US009926359B2

(12) United States Patent
Gross et al.

(10) Patent No.: US 9,926,359 B2
(45) Date of Patent: Mar. 27, 2018

(54) OPTOGENETIC INHIBITION OF OVERACTIVE NEURONAL ACTIVITY

(71) Applicant: EMORY UNIVERSITY, Atlanta, GA (US)

(72) Inventors: Robert E. Gross, Decatur, GA (US); Nealan G. Laxpati, Atlanta, GA (US); Jack Tung, Duluth, GA (US); Ken Berglund, Kennesaw, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/529,539

(22) Filed: Oct. 31, 2014

(65) Prior Publication Data

US 2015/0148407 A1 May 28, 2015

Related U.S. Application Data

(60) Provisional application No. 61/908,964, filed on Nov. 26, 2013.

(51) Int. Cl.
*C07K 14/705* (2006.01)
*C12N 9/02* (2006.01)
*A61K 31/4985* (2006.01)

(52) U.S. Cl.
CPC .......... *C07K 14/705* (2013.01); *C12N 9/0069* (2013.01); *A61K 31/4985* (2013.01); *C07K 2319/00* (2013.01); *C07K 2319/60* (2013.01); *C12Y 113/12005* (2013.01)

(58) Field of Classification Search
None
See application file for complete search history.

(56) References Cited

U.S. PATENT DOCUMENTS

2010/0145418 A1 * 6/2010 Zhang ...................... A61N 5/06 607/92
2015/0072394 A1 * 3/2015 Deisseroth ............... A61N 5/06 435/173.1
2016/0038755 A1 * 2/2016 Lundmark ........... A61N 1/0551 607/92

FOREIGN PATENT DOCUMENTS

JP 2011067190 * 7/2011
WO 2010011404 1/2010
WO WO 2010056970 * 5/2010
WO 2011005978 1/2011
WO 2013090356 6/2013

OTHER PUBLICATIONS

Contag In Vivo Pathology: Seeingwith Molecular Specificity and Cellular Resolutionin the Living Body Annu. Rev. Pathol. Mech. Dis. 2007. 2:277-305.*

Tung et al Optogenetic inhibition using a genetically encoded bioluminescent light source. Meeting Info: 2014 Biennial Meeting of the American Society for Stereotactic and Functional Neurosurgery. Washington, DC, United States. May 31, 2014-Jun. 3, 2014.*

Tung et al Optogenetic inhibition using a genetically encoded bioluminescent light source. Meeting Info.: 43rd Annual Meeting of the Society-for-Neuroscience. San Diego, CA, USA. Nov. 9-13, 2013. Soc Neuroscience.*

Inouye et al The Use of Renilla Luciferase, Oplophorus Luciferase, and Apoaequorin as Bioluminescent Reporter Protein in the Presence of Coelenterazine Analogues as SubstrateBiochemical and Biophysical Research Communications 233, 349-353 (1997).*

Acharya et al., Automated EEG analysis of epilepsy: A review Knowledge-Based Systems 45 (2013) 147-165.*

Epileptic seizure—Wikipedia p. 1-13 , downloaded on May 8, 2017.*

Rogers et al Progressive, Seizure-Like, Spike-Wave Discharges Are Common in Both Injured and Uninjured Sprague-Dawley Rats: Implications for the Fluid Percussion Injury Model of Post-Traumatic Epilepsy J. Neurosci., Jun. 17, 2015 • 35(24):9194-9204.*

Badea et al. "Calcium imaging of epileptiform events with single-cell resolution" J Neurobiol, 2001; 48: 215-227.

Berglund et al. "Light-Emitting Channelrhodopsins for Combined Optogenetic and Chemical-Genetic Control of Neurons" PLOS One, 2013; 8(3): e59759.

Bergland et al. "Lumigenetics: Multimodal control of neural circuits by combining optogenetics with bioluminescence" Soc for Neurosci Abstr, 2011.

Contag "In Vivo Pathology: Seeing with Molecular Specificity and Cellular Resolution in the Living Body" Annu. Rev. Pathol. Mech. Dis., 2007; 2: 277-305.

Desai et al. "Deep brain stimulation macroelectrodes compared to multiple microelectrodes in rat hippocampus" Frontiers in Neuroengineering, 2014; 7(16): 1-8.

Drobac et al. "Calcium imaging in single neurons from brain slices using bioluminescent reporters" J Neurosci Res., 2010; 88: 695-711.

Laxpati et al. "Optogenetic Activation of Hippocampal Pyramidal Cells is Highly Dependent on the Parameters of Stimulation" Soc for Neurosci Abstr, 2011.

Laxpati et al. "Deep Brain Stimulation for the Treatment of Epilepsy: Circuits, Targets, and Trials" Neurotherapeutics, 2014; 11: 508-526.

Saito et al. "Luminescent proteins for high-speed single-cell and whole-body imaging" Nat. Commun., 2012; 3: 1262.

Tung et al. "Optogenetic inhibition using a genetically encoded bioluminescent light source" Society for Neuroscience Abstract Viewer and Itinerary Planner, 2013; vol. 43.

Tung et al. "Inhibitory luminopsins: genetically encoded bioluminescent opsins for versatile, scalable, and hardware independent optogenetic inhibition" Scientific Reports, 2015; 5:14366.

(Continued)

*Primary Examiner* — Maria G Leavitt
(74) *Attorney, Agent, or Firm* — Emory Patent Group

(57) ABSTRACT

This disclosure relates to recombinant proteins, vectors, and methods of treating neurological conditions by exposing neurons to an opsin and luciferase in the presence of a luciferin. In certain embodiments, the disclosure relates to treating or preventing epilepsy or seizures comprising administering an effective amount of a vector that encodes an opsin and luciferase in combination with a luciferin to a subject in need thereof.

3 Claims, 5 Drawing Sheets

(56) References Cited

OTHER PUBLICATIONS

Verhaegen et al. "Recombinant Gaussia Luciferase. Overexpression, Purification, and Analytical Application of a Bioluminescent Reporter for DNA Hybridization" Anal. Chem., 2002; 74: 4378-4385.
Willie et al. "Real-Time Magnetic Resonance-Guided Stereotactic Laser Amygdalohippocampotomy for Mesial Temporal Lobe Epilepsy" Neurosurgery, 2014; 74: 569-585.
Zhang et al. "Multimodal fast optical interrogation of neural circuitry" Nature, 2007; 446: 633-639.
Zhao et al. "Improved expression of halorhodopsin for light-induced silencing of neuronal activity" Brain Cell Biol., 2008; 36(1-4): 141-154.

* cited by examiner

OPTOGENETIC INHIBITION OF OVERACTIVE NEURONAL ACTIVITY

CROSS REFERENCE TO RELATED APPLICATIONS

This Application claims priority to U.S. Provisional Application No. 61/908,964 filed Nov. 26, 2013, hereby incorporated by reference in its entirety.

STATEMENT REGARDING FEDERALLY FUNDED RESEARCH

This invention was made with government support under grants NS079268 and NS079757 awarded by the National Institutes of Health. The Government has certain rights in the invention.

BACKGROUND

Approximately 20-40% of patients with epilepsy have refractory seizures unresponsive to pharmacotherapy. Thus, there is a need to develop alternative treatments for this large population of people who are at higher risk of developing epilepsy-related disabilities.

Halorhodopsin is a membrane bound light-gated ion pump. Upon exposure to light, halorhodopsin moves chloride ions into a cell. Light induced halorhodopsin silences excitable neuronal cells. Zhao et al. reported the halorhodopsin from halophilic bacterium *Natronobacterium pharaonis* (NpHR) for light-induced silencing of neuronal activity. Brain Cell Biol, 2008, 36(1-4): 141-154. See also Zhang et al., Multimodal fast optical interrogation of neural circuitry. Nature, 2007, 446:633-639.

Luciferases produce light in the presence of luciferin. Coelenterazine (CTZ) is a substrate luciferin of Renilla reniformis luciferase (Rluc) and Gaussia luciferase (Gluc). Berglund et al. report using a luciferase for light-activating a channelrhodopsin for combined optogenetic and chemical-genetic control of neurons. *PLoS ONE,* 2013, 8(3): e59759. See also WO 2011/005978 and WO 2010/011404.

References cited herein are not an admission of prior art.

SUMMARY

This disclosure relates to recombinant proteins, vectors, and methods of treating neurological conditions by exposing neurons to an opsin and luciferase in the presence of a luciferin. In certain embodiments, the disclosure relates to treating or preventing epilepsy or seizures comprising administering an effective amount of a nucleic acid or vector that encodes an opsin and luciferase in combination with a luciferin to a subject in need thereof.

In certain embodiments, the disclosure relates to recombinant proteins comprising a light-activated opsin, termed Biologic Controller (BC), and a luciferase and typically comprising a second fluorescent sequence inserted between the C-terminal of the light-activated opsin and N-terminal of the luciferase. Typically the second fluorescent sequence is configured and capable of fluorescence resonance energy transfer (FRET) with the luciferase. In certain embodiments, the luciferase is activity-dependent (e.g. calcium-sensing), termed an Autonomous Biologic Controller (ABC).

In certain embodiments, the recombinant protein comprises SEQ ID NO: 1 or 11 or variant thereof having greater than 50, 60, 70, 80, 90, 95, 98 or 99% identity or similarity thereto. In certain embodiments, the light-activated opsin is halorhodopsin (NpHR), or an enhanced halorhodopsin (eNpHR2.0 and eNpHR3.0). In certain embodiments, the light-activated opsin is archaerhodopsin. In certain embodiments the luciferase is Renilla luciferase or Gaussia luciferase.

In certain embodiments, the disclosure relates to synthetic nucleic acids or vectors comprising a recombinant nucleic acid encoding a light-activated opsin and encoding a luciferase. In certain embodiments, the vector is a lentiviral vector, adenovirus, retrovirus, an adeno-associated virus (AAV), vaccinia virus, or poxvirus. In certain embodiments, the vector is a herpes simplex virus, e.g., HSV-1. Viral vectors may or may not be deficient or attenuated in their ability to replicate.

In certain embodiments, the light-activated opsin and the luciferase are encoded such that they would be expressed in the same polypeptide.

In certain embodiments, the light-activated opsin and the luciferase are encoded such that they would be expressed in different polypeptides.

In certain embodiments, the synthetic nucleic acid or vector encodes a polypeptide comprising SEQ ID NO: 1 or 11 or variant thereof having greater than 50, 60, 70, 80, 90, 95, 98, or 99% identity or similarity thereto.

In certain embodiments, the synthetic nucleic acid or vector comprises a c-fos promoter.

In certain embodiments, the luciferase is activity-dependent (e.g. responsive to calcium or chloride).

In certain embodiments, the disclosure relates to cells or other expression systems comprising nucleic acids and vectors disclosure herein.

In certain embodiments, the disclosure relates to methods of treating or preventing a neurological disease or condition comprising administering an effective amount of a nucleic acid or vector disclosed herein in combination with a luciferin to a subject in need thereof.

In certain embodiments, the neurological disease is epilepsy, retinal degeneration, Parkinson's disease, or cardiac dysrthymais.

In certain embodiments, the neurological condition is a seizure.

In certain embodiments, the luciferin is coelenterazine (CTZ) or derivative.

In certain embodiments, the subject is a human.

In certain embodiments the disclosure relates to recombinant or synthetic peptides, fusions, nucleic acids, or vectors comprising nucleic acid sequences discloses herein or variants thereof having greater than 50, 60, 70, 80, 90, 95, 98, or 99% identity or similarity thereto.

DETAILED DESCRIPTION

Figure 1A:
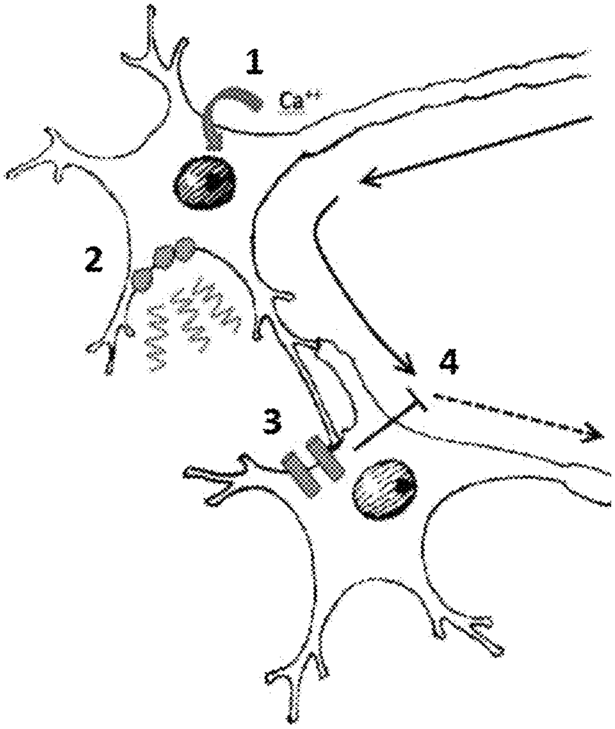
FIG. 1A illustrates an epileptic thermostat by showing how luciferase can be activated by neural activity (e.g. calcium influx) and activate a coupled opsin (Halorhodopsin). The luciferase and opsin are expressed separately (as illustrated in different neurons in this case, although it could also be in the same neuron). Propagating activity induces a Ca influx (1). A Ca-sensing luciferase (2) emits light in response to influx and activates an inhibitory opsin (3), which hyperpolarizes the downstream cell and prevents propagation of pathological activity (4). A calcium-sensitive luciferase senses pathological activity and responds by emitting light, thus activating an inhibitory opsin and arresting propagation of neural activity as the cell is hyperpolarized. Since the bioluminescence is tied to neural activity, as the latter decreases so will the former, as well as the consequent inhibition.
Figure 1B:
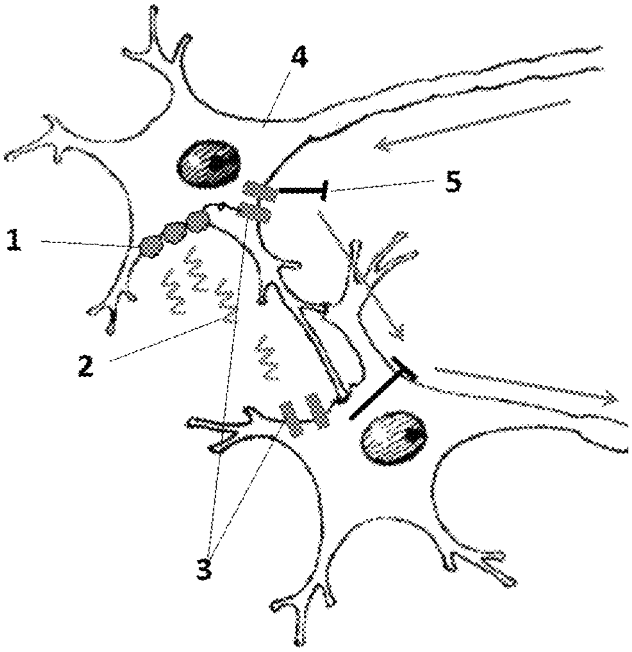
FIG. 1B illustrates a genetically-encoded light-activated opsin, e.g., halorhodopsin (NpHR), enhanced halorhodopsin (eNpHR2.0 and eNpHR3.0), or archaerhodopsin (Arch) (3) fused to a bioluminescent protein, e.g., luciferase (1). The luciferase and opsin are expressed together as a fusion protein. A fluorescent tag (5), e.g, TagBFP-TagGFP2 or EYFP, may also be conjugated to the fusion. See Subach et al. Conversion of Red Fluorescent Protein into a Bright Blue Probe. Chem Biol. 2008; 15 (10):1116-24.
Figure 2:
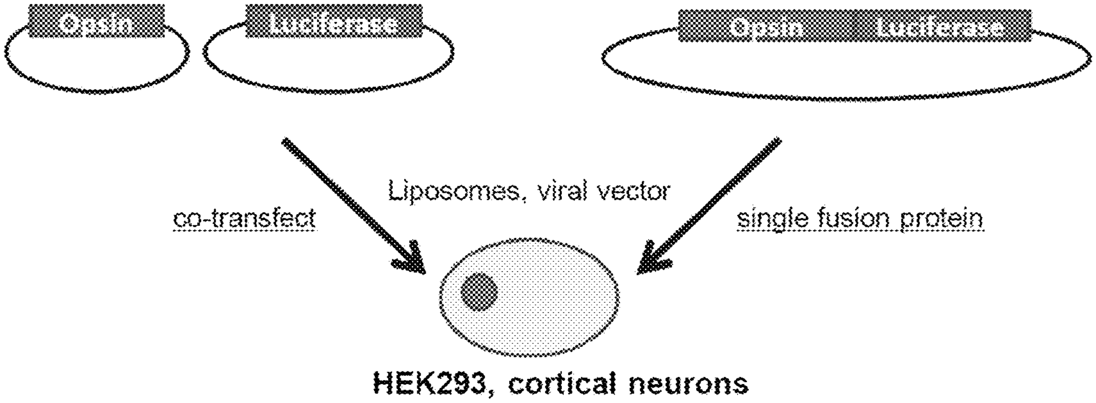
FIG. 2 illustrates Biologic Controllers (BC): BC1.0, Halorhodopsin and TagFPRluc; BC1.1, Halorhodopsin fused to TagFPRluc; BC2.0, Arch and TagFPRluc; BC2.1, Arch fused to TagFPRluc.
Figure 3A:
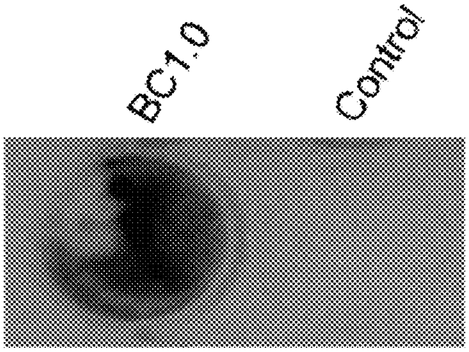
FIG. 3A shows transfected HEK293 cells express BC1.0 Biologic Controllers luminesce (black signal) after addition of CTZ.
Figure 3B:
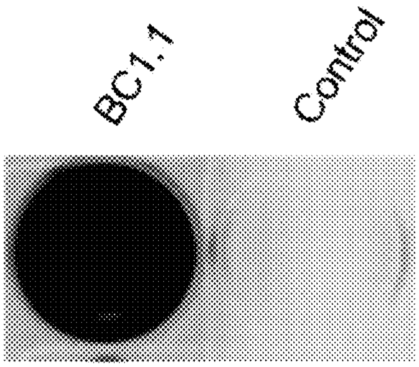
FIG. 3B shows transfected HEK293 cells express BC1.1 Biologic Controllers luminesce (black signal) after addition of CTZ.
Figure 4:
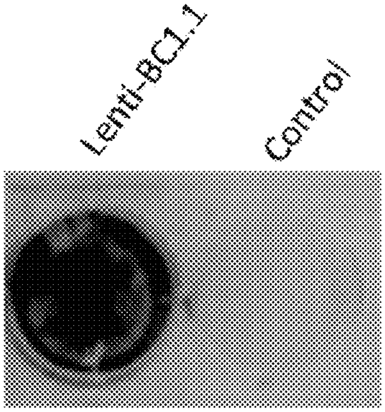
FIG. 4 illustrates Biologic Controller 1.1 was packaged into a lentiviral vector and used to infect dissociated cortical neurons. Infected neurons still luminesce (black signal) after addition of CTZ and hyperpolarize in response to green light illumination.
Figure 5:
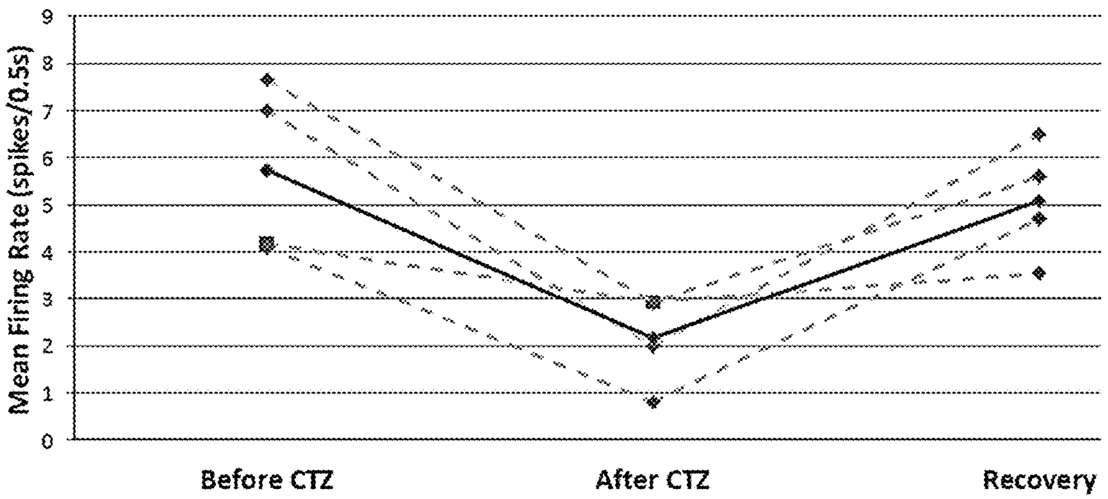
FIG. 5 shows data indicating Biologic Controller 1.1 was able to inhibit evoked activity in cortical neuron cultures. Trains of action potentials were evoked by 30 pA current injections. (A): Firing rate was significantly reduced during periods of green light illumination. (B): Firing rate was similarly reduced after CTZ addition. (C): Baseline activity was eventually recovered minutes after CTZ addition. CTZ did not have any significant effect on firing rate in control (uninfected) neurons.
Figure 6A:
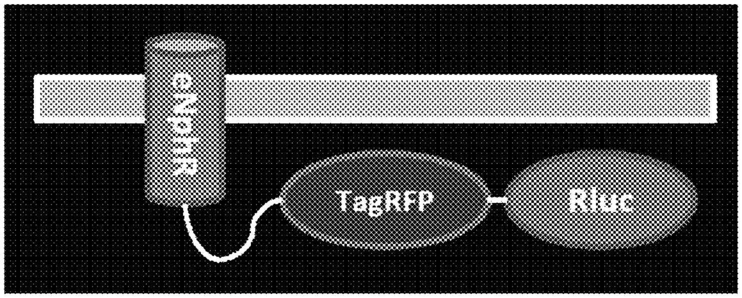
FIG. 6A illustrates an embodiment of the disclosure.
Figure 6B:
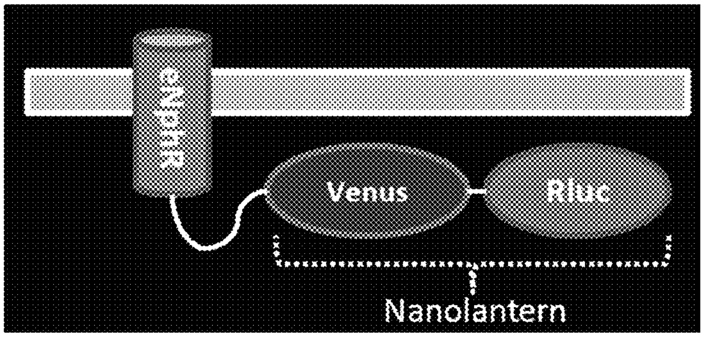
FIG. 6B illustrates an embodiment of the disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

The term "opsin" refers to light-sensitive membrane-bound channel polypeptides typically of 35-55 kDa. Examples include halorhodopsin (NpHR), or enhanced halorhodopsins (eNpHR2.0 and eNpHR3.0), archaerhodopsin, and variants thereof.

An example halorhodopsin (eNpHR2.0) has the following sequence (SEQ ID NO: 5), MTETLPPVTESAV-ALQAEVTQRELFEFVLNDPLLASSLYINIALAGLSILL-FVFMTRGLDDPRA KLIAVSTILVPVVSIASYTGLAS-GLTISVLEMPAGHFAEGSSVMLGGEEVDGVVTMW-GRYLT WALSTPMILLALGLLAGSNATKLFTAITFDI-AMCVTGLAAALTTSSHLMRWFWYAISCACFL VVLY-ILLVEWAQDAKAAGTADMFNTLKLLTVVM-WLGYPIVWALGVEGIAVLPVGVTSWG YSFLDIVAKYIFAFLLLNYLTSNESVVSGSILDVPSAS-GTPADD.

An example halorhodopsin (eNpHR3.0) has the following sequence (SEQ ID NO: 6). MTETLPPVTESAV-ALQAEVTQRELFEFVLNDPLLASSLYINIALAGLSILL-FVFMTRGLDDPRA KLIAVSTILVPVVSIASYTGLAS-GLTISVLEMPAGHFAEGSSVMLGGEEVDGVVTMW-GRYLT WALSTPMILLALGLLAGSNATKLFTAITFDI-AMCVTGLAAALTTSSHLMRWFWYAISCACFL VVLY-ILLVEWAQDAKAAGTADMFNTLKLLTVVM-WLGYPIVWALGVEGIAVLPVGVTSWG YSFLDIVAKYIFAFLLLNYLTSNESVVSGSILDVPSAS-GTPADD. Contemplated variants may have greater than 50, 60, 70, 80, 90, 95, 98 or 99% identity or similarity thereto.

An example archaerhodopsin has the following sequence (SEQ ID NO: 7), MDPIALQAGY DLLGDGRPET LWL- GIGTLLM LIGTFYFIVK GWGVTDKEAR EYYSITILVP GIASAAYLSM FFGIGLTEVT VAGEVLDIYY ARYADWLFTT PLLLLDLALL AKVDRVSIGT LVGVDALMIV TGLIGALSHT PLARYSWWLF STICMIVVLY FLATSLRAAA KERGPEVAST FNTLTALVLV LWTAYPILWI IGTEGAGVVG LGIETLLFMV LDVTAKVGFG FILLRSRAIL GDTEAPEP. Contemplated variants may have greater than 50, 60, 70, 80, 90, 95, 98 or 99% identity or similarity thereto.

The term "luciferase" refers to luciferin oxidative enzymes that function in bioluminescence. Luciferin refers to a compound that emits light due to a reaction with a luciferase. Coelenterazine and water soluble derivatives are known luciferins. A luciferase may be naturally occurring or a non-naturally occurring variant. Examples include Renilla reniformis luciferase, Gaussia luciferase, aequorin, firefly luciferase, Metridia luciferase (MetLuc) and variants thereof. An example Luciferase is RLuc8 has the following sequence (SEQ ID NO: 8) MASKVYDPEQ RKRMITGPQW WARCKQMNVL DSFINYYDSE KHAENAVIFL HGNATSSYLW RHVVPHIEPV ARCIIPDLIG MGKSGKSGNG SYRLLDHYKY LTAWFELLNL PKKIIFVGHD WGAALAFHYA YEHQDRIKAI VHMESVVDVI ESWDEWPDIE EDIALIKSEE GEKMVLENNF FVETVLPSKI MRKLEPEEFA AYLEPFKEKG EVRRPTLSWP REIPLVKGGK PDVVQIVRNY NAYLRASDDL PKLFIESDPG FFSNAIVEGA KKFPNTEFVK VKGLHFLQED APDEMGKYIK SFVERVLKNE Q. See Loening et al., Consensus guided mutagenesis of Renilla luciferase yields enhanced stability and light output. Prot. Eng. Des. Sel. 19, 391-400 (2006). Contemplated variants may have greater than 50, 60, 70, 80, 90, 95, 98 or 99% identity or similarity thereto.

A "fluorescent protein" refers to a polypeptide that upon expression maintains fluorescence upon exposure to light. The fluorescent protein may contain multiple or repeating sequences. Multiple sequences may be FRET pairs. Examples include yellow fluorescent protein and variants thereof such as yellow fluorescent protein (YFP) having mutation F46L and optionally other mutations, F64L, M153T, V163A, and/or S175G. See Nagai et al. A variant of yellow fluorescent protein with fast and efficient maturation for cell-biological applications. Nat. Biotechnol. 20, 87-90 (2002). An example YFP has the following sequence (SEQ ID NO: 9), MSKGEELFTG VVPILVELDG DVNGHKFSVS GEGEGDATYG KLTLKFICTT GKLPVPWPTL VTTFGYGLQC FARYPDHMKR HDFFKSAMPE GYVQERTIFF KDDGNYKTRA EVKFEGDTLV NRIELKGIDF KEDGNILGHK LEYNYNSHNV YIMADKQKNG IKVNFKIRHN IEDGSVQLAD HYQQNTPIGD GPVLLPDNHY LSYQSALSKD PNEKRDHMVL LEFVTAAGIT HGMDELYK. Contemplated variants may have greater than 50, 60, 70, 80, 90, 95, 98 or 99% identity or similarity thereto. "Venus" refers to a YFP variant having the following sequence (SEQ ID NO: 10) MVSKG EELFTGVVPI LVELDGDVNG HKFSVSGEGE GDATYGKLTL KLICTTGKLP VPWPTLVTTL GYGLQCFARY PDHMKQHDFF KSAMPEGYVQ ERTIFFKDDG NYKTRAEVKF EGDTLVNRIE LKGIDFKEDG NILGHKLEYN YNSHNVYITA DKQKNGIKAN FKIRHNIEDG GVQLADHYQQ NTPIGDGPVL LPDNHYLSYQ SALSKDPNEK RDHMVLLEFV TAAGITLGMD ELYK.

The term "a nucleic acid sequence encoding" a specified polypeptide refers to a nucleic acid sequence comprising the coding region of a gene or in other words the nucleic acid sequence which encodes a gene product. The coding region may be present in either a cDNA, synthetic copy or genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene.

Efficient expression of recombinant nucleic acid sequences in eukaryotic cells requires expression of signals directing the efficient termination and polyadenylation of the resulting transcript. Transcription termination signals are generally found downstream of the polyadenylation signal and are typically a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene.

Sequence "identity" refers to the number of exactly matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing an amino group with a hydroxyl group. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NR_aC(=O)NR_aNR_b$, $-NR_aC(=O)ORb$, $-NR_aSO_2R_b$, $-C(=O)R_a$, $-C(=O)OR_a$, $-C(=O)NR_aR_b$, $-OC(=O)NR_aRb$, $-OR_a$, $-SR_a$, $-SOR_a$, $-S(=O)_2R_a$, $-OS(=O)_2R_a$ and $-S(=O)_2ORa$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Optogenetic Vectors using Bioluminescent Light Sources

Light sensitive ion channels or pumps (opsins), when transduced into neural tissue, provide a means to selectively excite or inhibit cell-type specific subpopulations of neurons in vivo. Channelrhodopsin-2 (ChR2) is a cation channel that is activated by blue light, while Halorhodopsin (NpHR) is a chloride pump that when exposed to yellow light hyperpolarizes the cell. For in vitro preparations in the brain, activating light is conventionally delivered with halogen/xenon arc lamps and LEDs, with pulses generated via fast shutter or intensity modulation. In vivo light delivery is more complicated; superficial stimulation relying on small mounted LEDs above the brain, and optical fibers used to target deeper structures.

Distributed structures can thus be more easily interrogated in vitro than in vivo. For example, inhibition of pathologic activity in a slice model of hippocampal epilepsy allows for control of pyramidal neurons across the slice, and our own experiments in the hippocampus with AAV2-CaMK11a-ChR2 have shown similar results. However experiments in an awake, behaving Parkinson's disease model using optical fibers to direct light indicate that only approximately 0.7 $mm^3$ of tissue can be controlled in this fashion. Thus there is a need for distributed activation of opsins in vivo.

Bioluminescence from luciferase proteins offers an alternative light source for activation of opsins. Bioluminescence from luciferase proteins can be utilized to activate opsins. Coupling the expression of luciferase with opsin in neurons obviates the need for external light sources delivered through implanted optical fibers in vivo and facilitate clinical translation.

Activity-dependent luciferases couple to opsins may be achieved in several ways. Several calcium-sensing luciferases have been developed and used as bioluminescent reporters of neural activity (e.g. GFP-Aequorin, Nanolantern-Ca's). These reagents can be directly utilized to report neural activity in the form of bioluminescence and autonomously activate coupled opsins. One can express luciferase in an activity-dependent fashion. For example, When luciferase expression is driven by an immediate-early gene (c-fos) reporter, they can effectively reflect neuron activity. One illustration of how activity-dependent luminescence could be used to autonomously activate opsins could therefore be rats rendered epileptic with focal injections of tetanus toxin to the hippocampus may be simultaneously infected with viral vectors encoding activity-dependent luciferase (either Ca-sensing or c-fos driven expression), and CaMK11a-eNpHR. Overactivation of hippocampal neurons due to epileptiform activity would drive biolumniescense, which will then drive bioluminescence of those same neurons through activation of eNpHR, reducing their activity. Hyperpolarization will then bring luciferase activity back toward baseline reducing inhibitory current. This should lead to a steady-state situation, which will reduce pathologic activity and seizures.

EXAMPLES

Bioluminescent Resonance Energy Transfer (BRET) Based Reporter

BRET-based reporters are fusion proteins of a luciferase and a fluorescent protein; this fusion allows energy to be transferred from the luciferase to the fluorescent protein, enabling enhanced emission of bright light. Dragulescu-Andrasi et al. report a BRET systems consist of Renilla reniformis luciferase (RLuc) variants RLuc8 and RLuc8.6, used as BRET donors, combined with two red fluorescent proteins, TagRFP and TurboFP635, as BRET acceptors. Proc Natl Acad Sci USA, 2011, 108(29):12060-5.

A number of AAV and lentivirus-based vectors have been produced and tested for delivering optogenetic channels. Using viral vectors one can deliver a high copy number of transgene as well as allow cell-type specific expression in in vivo studies. One can transduce luciferase into primary cortical neurons, confirm transgene expression using fluorescence microscopy, and perform a titration experiment with coelanterazine substrate to determine the optimal parameters for producing bioluminescence. AAV encoding eNpHR3.0 and Arch under the control of the CAMKII promoter have been produced.

One delivers luciferase and inhibitory opsin to various primary cortical neuron cultures using the viral vectors. The viral titers used in these co-infections are varied to obtain a heterogeneous population of luciferase-expressing and opsin-expressing cells. Luciferase-expressing cells and opsin-expressing cells are identified by fluorescence microscopy. Coelenterazine substrate is added to the culture in various concentrations, and its effect on network activity is determined.

Simultaneous patch clamp studies is conducted to determine cellular responses in (1) cells expressing both opsin and luciferase (i.e. both components in cis) and (2) cells expressing only opsin (i.e. both components in trans). As an alternative to co-infection, one can also deliver luciferase and inhibitory opsin together as a fusion protein. Various molecular strategies can also be employed (such as adding dimerizing or transmembrane domains) to facilitate co-localization of the luciferase and inhibitory opsin to the cell membrane.

A BRET-based Auto-luminescent Calcium (BRAC) indicator as an bioluminescent reporter is used for several reasons: (1) BRAC has an emission spectrum (peak 530 nm) that overlaps closely with our inhibitory opsins; (2) BRAC has been shown to regenerate faster than other calcium indicators; (3) and BRAC exhibits resonance energy transfer, which produces robust bioluminescent signal. An alternative calcium-sensitive luciferase that can be used as a sensor for neural activity is GFP-aequorin or Nanolantern-Ca.

An exemplary BRET luciferase polypeptide is TagRFPR-luc has SEQ ID NO: 1, MVSKGEELIKENMHMK-LYMEGTVNNHHFKCTSEGEGKPYEGTQTMRIKV-VEGGPLPFAFDI LATSFMYGSRTFINHTQGIPDFFKQSFPEGFTWERVT-TYEDGGVLTATQDTSLQDGCLIYNVK IRGVNFPSNG-PVMQKKTLGWEANTEMLYPADGGLEGRSDMAL-KLVGGGHLICNFKTTYRSK KPAKNLKMPGVYYVDHRLERIKEADKE-TYVEQHEVAVARYCDLPSKLGHKLNSGLRSDIGP SRATMASKVYDPEQRKRMITGPQWWARCKQMNV-LDSFINYYDSEKHAENAVIFLHGNATSS YLWRHVV-PHIEPVARCIIPDLIGMGKSGKSGNGSYRLLDHYKYL-TAWFELLNLPKKIIFVGHD WGSALAFHYAYEHQDRIKAIVHMESVVDVIESWMG-WPDIEEELALIKSEEGEKMVLENNFF VETLLPSKIM-RKLEPEEFAAYLEPFKEKGEVRRPTLSWPREIPLVKG-GKPDVVQIVRNYNAYL RASDDLPKLFIESDPGFFSNAIVEGAKKFPNTEFVK-VKGLHFLQEDAPDEMGKYIKSFVERVL KNEQ.

An exemplary nucleic acid encoding a BRET luciferase polypeptide has SEQ ID NO: 2, ATGGTGTCTAAGGGC-GAAGAGCTGATTAAGGAGAACATGCACAT-GAAGCTGTACATGGA GGGCACCGTGAACAACCAC-CACTTCAAGTGCACATCCGAGGGCGAAGGCAAG-CCCTACG AGGGCACCCAGACCATGAGAAT-CAAGGTGGTCGAGGGCGGCCCTCTCCCCTTCGC-CTTC GACATCCTGGCTACCAGCTTCATGTACGGCA-GCAGAACCTTCATCAACCACACCCAGGGC ATCCCCGACTTCTTTAAGCAGTCCTTCCCT-GAGGGCTTCACATGGGAGAGAGTCACCACA TAC-GAAGACGGGGGCGTGCTGACCGCTACCCAGGA-CACCAGCCTCCAGGACGGCTGCCT CATCTACAACGTCAAGATCAGAGGGGTGAACTTC-CCATCCAACGGCCCTGTGATGCAGA AGAAAACACTCGGCTGGGAGGCCAACACCGAGAT-GCTGTACCCCGCTGACGGCGGCCTG GAAGGCA-GAAGCGACATGGCCCT-GAAGCTCGTGGGCGGGGGCCACCTGATCTGCAA-CTT CAAGACCACATACAGATCCAAGAAAC- CCGCTAAGAACCTCAAGATGCCCGGCGTCTACT ATGTGGACCACAGACTGGAAAGAATCAAGGAGGC-CGACAAAGAGACCTACGTCGAGCA GCACGAG-GTGGCTGTGGCCAGATACTGCGACCTCCCTAG-CAAACTGGGGCACAAACTTA ATTCCGGACTCAGATCTGATATCGGGCCCTCTA-GAGCCACCATGGCTTCCAAGGTGTACG ACCCCGAGCAACGCAAACGCATGATCACTGGGC-CTCAGTGGTGGGCTCGCTGCAAGCAA ATGAACGT-GCTGGACTCCTTCATCAACTACTATGATTCCGA-GAAGCACGCCGAGAACGCC GTGATTTTTCTGCATGGTAACGCTACCTCCAGCTAC-CTGTGGAGGCACGTCGTGCCTCAC ATCGAGC-CCGTGGCTAGATGCATCATCCCTGATCTGATCG-GAATGGGTAAGTCCGGCAA GAGCGGGAATGGCTCATATCGCCTCCTGGATCAC-TACAAGTACCTCACCGCTTGGTTCGA GCTGCT-GAACCTTCCAAAGAAAATCATCTTTGTGGGCCAC-GACTGGGGGAGCGCTCTGGC CTTTCACTACGCCTACGAGCACCAAGACAGGAT-CAAGGCCATCGTCCATATGGAGAGTG TCGTG-GACGTGATCGAGTCCTGGATGGGGTGGCCT-GACATCGAGGAGGAGCTGGCCCTG ATCAAGAGCGAAGAGGGCGAGAAAATGGTGCTT-GAGAATAACTTCTTCGTCGAGACCCT GTTGC-CAAGCAAGATCATGCGGAAACTGGAGCCTGAG-GAGTTCGCTGCCTACCTGGAGC CATTCAAGGAGAAGGGCGAGGTTAGACGGCCTAC-CCTCTCCTGGCCTCGCGAGATCCCTC TCGT-TAAGGGAGGCAAGCCCGACGTCGTCCAGATTGTC-CGCAACTACAACGCCTACCTTC GGGCCAGCGACGATCTGCCTAAGCTGTTCATC-GAGTCCGACCCTGGGTTCTTTTCCAACG CTATT-GTCGAGGGAGCTAAGAAGTTCCCTAACACCGAGT-TCGTGAAGGTGAAGGGCCTC CACTTCCTCCAGGAGGACGCTCCAGAT-GAAATGGGTAAGTACATCAAGAGCTTCGTGGA GCGCGTGCTGAAGAACGAGCAG An exemplary nucleic acid encoding a light-activated opsin is “eNphR3.0-TagRFPRluc” which has SEQ ID NO: 3, ATGACAGAGACCCTGCCTCCCGTGACCGAGAGT-GCCGTGGCCCTTCAAGCCGAGGTTAC CCAAAGGGAGTTGTTCGAGTTCGTGCTGAACGAC-CCTTTGCTTGCAAGCAGTCTCTATAT CAACATCG-CACTTGCAGGACTGAGTATACTGCTGTTCGTTTT-TATGACCCGAGGACTCGA TGATCCACGGGCAAAACTTATTGCTGTGTCAAC-CATCCTTGTGCCTGTCGTCAGCATTGC CTCCTA-CACTGGATTGGCGAGCGGCCTGACAATTTCCGT-TCTTGAAATGCCAGCGGGCCA TTTTGCAGAAGGCAGCTCAGTGATGCTGGGAGGA-GAAGAGGTAGATGGTGTAGTCACCA TGTGGGGACGGTATCTCACCTGGGCACTTTC-CACGCCCATGATTCTCCTCGCTCTGGGTCT CCTG-GCCGGAAGCAATGCTACAAAGCTCTTCACAGCTAT-CACTTTCGATATCGCTATGTG CGTGACTGGCCTTGCCGCGGCCCTGACTACCTC-CTCCCACCTCATGAGATGGTTCTGGTA CGCTATCA-GTTGTGCATGCTTTCTGGTGGTCTTGTATATCCT-GCTGGTGGAGTGGGCACA GGACGCCAAAGCCGCGGGAACCGCTGACATGT-TCAATACCCTGAAGCTGTTGACAGTAG TGATGTG-GCTGGGGTATCCAATTGTGTGGGCTCTTGGAGTC-GAGGGTATCGCGGTGTTGC CCGTTGGGGTGACGAGCTGGGGATATTCTTTCCTG-GATATCGTGGCAAAGTACATTTTCG CATTCTT- GCTCCTGAACTATCTGACGTCAAACGAATCT-
GTCGTGTCCGGCAGCATTTTGG ATGTTCCATCT-
GCTTCTGGGACCCCGGCTGATGATGCGGCCGC-
TATGGTGTCTAAGGGCG
AAGAGCTGATTAAGGAGAACATGCACATGAAGCT-
GTACATGGAGGGCACCGTGAACAAC CACCACT-
TCAAGTGCACATCCGAGGGCGAAGGCAAGC-
CCTACGAGGGCACCCAGACCAT
GAGAATCAAGGTGGTCGAGGGCGGCCCTCTC-
CCCTTCGCCTTCGACATCCTGGCTACCAG CTTCAT-
GTACGGCAGCAGAACCTTCATCAACCACACCCA-
GGGCATCCCCGACTTCTTTAA
GCAGTCCTTCCCTGAGGGCTTCACATGGGAGA-
GAGTCACCACATACGAAGACGGGGGCG TGCTGAC-
CGCTACCCAGGACACCAGCCTCCAGGACGGCTGC-
CTCATCTACAACGTCAAG
ATCAGAGGGGTGAACTTCCCATCCAACGGCCCTGT-
GATGCAGAAGAAAACACTCGGCTG GGAGGC-
CAACACCGAGATGCTGTACCCCGCTGACGGCGGC-
CTGGAAGGCAGAAGCGAC
ATGGCCCTGAAGCTCGTGGGCGGGGGCCACCT-
GATCTGCAACTTCAAGACCACATACAG ATC-
CAAGAAACCCGCTAAGAACCTCAAGATGCCCG-
GCGTCTACTATGTGGACCACAGAC
TGGAAAGAATCAAGGAGGCCGACAAAGAGAC-
CTACGTCGAGCAGCACGAGGTGGCTGT GGCCAGA-
TACTGCGACCTCCCTAGCAAACTGGGGCA-
CAAACTTAATTCCGGACTCAGAT
CTGATATCGGGCCCTCTAGAGCCACCATGGCTTC-
CAAGGTGTACGACCCCGAGCAACGC AAACGCAT-
GATCACTGGGCCTCAGTGGTGGGCTCGCTG-
CAAGCAAATGAACGTGCTGGA
CTCCTTCATCAACTACTATGATTCCGA-
GAAGCACGCCGAGAACGCCGTGATTTTTCTGCA
TGGTAACGCTACCTCCAGCTACCTGTGGAG-
GCACGTCGTGCCTCACATCGAGCCCGTGGC TAGAT-
GCATCATCCCTGATCTGATCGGAATGGGTAAGTC-
CGGCAAGAGCGGGAATGGCT
CATATCGCCTCCTGGATCACTACAAGTACCTCAC-
CGCTTGGTTCGAGCTGCTGAACCTTC
CAAAGAAAATCATCTTTGTGGGCCAC-
GACTGGGGGAGCGCTCTGGCCTTTCACTACGCCT
ACGAGCACCAAGACAGGATCAAGGCCATCGTC-
CATATGGAGAGTGTCGTGGACGTGATC GAGTC-
CTGGATGGGGTGGCCTGACATCGAGGAGGAGCTG-
GCCCTGATCAAGAGCGAAGA
GGGCGAGAAAATGGTGCTTGAGAATAACTTCT-
TCGTCGAGACCCTGTTGCCAAGCAAGA TCATGCG-
GAAACTGGAGCCTGAGGAGTTCGCTGCCTACCTG-
GAGCCATTCAAGGAGAAG
GGCGAGGTTAGACGGCCTACCCTCTCCTGGC-
CTCGCGAGATCCCTCTCGTTAAGGGAGGC AAGC-
CCGACGTCGTCCAGATTGTCCGCAACTACAACGC-
CTACCTTCGGGCCAGCGACGAT
CTGCCTAAGCTGTTCATCGAGTCCGACCCTGGGT-
TCTTTTCCAACGCTATTGTCGAGGGA
GCTAAGAAGTTCCCTAACACCGAGTTCGT-
GAAGGTGAAGGGCCTCCACTTCCTCCAGGA
GGACGCTCCAGATGAAATGGGTAAGTACAT-
CAAGAGCTTCGTGGAGCGCGTGCTGAAGA
ACGAGCAGTAA.

Figure 7A:
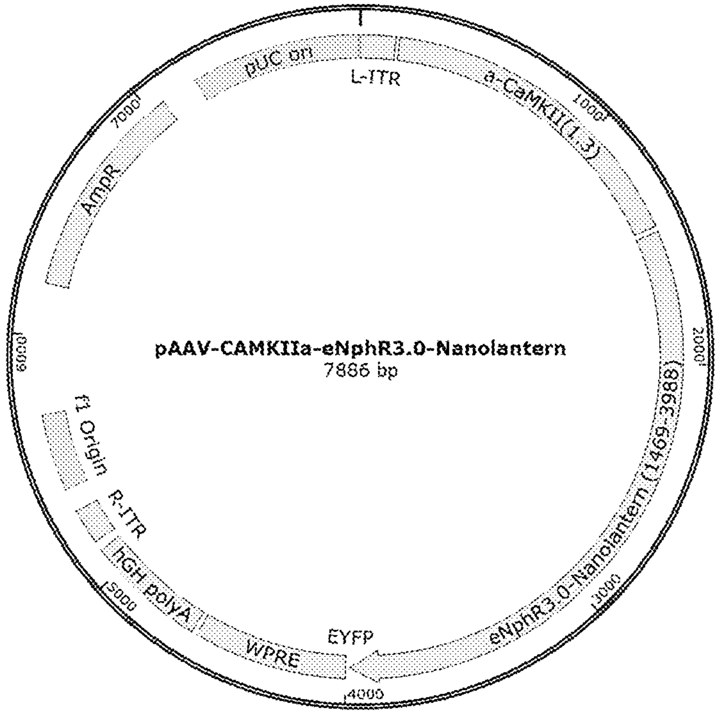
FIG. 7A illustrates a vector map for pAAV-CAMKIIa-eNphR3.0-Nanolantern.
Figure 7B:
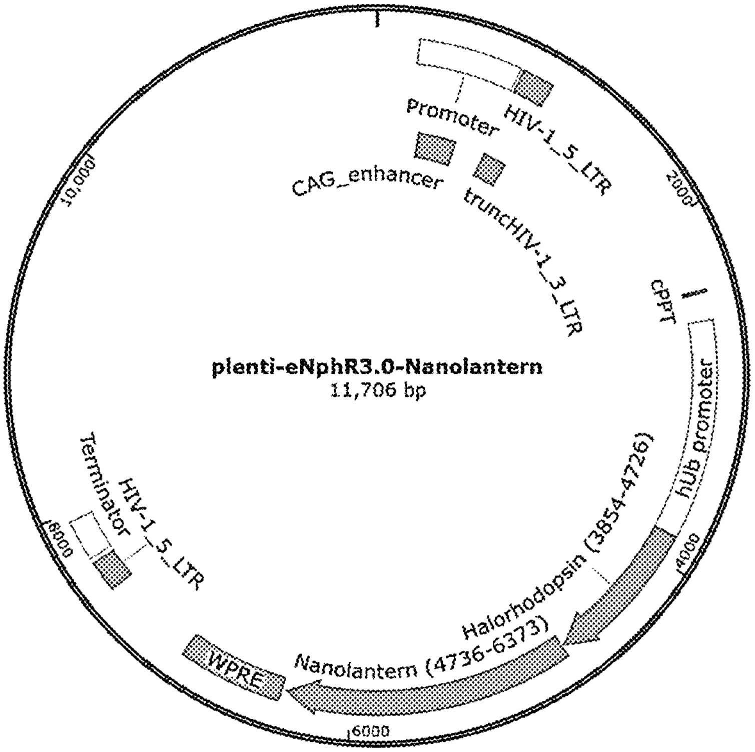
FIG. 7B illustrates a vector map for plenti-eNphR3.0-Nanolantern.
Figure 7C:
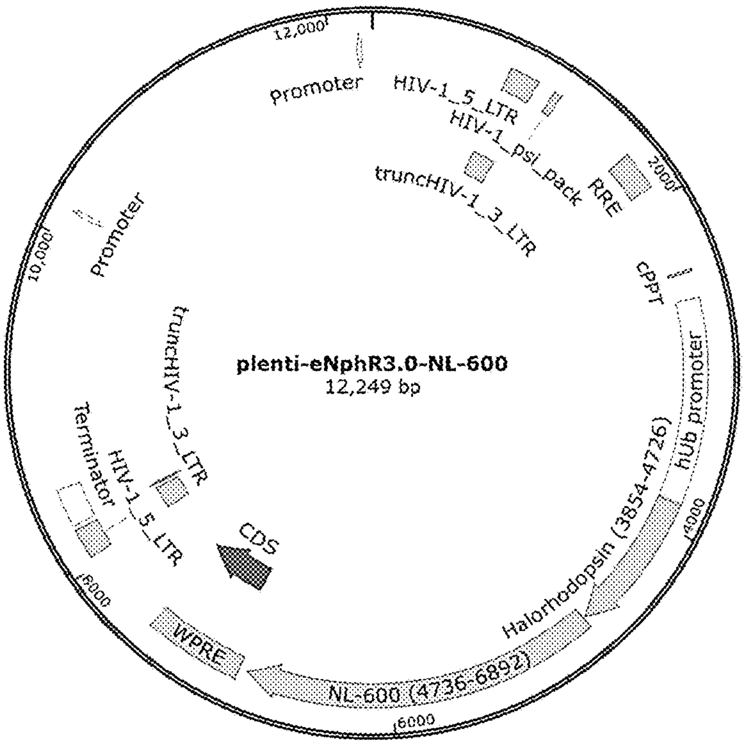
FIG. 7C illustrates a vector map for plenti-eNphR3.0-NL-600.
Figure 8:
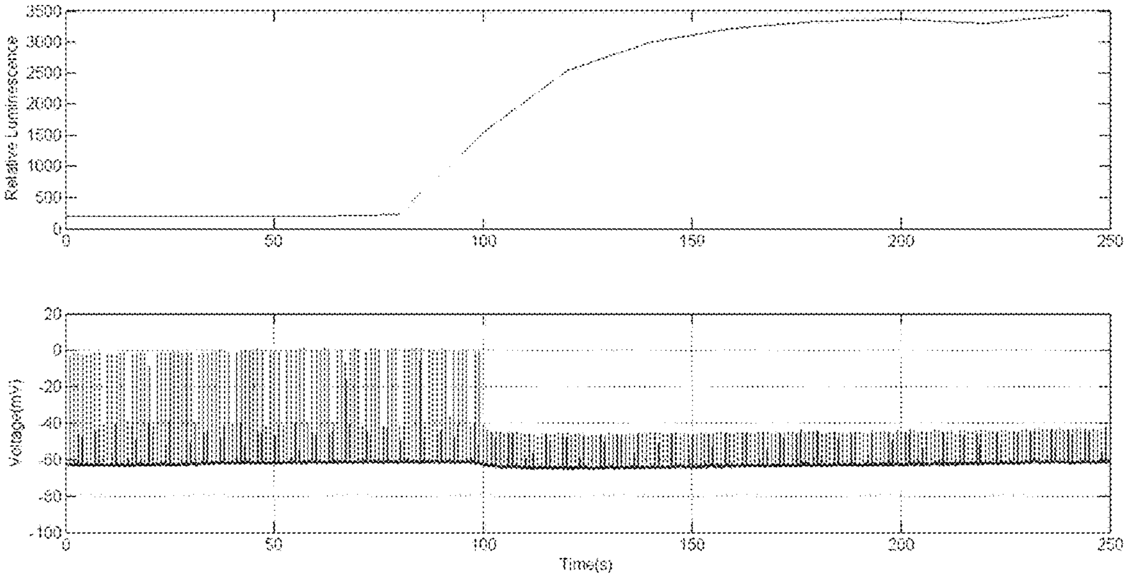
FIG. 8 shows data indicating the inhibition of evoked spikes in a neuron expressing eNpHR3.0-Nanolantern. When a neuron is given a sub-threshold depolarizing current injection (not every current injection induces an action potential), CTZ is able to completely attenuate evoked action potentials. This inhibition of evoked activity corresponds to an increase in luminescence signal (top).

An exemplary lentiviral vector is plenti-FU-eNphR3.0-TagRFP-Rluc-WPRE (See Lois et al., Germline transmission and tissue-specific expression of transgenes delivered by lentiviral vectors, 2002, Science, 295(5556):868-72) which has SEQ ID NO: 4, (hUB promoter: 2618-3846 and eNphR3.0-TagRFPRluc: 3863-643) GTCGACG-
GATCGGGAGATCTCCCGATCCCCTATGGTG-
CACTCTCAGTACAATCTGCTCTG ATGCCGCATAGT-
TAAGCCAGTATCTGCTCCCTGCTTGTGTGTTGGAG-
GTCGCTGAGTAGT GCGCGAGCAAAATTTAAGCTA-
CAACAAGGCAAGGCTTGACCGACAATTGCAT-
GAAGAAT CTGCTTAGGGTTAGGCGTTTTGCGCT-
GCTTCGCGATGTACGGGCCAGATATACGCGTTGA
CATTGATTATTGACTAGTTATTAATAGTAATCAAT-
TACGGGGTCATTAGTTCATAGCCCAT ATATGGAGT-
TCCGCGTTACATAACTTACGGTAAATGGCCCGC-
CTGGCTGACCGCCCAACG
ACCCCCGCCCATTGACGTCAATAATGACGTATGT-
TCCCATAGTAACGCCAATAGGGACTT TCCATT-
GACGTCAATGGGTGGAGTATTTACGGTAAACTGC-
CCACTTGGCAGTACATCAAG
TGTATCATATGCCAAGTACGCCCCCTATTGACGT-
CAATGACGGTAAATGGCCCGCCTGGC ATTATGC-
CCAGTACATGACCTTATGGGACTTTCCTACTTG-
GCAGTACATCTACGTATTAGT
CATCGCTATTACCATGGTGATGCGGTTTTGGCAGTA-
CATCAATGGGCGTGGATAGCGGTT TGACT-
CACGGGGATTTCCAAGTCTCCACCCCATTGACGT-
CAATGGGAGTTTGTTTTGGCA
CCAAAATCAACGGGACTTTCCAAAATGTCG-
TAACAACTCCGCCCCATTGACGCAAATGG GCGG-
TAGGCGTGTACGGTGGGAGGTCTATATAAGCA-
GCGCGTTTTGCCTGTACTGGGTCT
CTCTGGTTAGACCAGATCTGAGC-
CTGGGAGCTCTCTGGCTAACTAGGGAACCCACT-
GCTT AAGCCTCAATAAAGCTTGCCTTGAGTGCT-
TCAAGTAGTGTGTGCCCGTCTGTTGTGTGAC
TCTGGTAACTAGAGATCCCTCAGACCCTTT-
TAGTCAGTGTGGAAAATCTCTAGCAGTGGC
GCCCGAACAGGGACTTGAAAGCGAAAGGGAAAC-
CAGAGGAGCTCTCTCGACGCAGGAC TCGGCTT-
GCTGAAGCGCGCACGGCAAGAGGCGAGGGGCG-
GCGACTGGTGAGTACGCCAA
AAATTTTGACTAGCGGAGGCTAGAAGGAGAGA-
GATGGGTGCGAGAGCGTCAGTATTAAG CGGGGGA-
GAATTAGATCGCGATGGGAAAAAATTCGGT-
TAAGGCCAGGGGGAAAGAAAA
AATATAAATTAAAACATATAGTATGGGCAAGCA-
GGGAGCTAGAACGATTCGCAGTTAAT CCTGGCCT-
GTTAGAAACATCAGAAGGCTGTAGA-
CAAATACTGGGACAGCTACAACCATC
CCTTCAGACAGGATCAGAAGAACTTAGATCAT-
TATATAATACAGTAGCAACCCTCTATTG TGTGCAT-
CAAAGGATAGAGATAAAAGACACCAAGGAAGCTT-
TAGACAAGATAGAGGAA
GAGCAAAACAAAAGTAAGACCACCGCACAG-
CAAGCGGCCGCTGATCTTCAGACCTGGAG GAGGA-
GATATGAGGGACAATTGGAGAAGTGAAT-
TATATAAATATAAAGTAGTAAAAATT
GAACCATTAGGAGTAGCACCCACCAAGGCAAAGA-
GAAGAGTGGTGCAGAGAGAAAAAA GAGCA-
GTGGGAATAGGAGCTTTGTTCCTTGGGTTCT-
TGGGAGCAGCAGGAAGCACTATG
GGCGCAGCGTCAATGACGCTGACGGTACAGGCCA-
GACAATTATTGTCTGGTATAGTGCA GCAGCA-
GAACAATTTGCTGAGGGCTATTGAGGCGCAACAG-
CATCTGTTGCAACTCACAG
TCTGGGGCATCAAGCAGCTCCAGGCAAGAATC-
CTGGCTGTGGAAAGATACCTAAAGGAT CAACA-
GCTCCTGGGGATTTGGGGTTGCTCTGGAAAACT-
CATTTGCACCACTGCTGTGCCT
TGGAATGCTAGTTGGAGTAATAAATCTCTGGAACA- GATTTGGAATCACACGACCTGGAT
GGAGTGGGACAGAGAAATTAACAATTACA-
CAAGCTTAATACACTCCTTAATTGAAGAAT
CGCAAAACCAGCAAGAAAAGAATGAACAAGAATT-
ATTGGAATTAGATAAATGGGCAAG TTTGTGGAAT-
TGGTTTAACATAACAAATTGGCTGTGG-
TATATAAAATTATTCATAATGAT
AGTAGGAGGCTTGGTAGGTTTAAGAATAGTTTTT-
GCTGTACTTTCTATAGTGAATAGAGT TAGGCA-
GGGATATTCACCATTATCGTTTCAGACCCACCTC-
CCAACCCCGAGGGGACCCGA
CAGGCCCGAAGGAATAGAAGAAGAAGGTGGAGA-
GAGAGACAGAGACAGATCCATTCGA TTAGT-
GAACGGATCGGCACTGCGTGCGCCAATTCTGCA-
GACAAATGGCAGTATTCATCCA
CAATTTTAAAAGAAAAGGGGGGATTGGGGGGTA-
CAGTGCAGGGGAAAGAATAGTAGAC ATAATAG-
CAACAGACATACAAACTAAAGAATTA-
CAAAAACAAATTACAAAAATTCAAAA
TTTTCGGGTTTATTACAGGGACAGCAGAGATCCA-
GTTTGGTTAATTAAGGGTGCAGCGGC CTCCGCGC-
CGGGTTTTGGCGCCTCCCGCGGGCGCCCCCCTCCT-
CACGGCGAGCGCTGCCA
CGTCAGACGAAGGGCGCAGGAGCGTTCCTGATC-
CTTCCGCCCGGACGCTCAGGACAGCG GCCCGCT-
GCTCATAAGACTCGGCCTTAGAACCCCAGTATCA-
GCAGAAGGACATTTTAGG
ACGGGACTTGGGTGACTCTAGGGCACTG-
GTTTTCTTTCCAGAGAGCGGAACAGGCGAGG
AAAAGTAGTCCCTTCTCGGCGATTCTGCG-
GAGGGATCTCCGTGGGGCGGTGAACGCCGA TGAT-
TATATAAGGACGCGCCGGGTGTGGCACAGCTAGT-
TCCGTCGCAGCCGGGATTTGG
GTCGCGGTTCTTGTTTGTGGATCGCTGTGATCGT-
CACTTGGTGAGTTGCGGGCTGCTGGG CTGGC-
CGGGGCTTTCGTGGCCGCCGGGCCGCTCG-
GTGGGACGGAAGCGTGTGGAGAGAC
CGCCAAGGGCTGTAGTCTGGGTCCGCGAG-
CAAGGTTGCCCTGAACTGGGGGTTGGGGGG
AGCGCACAAAATGGCGGCTGTTCCCGAGTCTT-
GAATGGAAGACGCTTGTAAGGCGGGCT GTGAG-
GTCGTTGAAACAAGGTGGGGGGCATGGTGGGCG-
GCAAGAACCCAAGGTCTTGAG
GCCTTCGCTAATGCGGGAAAGCTCTTATTCGGGT-
GAGATGGGCTGGGGCACCATCTGGG GACCCT-
GACGTGAAGTTTGTCACTGACTGGA-
GAACTCGGGTTTGTCGTCTGGTTGCGGGG
GCGGCAGTTATGCGGTGCCGTTGGGCAGTGCAC-
CCGTACCTTTGGGAGCGCGCGCCTCGT CGTGTCGT-
GACGTCACCCGTTCTGTTGGCTTATAATGCA-
GGGTGGGGCCACCTGCCGGTA
GGTGTGCGGTAGGCTTTTCTCCGTCGCAG-
GACGCAGGGTTCGGGCCTAGGGTAGGCTCTC
CTGAATCGACAGGCGCCGGACCTCTGGT-
GAGGGGAGGGATAAGTGAGGCGTCAGTTTCT TTG-
GTCGGTTTTATGTACCTATCTTCTTAAGTAGCT-
GAAGCTCCGGTTTTGAACTATGCGC
TCGGGGTTGGCGAGTGTGTTTTGTGAAGTTTTT-
TAGGCACCTTTTGAAATGTAATCATTTG GGT-
CAATATGTAATTTTCAGTGTTAGACTAGTAAAGCT-
TCTGCAGGTCGACTCTAGAAAA
TTGTCCGCTAAATTCTGGCCGTTTTTGGCTTTTTT-
GTTAGACAGGATCCCCGGGTACCATG ACAGAGAC-
CCTGCCTCCCGTGACCGAGAGTGCCGTGGCCCT-
TCAAGCCGAGGTTACCCA
AAGGGAGTTGTTCGAGTTCGTGCTGAACGAC-
CCTTTGCTTGCAAGCAGTCTCTATATCAA CATCG-
CACTTGCAGGACTGAGTATACTGCTGTTCGTTTT-
TATGACCCGAGGACTCGATGA
TCCACGGGCAAAACTTATTGCTGTGTCAACCATC-
CTTGTGCCTGTCGTCAGCATTGCCTCC TACACTG-
GATTGGCGAGCGGCCTGACAATTTCCGTTCTT-
GAAATGCCAGCGGGCCATTTT
GCAGAAGGCAGCTCAGTGATGCTGGGAGGA-
GAAGAGGTAGATGGTGTAGTCACCATGTG
GGGACGGTATCTCACCTGGGCACTTTCCACGC-
CCATGATTCTCCTCGCTCTGGGTCTCCTG GCCG-
GAAGCAATGCTACAAAGCTCTTCACAGCTAT-
CACTTTCGATATCGCTATGTGCGTG
ACTGGCCTTGCCGCGGCCCTGACTACCTCCTC-
CCACCTCATGAGATGGTTCTGGTACGCT ATCAGTT-
GTGCATGCTTTCTGGTGGTCTTGTATATCCTGCTG-
GTGGAGTGGGCACAGGAC
GCCAAAGCCGCGGGAACCGCTGACATGT-
TCAATACCCTGAAGCTGTTGACAGTAGTGAT GTG-
GCTGGGGTATCCAATTGTGTGGGCTCTTGGAGTC-
GAGGGTATCGCGGTGTTGCCCGT
TGGGGTGACGAGCTGGGGATATTCTTTCCTGGA-
TATCGTGGCAAAGTACATTTTCGCATT CTTGCTCCT-
GAACTATCTGACGTCAAACGAATCTGTCGTGTCCG-
GCAGCATTTTGGATGTT
CCATCTGCTTCTGGGACCCCGGCTGATGATGCGGC-
CGCTATGGTGTCTAAGGGCGAAGAG CTGAT-
TAAGGAGAACATGCACATGAAGCTGTACATG-
GAGGGCACCGTGAACAACCACCA
CTTCAAGTGCACATCCGAGGGCGAAGGCAAGC-
CCTACGAGGGCACCCAGACCATGAGAA
TCAAGGTGGTCGAGGGCGGCCCTCTCCCCTTCGC-
CTTCGACATCCTGGCTACCAGCTTCA TGTACGGCA-
GCAGAACCTTCATCAACCACACCCAGGGCATC-
CCCGACTTCTTTAAGCAGT
CCTTCCCTGAGGGCTTCACATGGGAGAGAGTCAC-
CACATACGAAGACGGGGGCGTGCTG ACCGCTAC-
CCAGGACACCAGCCTCCAGGACGGCTGCCTCATC-
TACAACGTCAAGATCAG
AGGGGTGAACTTCCCATCCAACGGCCCTGTGAT-
GCAGAAGAAAACACTCGGCTGGGAGG CCAACAC-
CGAGATGCTGTACCCCGCTGACGGCGGCCTG-
GAAGGCAGAAGCGACATGGCC
CTGAAGCTCGTGGGCGGGGGCCACCTGATCTG-
CAACTTCAAGACCACATACAGATCCAA GAAAC-
CCGCTAAGAACCTCAAGATGCCCGGCGTCTACTAT-
GTGGACCACAGACTGGAAA
GAATCAAGGAGGCCGACAAAGAGACCTACGTC-
GAGCAGCACGAGGTGGCTGTGGCCAG ATACTGC-
GACCTCCCTAGCAAACTGGGGCACAAACTTAATTC-
CGGACTCAGATCTGATAT
CGGGCCCTCTAGAGCCACCATGGCTTCCAAGGTG-
TACGACCCCGAGCAACGCAAACGCA TGAT-
CACTGGGCCTCAGTGGTGGGCTCGCTG-
CAAGCAAATGAACGTGCTGGACTCCTTCA
TCAACTACTATGATTCCGAGAAGCACGCCGA-
GAACGCCGTGATTTTTCTGCATGGTAACG CTAC-
CTCCAGCTACCTGTGGAGGCACGTCGTGCCTCA-
CATCGAGCCCGTGGCTAGATGCA
TCATCCCTGATCTGATCGGAATGGGTAAGTCCG-
GCAAGAGCGGGAATGGCTCATATCGC CTCCTGGAT-
CACTACAAGTACCTCACCGCTTGGTTCGAGCTGCT-
GAACCTTCCAAAGAAA
ATCATCTTTGTGGGCCAC-
GACTGGGGGAGCGCTCTGGCCTTTCACTACGC-
CTACGAGCAC CAAGACAGGATCAAGGCCATCGTC-
CATATGGAGAGTGTCGTGGACGTGATCGAGTCCTG
GATGGGGTGGCCTGACATCGAGGAGGAGCTGGC- CCTGATCAAGAGCGAAGAGGGCGAG AAAATGGT-
GCTTGAGAATAACTTCTTCGTCGAGACCCTGTTGC-
CAAGCAAGATCATGCGG
AAACTGGAGCCTGAGGAGTTCGCTGCCTACCTG-
GAGCCATTCAAGGAGAAGGGCGAGGT TAGACG-
GCCTACCCTCTCCTGGCCTCGCGAGATC-
CCTCTCGTTAAGGGAGGCAAGCCCGA
CGTCGTCCAGATTGTCCGCAACTACAACGCCTAC-
CTTCGGGCCAGCGACGATCTGCCTAA GCTGT-
TCATCGAGTCCGACCCTGGGTTCTTTTCCAACGCT-
ATTGTCGAGGGAGCTAAGAA
GTTCCCTAACACCGAGTTCGTGAAGGTGAAGGGC-
CTCCACTTCCTCCAGGAGGACGCTCC AGAT-
GAAATGGGTAAGTACATCAAGAGCTTCGTG-
GAGCGCGTGCTGAAGAACGAGCAGT
AAGAATTCGATATCAAGCTTATCGATAATCAAC-
CTCTGGATTACAAAATTTGTGAAAGAT TGACTGGT-
ATTCTTAACTATGTTGCTCCTTTTACGCTATGTGGA-
TACGCTGCTTTAATGCC
TTTGTATCATGCTATTGCTTCCCGTATG-
GCTTTCATTTTCTCCTCCTTGTATAAATCCTGGT
TGCTGTCTCTTTATGAGGAGTTGTGGCCCGTT-
GTCAGGCAACGTGGCGTGGTGTGCACTG TGTTT-
GCTGACGCAACCCCCACTGGTTGGGGCATTGC-
CACCACCTGTCAGCTCCTTTCCG
GGACTTTCGCTTTCCCCCTCCCTATTGCCACGGCG-
GAACTCATCGCCGCCTGCCTTGCCCG CTGCTG-
GACAGGGGCTCGGCTGTTGGGCACTGACAATTC-
CGTGGTGTTGTCGGGGAAATC
ATCGTCCTTTCCTTGGCTGCTCGCCTGTGTTGC-
CACCTGGATTCTGCGCGGGACGTCCTTC TGC-
TACGTCCCTTCGGCCCTCAATCCAGCGGACCTTC-
CTTCCCGCGGCCTGCTGCCGGCTC
TGCGGCCTCTTCCGCGTCTTCGCCTTCGCCCTCA-
GACGAGTCGGATCTCCCTTTGGGCCGC CTCCCCG-
CATCGATACCGTCGACCTCGAGACCTA-
GAAAAACATGGAGCAATCACAAGTA
GCAATACAGCAGCTACCAATGCTGATTGTGCCTG-
GCTAGAAGCACAAGAGGAGGAGGAG
GTGGGTTTTCCAGTCACACCTCAGGTACCTT-
TAAGACCAATGACTTACAAGGCAGCTGTA GATCT-
TAGCCACTTTTTAAAAGAAAAGGGGGGACTG-
GAAGGGCTAATTCACTCCCAACG
AAGACAAGATATCCTTGATCTGTGGATCTACCACA-
CACAAGGCTACTTCCCTGATTGGCA GAACTACA-
CACCAGGGCCAGGGATCAGATATCCACTGAC-
CTTTGGATGGTGCTACAAGC
TAGTACCAGTTGAGCAAGAGAAGGTAGAAGAAGC-
CAATGAAGGAGAGAACACCCGCTT GTTACACCCT-
GTGAGCCTGCATGGGATGGATGACCCGGAGAGA-
GAAGTATTAGAGTGGA
GGTTTGACAGCCGCCTAGCATTTCATCACATGGC-
CCGAGAGCTGCATCCGGACTGTACTG
GGTCTCTCTGGTTAGACCAGATCTGAGC-
CTGGGAGCTCTCTGGCTAACTAGGGAACCCAC
TGCTTAAGCCTCAATAAAGCTTGCCTTGAGTGCT-
TCAAGTAGTGTGTGCCCGTCTGTTGTG TGACTCTG-
GTAACTAGAGATCCCTCAGACCCTTTTAGTCAGT-
GTGGAAAATCTCTAGCAG
GGCCCGTTTAAACCCGCTGATCAGCCTCGACTGT-
GCCTTCTAGTTGCCAGCCATCTGTTGT TTGC-
CCCTCCCCCGTGCCTTCCTTGACCCTGGAAGGTGC-
CACTCCCACTGTCCTTTCCTAA
TAAAATGAGGAAATTGCATCGCATTGTCTGAGTAG-
GTGTCATTCTATTCTGGGGGGTGGG GTGGGGCAG-
GACAGCAAGGGGGAGGATTGGGAAGA-
CAATAGCAGGCATGCTGGGGATG CGGTGGGCTC-
TATGGCTTCTGAGGCGGAAAGAACCA-
GCTGGGGCTCTAGGGGGTATCCC
CACGCGCCCTGTAGCGGCGCATTAAGCGCG-
GCGGGTGTGGTGGTTACGCGCAGCGTGAC CGCTA-
CACTTGCCAGCGCCCTAGCGCCCGCTC-
CTTTCGCTTTCTTCCCTTCCTTTCTCGCC
ACGTTCGCCGGCTTTCCCCGT-
CAAGCTCTAAATCGGGGGCTCCCTTTAGGGTTC-
CGATTTA GTGCTTTACGGCACCTCGAC-
CCCAAAAAACTTGATTAGGGTGATGGTTCACGTA-
GTGGGC CATCGCCCTGATAGACGGTTTTTCGC-
CCTTTGACGTTGGAGTCCACGTTCTTTAATAGTGG
ACTCTTGTTCCAAACTGGAACAACACTCAAC-
CCTATCTCGGTCTATTCTTTTGATTTATAA
GGGATTTTGCCGATTTCGGCCTATTGGTTAAAAAAT-
GAGCTGATTTAACAAAAATTTAAC GCGAATTAAT-
TCTGTGGAATGTGTGTCAGTTAGGGTGTG-
GAAAGTCCCCAGGCTCCCCAG
CAGGCAGAAGTATGCAAAGCATGCATCTCAATT-
AGTCAGCAACCAGGTGTGGAAAGTCC CCAGGCTC-
CCCAGCAGGCAGAAGTATGCAAAGCATGCATCT-
CAATTAGTCAGCAACCAT
AGTCCCGCCCCTAACTCCGCCCATCCCGC-
CCCTAACTCCGCCCAGTTCCGCCCATTCTCCG
CCCCATGGCTGACTAATTTTTTTTATTTATGCAGAG-
GCCGAGGCCGCCTCTGCCTCTGAGC TATTCCA-
GAAGTAGTGAGGAGGCTTTTTTGGAGGCCTAG-
GCTTTTGCAAAAAGCTCCCGG
GAGCTTGTATATCCATTTTCGGATCTGATCAG-
CACGTGTTGACAATTAATCATCGGCATA GTATATCG-
GCATAGTATAATACGACAAGGTGAGGAACTAAAC-
CATGGCCAAGTTGACCA
GTGCCGTTCCGGTGCTCACCGCGCGCGACGTCGC-
CGGAGCGGTCGAGTTCTGGACCGACC
GGCTCGGGTTCTCCCGGGACTTCGTGGAGGAC-
GACTTCGCCGGTGTGGTCCGGGACGAC GTGAC-
CCTGTTCATCAGCGCGGTCCAGGACCAGGTGGT-
GCCGGACAACACCCTGGCCTG
GGTGTGGGTGCGCGGCCTGGACGAGCTGTACGC-
CGAGTGGTCGGAGGTCGTGTCCACGA ACTTC-
CGGGACGCCTCCGGGCCGGCCATGACCGAGATCG-
GCGAGCAGCCGTGGGGGCGG
GAGTTCGCCCTGCGCGACCCGGCCGGCAACT-
GCGTGCACTTCGTGGCCGAGGAGCAGGA
CTGACACGTGCTACGAGATTTCGATTCCACCGC-
CGCCTTCTATGAAAGGTTGGGCTTCGG
AATCGTTTTCCGGGACGCCGGCTGGATGATCCTC-
CAGCGCGGGGATCTCATGCTGGAGTT CTTCGC-
CCACCCCAACTTGTTTATTGCAGCTTATAATGGTTA-
CAAATAAAGCAATAGCAT
CACAAATTTCACAAATAAAGCATTTTTTTCACTG-
CATTCTAGTTGTGGTTTGTCCAAACTC ATCAATG-
TATCTTATCATGTCTGTATACCGTCGAC-
CTCTAGCTAGAGCTTGGCGTAATCAT
GGTCATAGCTGTTTCCTGTGTGAAATTGTTATC-
CGCTCACAATTCCACACAACATACGAG CCG-
GAAGCATAAAGTGTAAAGCCTGGGGTGCCTAAT-
GAGTGAGCTAACTCACATTAATT
GCGTTGCGCTCACTGCCCGCTTTCCA-
GTCGGGAAACCTGTCGTGCCAGCTGCATTAATGA
ATCGGCCAACGCGCGGGGAGAGGCGGTTTGCGT-
ATTGGGCGCTCTTCCGCTTCCTCGCTC ACT-
GACTCGCTGCGCTCGGTCGTTCGGCTGCGGC-
GAGCGGTATCAGCTCACTCAAAGGCG
GTAATACGGTTATCCACAGAATCAGGGGA-
TAACGCAGGAAAGAACATGTGAGCAAAAG GCCA-
GCAAAAGGCCAGGAACCGTAAAAAGGCCGCGTT- GCTGGCGTTTTTCCATAGGCTC
CGCCCCCCTGACGAGCATCACAAAAATCGACGCT-
CAAGTCAGAGGTGGCGAAACCCGAC AGGAC-
TATAAAGATACCAGGCGTTTCCCCCTGGAAGCTC-
CCTCGTGCGCTCTCCTGTTCC
GACCCTGCCGCTTACCGGATACCTGTCCGC-
CTTTCTCCCTTCGGGAAGCGTGGCGCTTTCT
CATAGCTCACGCTGTAGGTATCTCAGTTCGGTG-
TAGGTCGTTCGCTCCAAGCTGGGCTGT GTGCAC-
GAACCCCCCGTTCAGCCCGACCGCTGCGCCTTATC-
CGGTAACTATCGTCTTGAG
TCCAACCCGGTAAGACACGACTTATCGCCACTG-
GCAGCAGCCACTGGTAACAGGATTAG CAGAGC-
GAGGTATGTAGGCGGTGCTACAGAGTTCTT-
GAAGTGGTGGCCTAACTACGGCT
ACACTAGAAGAACAGTATTTGGTATCTGCGCTCT-
GCTGAAGCCAGTTACCTTCGGAAAAA GAGTTGG-
TAGCTCTTGATCCGGCAAACAAACCACCGCTGG-
TAGCGGTGGTTTTTTTGTTT
GCAAGCAGCAGATTACGCGCA-
GAAAAAAAGGATCTCAAGAAGATCCTTT-
GATCTTTTCT ACGGGGTCTGACGCTCAGTGGAAC-
GAAAACTCACGTTAAGGGATTTTGGTCATGAGATT
ATCAAAAAGGATCTTCACCTAGATCCTTTTAAAT-
TAAAAATGAAGTTTTAAATCAATCTA AAGTATATAT-
GAGTAAACTTGGTCTGACAGTTACCAATGCT-
TAATCAGTGAGGCACCTAT
CTCAGCGATCTGTCTATTTCGTTCATCCATAGTTGC-
CTGACTCCCCGTCGTGTAGATAACT ACGA-
TACGGGAGGGCTTACCATCTGGCCCCAGTGCTG-
CAATGATACCGCGAGACCCACG
CTCACCGGCTCCAGATTTATCAGCAATAAACCAGC-
CAGCCGGAAGGGCCGAGCGCAGAA GTGGTCCTG-
CAACTTTATCCGCCTCCATCCAGTCTATTAATTGTT-
GCCGGGAAGCTAGAG
TAAGTAGTTCGCCAGTTAATAGTTTGCGCAACGTT-
GTTGCCATTGCTACAGGCATCGTGG TGT-
CACGCTCGTCGTTTGGTATGGCTTCATTCAGCTC-
CGGTTCCCAACGATCAAGGCGAG
TTACATGATCCCCCATGTTGTGCAAAAAAGCGGT-
TAGCTCCTTCGGTCCTCCGATCGTTGT CAGAAG-
TAAGTTGGCCGCAGTGTTATCACTCATGGTTATG-
GCAGCACTGCATAATTCTCT
TACTGTCATGCCATCCGTAAGATGCTTTTCTGT-
GACTGGTGAGTACTCAACCAAGTCATTC
TGAGAATAGTGTATGCGGCGACCGAGTTGCTCTT-
GCCCGGCGTCAATACGGGATAATACC GCGCCA-
CATAGCAGAACTTTAAAAGTGCTCATCATTG-
GAAAACGTTCTTCGGGGCGAAA
ACTCTCAAGGATCTTACCGCTGTTGAGATCCAGT-
TCGATGTAACCCACTCGTGCACCCAA CTGATCT-
TCAGCATCTTTTACTTTCACCAGCGTTTCTGGGT-
GAGCAAAAACAGGAAGGCA
AAATGCCGCAAAAAAGGGAATAAGGGCGACACG-
GAAATGTTGAATACTCATACTCTTCC TTTTTCAAT-
ATTATTGAAGCATTTATCAGGGTTATTGTCTCAT-
GAGCGGATACATATTTGA
ATGTATTTAGAAAAATAAACAAATAGGGGTTC-
CGCGCACATTTCCCCGAAAAGTGCCAC CTGAC Other exemplary vectors are pAAV-CAMKIIa-eNphR3.0-Nanolantern (SEQ ID NO: 14) shown in FIG. 7A, plenti-eNphR3.0-Nanolantern (SEQ ID NO: 13) in FIG. 7B, and plenti-eNphR3.0-NL-600 (SEQ ID NO: 12) in FIG. 7C.

The amino acid sequence for the eNpHR3.0-Nanolantern cassette is (SEQ ID NO: 11) MTETLPPVTESAV-
ALQAEVTQRELFEFVLNDPLLASSLYINIALAGLSILL-
FVFMTRGLDDPRA KLIAVSTILVPVVSIASYTGLAS-
GLTISVLEMPAGHFAEGSSVMLGGEEVDGVVTMW-
GRYLT WALSTPMILLALGLLAGSNATKLFTAITFDI-
AMCVTGLAAALTTSSHLMRWFWYAISCACFL VVLY-
ILLVEWAQDAKAAGTADMFNTLKLLTVVM-
WLGYPIVWALGVEGIAVLPVGVTSWG
YSFLDIVAKYIFAFLLLNYLTSNESVVSGSILDVPSAS-
GTPADDAAAVSKGEELFTGVVPILVE LDGDVNGH-
KFSVSGEGEGDATYGKLTLKLICTTGKLPVPWPTLVT-
TLGYGLQCFARYPDHM
KQHDFFKSAMPEGYVQERTIFFKDDGNYKTRAEVK-
FEGDTLVNRIELKGIDFKEDGNILGHK LEYNYNSHN-
VYITADKQKNGIKANFKIRHNIEDGGVQLADHY-
QQNTPIGDGPVLLPDNHYLS
YQSKLSKDPNEKRDHMVLLEFVTAAGGTKVYD-
PEQRKRMITGPQWWARCKQMNVLDSFIN YYD-
SEKHAENAVIFLHGNATSSYLWRHVVPHIEPVARCIIP-
DLIGMGKSGKSGNGSYRLLDH
YKYLTAWFELLNLPKKIIFVGHDWGAALAF-
HYAYEHQDRIKAIVHMESVVDVIESWDEWPD IEEDI-
ALIKSEEGEKMVLENNFFVETVLPSKIMRKLE-
PEEFAAYLEPFKEKGEVRRPTLSWPREI
PLVKGGKPDVVQIVRNYNAYLRASDDLPKLFIEGD-
PGFFSNAIVEGAKKFPNTEFVKVKGLH FLQEDAP-
DEMGKYIKSFVERVLKNEQFCYENEV.

Tetracycline Transactivator (tTA) Driven by a c-fos Promoter

Another approach one can take for activity-dependent luminescence is to temporally define the expression of luciferase during periods of high neural activity. C-fos is an immediate-early gene that has been used as a marker of recent neural activity. One can drive luciferase expression under the control of a c-fos promoter. The presence of Dox inhibits c-fos-promoter-driven tTA from binding to its target tetracycline-responsive element (TRE) site, which in turn prevents it from driving protein expression. See Liu, X. et al. Optogenetic stimulation of a hippocampal engram activates fear memory recall. Nature 484, 381-385, (2012).

One can demonstrate activity-dependent expression of luciferase in dissociated cortical neuron cultures grown on multielectrode arrays (MEAs). Desirable constructs are delivered to cultures using viral vectors such as tetracycline transactivator (tTA) driven by a c-fos promoter and a luciferase driven by the tetracycline regulator element (TRE). In cells expressing both constructs, Doxycyline (Dox) inhibits c-fos driven tTA from binding to its target TRE, which would prevent it from driving expression of the luciferase. In the absence of Dox, luciferase expression can be driven by c-fos activity. Thus, one can define luciferase expression only during periods where Dox is not present and neuronal activity is high.

Activity-dependent luminescence may be assessed by evoking spiking activity in the MEA cultures through electrical stimulation in the presence and absence of doxycycline. Only a subset of contacts in the MEA can be stimulated to produce differential levels of spiking activity throughout the culture. One can see luciferase expression (as determined by fluorescence microscopy) and luminescence (as determined by bioluminescence imaging) when spiking activity is high in the absence of doxycycline. The duration of electrical stimulation and doxycycline removal time may be assessed to determine the optimal conditions for activity-dependent labeling.

This approach may be easily translatable to in vivo models with the use of transgenic c-fos-tTA animals.

In Vivo Evaluation of Optogenetic Inhibition

One stereotactically injects viruses carrying the autonomous biologic controller to the hippocampus of non-epileptic rats. One confirms coexpression of the transgenes in the dorsal hippocampus, characterizes expression levels and determines cell type specificity using histologic methods. In addition, animals are co-infected with the viral vectors, and epilepsy will be induced via stereotactic injection of tetanus toxin to the hippocampus. One examines single-unit and local field potential recordings for evidence of epileptic activity, such as seizures, interictal spikes, and high frequency oscillations. These are correlated with behavioral manifestations of epilepsy, with continuous video recording, as Racine level 5 seizures are common in the tetanus toxin model.

An acute seizure model is intracerebral injection of 4-aminopyridine or bicuculline.

The invention claimed is:

1. A method of treating a seizure comprising administering to a subject in need thereof an effective amount of a recombinant vector comprising a nucleic acid sequence encoding a recombinant protein comprising the amino acid sequence of SEQ ID NO: 11, wherein expression of the recombinant protein in a neuronal cell in combination with luciferin reduces neuronal firing rate relative to uninfected neuronal cells.

2. The method of claim 1 wherein the luciferin is coelenterazine (CTZ) or derivative.

3. The method of claim 1 wherein the subject is a human.

* * * * *

SEQUENCE LISTING

```
<160> NUMBER OF SEQ ID NOS: 14

<210> SEQ ID NO 1
<211> LENGTH: 561
<212> TYPE: PRT
<213> ORGANISM: Artificial Sequence
<220> FEATURE:
<223> OTHER INFORMATION: synthetic constructs

<400> SEQUENCE: 1

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Met Tyr Gly Ser Arg Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Pro Ser Asn Gly Pro Val Met Gln Lys Lys Thr Leu Gly Trp
    130                 135                 140

Glu Ala Asn Thr Glu Met Leu Tyr Pro Ala Asp Gly Gly Leu Glu Gly
145                 150                 155                 160

Arg Ser Asp Met Ala Leu Lys Leu Val Gly Gly Gly His Leu Ile Cys
                165                 170                 175

Asn Phe Lys Thr Thr Tyr Arg Ser Lys Lys Pro Ala Lys Asn Leu Lys
            180                 185                 190

Met Pro Gly Val Tyr Tyr Val Asp His Arg Leu Glu Arg Ile Lys Glu
        195                 200                 205

Ala Asp Lys Glu Thr Tyr Val Glu Gln His Glu Val Ala Val Ala Arg
    210                 215                 220

Tyr Cys Asp Leu Pro Ser Lys Leu Gly His Lys Leu Asn Ser Gly Leu
225                 230                 235                 240

Arg Ser Asp Ile Gly Pro Ser Arg Ala Thr Met Ala Ser Lys Val Tyr
                245                 250                 255

Asp Pro Glu Gln Arg Lys Arg Met Ile Thr Gly Pro Gln Trp Trp Ala
            260                 265                 270

Arg Cys Lys Gln Met Asn Val Leu Asp Ser Phe Ile Asn Tyr Tyr Asp
        275                 280                 285

Ser Glu Lys His Ala Glu Asn Ala Val Ile Phe Leu His Gly Asn Ala
    290                 295                 300
```

Thr Ser Ser Tyr Leu Trp Arg His Val Val Pro His Ile Glu Pro Val
305 310 315 320

Ala Arg Cys Ile Ile Pro Asp Leu Ile Gly Met Gly Lys Ser Gly Lys
325 330 335

Ser Gly Asn Gly Ser Tyr Arg Leu Leu Asp His Tyr Lys Tyr Leu Thr
340 345 350

Ala Trp Phe Glu Leu Leu Asn Leu Pro Lys Lys Ile Ile Phe Val Gly
355 360 365

His Asp Trp Gly Ser Ala Leu Ala Phe His Tyr Ala Tyr Glu His Gln
370 375 380

Asp Arg Ile Lys Ala Ile Val His Met Glu Ser Val Val Asp Val Ile
385 390 395 400

Glu Ser Trp Met Gly Trp Pro Asp Ile Glu Glu Glu Leu Ala Leu Ile
405 410 415

Lys Ser Glu Glu Gly Glu Lys Met Val Leu Glu Asn Asn Phe Phe Val
420 425 430

Glu Thr Leu Leu Pro Ser Lys Ile Met Arg Lys Leu Glu Pro Glu Glu
435 440 445

Phe Ala Ala Tyr Leu Glu Pro Phe Lys Glu Lys Gly Glu Val Arg Arg
450 455 460

Pro Thr Leu Ser Trp Pro Arg Glu Ile Pro Leu Val Lys Gly Gly Lys
465 470 475 480

Pro Asp Val Val Gln Ile Val Arg Asn Tyr Asn Ala Tyr Leu Arg Ala
485 490 495

Ser Asp Asp Leu Pro Lys Leu Phe Ile Glu Ser Asp Pro Gly Phe Phe
500 505 510

Ser Asn Ala Ile Val Glu Gly Ala Lys Lys Phe Pro Asn Thr Glu Phe
515 520 525

Val Lys Val Lys Gly Leu His Phe Leu Gln Glu Asp Ala Pro Asp Glu
530 535 540

Met Gly Lys Tyr Ile Lys Ser Phe Val Glu Arg Val Leu Lys Asn Glu
545 550 555 560

Gln

<210> SEQ ID NO 2
<211> LENGTH: 1683
<212> TYPE: PRT
<213> ORGANISM: Artificial Sequence
<220> FEATURE:
<223> OTHER INFORMATION: synthetic constructs

<400> SEQUENCE: 2

Ala Thr Gly Gly Thr Gly Thr Cys Thr Ala Ala Gly Gly Gly Cys Gly
1 5 10 15

Ala Ala Gly Ala Gly Cys Thr Gly Ala Thr Thr Ala Ala Gly Gly Ala
20 25 30

Gly Ala Ala Cys Ala Thr Gly Cys Ala Cys Ala Thr Gly Ala Ala Gly
35 40 45

Cys Thr Gly Thr Ala Cys Ala Thr Gly Gly Ala Gly Gly Gly Cys Ala
50 55 60

Cys Cys Gly Thr Gly Ala Ala Cys Ala Ala Cys Cys Ala Cys Cys Ala
65 70 75 80

Cys Thr Thr Cys Ala Ala Gly Thr Gly Cys Ala Cys Ala Thr Cys Cys
85 90 95

Gly Ala Gly Gly Gly Cys Gly Ala Ala Gly Gly Cys Ala Ala Gly Cys

```
            100                 105                 110

Cys Cys Thr Ala Cys Gly Ala Gly Gly Gly Cys Ala Cys Cys Cys Ala
        115                 120                 125

Gly Ala Cys Cys Ala Thr Gly Ala Gly Ala Ala Thr Cys Ala Ala Gly
    130                 135                 140

Gly Thr Gly Gly Thr Cys Gly Ala Gly Gly Gly Cys Gly Gly Cys Cys
145                 150                 155                 160

Cys Thr Cys Thr Cys Cys Cys Cys Thr Thr Cys Gly Cys Cys Thr Thr
                165                 170                 175

Cys Gly Ala Cys Ala Thr Cys Cys Thr Gly Gly Cys Thr Ala Cys Cys
            180                 185                 190

Ala Gly Cys Thr Thr Cys Ala Thr Gly Thr Ala Cys Gly Gly Cys Ala
        195                 200                 205

Gly Cys Ala Gly Ala Ala Cys Cys Thr Thr Cys Ala Thr Cys Ala Ala
    210                 215                 220

Cys Cys Ala Cys Ala Cys Cys Cys Ala Gly Gly Gly Cys Ala Thr Cys
225                 230                 235                 240

Cys Cys Cys Gly Ala Cys Thr Thr Cys Thr Thr Thr Ala Ala Gly Cys
                245                 250                 255

Ala Gly Thr Cys Cys Thr Thr Cys Cys Cys Thr Gly Ala Gly Gly Gly
            260                 265                 270

Cys Thr Thr Cys Ala Cys Ala Thr Gly Gly Gly Ala Gly Ala Gly Ala
        275                 280                 285

Gly Thr Cys Ala Cys Cys Ala Cys Ala Thr Ala Cys Gly Ala Ala Gly
    290                 295                 300

Ala Cys Gly Gly Gly Gly Gly Cys Gly Thr Gly Cys Thr Gly Ala Cys
305                 310                 315                 320

Cys Gly Cys Thr Ala Cys Cys Cys Ala Gly Gly Ala Cys Ala Cys Cys
                325                 330                 335

Ala Gly Cys Cys Thr Cys Cys Ala Gly Gly Ala Cys Gly Gly Cys Thr
            340                 345                 350

Gly Cys Cys Thr Cys Ala Thr Cys Thr Ala Cys Ala Ala Cys Gly Thr
        355                 360                 365

Cys Ala Ala Gly Ala Thr Cys Ala Gly Ala Gly Gly Gly Gly Thr Gly
    370                 375                 380

Ala Ala Cys Thr Thr Cys Cys Cys Ala Thr Cys Cys Ala Ala Cys Gly
385                 390                 395                 400

Gly Cys Cys Cys Thr Gly Thr Gly Ala Thr Gly Cys Ala Gly Ala Ala
                405                 410                 415

Gly Ala Ala Ala Ala Cys Ala Cys Thr Cys Gly Gly Cys Thr Gly Gly
            420                 425                 430

Gly Ala Gly Gly Cys Cys Ala Ala Cys Ala Cys Cys Gly Ala Gly Ala
        435                 440                 445

Thr Gly Cys Thr Gly Thr Ala Cys Cys Cys Cys Gly Cys Thr Gly Ala
    450                 455                 460

Cys Gly Gly Cys Gly Gly Cys Cys Thr Gly Gly Ala Ala Gly Gly Cys
465                 470                 475                 480

Ala Gly Ala Ala Gly Cys Gly Ala Cys Ala Thr Gly Gly Cys Cys Cys
                485                 490                 495

Thr Gly Ala Ala Gly Cys Thr Cys Gly Thr Gly Gly Gly Cys Gly Gly
            500                 505                 510

Gly Gly Gly Cys Cys Ala Cys Cys Thr Gly Ala Thr Cys Thr Gly Cys
        515                 520                 525
```

-continued

```
Ala Ala Cys Thr Thr Cys Ala Ala Gly Ala Cys Cys Ala Cys Ala Thr
    530                 535                 540

Ala Cys Ala Gly Ala Thr Cys Cys Ala Ala Gly Ala Ala Ala Cys Cys
545                 550                 555                 560

Cys Gly Cys Thr Ala Ala Gly Ala Ala Cys Cys Thr Cys Ala Ala Gly
                565                 570                 575

Ala Thr Gly Cys Cys Cys Gly Gly Cys Gly Thr Cys Thr Ala Cys Thr
            580                 585                 590

Ala Thr Gly Thr Gly Gly Ala Cys Cys Ala Cys Ala Gly Ala Cys Thr
        595                 600                 605

Gly Gly Ala Ala Ala Gly Ala Ala Thr Cys Ala Ala Gly Gly Ala Gly
    610                 615                 620

Gly Cys Cys Gly Ala Cys Ala Ala Ala Gly Ala Gly Ala Cys Cys Thr
625                 630                 635                 640

Ala Cys Gly Thr Cys Gly Ala Gly Cys Ala Gly Cys Ala Cys Gly Ala
                645                 650                 655

Gly Gly Thr Gly Gly Cys Thr Gly Thr Gly Gly Cys Cys Ala Gly Ala
            660                 665                 670

Thr Ala Cys Thr Gly Cys Gly Ala Cys Cys Thr Cys Cys Cys Thr Ala
        675                 680                 685

Gly Cys Ala Ala Ala Cys Thr Gly Gly Gly Gly Cys Ala Cys Ala Ala
    690                 695                 700

Ala Cys Thr Thr Ala Ala Thr Thr Cys Cys Gly Gly Ala Cys Thr Cys
705                 710                 715                 720

Ala Gly Ala Thr Cys Thr Gly Ala Thr Ala Thr Cys Gly Gly Gly Cys
                725                 730                 735

Cys Cys Thr Cys Thr Ala Gly Ala Gly Cys Cys Ala Cys Cys Ala Thr
            740                 745                 750

Gly Gly Cys Thr Thr Cys Cys Ala Ala Gly Gly Thr Gly Thr Ala Cys
        755                 760                 765

Gly Ala Cys Cys Cys Cys Gly Ala Gly Cys Ala Ala Cys Gly Cys Ala
    770                 775                 780

Ala Ala Cys Gly Cys Ala Thr Gly Ala Thr Cys Ala Cys Thr Gly Gly
785                 790                 795                 800

Gly Cys Cys Thr Cys Ala Gly Thr Gly Gly Thr Gly Gly Gly Cys Thr
                805                 810                 815

Cys Gly Cys Thr Gly Cys Ala Ala Gly Cys Ala Ala Ala Thr Gly Ala
            820                 825                 830

Ala Cys Gly Thr Gly Cys Thr Gly Gly Ala Cys Thr Cys Cys Thr Thr
        835                 840                 845

Cys Ala Thr Cys Ala Ala Cys Thr Ala Cys Thr Ala Thr Gly Ala Thr
    850                 855                 860

Thr Cys Cys Gly Ala Gly Ala Ala Gly Cys Ala Cys Gly Cys Cys Gly
865                 870                 875                 880

Ala Gly Ala Ala Cys Gly Cys Cys Gly Thr Gly Ala Thr Thr Thr Thr
                885                 890                 895

Thr Cys Thr Gly Cys Ala Thr Gly Gly Thr Ala Ala Cys Gly Cys Thr
            900                 905                 910

Ala Cys Cys Thr Cys Cys Ala Gly Cys Thr Ala Cys Cys Thr Gly Thr
        915                 920                 925

Gly Gly Ala Gly Gly Cys Ala Cys Gly Thr Cys Gly Thr Gly Cys Cys
    930                 935                 940
```

-continued

```
Thr Cys Ala Cys Ala Thr Cys Gly Ala Gly Cys Cys Cys Gly Thr Gly
945                 950                 955                 960

Gly Cys Thr Ala Gly Ala Thr Gly Cys Ala Thr Cys Ala Thr Cys Cys
                965                 970                 975

Cys Thr Gly Ala Thr Cys Thr Gly Ala Thr Cys Gly Gly Ala Ala Thr
            980                 985                 990

Gly Gly Gly Thr Ala Ala Gly Thr  Cys Cys Gly Gly Cys  Ala Ala Gly
        995                 1000                 1005

Ala Gly  Cys Gly Gly Gly Ala  Ala Thr Gly Gly Cys  Thr Cys Ala
    1010                 1015                 1020

Thr Ala  Thr Cys Gly Cys Cys  Thr Cys Cys Thr Gly  Gly Ala Thr
    1025                 1030                 1035

Cys Ala  Cys Thr Ala Cys Ala  Ala Gly Thr Ala Cys  Cys Thr Cys
    1040                 1045                 1050

Ala Cys  Cys Gly Cys Thr Thr  Gly Gly Thr Thr Cys  Gly Ala Gly
    1055                 1060                 1065

Cys Thr  Gly Cys Thr Gly Ala  Ala Cys Cys Thr Thr  Cys Cys Ala
    1070                 1075                 1080

Ala Ala  Gly Ala Ala Ala Ala  Thr Cys Ala Thr Cys  Thr Thr Thr
    1085                 1090                 1095

Gly Thr  Gly Gly Gly Cys Cys  Ala Cys Gly Ala Cys  Thr Gly Gly
    1100                 1105                 1110

Gly Gly  Gly Ala Gly Cys Gly  Cys Thr Cys Thr Gly  Gly Cys Cys
    1115                 1120                 1125

Thr Thr  Thr Cys Ala Cys Thr  Ala Cys Gly Cys Cys  Thr Ala Cys
    1130                 1135                 1140

Gly Ala  Gly Cys Ala Cys Cys  Ala Ala Gly Ala Cys  Ala Gly Gly
    1145                 1150                 1155

Ala Thr  Cys Ala Ala Gly Gly  Cys Cys Ala Thr Cys  Gly Thr Cys
    1160                 1165                 1170

Cys Ala  Thr Ala Thr Gly Gly  Ala Gly Ala Gly Thr  Gly Thr Cys
    1175                 1180                 1185

Gly Thr  Gly Gly Ala Cys Gly  Thr Gly Ala Thr Cys  Gly Ala Gly
    1190                 1195                 1200

Thr Cys  Cys Thr Gly Gly Ala  Thr Gly Gly Gly Gly  Thr Gly Gly
    1205                 1210                 1215

Cys Cys  Thr Gly Ala Cys Ala  Thr Cys Gly Ala Gly  Gly Ala Gly
    1220                 1225                 1230

Gly Ala  Gly Cys Thr Gly Gly  Cys Cys Cys Thr Gly  Ala Thr Cys
    1235                 1240                 1245

Ala Ala  Gly Ala Gly Cys Gly  Ala Ala Gly Ala Gly  Gly Gly Cys
    1250                 1255                 1260

Gly Ala  Gly Ala Ala Ala Ala  Thr Gly Gly Thr Gly  Cys Thr Thr
    1265                 1270                 1275

Gly Ala  Gly Ala Ala Thr Ala  Ala Cys Thr Thr Cys  Thr Thr Cys
    1280                 1285                 1290

Gly Thr  Cys Gly Ala Gly Ala  Cys Cys Cys Thr Gly  Thr Thr Gly
    1295                 1300                 1305

Cys Cys  Ala Ala Gly Cys Ala  Ala Gly Ala Thr Cys  Ala Thr Gly
    1310                 1315                 1320

Cys Gly  Gly Ala Ala Ala Cys  Thr Gly Gly Ala Gly  Cys Cys Thr
    1325                 1330                 1335

Gly Ala  Gly Gly Ala Gly Thr  Thr Cys Gly Cys Thr  Gly Cys Cys
```

1340 1345 1350

Thr Ala Cys Cys Thr Gly Gly Ala Gly Cys Cys Ala Thr Thr Cys
1355 1360 1365

Ala Ala Gly Gly Ala Gly Ala Ala Gly Gly Gly Cys Gly Ala Gly
1370 1375 1380

Gly Thr Thr Ala Gly Ala Cys Gly Gly Cys Cys Thr Ala Cys Cys
1385 1390 1395

Cys Thr Cys Thr Cys Cys Thr Gly Gly Cys Cys Thr Cys Gly Cys
1400 1405 1410

Gly Ala Gly Ala Thr Cys Cys Cys Thr Cys Thr Cys Gly Thr Thr
1415 1420 1425

Ala Ala Gly Gly Gly Ala Gly Gly Cys Ala Ala Gly Cys Cys Cys
1430 1435 1440

Gly Ala Cys Gly Thr Cys Gly Thr Cys Cys Ala Gly Ala Thr Thr
1445 1450 1455

Gly Thr Cys Cys Gly Cys Ala Ala Cys Thr Ala Cys Ala Ala Cys
1460 1465 1470

Gly Cys Cys Thr Ala Cys Cys Thr Thr Cys Gly Gly Gly Cys Cys
1475 1480 1485

Ala Gly Cys Gly Ala Cys Gly Ala Thr Cys Thr Gly Cys Cys Thr
1490 1495 1500

Ala Ala Gly Cys Thr Gly Thr Thr Cys Ala Thr Cys Gly Ala Gly
1505 1510 1515

Thr Cys Cys Gly Ala Cys Cys Cys Thr Gly Gly Gly Thr Thr Cys
1520 1525 1530

Thr Thr Thr Thr Cys Cys Ala Ala Cys Gly Cys Thr Ala Thr Thr
1535 1540 1545

Gly Thr Cys Gly Ala Gly Gly Gly Ala Gly Cys Thr Ala Ala Gly
1550 1555 1560

Ala Ala Gly Thr Thr Cys Cys Cys Thr Ala Ala Cys Ala Cys Cys
1565 1570 1575

Gly Ala Gly Thr Thr Cys Gly Thr Gly Ala Ala Gly Gly Thr Gly
1580 1585 1590

Ala Ala Gly Gly Gly Cys Cys Thr Cys Cys Ala Cys Thr Thr Cys
1595 1600 1605

Cys Thr Cys Cys Ala Gly Gly Ala Gly Gly Ala Cys Gly Cys Thr
1610 1615 1620

Cys Cys Ala Gly Ala Thr Gly Ala Ala Ala Thr Gly Gly Gly Thr
1625 1630 1635

Ala Ala Gly Thr Ala Cys Ala Thr Cys Ala Ala Gly Ala Gly Cys
1640 1645 1650

Thr Thr Cys Gly Thr Gly Gly Ala Gly Cys Gly Cys Gly Thr Gly
1655 1660 1665

Cys Thr Gly Ala Ala Gly Ala Ala Cys Gly Ala Gly Cys Ala Gly
1670 1675 1680

<210> SEQ ID NO 3
<211> LENGTH: 2568
<212> TYPE: PRT
<213> ORGANISM: Artificial Sequence
<220> FEATURE:
<223> OTHER INFORMATION: synthetic constructs

<400> SEQUENCE: 3

Ala Thr Gly Ala Cys Ala Gly Ala Gly Ala Cys Cys Cys Thr Gly Cys

-continued

```
1               5                   10                  15

Cys Thr Cys Cys Cys Gly Thr Gly Ala Cys Cys Gly Ala Gly Ala Gly
            20                  25                  30

Thr Gly Cys Cys Gly Thr Gly Gly Cys Cys Cys Thr Thr Cys Ala Ala
        35                  40                  45

Gly Cys Cys Gly Ala Gly Gly Thr Thr Ala Cys Cys Cys Ala Ala Ala
    50                  55                  60

Gly Gly Gly Ala Gly Thr Thr Gly Thr Thr Cys Gly Ala Gly Thr Thr
65                  70                  75                  80

Cys Gly Thr Gly Cys Thr Gly Ala Ala Cys Gly Ala Cys Cys Cys Thr
                85                  90                  95

Thr Thr Gly Cys Thr Thr Gly Cys Ala Ala Gly Cys Ala Gly Thr Cys
            100                 105                 110

Thr Cys Thr Ala Thr Ala Thr Cys Ala Ala Cys Ala Thr Cys Gly Cys
        115                 120                 125

Ala Cys Thr Thr Gly Cys Ala Gly Gly Ala Cys Thr Gly Ala Gly Thr
    130                 135                 140

Ala Thr Ala Cys Thr Gly Cys Thr Gly Thr Thr Cys Gly Thr Thr Thr
145                 150                 155                 160

Thr Thr Ala Thr Gly Ala Cys Cys Cys Gly Ala Gly Gly Ala Cys Thr
                165                 170                 175

Cys Gly Ala Thr Gly Ala Thr Cys Cys Ala Cys Gly Gly Gly Cys Ala
            180                 185                 190

Ala Ala Ala Cys Thr Thr Ala Thr Thr Gly Cys Thr Gly Thr Gly Thr
        195                 200                 205

Cys Ala Ala Cys Cys Ala Thr Cys Cys Thr Thr Gly Thr Gly Cys Cys
    210                 215                 220

Thr Gly Thr Cys Gly Thr Cys Ala Gly Cys Ala Thr Thr Gly Cys Cys
225                 230                 235                 240

Thr Cys Cys Thr Ala Cys Ala Cys Thr Gly Gly Ala Thr Thr Gly Gly
                245                 250                 255

Cys Gly Ala Gly Cys Gly Gly Cys Cys Thr Gly Ala Cys Ala Ala Thr
            260                 265                 270

Thr Thr Cys Cys Gly Thr Thr Cys Thr Thr Gly Ala Ala Ala Thr Gly
        275                 280                 285

Cys Cys Ala Gly Cys Gly Gly Gly Cys Cys Ala Thr Thr Thr Thr Gly
    290                 295                 300

Cys Ala Gly Ala Ala Gly Gly Cys Ala Gly Cys Thr Cys Ala Gly Thr
305                 310                 315                 320

Gly Ala Thr Gly Cys Thr Gly Gly Gly Ala Gly Gly Ala Gly Ala Ala
                325                 330                 335

Gly Ala Gly Gly Thr Ala Gly Ala Thr Gly Gly Thr Gly Thr Ala Gly
            340                 345                 350

Thr Cys Ala Cys Cys Ala Thr Gly Thr Gly Gly Gly Gly Ala Cys Gly
        355                 360                 365

Gly Thr Ala Thr Cys Thr Cys Ala Cys Cys Thr Gly Gly Gly Cys Ala
    370                 375                 380

Cys Thr Thr Thr Cys Cys Ala Cys Gly Cys Cys Cys Ala Thr Gly Ala
385                 390                 395                 400

Thr Thr Cys Thr Cys Cys Thr Cys Gly Cys Thr Cys Thr Gly Gly Gly
                405                 410                 415

Thr Cys Thr Cys Cys Thr Gly Gly Cys Cys Gly Gly Ala Ala Gly Cys
            420                 425                 430
```

-continued

```
Ala Ala Thr Gly Cys Thr Ala Cys Ala Ala Ala Gly Cys Thr Cys Thr
        435                 440                 445

Thr Cys Ala Cys Ala Gly Cys Thr Ala Thr Cys Ala Cys Thr Thr Thr
    450                 455                 460

Cys Gly Ala Thr Ala Thr Cys Gly Cys Thr Ala Thr Gly Thr Gly Cys
465                 470                 475                 480

Gly Thr Gly Ala Cys Thr Gly Gly Cys Cys Thr Thr Gly Cys Cys Gly
                485                 490                 495

Cys Gly Gly Cys Cys Cys Thr Gly Ala Cys Thr Ala Cys Cys Thr Cys
            500                 505                 510

Cys Thr Cys Cys Cys Ala Cys Cys Thr Cys Ala Thr Gly Ala Gly Ala
        515                 520                 525

Thr Gly Gly Thr Thr Cys Thr Gly Gly Thr Ala Cys Gly Cys Thr Ala
    530                 535                 540

Thr Cys Ala Gly Thr Thr Gly Thr Gly Cys Ala Thr Gly Cys Thr Thr
545                 550                 555                 560

Thr Cys Thr Gly Gly Thr Gly Gly Thr Cys Thr Thr Gly Thr Ala Thr
                565                 570                 575

Ala Thr Cys Cys Thr Gly Cys Thr Gly Gly Thr Gly Gly Ala Gly Thr
            580                 585                 590

Gly Gly Gly Cys Ala Cys Ala Gly Gly Ala Cys Gly Cys Cys Ala Ala
        595                 600                 605

Ala Gly Cys Cys Gly Cys Gly Gly Gly Ala Ala Cys Cys Gly Cys Thr
    610                 615                 620

Gly Ala Cys Ala Thr Gly Thr Thr Cys Ala Ala Thr Ala Cys Cys Cys
625                 630                 635                 640

Thr Gly Ala Ala Gly Cys Thr Gly Thr Thr Gly Ala Cys Ala Gly Thr
                645                 650                 655

Ala Gly Thr Gly Ala Thr Gly Thr Gly Gly Cys Thr Gly Gly Gly Gly
            660                 665                 670

Thr Ala Thr Cys Cys Ala Ala Thr Thr Gly Thr Gly Thr Gly Gly Gly
        675                 680                 685

Cys Thr Cys Thr Thr Gly Gly Ala Gly Thr Cys Gly Ala Gly Gly Gly
    690                 695                 700

Thr Ala Thr Cys Gly Cys Gly Gly Thr Gly Thr Thr Gly Cys Cys Cys
705                 710                 715                 720

Gly Thr Thr Gly Gly Gly Gly Thr Gly Ala Cys Gly Ala Gly Cys Thr
                725                 730                 735

Gly Gly Gly Gly Ala Thr Ala Thr Thr Cys Thr Thr Thr Cys Cys Thr
            740                 745                 750

Gly Gly Ala Thr Ala Thr Cys Gly Thr Gly Gly Cys Ala Ala Ala Gly
        755                 760                 765

Thr Ala Cys Ala Thr Thr Thr Thr Cys Gly Cys Ala Thr Thr Cys Thr
    770                 775                 780

Thr Gly Cys Thr Cys Cys Thr Gly Ala Ala Cys Thr Ala Thr Cys Thr
785                 790                 795                 800

Gly Ala Cys Gly Thr Cys Ala Ala Ala Cys Gly Ala Ala Thr Cys Thr
                805                 810                 815

Gly Thr Cys Gly Thr Gly Thr Cys Cys Gly Gly Cys Ala Gly Cys Ala
            820                 825                 830

Thr Thr Thr Thr Gly Gly Ala Thr Gly Thr Thr Cys Cys Ala Thr Cys
        835                 840                 845
```

```
Thr Gly Cys Thr Thr Cys Thr Gly Gly Gly Ala Cys Cys Cys Cys Gly
    850                 855                 860

Gly Cys Thr Gly Ala Thr Gly Ala Thr Gly Cys Gly Gly Cys Cys Gly
865                 870                 875                 880

Cys Thr Ala Thr Gly Gly Thr Gly Thr Cys Thr Ala Ala Gly Gly Gly
                885                 890                 895

Cys Gly Ala Ala Gly Ala Gly Cys Thr Gly Ala Thr Thr Ala Ala Gly
            900                 905                 910

Gly Ala Gly Ala Ala Cys Ala Thr Gly Cys Ala Cys Ala Thr Gly Ala
        915                 920                 925

Ala Gly Cys Thr Gly Thr Ala Cys Ala Thr Gly Gly Ala Gly Gly Gly
    930                 935                 940

Cys Ala Cys Cys Gly Thr Gly Ala Ala Cys Ala Ala Cys Cys Ala Cys
945                 950                 955                 960

Cys Ala Cys Thr Thr Cys Ala Ala Gly Thr Gly Cys Ala Cys Ala Thr
                965                 970                 975

Cys Cys Gly Ala Gly Gly Gly Cys Gly Ala Ala Gly Gly Cys Ala Ala
            980                 985                 990

Gly Cys Cys Cys Thr Ala Cys Gly  Ala Gly Gly Gly Cys  Ala Cys Cys
        995                 1000                1005

Cys Ala  Gly Ala Cys Cys Ala  Thr Gly Ala Gly Ala  Ala Thr Cys
    1010                 1015                 1020

Ala Ala  Gly Gly Thr Gly Gly  Thr Cys Gly Ala Gly  Gly Gly Cys
    1025                 1030                 1035

Gly Gly  Cys Cys Cys Thr Cys  Thr Cys Cys Cys Cys  Thr Thr Cys
    1040                 1045                 1050

Gly Cys  Cys Thr Thr Cys Gly  Ala Cys Ala Thr Cys  Cys Thr Gly
    1055                 1060                 1065

Gly Cys  Thr Ala Cys Cys Ala  Gly Cys Thr Thr Cys  Ala Thr Gly
    1070                 1075                 1080

Thr Ala  Cys Gly Gly Cys Ala  Gly Cys Ala Gly Ala  Ala Cys Cys
    1085                 1090                 1095

Thr Thr  Cys Ala Thr Cys Ala  Ala Cys Cys Ala Cys  Ala Cys Cys
    1100                 1105                 1110

Cys Ala  Gly Gly Gly Cys Ala  Thr Cys Cys Cys Cys  Gly Ala Cys
    1115                 1120                 1125

Thr Thr  Cys Thr Thr Thr Ala  Ala Gly Cys Ala Gly  Thr Cys Cys
    1130                 1135                 1140

Thr Thr  Cys Cys Cys Thr Gly  Ala Gly Gly Gly Cys  Thr Thr Cys
    1145                 1150                 1155

Ala Cys  Ala Thr Gly Gly Gly  Ala Gly Ala Gly Ala  Gly Thr Cys
    1160                 1165                 1170

Ala Cys  Cys Ala Cys Ala Thr  Ala Cys Gly Ala Ala  Gly Ala Cys
    1175                 1180                 1185

Gly Gly  Gly Gly Gly Cys Gly  Thr Gly Cys Thr Gly  Ala Cys Cys
    1190                 1195                 1200

Gly Cys  Thr Ala Cys Cys Cys  Ala Gly Gly Ala Cys  Ala Cys Cys
    1205                 1210                 1215

Ala Gly  Cys Cys Thr Cys Cys  Ala Gly Gly Ala Cys  Gly Gly Cys
    1220                 1225                 1230

Thr Gly  Cys Cys Thr Cys Ala  Thr Cys Thr Ala Cys  Ala Ala Cys
    1235                 1240                 1245

Gly Thr  Cys Ala Ala Gly Ala  Thr Cys Ala Gly Ala  Gly Gly Gly
```

-continued

```
    1250                1255                1260

Gly Thr  Gly Ala Ala Cys Thr  Thr Cys Cys Cys Ala  Thr Cys Cys
    1265                1270                1275

Ala Ala  Cys Gly Gly Cys Cys  Cys Thr Gly Thr Gly  Ala Thr Gly
    1280                1285                1290

Cys Ala  Gly Ala Ala Gly Ala  Ala Ala Ala Cys Ala  Cys Thr Cys
    1295                1300                1305

Gly Gly  Cys Thr Gly Gly Gly  Ala Gly Gly Cys Cys  Ala Ala Cys
    1310                1315                1320

Ala Cys  Cys Gly Ala Gly Ala  Thr Gly Cys Thr Gly  Thr Ala Cys
    1325                1330                1335

Cys Cys  Cys Gly Cys Thr Gly  Ala Cys Gly Gly Cys  Gly Gly Cys
    1340                1345                1350

Cys Thr  Gly Gly Ala Ala Gly  Gly Cys Ala Gly Ala  Ala Gly Cys
    1355                1360                1365

Gly Ala  Cys Ala Thr Gly Gly  Cys Cys Cys Thr Gly  Ala Ala Gly
    1370                1375                1380

Cys Thr  Cys Gly Thr Gly Gly  Gly Cys Gly Gly Gly  Gly Gly Cys
    1385                1390                1395

Cys Ala  Cys Cys Thr Gly Ala  Thr Cys Thr Gly Cys  Ala Ala Cys
    1400                1405                1410

Thr Thr  Cys Ala Ala Gly Ala  Cys Cys Ala Cys Ala  Thr Ala Cys
    1415                1420                1425

Ala Gly  Ala Thr Cys Cys Ala  Ala Gly Ala Ala Ala  Cys Cys Cys
    1430                1435                1440

Gly Cys  Thr Ala Ala Gly Ala  Ala Cys Cys Thr Cys  Ala Ala Gly
    1445                1450                1455

Ala Thr  Gly Cys Cys Cys Gly  Gly Cys Gly Thr Cys  Thr Ala Cys
    1460                1465                1470

Thr Ala  Thr Gly Thr Gly Gly  Ala Cys Cys Ala Cys  Ala Gly Ala
    1475                1480                1485

Cys Thr  Gly Gly Ala Ala Ala  Gly Ala Ala Thr Cys  Ala Ala Gly
    1490                1495                1500

Gly Ala  Gly Gly Cys Cys Gly  Ala Cys Ala Ala Ala  Gly Ala Gly
    1505                1510                1515

Ala Cys  Cys Thr Ala Cys Gly  Thr Cys Gly Ala Gly  Cys Ala Gly
    1520                1525                1530

Cys Ala  Cys Gly Ala Gly Gly  Thr Gly Gly Cys Thr  Gly Thr Gly
    1535                1540                1545

Gly Cys  Cys Ala Gly Ala Thr  Ala Cys Thr Gly Cys  Gly Ala Cys
    1550                1555                1560

Cys Thr  Cys Cys Cys Thr Ala  Gly Cys Ala Ala Ala  Cys Thr Gly
    1565                1570                1575

Gly Gly  Gly Cys Ala Cys Ala  Ala Ala Cys Thr Thr  Ala Ala Thr
    1580                1585                1590

Thr Cys  Cys Gly Gly Ala Cys  Thr Cys Ala Gly Ala  Thr Cys Thr
    1595                1600                1605

Gly Ala  Thr Ala Thr Cys Gly  Gly Gly Cys Cys Cys  Thr Cys Thr
    1610                1615                1620

Ala Gly  Ala Gly Cys Cys Ala  Cys Cys Ala Thr Gly  Gly Cys Thr
    1625                1630                1635

Thr Cys  Cys Ala Ala Gly Gly  Thr Gly Thr Ala Cys  Gly Ala Cys
    1640                1645                1650
```

Cys Cys Cys Gly Ala Gly Cys Ala Ala Cys Gly Cys Ala Ala Ala
1655 1660 1665

Cys Gly Cys Ala Thr Gly Ala Thr Cys Ala Cys Thr Gly Gly Gly
1670 1675 1680

Cys Cys Thr Cys Ala Gly Thr Gly Gly Thr Gly Gly Gly Cys Thr
1685 1690 1695

Cys Gly Cys Thr Gly Cys Ala Ala Gly Cys Ala Ala Ala Thr Gly
1700 1705 1710

Ala Ala Cys Gly Thr Gly Cys Thr Gly Gly Ala Cys Thr Cys Cys
1715 1720 1725

Thr Thr Cys Ala Thr Cys Ala Ala Cys Thr Ala Cys Thr Ala Thr
1730 1735 1740

Gly Ala Thr Thr Cys Cys Gly Ala Gly Ala Ala Gly Cys Ala Cys
1745 1750 1755

Gly Cys Cys Gly Ala Gly Ala Ala Cys Gly Cys Cys Gly Thr Gly
1760 1765 1770

Ala Thr Thr Thr Thr Thr Cys Thr Gly Cys Ala Thr Gly Gly Thr
1775 1780 1785

Ala Ala Cys Gly Cys Thr Ala Cys Cys Thr Cys Cys Ala Gly Cys
1790 1795 1800

Thr Ala Cys Cys Thr Gly Thr Gly Gly Ala Gly Gly Cys Ala Cys
1805 1810 1815

Gly Thr Cys Gly Thr Gly Cys Cys Thr Cys Ala Cys Ala Thr Cys
1820 1825 1830

Gly Ala Gly Cys Cys Cys Gly Thr Gly Gly Cys Thr Ala Gly Ala
1835 1840 1845

Thr Gly Cys Ala Thr Cys Ala Thr Cys Cys Cys Thr Gly Ala Thr
1850 1855 1860

Cys Thr Gly Ala Thr Cys Gly Gly Ala Ala Thr Gly Gly Gly Thr
1865 1870 1875

Ala Ala Gly Thr Cys Cys Gly Gly Cys Ala Ala Gly Ala Gly Cys
1880 1885 1890

Gly Gly Gly Ala Ala Thr Gly Gly Cys Thr Cys Ala Thr Ala Thr
1895 1900 1905

Cys Gly Cys Cys Thr Cys Cys Thr Gly Gly Ala Thr Cys Ala Cys
1910 1915 1920

Thr Ala Cys Ala Ala Gly Thr Ala Cys Cys Thr Cys Ala Cys Cys
1925 1930 1935

Gly Cys Thr Thr Gly Gly Thr Thr Cys Gly Ala Gly Cys Thr Gly
1940 1945 1950

Cys Thr Gly Ala Ala Cys Cys Thr Thr Cys Cys Ala Ala Ala Gly
1955 1960 1965

Ala Ala Ala Ala Thr Cys Ala Thr Cys Thr Thr Thr Gly Thr Gly
1970 1975 1980

Gly Gly Cys Cys Ala Cys Gly Ala Cys Thr Gly Gly Gly Gly Gly
1985 1990 1995

Ala Gly Cys Gly Cys Thr Cys Thr Gly Gly Cys Cys Thr Thr Thr
2000 2005 2010

Cys Ala Cys Thr Ala Cys Gly Cys Cys Thr Ala Cys Gly Ala Gly
2015 2020 2025

Cys Ala Cys Cys Ala Ala Gly Ala Cys Ala Gly Gly Ala Thr Cys
2030 2035 2040

```
Ala Ala Gly Gly Cys Cys Ala Thr Cys Gly Thr Cys Cys Ala Thr
    2045                2050                2055

Ala Thr Gly Gly Ala Gly Ala Gly Thr Gly Thr Cys Gly Thr Gly
    2060                2065                2070

Gly Ala Cys Gly Thr Gly Ala Thr Cys Gly Ala Gly Thr Cys Cys
    2075                2080                2085

Thr Gly Gly Ala Thr Gly Gly Gly Gly Thr Gly Gly Cys Cys Thr
    2090                2095                2100

Gly Ala Cys Ala Thr Cys Gly Ala Gly Gly Ala Gly Gly Ala Gly
    2105                2110                2115

Cys Thr Gly Gly Cys Cys Cys Thr Gly Ala Thr Cys Ala Ala Gly
    2120                2125                2130

Ala Gly Cys Gly Ala Ala Gly Ala Gly Gly Gly Cys Gly Ala Gly
    2135                2140                2145

Ala Ala Ala Ala Thr Gly Gly Thr Gly Cys Thr Thr Gly Ala Gly
    2150                2155                2160

Ala Ala Thr Ala Ala Cys Thr Thr Cys Thr Thr Cys Gly Thr Cys
    2165                2170                2175

Gly Ala Gly Ala Cys Cys Cys Thr Gly Thr Thr Gly Cys Cys Ala
    2180                2185                2190

Ala Gly Cys Ala Ala Gly Ala Thr Cys Ala Thr Gly Cys Gly Gly
    2195                2200                2205

Ala Ala Ala Cys Thr Gly Gly Ala Gly Cys Cys Thr Gly Ala Gly
    2210                2215                2220

Gly Ala Gly Thr Thr Cys Gly Cys Thr Gly Cys Cys Thr Ala Cys
    2225                2230                2235

Cys Thr Gly Gly Ala Gly Cys Cys Ala Thr Thr Cys Ala Ala Gly
    2240                2245                2250

Gly Ala Gly Ala Ala Gly Gly Gly Cys Gly Ala Gly Gly Thr Thr
    2255                2260                2265

Ala Gly Ala Cys Gly Gly Cys Cys Thr Ala Cys Cys Cys Thr Cys
    2270                2275                2280

Thr Cys Cys Thr Gly Gly Cys Cys Thr Cys Gly Cys Gly Ala Gly
    2285                2290                2295

Ala Thr Cys Cys Cys Thr Cys Thr Cys Gly Thr Thr Ala Ala Gly
    2300                2305                2310

Gly Gly Ala Gly Gly Cys Ala Ala Gly Cys Cys Cys Gly Ala Cys
    2315                2320                2325

Gly Thr Cys Gly Thr Cys Cys Ala Gly Ala Thr Thr Gly Thr Cys
    2330                2335                2340

Cys Gly Cys Ala Ala Cys Thr Ala Cys Ala Ala Cys Gly Cys Cys
    2345                2350                2355

Thr Ala Cys Cys Thr Thr Cys Gly Gly Gly Cys Cys Ala Gly Cys
    2360                2365                2370

Gly Ala Cys Gly Ala Thr Cys Thr Gly Cys Cys Thr Ala Ala Gly
    2375                2380                2385

Cys Thr Gly Thr Thr Cys Ala Thr Cys Gly Ala Gly Thr Cys Cys
    2390                2395                2400

Gly Ala Cys Cys Cys Thr Gly Gly Gly Thr Thr Cys Thr Thr Thr
    2405                2410                2415

Thr Cys Cys Ala Ala Cys Gly Cys Thr Ala Thr Thr Gly Thr Cys
    2420                2425                2430

Gly Ala Gly Gly Gly Ala Gly Cys Thr Ala Ala Gly Ala Ala Gly
```

2435 2440 2445

Thr Thr Cys Cys Cys Thr Ala Ala Cys Ala Cys Cys Gly Ala Gly
2450 2455 2460

Thr Thr Cys Gly Thr Gly Ala Ala Gly Gly Thr Gly Ala Ala Gly
2465 2470 2475

Gly Gly Cys Cys Thr Cys Cys Ala Cys Thr Thr Cys Cys Thr Cys
2480 2485 2490

Cys Ala Gly Gly Ala Gly Gly Ala Cys Gly Cys Thr Cys Cys Ala
2495 2500 2505

Gly Ala Thr Gly Ala Ala Ala Thr Gly Gly Gly Thr Ala Ala Gly
2510 2515 2520

Thr Ala Cys Ala Thr Cys Ala Ala Gly Ala Gly Cys Thr Thr Cys
2525 2530 2535

Gly Thr Gly Gly Ala Gly Cys Gly Cys Gly Thr Gly Cys Thr Gly
2540 2545 2550

Ala Ala Gly Ala Ala Cys Gly Ala Gly Cys Ala Gly Thr Ala Ala
2555 2560 2565

<210> SEQ ID NO 4
<211> LENGTH: 11763
<212> TYPE: PRT
<213> ORGANISM: Artificial Sequence
<220> FEATURE:
<223> OTHER INFORMATION: synthetic constructs

<400> SEQUENCE: 4

Gly Thr Cys Gly Ala Cys Gly Gly Ala Thr Cys Gly Gly Gly Ala Gly
1 5 10 15

Ala Thr Cys Thr Cys Cys Cys Gly Ala Thr Cys Cys Cys Cys Thr Ala
20 25 30

Thr Gly Gly Thr Gly Cys Ala Cys Thr Cys Thr Cys Ala Gly Thr Ala
35 40 45

Cys Ala Ala Thr Cys Thr Gly Cys Thr Cys Thr Gly Ala Thr Gly Cys
50 55 60

Cys Gly Cys Ala Thr Ala Gly Thr Thr Ala Ala Gly Cys Cys Ala Gly
65 70 75 80

Thr Ala Thr Cys Thr Gly Cys Thr Cys Cys Cys Thr Gly Cys Thr Thr
85 90 95

Gly Thr Gly Thr Gly Thr Thr Gly Gly Ala Gly Gly Thr Cys Gly Cys
100 105 110

Thr Gly Ala Gly Thr Ala Gly Thr Gly Cys Gly Cys Gly Ala Gly Cys
115 120 125

Ala Ala Ala Ala Thr Thr Thr Ala Ala Gly Cys Thr Ala Cys Ala Ala
130 135 140

Cys Ala Ala Gly Gly Cys Ala Ala Gly Gly Cys Thr Thr Gly Ala Cys
145 150 155 160

Cys Gly Ala Cys Ala Ala Thr Thr Gly Cys Ala Thr Gly Ala Ala Gly
165 170 175

Ala Ala Thr Cys Thr Gly Cys Thr Thr Ala Gly Gly Gly Thr Thr Ala
180 185 190

Gly Gly Cys Gly Thr Thr Thr Thr Gly Cys Gly Cys Thr Gly Cys Thr
195 200 205

Thr Cys Gly Cys Gly Ala Thr Gly Thr Ala Cys Gly Gly Gly Cys Cys
210 215 220

Ala Gly Ala Thr Ala Thr Ala Cys Gly Cys Gly Thr Thr Gly Ala Cys

-continued

```
225                 230                 235                 240

Ala Thr Thr Gly Ala Thr Thr Ala Thr Thr Gly Ala Cys Thr Ala Gly
                245                 250                 255

Thr Thr Ala Thr Thr Ala Ala Thr Ala Gly Thr Ala Ala Thr Cys Ala
            260                 265                 270

Ala Thr Thr Ala Cys Gly Gly Gly Gly Thr Cys Ala Thr Thr Ala Gly
        275                 280                 285

Thr Thr Cys Ala Thr Ala Gly Cys Cys Cys Ala Thr Ala Thr Ala Thr
    290                 295                 300

Gly Gly Ala Gly Thr Thr Cys Cys Gly Cys Gly Thr Thr Ala Cys Ala
305                 310                 315                 320

Thr Ala Ala Cys Thr Thr Ala Cys Gly Gly Thr Ala Ala Ala Thr Gly
                325                 330                 335

Gly Cys Cys Cys Gly Cys Cys Thr Gly Gly Cys Thr Gly Ala Cys Cys
            340                 345                 350

Gly Cys Cys Cys Ala Ala Cys Gly Ala Cys Cys Cys Cys Cys Gly Cys
        355                 360                 365

Cys Cys Ala Thr Thr Gly Ala Cys Gly Thr Cys Ala Ala Thr Ala Ala
    370                 375                 380

Thr Gly Ala Cys Gly Thr Ala Thr Gly Thr Thr Cys Cys Cys Ala Thr
385                 390                 395                 400

Ala Gly Thr Ala Ala Cys Gly Cys Cys Ala Ala Thr Ala Gly Gly Gly
                405                 410                 415

Ala Cys Thr Thr Thr Cys Cys Ala Thr Thr Gly Ala Cys Gly Thr Cys
            420                 425                 430

Ala Ala Thr Gly Gly Gly Thr Gly Gly Ala Gly Thr Ala Thr Thr Thr
        435                 440                 445

Ala Cys Gly Gly Thr Ala Ala Ala Cys Thr Gly Cys Cys Cys Ala Cys
    450                 455                 460

Thr Thr Gly Gly Cys Ala Gly Thr Ala Cys Ala Thr Cys Ala Ala Gly
465                 470                 475                 480

Thr Gly Thr Ala Thr Cys Ala Thr Ala Thr Gly Cys Cys Ala Ala Gly
                485                 490                 495

Thr Ala Cys Gly Cys Cys Cys Cys Cys Thr Ala Thr Thr Gly Ala Cys
            500                 505                 510

Gly Thr Cys Ala Ala Thr Gly Ala Cys Gly Gly Thr Ala Ala Ala Thr
        515                 520                 525

Gly Gly Cys Cys Cys Gly Cys Cys Thr Gly Gly Cys Ala Thr Thr Ala
    530                 535                 540

Thr Gly Cys Cys Cys Ala Gly Thr Ala Cys Ala Thr Gly Ala Cys Cys
545                 550                 555                 560

Thr Thr Ala Thr Gly Gly Gly Ala Cys Thr Thr Thr Cys Cys Thr Ala
                565                 570                 575

Cys Thr Thr Gly Gly Cys Ala Gly Thr Ala Cys Ala Thr Cys Thr Ala
            580                 585                 590

Cys Gly Thr Ala Thr Thr Ala Gly Thr Cys Ala Thr Cys Gly Cys Thr
        595                 600                 605

Ala Thr Thr Ala Cys Cys Ala Thr Gly Gly Thr Gly Ala Thr Gly Cys
    610                 615                 620

Gly Gly Thr Thr Thr Thr Gly Gly Cys Ala Gly Thr Ala Cys Ala Thr
625                 630                 635                 640

Cys Ala Ala Thr Gly Gly Gly Cys Gly Thr Gly Gly Ala Thr Ala Gly
                645                 650                 655
```

-continued

```
Cys Gly Gly Thr Thr Thr Gly Ala Cys Thr Cys Ala Cys Gly Gly Gly
            660                 665                 670

Gly Ala Thr Thr Thr Cys Cys Ala Ala Gly Thr Cys Thr Cys Cys Ala
        675                 680                 685

Cys Cys Cys Cys Ala Thr Thr Gly Ala Cys Gly Thr Cys Ala Ala Thr
    690                 695                 700

Gly Gly Gly Ala Gly Thr Thr Thr Gly Thr Thr Thr Thr Gly Gly Cys
705                 710                 715                 720

Ala Cys Cys Ala Ala Ala Ala Thr Cys Ala Ala Cys Gly Gly Gly Ala
                725                 730                 735

Cys Thr Thr Thr Cys Cys Ala Ala Ala Ala Thr Gly Thr Cys Gly Thr
            740                 745                 750

Ala Ala Cys Ala Ala Cys Thr Cys Cys Gly Cys Cys Cys Cys Ala Thr
        755                 760                 765

Thr Gly Ala Cys Gly Cys Ala Ala Ala Thr Gly Gly Gly Cys Gly Gly
    770                 775                 780

Thr Ala Gly Gly Cys Gly Thr Gly Thr Ala Cys Gly Gly Thr Gly Gly
785                 790                 795                 800

Gly Ala Gly Gly Thr Cys Thr Ala Thr Ala Thr Ala Ala Gly Cys Ala
                805                 810                 815

Gly Cys Gly Cys Gly Thr Thr Thr Thr Gly Cys Cys Thr Gly Thr Ala
            820                 825                 830

Cys Thr Gly Gly Gly Thr Cys Thr Cys Thr Cys Thr Gly Gly Thr Thr
        835                 840                 845

Ala Gly Ala Cys Cys Ala Gly Ala Thr Cys Thr Gly Ala Gly Cys Cys
    850                 855                 860

Thr Gly Gly Gly Ala Gly Cys Thr Cys Thr Cys Thr Gly Gly Cys Thr
865                 870                 875                 880

Ala Ala Cys Thr Ala Gly Gly Gly Ala Ala Cys Cys Cys Ala Cys Thr
                885                 890                 895

Gly Cys Thr Thr Ala Ala Gly Cys Cys Thr Cys Ala Ala Thr Ala Ala
            900                 905                 910

Ala Gly Cys Thr Thr Gly Cys Cys Thr Thr Gly Ala Gly Thr Gly Cys
        915                 920                 925

Thr Thr Cys Ala Ala Gly Thr Ala Gly Thr Gly Thr Gly Thr Gly Cys
    930                 935                 940

Cys Cys Gly Thr Cys Thr Gly Thr Thr Gly Thr Gly Thr Gly Ala Cys
945                 950                 955                 960

Thr Cys Thr Gly Gly Thr Ala Ala Cys Thr Ala Gly Ala Gly Ala Thr
                965                 970                 975

Cys Cys Cys Thr Cys Ala Gly Ala Cys Cys Cys Thr Thr Thr Thr Ala
            980                 985                 990

Gly Thr Cys Ala Gly Thr Gly Thr  Gly Gly Ala Ala Ala  Ala Thr Cys
        995                 1000                1005

Thr Cys  Thr Ala Gly Cys Ala  Gly Thr Gly Gly Cys  Gly Cys Cys
    1010                 1015                 1020

Cys Gly  Ala Ala Cys Ala Gly  Gly Gly Ala Cys Thr  Thr Gly Ala
    1025                 1030                 1035

Ala Ala  Gly Cys Gly Ala Ala  Ala Gly Gly Gly Ala  Ala Ala Cys
    1040                 1045                 1050

Cys Ala  Gly Ala Gly Gly Ala  Gly Cys Thr Cys Thr  Cys Thr Cys
    1055                 1060                 1065
```

-continued

```
Gly Ala  Cys Gly Cys Ala Gly  Gly Ala Cys Thr Cys  Gly Gly Cys
    1070                 1075                 1080

Thr Thr  Gly Cys Thr Gly Ala  Ala Gly Cys Gly Cys  Gly Cys Ala
    1085                 1090                 1095

Cys Gly  Gly Cys Ala Ala Gly  Ala Gly Gly Cys Gly  Ala Gly Gly
    1100                 1105                 1110

Gly Gly  Cys Gly Gly Cys Gly  Ala Cys Thr Gly Gly  Thr Gly Ala
    1115                 1120                 1125

Gly Thr  Ala Cys Gly Cys Cys  Ala Ala Ala Ala Ala  Thr Thr Thr
    1130                 1135                 1140

Thr Gly  Ala Cys Thr Ala Gly  Cys Gly Gly Ala Gly  Gly Cys Thr
    1145                 1150                 1155

Ala Gly  Ala Ala Gly Gly Ala  Gly Ala Gly Ala Gly  Ala Thr Gly
    1160                 1165                 1170

Gly Gly  Thr Gly Cys Gly Ala  Gly Ala Gly Cys Gly  Thr Cys Ala
    1175                 1180                 1185

Gly Thr  Ala Thr Thr Ala Ala  Gly Cys Gly Gly Gly  Gly Gly Ala
    1190                 1195                 1200

Gly Ala  Ala Thr Thr Ala Gly  Ala Thr Cys Gly Cys  Gly Ala Thr
    1205                 1210                 1215

Gly Gly  Gly Ala Ala Ala Ala  Ala Ala Thr Thr Cys  Gly Gly Thr
    1220                 1225                 1230

Thr Ala  Ala Gly Gly Cys Cys  Ala Gly Gly Gly Gly  Gly Ala Ala
    1235                 1240                 1245

Ala Gly  Ala Ala Ala Ala Ala  Ala Thr Ala Thr Ala  Ala Ala Thr
    1250                 1255                 1260

Thr Ala  Ala Ala Ala Cys Ala  Thr Ala Thr Ala Gly  Thr Ala Thr
    1265                 1270                 1275

Gly Gly  Gly Cys Ala Ala Gly  Cys Ala Gly Gly Gly  Ala Gly Cys
    1280                 1285                 1290

Thr Ala  Gly Ala Ala Cys Gly  Ala Thr Thr Cys Gly  Cys Ala Gly
    1295                 1300                 1305

Thr Thr  Ala Ala Thr Cys Cys  Thr Gly Gly Cys Cys  Thr Gly Thr
    1310                 1315                 1320

Thr Ala  Gly Ala Ala Ala Cys  Ala Thr Cys Ala Gly  Ala Ala Gly
    1325                 1330                 1335

Gly Cys  Thr Gly Thr Ala Gly  Ala Cys Ala Ala Ala  Thr Ala Cys
    1340                 1345                 1350

Thr Gly  Gly Gly Ala Cys Ala  Gly Cys Thr Ala Cys  Ala Ala Cys
    1355                 1360                 1365

Cys Ala  Thr Cys Cys Cys Thr  Thr Cys Ala Gly Ala  Cys Ala Gly
    1370                 1375                 1380

Gly Ala  Thr Cys Ala Gly Ala  Ala Gly Ala Ala Cys  Thr Thr Ala
    1385                 1390                 1395

Gly Ala  Thr Cys Ala Thr Thr  Ala Thr Ala Thr Ala  Ala Thr Ala
    1400                 1405                 1410

Cys Ala  Gly Thr Ala Gly Cys  Ala Ala Cys Cys Cys  Thr Cys Thr
    1415                 1420                 1425

Ala Thr  Thr Gly Thr Gly Thr  Gly Cys Ala Thr Cys  Ala Ala Ala
    1430                 1435                 1440

Gly Gly  Ala Thr Ala Gly Ala  Gly Ala Thr Ala Ala  Ala Ala Gly
    1445                 1450                 1455

Ala Cys  Ala Cys Cys Ala Ala  Gly Gly Ala Ala Gly  Cys Thr Thr
```

```
    1460                1465                1470

Thr Ala  Gly Ala Cys Ala Ala  Gly Ala Thr Ala Gly  Ala Gly Gly
    1475                1480                1485

Ala Ala  Gly Ala Gly Cys Ala  Ala Ala Ala Cys Ala  Ala Ala Ala
    1490                1495                1500

Gly Thr  Ala Ala Gly Ala Cys  Cys Ala Cys Cys Gly  Cys Ala Cys
    1505                1510                1515

Ala Gly  Cys Ala Ala Gly Cys  Gly Gly Cys Cys Gly  Cys Thr Gly
    1520                1525                1530

Ala Thr  Cys Thr Thr Cys Ala  Gly Ala Cys Cys Thr  Gly Gly Ala
    1535                1540                1545

Gly Gly  Ala Gly Gly Ala Gly  Ala Thr Ala Thr Gly  Ala Gly Gly
    1550                1555                1560

Gly Ala  Cys Ala Ala Thr Thr  Gly Gly Ala Gly Ala  Ala Gly Thr
    1565                1570                1575

Gly Ala  Ala Thr Thr Ala Thr  Ala Thr Ala Ala Ala  Thr Ala Thr
    1580                1585                1590

Ala Ala  Ala Gly Thr Ala Gly  Thr Ala Ala Ala Ala  Ala Thr Thr
    1595                1600                1605

Gly Ala  Ala Cys Cys Ala Thr  Thr Ala Gly Gly Ala  Gly Thr Ala
    1610                1615                1620

Gly Cys  Ala Cys Cys Cys Ala  Cys Cys Ala Ala Gly  Gly Cys Ala
    1625                1630                1635

Ala Ala  Gly Ala Gly Ala Ala  Gly Ala Gly Thr Gly  Gly Thr Gly
    1640                1645                1650

Cys Ala  Gly Ala Gly Ala Gly  Ala Ala Ala Ala Ala  Ala Gly Ala
    1655                1660                1665

Gly Cys  Ala Gly Thr Gly Gly  Gly Ala Ala Thr Ala  Gly Gly Ala
    1670                1675                1680

Gly Cys  Thr Thr Thr Gly Thr  Thr Cys Cys Thr Thr  Gly Gly Gly
    1685                1690                1695

Thr Thr  Cys Thr Thr Gly Gly  Gly Ala Gly Cys Ala  Gly Cys Ala
    1700                1705                1710

Gly Gly  Ala Ala Gly Cys Ala  Cys Thr Ala Thr Gly  Gly Gly Cys
    1715                1720                1725

Gly Cys  Ala Gly Cys Gly Thr  Cys Ala Ala Thr Gly  Ala Cys Gly
    1730                1735                1740

Cys Thr  Gly Ala Cys Gly Gly  Thr Ala Cys Ala Gly  Gly Cys Cys
    1745                1750                1755

Ala Gly  Ala Cys Ala Ala Thr  Thr Ala Thr Thr Gly  Thr Cys Thr
    1760                1765                1770

Gly Gly  Thr Ala Thr Ala Gly  Thr Gly Cys Ala Gly  Cys Ala Gly
    1775                1780                1785

Cys Ala  Gly Ala Ala Cys Ala  Ala Thr Thr Thr Gly  Cys Thr Gly
    1790                1795                1800

Ala Gly  Gly Gly Cys Thr Ala  Thr Thr Gly Ala Gly  Gly Cys Gly
    1805                1810                1815

Cys Ala  Ala Cys Ala Gly Cys  Ala Thr Cys Thr Gly  Thr Thr Gly
    1820                1825                1830

Cys Ala  Ala Cys Thr Cys Ala  Cys Ala Gly Thr Cys  Thr Gly Gly
    1835                1840                1845

Gly Gly  Cys Ala Thr Cys Ala  Ala Gly Cys Ala Gly  Cys Thr Cys
    1850                1855                1860
```

-continued

```
Cys Ala  Gly Gly Cys Ala Ala  Gly Ala Ala Thr Cys  Cys Thr Gly
    1865                 1870                 1875

Gly Cys  Thr Gly Thr Gly Gly  Ala Ala Ala Gly Ala  Thr Ala Cys
    1880                 1885                 1890

Cys Thr  Ala Ala Ala Gly Gly  Ala Thr Cys Ala Ala  Cys Ala Gly
    1895                 1900                 1905

Cys Thr  Cys Cys Thr Gly Gly  Gly Gly Ala Thr Thr  Thr Gly Gly
    1910                 1915                 1920

Gly Gly  Thr Thr Gly Cys Thr  Cys Thr Gly Gly Ala  Ala Ala Ala
    1925                 1930                 1935

Cys Thr  Cys Ala Thr Thr Thr  Gly Cys Ala Cys Cys  Ala Cys Thr
    1940                 1945                 1950

Gly Cys  Thr Gly Thr Gly Cys  Cys Thr Thr Gly Gly  Ala Ala Thr
    1955                 1960                 1965

Gly Cys  Thr Ala Gly Thr Thr  Gly Gly Ala Gly Thr  Ala Ala Thr
    1970                 1975                 1980

Ala Ala  Ala Thr Cys Thr Cys  Thr Gly Gly Ala Ala  Cys Ala Gly
    1985                 1990                 1995

Ala Thr  Thr Thr Gly Gly Ala  Ala Thr Cys Ala Cys  Ala Cys Gly
    2000                 2005                 2010

Ala Cys  Cys Thr Gly Gly Ala  Thr Gly Gly Ala Gly  Thr Gly Gly
    2015                 2020                 2025

Gly Ala  Cys Ala Gly Ala Gly  Ala Ala Ala Thr Thr  Ala Ala Cys
    2030                 2035                 2040

Ala Ala  Thr Thr Ala Cys Ala  Cys Ala Ala Gly Cys  Thr Thr Ala
    2045                 2050                 2055

Ala Thr  Ala Cys Ala Cys Thr  Cys Cys Thr Thr Ala  Ala Thr Thr
    2060                 2065                 2070

Gly Ala  Ala Gly Ala Ala Thr  Cys Gly Cys Ala Ala  Ala Ala Cys
    2075                 2080                 2085

Cys Ala  Gly Cys Ala Ala Gly  Ala Ala Ala Ala Gly  Ala Ala Thr
    2090                 2095                 2100

Gly Ala  Ala Cys Ala Ala Gly  Ala Ala Thr Thr Ala  Thr Thr Gly
    2105                 2110                 2115

Gly Ala  Ala Thr Thr Ala Gly  Ala Thr Ala Ala Ala  Thr Gly Gly
    2120                 2125                 2130

Gly Cys  Ala Ala Gly Thr Thr  Thr Gly Thr Gly Gly  Ala Ala Thr
    2135                 2140                 2145

Thr Gly  Gly Thr Thr Thr Ala  Ala Cys Ala Thr Ala  Ala Cys Ala
    2150                 2155                 2160

Ala Ala  Thr Thr Gly Gly Cys  Thr Gly Thr Gly Gly  Thr Ala Thr
    2165                 2170                 2175

Ala Thr  Ala Ala Ala Ala Thr  Thr Ala Thr Thr Cys  Ala Thr Ala
    2180                 2185                 2190

Ala Thr  Gly Ala Thr Ala Gly  Thr Ala Gly Gly Ala  Gly Gly Cys
    2195                 2200                 2205

Thr Thr  Gly Gly Thr Ala Gly  Gly Thr Thr Thr Ala  Ala Gly Ala
    2210                 2215                 2220

Ala Thr  Ala Gly Thr Thr Thr  Thr Thr Gly Cys Thr  Gly Thr Ala
    2225                 2230                 2235

Cys Thr  Thr Thr Cys Thr Ala  Thr Ala Gly Thr Gly  Ala Ala Thr
    2240                 2245                 2250
```

-continued

```
Ala Gly  Ala Gly Thr Thr Ala  Gly Gly Cys Ala Gly  Gly Gly Ala
    2255                 2260                 2265

Thr Ala  Thr Thr Cys Ala Cys  Cys Ala Thr Thr Ala  Thr Cys Gly
    2270                 2275                 2280

Thr Thr  Thr Cys Ala Gly Ala  Cys Cys Cys Ala Cys  Cys Thr Cys
    2285                 2290                 2295

Cys Cys  Ala Ala Cys Cys Cys  Cys Gly Ala Gly Gly  Gly Gly Ala
    2300                 2305                 2310

Cys Cys  Cys Gly Ala Cys Ala  Gly Gly Cys Cys Cys  Gly Ala Ala
    2315                 2320                 2325

Gly Gly  Ala Ala Thr Ala Gly  Ala Ala Gly Ala Ala  Gly Ala Ala
    2330                 2335                 2340

Gly Gly  Thr Gly Gly Ala Gly  Ala Gly Ala Gly Ala  Gly Ala Cys
    2345                 2350                 2355

Ala Gly  Ala Gly Ala Cys Ala  Gly Ala Thr Cys Cys  Ala Thr Thr
    2360                 2365                 2370

Cys Gly  Ala Thr Thr Ala Gly  Thr Gly Ala Ala Cys  Gly Gly Ala
    2375                 2380                 2385

Thr Cys  Gly Gly Cys Ala Cys  Thr Gly Cys Gly Thr  Gly Cys Gly
    2390                 2395                 2400

Cys Cys  Ala Ala Thr Thr Cys  Thr Gly Cys Ala Gly  Ala Cys Ala
    2405                 2410                 2415

Ala Ala  Thr Gly Gly Cys Ala  Gly Thr Ala Thr Thr  Cys Ala Thr
    2420                 2425                 2430

Cys Cys  Ala Cys Ala Ala Thr  Thr Thr Thr Ala Ala  Ala Ala Gly
    2435                 2440                 2445

Ala Ala  Ala Ala Gly Gly Gly  Gly Gly Gly Ala Thr  Thr Gly Gly
    2450                 2455                 2460

Gly Gly  Gly Gly Thr Ala Cys  Ala Gly Thr Gly Cys  Ala Gly Gly
    2465                 2470                 2475

Gly Gly  Ala Ala Ala Gly Ala  Ala Thr Ala Gly Thr  Ala Gly Ala
    2480                 2485                 2490

Cys Ala  Thr Ala Ala Thr Ala  Gly Cys Ala Ala Cys  Ala Gly Ala
    2495                 2500                 2505

Cys Ala  Thr Ala Cys Ala Ala  Ala Cys Thr Ala Ala  Ala Gly Ala
    2510                 2515                 2520

Ala Thr  Thr Ala Cys Ala Ala  Ala Ala Ala Cys Ala  Ala Ala Thr
    2525                 2530                 2535

Thr Ala  Cys Ala Ala Ala Ala  Ala Thr Thr Cys Ala  Ala Ala Ala
    2540                 2545                 2550

Thr Thr  Thr Thr Cys Gly Gly  Gly Thr Thr Thr Ala  Thr Thr Ala
    2555                 2560                 2565

Cys Ala  Gly Gly Gly Ala Cys  Ala Gly Cys Ala Gly  Ala Gly Ala
    2570                 2575                 2580

Thr Cys  Cys Ala Gly Thr Thr  Thr Gly Gly Thr Thr  Ala Ala Thr
    2585                 2590                 2595

Thr Ala  Ala Gly Gly Gly Thr  Gly Cys Ala Gly Cys  Gly Gly Cys
    2600                 2605                 2610

Cys Thr  Cys Cys Gly Cys Gly  Cys Cys Gly Gly Gly  Thr Thr Thr
    2615                 2620                 2625

Thr Gly  Gly Cys Gly Cys Cys  Thr Cys Cys Cys Gly  Cys Gly Gly
    2630                 2635                 2640

Gly Cys  Gly Cys Cys Cys Cys  Cys Cys Thr Cys Cys  Thr Cys Ala
```

-continued

```
    2645                2650                2655

Cys Gly  Gly Cys Gly Ala Gly  Cys Gly Cys Thr Gly  Cys Cys Ala
    2660                2665                2670

Cys Gly  Thr Cys Ala Gly Ala  Cys Gly Ala Ala Gly  Gly Gly Cys
    2675                2680                2685

Gly Cys  Ala Gly Gly Ala Gly  Cys Gly Thr Thr Cys  Cys Thr Gly
    2690                2695                2700

Ala Thr  Cys Cys Thr Thr Cys  Cys Gly Cys Cys Cys  Gly Gly Ala
    2705                2710                2715

Cys Gly  Cys Thr Cys Ala Gly  Gly Ala Cys Ala Gly  Cys Gly Gly
    2720                2725                2730

Cys Cys  Cys Gly Cys Thr Gly  Cys Thr Cys Ala Thr  Ala Ala Gly
    2735                2740                2745

Ala Cys  Thr Cys Gly Gly Cys  Cys Thr Thr Ala Gly  Ala Ala Cys
    2750                2755                2760

Cys Cys  Cys Ala Gly Thr Ala  Thr Cys Ala Gly Cys  Ala Gly Ala
    2765                2770                2775

Ala Gly  Gly Ala Cys Ala Thr  Thr Thr Thr Ala Gly  Gly Ala Cys
    2780                2785                2790

Gly Gly  Gly Ala Cys Thr Thr  Gly Gly Gly Thr Gly  Ala Cys Thr
    2795                2800                2805

Cys Thr  Ala Gly Gly Gly Cys  Ala Cys Thr Gly Gly  Thr Thr Thr
    2810                2815                2820

Thr Cys  Thr Thr Thr Cys Cys  Ala Gly Ala Gly Ala  Gly Cys Gly
    2825                2830                2835

Gly Ala  Ala Cys Ala Gly Gly  Cys Gly Ala Gly Gly  Ala Ala Ala
    2840                2845                2850

Ala Gly  Thr Ala Gly Thr Cys  Cys Cys Thr Thr Cys  Thr Cys Gly
    2855                2860                2865

Gly Cys  Gly Ala Thr Thr Cys  Thr Gly Cys Gly Gly  Ala Gly Gly
    2870                2875                2880

Gly Ala  Thr Cys Thr Cys Cys  Gly Thr Gly Gly Gly  Gly Cys Gly
    2885                2890                2895

Gly Thr  Gly Ala Ala Cys Gly  Cys Cys Gly Ala Thr  Gly Ala Thr
    2900                2905                2910

Thr Ala  Thr Ala Thr Ala Ala  Gly Gly Ala Cys Gly  Cys Gly Cys
    2915                2920                2925

Cys Gly  Gly Gly Thr Gly Thr  Gly Gly Cys Ala Cys  Ala Gly Cys
    2930                2935                2940

Thr Ala  Gly Thr Thr Cys Cys  Gly Thr Cys Gly Cys  Ala Gly Cys
    2945                2950                2955

Cys Gly  Gly Gly Ala Thr Thr  Thr Gly Gly Gly Thr  Cys Gly Cys
    2960                2965                2970

Gly Gly  Thr Thr Cys Thr Thr  Gly Thr Thr Thr Gly  Thr Gly Gly
    2975                2980                2985

Ala Thr  Cys Gly Cys Thr Gly  Thr Gly Ala Thr Cys  Gly Thr Cys
    2990                2995                3000

Ala Cys  Thr Thr Gly Gly Thr  Gly Ala Gly Thr Thr  Gly Cys Gly
    3005                3010                3015

Gly Gly  Cys Thr Gly Cys Thr  Gly Gly Gly Cys Thr  Gly Gly Cys
    3020                3025                3030

Cys Gly  Gly Gly Gly Cys Thr  Thr Thr Cys Gly Thr  Gly Gly Cys
    3035                3040                3045
```

Cys Gly Cys Cys Gly Gly Gly Cys Cys Gly Cys Thr Cys Gly Gly
3050 3055 3060

Thr Gly Gly Gly Ala Cys Gly Gly Ala Ala Gly Cys Gly Thr Gly
3065 3070 3075

Thr Gly Gly Ala Gly Ala Gly Ala Cys Cys Gly Cys Cys Ala Ala
3080 3085 3090

Gly Gly Gly Cys Thr Gly Thr Ala Gly Thr Cys Thr Gly Gly Gly
3095 3100 3105

Thr Cys Cys Gly Cys Gly Ala Gly Cys Ala Ala Gly Gly Thr Thr
3110 3115 3120

Gly Cys Cys Cys Thr Gly Ala Ala Cys Thr Gly Gly Gly Gly Gly
3125 3130 3135

Thr Thr Gly Gly Gly Gly Gly Gly Ala Gly Cys Gly Cys Ala Cys
3140 3145 3150

Ala Ala Ala Ala Thr Gly Gly Cys Gly Gly Cys Thr Gly Thr Thr
3155 3160 3165

Cys Cys Cys Gly Ala Gly Thr Cys Thr Thr Gly Ala Ala Thr Gly
3170 3175 3180

Gly Ala Ala Gly Ala Cys Gly Cys Thr Thr Gly Thr Ala Ala Gly
3185 3190 3195

Gly Cys Gly Gly Gly Cys Thr Gly Thr Gly Ala Gly Gly Thr Cys
3200 3205 3210

Gly Thr Thr Gly Ala Ala Ala Cys Ala Ala Gly Gly Thr Gly Gly
3215 3220 3225

Gly Gly Gly Gly Cys Ala Thr Gly Gly Thr Gly Gly Gly Cys Gly
3230 3235 3240

Gly Cys Ala Ala Gly Ala Ala Cys Cys Cys Ala Ala Gly Gly Thr
3245 3250 3255

Cys Thr Thr Gly Ala Gly Gly Cys Cys Thr Thr Cys Gly Cys Thr
3260 3265 3270

Ala Ala Thr Gly Cys Gly Gly Gly Ala Ala Ala Gly Cys Thr Cys
3275 3280 3285

Thr Thr Ala Thr Thr Cys Gly Gly Gly Thr Gly Ala Gly Ala Thr
3290 3295 3300

Gly Gly Gly Cys Thr Gly Gly Gly Gly Cys Ala Cys Cys Ala Thr
3305 3310 3315

Cys Thr Gly Gly Gly Gly Ala Cys Cys Cys Thr Gly Ala Cys Gly
3320 3325 3330

Thr Gly Ala Ala Gly Thr Thr Thr Gly Thr Cys Ala Cys Thr Gly
3335 3340 3345

Ala Cys Thr Gly Gly Ala Gly Ala Ala Cys Thr Cys Gly Gly Gly
3350 3355 3360

Thr Thr Thr Gly Thr Cys Gly Thr Cys Thr Gly Gly Thr Thr Gly
3365 3370 3375

Cys Gly Gly Gly Gly Gly Cys Gly Gly Cys Ala Gly Thr Thr Ala
3380 3385 3390

Thr Gly Cys Gly Gly Thr Gly Cys Cys Gly Thr Thr Gly Gly Gly
3395 3400 3405

Cys Ala Gly Thr Gly Cys Ala Cys Cys Cys Gly Thr Ala Cys Cys
3410 3415 3420

Thr Thr Thr Gly Gly Gly Ala Gly Cys Gly Cys Gly Cys Gly Cys
3425 3430 3435

```
Cys Thr  Cys Gly Thr Cys Gly  Thr Gly Thr Cys Gly  Thr Gly Ala
    3440                 3445                 3450

Cys Gly  Thr Cys Ala Cys Cys  Cys Gly Thr Thr Cys  Thr Gly Thr
    3455                 3460                 3465

Thr Gly  Gly Cys Thr Thr Ala  Thr Ala Ala Thr Gly  Cys Ala Gly
    3470                 3475                 3480

Gly Gly  Thr Gly Gly Gly Gly  Cys Cys Ala Cys Cys  Thr Gly Cys
    3485                 3490                 3495

Cys Gly  Gly Thr Ala Gly Gly  Thr Gly Thr Gly Cys  Gly Gly Thr
    3500                 3505                 3510

Ala Gly  Gly Cys Thr Thr Thr  Thr Cys Thr Cys Cys  Gly Thr Cys
    3515                 3520                 3525

Gly Cys  Ala Gly Gly Ala Cys  Gly Cys Ala Gly Gly  Gly Thr Thr
    3530                 3535                 3540

Cys Gly  Gly Gly Cys Cys Thr  Ala Gly Gly Gly Thr  Ala Gly Gly
    3545                 3550                 3555

Cys Thr  Cys Thr Cys Cys Thr  Gly Ala Ala Thr Cys  Gly Ala Cys
    3560                 3565                 3570

Ala Gly  Gly Cys Gly Cys Cys  Gly Gly Ala Cys Cys  Thr Cys Thr
    3575                 3580                 3585

Gly Gly  Thr Gly Ala Gly Gly  Gly Gly Ala Gly Gly  Gly Ala Thr
    3590                 3595                 3600

Ala Ala  Gly Thr Gly Ala Gly  Gly Cys Gly Thr Cys  Ala Gly Thr
    3605                 3610                 3615

Thr Thr  Cys Thr Thr Thr Gly  Gly Thr Cys Gly Gly  Thr Thr Thr
    3620                 3625                 3630

Thr Ala  Thr Gly Thr Ala Cys  Cys Thr Ala Thr Cys  Thr Thr Cys
    3635                 3640                 3645

Thr Thr  Ala Ala Gly Thr Ala  Gly Cys Thr Gly Ala  Ala Gly Cys
    3650                 3655                 3660

Thr Cys  Cys Gly Gly Thr Thr  Thr Thr Gly Ala Ala  Cys Thr Ala
    3665                 3670                 3675

Thr Gly  Cys Gly Cys Thr Cys  Gly Gly Gly Gly Thr  Thr Gly Gly
    3680                 3685                 3690

Cys Gly  Ala Gly Thr Gly Thr  Gly Thr Thr Thr Thr  Gly Thr Gly
    3695                 3700                 3705

Ala Ala  Gly Thr Thr Thr Thr  Thr Thr Ala Gly Gly  Cys Ala Cys
    3710                 3715                 3720

Cys Thr  Thr Thr Thr Gly Ala  Ala Ala Thr Gly Thr  Ala Ala Thr
    3725                 3730                 3735

Cys Ala  Thr Thr Thr Gly Gly  Gly Thr Cys Ala Ala  Thr Ala Thr
    3740                 3745                 3750

Gly Thr  Ala Ala Thr Thr Thr  Thr Cys Ala Gly Thr  Gly Thr Thr
    3755                 3760                 3765

Ala Gly  Ala Cys Thr Ala Gly  Thr Ala Ala Ala Gly  Cys Thr Thr
    3770                 3775                 3780

Cys Thr  Gly Cys Ala Gly Gly  Thr Cys Gly Ala Cys  Thr Cys Thr
    3785                 3790                 3795

Ala Gly  Ala Ala Ala Ala Thr  Thr Gly Thr Cys Cys  Gly Cys Thr
    3800                 3805                 3810

Ala Ala  Ala Thr Thr Cys Thr  Gly Gly Cys Cys Gly  Thr Thr Thr
    3815                 3820                 3825

Thr Thr  Gly Gly Cys Thr Thr  Thr Thr Thr Thr Gly  Thr Thr Ala
```

-continued

```
    3830                3835                3840

Gly Ala  Cys Ala Gly Gly Ala  Thr Cys Cys Cys Cys  Gly Gly Gly
    3845                3850                3855

Thr Ala  Cys Cys Ala Thr Gly  Ala Cys Ala Gly Ala  Gly Ala Cys
    3860                3865                3870

Cys Cys  Thr Gly Cys Cys Thr  Cys Cys Cys Gly Thr  Gly Ala Cys
    3875                3880                3885

Cys Gly  Ala Gly Ala Gly Thr  Gly Cys Cys Gly Thr  Gly Gly Cys
    3890                3895                3900

Cys Cys  Thr Thr Cys Ala Ala  Gly Cys Cys Gly Ala  Gly Gly Thr
    3905                3910                3915

Thr Ala  Cys Cys Cys Ala Ala  Ala Gly Gly Gly Ala  Gly Thr Thr
    3920                3925                3930

Gly Thr  Thr Cys Gly Ala Gly  Thr Thr Cys Gly Thr  Gly Cys Thr
    3935                3940                3945

Gly Ala  Ala Cys Gly Ala Cys  Cys Cys Thr Thr Thr  Gly Cys Thr
    3950                3955                3960

Thr Gly  Cys Ala Ala Gly Cys  Ala Gly Thr Cys Thr  Cys Thr Ala
    3965                3970                3975

Thr Ala  Thr Cys Ala Ala Cys  Ala Thr Cys Gly Cys  Ala Cys Thr
    3980                3985                3990

Thr Gly  Cys Ala Gly Gly Ala  Cys Thr Gly Ala Gly  Thr Ala Thr
    3995                4000                4005

Ala Cys  Thr Gly Cys Thr Gly  Thr Thr Cys Gly Thr  Thr Thr Thr
    4010                4015                4020

Thr Ala  Thr Gly Ala Cys Cys  Cys Gly Ala Gly Gly  Ala Cys Thr
    4025                4030                4035

Cys Gly  Ala Thr Gly Ala Thr  Cys Cys Ala Cys Gly  Gly Gly Cys
    4040                4045                4050

Ala Ala  Ala Ala Cys Thr Thr  Ala Thr Thr Gly Cys  Thr Gly Thr
    4055                4060                4065

Gly Thr  Cys Ala Ala Cys Cys  Ala Thr Cys Cys Thr  Thr Gly Thr
    4070                4075                4080

Gly Cys  Cys Thr Gly Thr Cys  Gly Thr Cys Ala Gly  Cys Ala Thr
    4085                4090                4095

Thr Gly  Cys Cys Thr Cys Cys  Thr Ala Cys Ala Cys  Thr Gly Gly
    4100                4105                4110

Ala Thr  Thr Gly Gly Cys Gly  Ala Gly Cys Gly Gly  Cys Cys Thr
    4115                4120                4125

Gly Ala  Cys Ala Ala Thr Thr  Thr Cys Cys Gly Thr  Thr Cys Thr
    4130                4135                4140

Thr Gly  Ala Ala Ala Thr Gly  Cys Cys Ala Gly Cys  Gly Gly Gly
    4145                4150                4155

Cys Cys  Ala Thr Thr Thr Thr  Gly Cys Ala Gly Ala  Ala Gly Gly
    4160                4165                4170

Cys Ala  Gly Cys Thr Cys Ala  Gly Thr Gly Ala Thr  Gly Cys Thr
    4175                4180                4185

Gly Gly  Gly Ala Gly Gly Ala  Gly Ala Ala Gly Ala  Gly Gly Thr
    4190                4195                4200

Ala Gly  Ala Thr Gly Gly Thr  Gly Thr Ala Gly Thr  Cys Ala Cys
    4205                4210                4215

Cys Ala  Thr Gly Thr Gly Gly  Gly Gly Ala Cys Gly  Gly Thr Ala
    4220                4225                4230
```

Thr Cys Thr Cys Ala Cys Cys Thr Gly Gly Gly Cys Ala Cys Thr
4235 4240 4245

Thr Thr Cys Cys Ala Cys Gly Cys Cys Cys Ala Thr Gly Ala Thr
4250 4255 4260

Thr Cys Thr Cys Cys Thr Cys Gly Cys Thr Cys Thr Gly Gly Gly
4265 4270 4275

Thr Cys Thr Cys Cys Thr Gly Gly Cys Cys Gly Gly Ala Ala Gly
4280 4285 4290

Cys Ala Ala Thr Gly Cys Thr Ala Cys Ala Ala Ala Gly Cys Thr
4295 4300 4305

Cys Thr Thr Cys Ala Cys Ala Gly Cys Thr Ala Thr Cys Ala Cys
4310 4315 4320

Thr Thr Thr Cys Gly Ala Thr Ala Thr Cys Gly Cys Thr Ala Thr
4325 4330 4335

Gly Thr Gly Cys Gly Thr Gly Ala Cys Thr Gly Gly Cys Cys Thr
4340 4345 4350

Thr Gly Cys Cys Gly Cys Gly Gly Cys Cys Cys Thr Gly Ala Cys
4355 4360 4365

Thr Ala Cys Cys Thr Cys Cys Thr Cys Cys Cys Ala Cys Cys Thr
4370 4375 4380

Cys Ala Thr Gly Ala Gly Ala Thr Gly Gly Thr Thr Cys Thr Gly
4385 4390 4395

Gly Thr Ala Cys Gly Cys Thr Ala Thr Cys Ala Gly Thr Thr Gly
4400 4405 4410

Thr Gly Cys Ala Thr Gly Cys Thr Thr Thr Cys Thr Gly Gly Thr
4415 4420 4425

Gly Gly Thr Cys Thr Thr Gly Thr Ala Thr Ala Thr Cys Cys Thr
4430 4435 4440

Gly Cys Thr Gly Gly Thr Gly Gly Ala Gly Thr Gly Gly Gly Cys
4445 4450 4455

Ala Cys Ala Gly Gly Ala Cys Gly Cys Cys Ala Ala Ala Gly Cys
4460 4465 4470

Cys Gly Cys Gly Gly Gly Ala Ala Cys Cys Gly Cys Thr Gly Ala
4475 4480 4485

Cys Ala Thr Gly Thr Thr Cys Ala Ala Thr Ala Cys Cys Cys Thr
4490 4495 4500

Gly Ala Ala Gly Cys Thr Gly Thr Thr Gly Ala Cys Ala Gly Thr
4505 4510 4515

Ala Gly Thr Gly Ala Thr Gly Thr Gly Gly Cys Thr Gly Gly Gly
4520 4525 4530

Gly Thr Ala Thr Cys Cys Ala Ala Thr Thr Gly Thr Gly Thr Gly
4535 4540 4545

Gly Gly Cys Thr Cys Thr Thr Gly Gly Ala Gly Thr Cys Gly Ala
4550 4555 4560

Gly Gly Gly Thr Ala Thr Cys Gly Cys Gly Gly Thr Gly Thr Thr
4565 4570 4575

Gly Cys Cys Cys Gly Thr Thr Gly Gly Gly Gly Thr Gly Ala Cys
4580 4585 4590

Gly Ala Gly Cys Thr Gly Gly Gly Gly Ala Thr Ala Thr Thr Cys
4595 4600 4605

Thr Thr Thr Cys Cys Thr Gly Gly Ala Thr Ala Thr Cys Gly Thr
4610 4615 4620

```
Gly Gly  Cys Ala Ala Ala Gly  Thr Ala Cys Ala Thr  Thr Thr Thr
    4625                 4630                 4635

Cys Gly  Cys Ala Thr Thr Cys  Thr Thr Gly Cys Thr  Cys Cys Thr
    4640                 4645                 4650

Gly Ala  Ala Cys Thr Ala Thr  Cys Thr Gly Ala Cys  Gly Thr Cys
    4655                 4660                 4665

Ala Ala  Ala Cys Gly Ala Ala  Thr Cys Thr Gly Thr  Cys Gly Thr
    4670                 4675                 4680

Gly Thr  Cys Cys Gly Gly Cys  Ala Gly Cys Ala Thr  Thr Thr Thr
    4685                 4690                 4695

Gly Gly  Ala Thr Gly Thr Thr  Cys Cys Ala Thr Cys  Thr Gly Cys
    4700                 4705                 4710

Thr Thr  Cys Thr Gly Gly Gly  Ala Cys Cys Cys Cys  Gly Gly Cys
    4715                 4720                 4725

Thr Gly  Ala Thr Gly Ala Thr  Gly Cys Gly Gly Cys  Cys Gly Cys
    4730                 4735                 4740

Thr Ala  Thr Gly Gly Thr Gly  Thr Cys Thr Ala Ala  Gly Gly Gly
    4745                 4750                 4755

Cys Gly  Ala Ala Gly Ala Gly  Cys Thr Gly Ala Thr  Thr Ala Ala
    4760                 4765                 4770

Gly Gly  Ala Gly Ala Ala Cys  Ala Thr Gly Cys Ala  Cys Ala Thr
    4775                 4780                 4785

Gly Ala  Ala Gly Cys Thr Gly  Thr Ala Cys Ala Thr  Gly Gly Ala
    4790                 4795                 4800

Gly Gly  Gly Cys Ala Cys Cys  Gly Thr Gly Ala Ala  Cys Ala Ala
    4805                 4810                 4815

Cys Cys  Ala Cys Cys Ala Cys  Thr Thr Cys Ala Ala  Gly Thr Gly
    4820                 4825                 4830

Cys Ala  Cys Ala Thr Cys Cys  Gly Ala Gly Gly Gly  Cys Gly Ala
    4835                 4840                 4845

Ala Gly  Gly Cys Ala Ala Gly  Cys Cys Cys Thr Ala  Cys Gly Ala
    4850                 4855                 4860

Gly Gly  Gly Cys Ala Cys Cys  Cys Ala Gly Ala Cys  Cys Ala Thr
    4865                 4870                 4875

Gly Ala  Gly Ala Ala Thr Cys  Ala Ala Gly Gly Thr  Gly Gly Thr
    4880                 4885                 4890

Cys Gly  Ala Gly Gly Gly Cys  Gly Gly Cys Cys Cys  Thr Cys Thr
    4895                 4900                 4905

Cys Cys  Cys Cys Thr Thr Cys  Gly Cys Cys Thr Thr  Cys Gly Ala
    4910                 4915                 4920

Cys Ala  Thr Cys Cys Thr Gly  Gly Cys Thr Ala Cys  Cys Ala Gly
    4925                 4930                 4935

Cys Thr  Thr Cys Ala Thr Gly  Thr Ala Cys Gly Gly  Cys Ala Gly
    4940                 4945                 4950

Cys Ala  Gly Ala Ala Cys Cys  Thr Thr Cys Ala Thr  Cys Ala Ala
    4955                 4960                 4965

Cys Cys  Ala Cys Ala Cys Cys  Cys Ala Gly Gly Gly  Cys Ala Thr
    4970                 4975                 4980

Cys Cys  Cys Cys Gly Ala Cys  Thr Thr Cys Thr Thr  Thr Ala Ala
    4985                 4990                 4995

Gly Cys  Ala Gly Thr Cys Cys  Thr Thr Cys Cys Cys  Thr Gly Ala
    5000                 5005                 5010

Gly Gly  Gly Cys Thr Thr Cys  Ala Cys Ala Thr Gly  Gly Gly Ala
```

```
    5015                5020                5025

Gly Ala  Gly Ala Gly Thr Cys  Ala Cys Cys Ala Cys  Ala Thr Ala
    5030                5035                5040

Cys Gly  Ala Ala Gly Ala Cys  Gly Gly Gly Gly Gly  Cys Gly Thr
    5045                5050                5055

Gly Cys  Thr Gly Ala Cys Cys  Gly Cys Thr Ala Cys  Cys Cys Ala
    5060                5065                5070

Gly Gly  Ala Cys Ala Cys Cys  Ala Gly Cys Cys Thr  Cys Cys Ala
    5075                5080                5085

Gly Gly  Ala Cys Gly Gly Cys  Thr Gly Cys Cys Thr  Cys Ala Thr
    5090                5095                5100

Cys Thr  Ala Cys Ala Ala Cys  Gly Thr Cys Ala Ala  Gly Ala Thr
    5105                5110                5115

Cys Ala  Gly Ala Gly Gly Gly  Gly Thr Gly Ala Ala  Cys Thr Thr
    5120                5125                5130

Cys Cys  Cys Ala Thr Cys Cys  Ala Ala Cys Gly Gly  Cys Cys Cys
    5135                5140                5145

Thr Gly  Thr Gly Ala Thr Gly  Cys Ala Gly Ala Ala  Gly Ala Ala
    5150                5155                5160

Ala Ala  Cys Ala Cys Thr Cys  Gly Gly Cys Thr Gly  Gly Gly Ala
    5165                5170                5175

Gly Gly  Cys Cys Ala Ala Cys  Ala Cys Cys Gly Ala  Gly Ala Thr
    5180                5185                5190

Gly Cys  Thr Gly Thr Ala Cys  Cys Cys Cys Gly Cys  Thr Gly Ala
    5195                5200                5205

Cys Gly  Gly Cys Gly Gly Cys  Cys Thr Gly Gly Ala  Ala Gly Gly
    5210                5215                5220

Cys Ala  Gly Ala Ala Gly Cys  Gly Ala Cys Ala Thr  Gly Gly Cys
    5225                5230                5235

Cys Cys  Thr Gly Ala Ala Gly  Cys Thr Cys Gly Thr  Gly Gly Gly
    5240                5245                5250

Cys Gly  Gly Gly Gly Gly Cys  Cys Ala Cys Cys Thr  Gly Ala Thr
    5255                5260                5265

Cys Thr  Gly Cys Ala Ala Cys  Thr Thr Cys Ala Ala  Gly Ala Cys
    5270                5275                5280

Cys Ala  Cys Ala Thr Ala Cys  Ala Gly Ala Thr Cys  Cys Ala Ala
    5285                5290                5295

Gly Ala  Ala Ala Cys Cys Cys  Gly Cys Thr Ala Ala  Gly Ala Ala
    5300                5305                5310

Cys Cys  Thr Cys Ala Ala Gly  Ala Thr Gly Cys Cys  Cys Gly Gly
    5315                5320                5325

Cys Gly  Thr Cys Thr Ala Cys  Thr Ala Thr Gly Thr  Gly Gly Ala
    5330                5335                5340

Cys Cys  Ala Cys Ala Gly Ala  Cys Thr Gly Gly Ala  Ala Ala Gly
    5345                5350                5355

Ala Ala  Thr Cys Ala Ala Gly  Gly Ala Gly Gly Cys  Cys Gly Ala
    5360                5365                5370

Cys Ala  Ala Ala Gly Ala Gly  Ala Cys Cys Thr Ala  Cys Gly Thr
    5375                5380                5385

Cys Gly  Ala Gly Cys Ala Gly  Cys Ala Cys Gly Ala  Gly Gly Thr
    5390                5395                5400

Gly Gly  Cys Thr Gly Thr Gly  Gly Cys Cys Ala Gly  Ala Thr Ala
    5405                5410                5415
```

```
Cys Thr Gly Cys Gly Ala Cys Cys Thr Cys Cys Cys Thr Ala Gly
    5420                5425                5430

Cys Ala Ala Ala Cys Thr Gly Gly Gly Gly Cys Ala Cys Ala Ala
    5435                5440                5445

Ala Cys Thr Thr Ala Ala Thr Thr Cys Cys Gly Gly Ala Cys Thr
    5450                5455                5460

Cys Ala Gly Ala Thr Cys Thr Gly Ala Thr Ala Thr Cys Gly Gly
    5465                5470                5475

Gly Cys Cys Cys Thr Cys Thr Ala Gly Ala Gly Cys Cys Ala Cys
    5480                5485                5490

Cys Ala Thr Gly Gly Cys Thr Thr Cys Cys Ala Ala Gly Gly Thr
    5495                5500                5505

Gly Thr Ala Cys Gly Ala Cys Cys Cys Cys Gly Ala Gly Cys Ala
    5510                5515                5520

Ala Cys Gly Cys Ala Ala Ala Cys Gly Cys Ala Thr Gly Ala Thr
    5525                5530                5535

Cys Ala Cys Thr Gly Gly Gly Cys Cys Thr Cys Ala Gly Thr Gly
    5540                5545                5550

Gly Thr Gly Gly Gly Cys Thr Cys Gly Cys Thr Gly Cys Ala Ala
    5555                5560                5565

Gly Cys Ala Ala Ala Thr Gly Ala Ala Cys Gly Thr Gly Cys Thr
    5570                5575                5580

Gly Gly Ala Cys Thr Cys Cys Thr Thr Cys Ala Thr Cys Ala Ala
    5585                5590                5595

Cys Thr Ala Cys Thr Ala Thr Gly Ala Thr Thr Cys Cys Gly Ala
    5600                5605                5610

Gly Ala Ala Gly Cys Ala Cys Gly Cys Cys Gly Ala Gly Ala Ala
    5615                5620                5625

Cys Gly Cys Cys Gly Thr Gly Ala Thr Thr Thr Thr Thr Cys Thr
    5630                5635                5640

Gly Cys Ala Thr Gly Gly Thr Ala Ala Cys Gly Cys Thr Ala Cys
    5645                5650                5655

Cys Thr Cys Cys Ala Gly Cys Thr Ala Cys Cys Thr Gly Thr Gly
    5660                5665                5670

Gly Ala Gly Gly Cys Ala Cys Gly Thr Cys Gly Thr Gly Cys Cys
    5675                5680                5685

Thr Cys Ala Cys Ala Thr Cys Gly Ala Gly Cys Cys Cys Gly Thr
    5690                5695                5700

Gly Gly Cys Thr Ala Gly Ala Thr Gly Cys Ala Thr Cys Ala Thr
    5705                5710                5715

Cys Cys Cys Thr Gly Ala Thr Cys Thr Gly Ala Thr Cys Gly Gly
    5720                5725                5730

Ala Ala Thr Gly Gly Gly Thr Ala Ala Gly Thr Cys Cys Gly Gly
    5735                5740                5745

Cys Ala Ala Gly Ala Gly Cys Gly Gly Gly Ala Ala Thr Gly Gly
    5750                5755                5760

Cys Thr Cys Ala Thr Ala Thr Cys Gly Cys Cys Thr Cys Cys Thr
    5765                5770                5775

Gly Gly Ala Thr Cys Ala Cys Thr Ala Cys Ala Ala Gly Thr Ala
    5780                5785                5790

Cys Cys Thr Cys Ala Cys Cys Gly Cys Thr Thr Gly Gly Thr Thr
    5795                5800                5805
```

Cys Gly Ala Gly Cys Thr Gly Cys Thr Gly Ala Ala Cys Cys Thr
5810 5815 5820

Thr Cys Cys Ala Ala Ala Gly Ala Ala Ala Ala Thr Cys Ala Thr
5825 5830 5835

Cys Thr Thr Thr Gly Thr Gly Gly Gly Cys Cys Ala Cys Gly Ala
5840 5845 5850

Cys Thr Gly Gly Gly Gly Gly Ala Gly Cys Gly Cys Thr Cys Thr
5855 5860 5865

Gly Gly Cys Cys Thr Thr Thr Cys Ala Cys Thr Ala Cys Gly Cys
5870 5875 5880

Cys Thr Ala Cys Gly Ala Gly Cys Ala Cys Cys Ala Ala Gly Ala
5885 5890 5895

Cys Ala Gly Gly Ala Thr Cys Ala Ala Gly Gly Cys Cys Ala Thr
5900 5905 5910

Cys Gly Thr Cys Cys Ala Thr Ala Thr Gly Gly Ala Gly Ala Gly
5915 5920 5925

Thr Gly Thr Cys Gly Thr Gly Gly Ala Cys Gly Thr Gly Ala Thr
5930 5935 5940

Cys Gly Ala Gly Thr Cys Cys Thr Gly Gly Ala Thr Gly Gly Gly
5945 5950 5955

Gly Thr Gly Gly Cys Cys Thr Gly Ala Cys Ala Thr Cys Gly Ala
5960 5965 5970

Gly Gly Ala Gly Gly Ala Gly Cys Thr Gly Gly Cys Cys Cys Thr
5975 5980 5985

Gly Ala Thr Cys Ala Ala Gly Ala Gly Cys Gly Ala Ala Gly Ala
5990 5995 6000

Gly Gly Gly Cys Gly Ala Gly Ala Ala Ala Ala Thr Gly Gly Thr
6005 6010 6015

Gly Cys Thr Thr Gly Ala Gly Ala Ala Thr Ala Ala Cys Thr Thr
6020 6025 6030

Cys Thr Thr Cys Gly Thr Cys Gly Ala Gly Ala Cys Cys Cys Thr
6035 6040 6045

Gly Thr Thr Gly Cys Cys Ala Ala Gly Cys Ala Ala Gly Ala Thr
6050 6055 6060

Cys Ala Thr Gly Cys Gly Gly Ala Ala Ala Cys Thr Gly Gly Ala
6065 6070 6075

Gly Cys Cys Thr Gly Ala Gly Gly Ala Gly Thr Thr Cys Gly Cys
6080 6085 6090

Thr Gly Cys Cys Thr Ala Cys Cys Thr Gly Gly Ala Gly Cys Cys
6095 6100 6105

Ala Thr Thr Cys Ala Ala Gly Gly Ala Gly Ala Ala Gly Gly Gly
6110 6115 6120

Cys Gly Ala Gly Gly Thr Thr Ala Gly Ala Cys Gly Gly Cys Cys
6125 6130 6135

Thr Ala Cys Cys Cys Thr Cys Thr Cys Cys Thr Gly Gly Cys Cys
6140 6145 6150

Thr Cys Gly Cys Gly Ala Gly Ala Thr Cys Cys Cys Thr Cys Thr
6155 6160 6165

Cys Gly Thr Thr Ala Ala Gly Gly Gly Ala Gly Gly Cys Ala Ala
6170 6175 6180

Gly Cys Cys Cys Gly Ala Cys Gly Thr Cys Gly Thr Cys Cys Ala
6185 6190 6195

Gly Ala Thr Thr Gly Thr Cys Cys Gly Cys Ala Ala Cys Thr Ala

-continued

```
    6200                6205                6210

Cys Ala  Ala Cys Gly Cys Cys  Thr Ala Cys Cys Thr  Thr Cys Gly
    6215                6220                6225

Gly Gly  Cys Cys Ala Gly Cys  Gly Ala Cys Gly Ala  Thr Cys Thr
    6230                6235                6240

Gly Cys  Cys Thr Ala Ala Gly  Cys Thr Gly Thr Thr  Cys Ala Thr
    6245                6250                6255

Cys Gly  Ala Gly Thr Cys Cys  Gly Ala Cys Cys Cys  Thr Gly Gly
    6260                6265                6270

Gly Thr  Thr Cys Thr Thr Thr  Thr Cys Cys Ala Ala  Cys Gly Cys
    6275                6280                6285

Thr Ala  Thr Thr Gly Thr Cys  Gly Ala Gly Gly Gly  Ala Gly Cys
    6290                6295                6300

Thr Ala  Ala Gly Ala Ala Gly  Thr Thr Cys Cys Cys  Thr Ala Ala
    6305                6310                6315

Cys Ala  Cys Cys Gly Ala Gly  Thr Thr Cys Gly Thr  Gly Ala Ala
    6320                6325                6330

Gly Gly  Thr Gly Ala Ala Gly  Gly Gly Cys Cys Thr  Cys Cys Ala
    6335                6340                6345

Cys Thr  Thr Cys Cys Thr Cys  Cys Ala Gly Gly Ala  Gly Gly Ala
    6350                6355                6360

Cys Gly  Cys Thr Cys Cys Ala  Gly Ala Thr Gly Ala  Ala Ala Thr
    6365                6370                6375

Gly Gly  Gly Thr Ala Ala Gly  Thr Ala Cys Ala Thr  Cys Ala Ala
    6380                6385                6390

Gly Ala  Gly Cys Thr Thr Cys  Gly Thr Gly Gly Ala  Gly Cys Gly
    6395                6400                6405

Cys Gly  Thr Gly Cys Thr Gly  Ala Ala Gly Ala Ala  Cys Gly Ala
    6410                6415                6420

Gly Cys  Ala Gly Thr Ala Ala  Gly Ala Ala Thr Thr  Cys Gly Ala
    6425                6430                6435

Thr Ala  Thr Cys Ala Ala Gly  Cys Thr Thr Ala Thr  Cys Gly Ala
    6440                6445                6450

Thr Ala  Ala Thr Cys Ala Ala  Cys Cys Thr Cys Thr  Gly Gly Ala
    6455                6460                6465

Thr Thr  Ala Cys Ala Ala Ala  Ala Thr Thr Thr Gly  Thr Gly Ala
    6470                6475                6480

Ala Ala  Gly Ala Thr Thr Gly  Ala Cys Thr Gly Gly  Thr Ala Thr
    6485                6490                6495

Thr Cys  Thr Thr Ala Ala Cys  Thr Ala Thr Gly Thr  Thr Gly Cys
    6500                6505                6510

Thr Cys  Cys Thr Thr Thr Thr  Ala Cys Gly Cys Thr  Ala Thr Gly
    6515                6520                6525

Thr Gly  Gly Ala Thr Ala Cys  Gly Cys Thr Gly Cys  Thr Thr Thr
    6530                6535                6540

Ala Ala  Thr Gly Cys Cys Thr  Thr Thr Gly Thr Ala  Thr Cys Ala
    6545                6550                6555

Thr Gly  Cys Thr Ala Thr Thr  Gly Cys Thr Thr Cys  Cys Cys Gly
    6560                6565                6570

Thr Ala  Thr Gly Gly Cys Thr  Thr Thr Cys Ala Thr  Thr Thr Thr
    6575                6580                6585

Cys Thr  Cys Cys Thr Cys Cys  Thr Thr Gly Thr Ala  Thr Ala Ala
    6590                6595                6600
```

-continued

```
Ala Thr Cys Cys Thr Gly Gly Thr Thr Gly Cys Thr Gly Thr Cys
    6605                6610                6615

Thr Cys Thr Thr Thr Ala Thr Gly Ala Gly Gly Ala Gly Thr Thr
    6620                6625                6630

Gly Thr Gly Gly Cys Cys Cys Gly Thr Thr Gly Thr Cys Ala Gly
    6635                6640                6645

Gly Cys Ala Ala Cys Gly Thr Gly Gly Cys Gly Thr Gly Gly Thr
    6650                6655                6660

Gly Thr Gly Cys Ala Cys Thr Gly Thr Gly Thr Thr Thr Gly Cys
    6665                6670                6675

Thr Gly Ala Cys Gly Cys Ala Ala Cys Cys Cys Cys Cys Ala Cys
    6680                6685                6690

Thr Gly Gly Thr Thr Gly Gly Gly Gly Cys Ala Thr Thr Gly Cys
    6695                6700                6705

Cys Ala Cys Cys Ala Cys Cys Thr Gly Thr Cys Ala Gly Cys Thr
    6710                6715                6720

Cys Cys Thr Thr Thr Cys Cys Gly Gly Gly Ala Cys Thr Thr Thr
    6725                6730                6735

Cys Gly Cys Thr Thr Thr Cys Cys Cys Cys Cys Thr Cys Cys Cys
    6740                6745                6750

Thr Ala Thr Thr Gly Cys Cys Ala Cys Gly Gly Cys Gly Gly Ala
    6755                6760                6765

Ala Cys Thr Cys Ala Thr Cys Gly Cys Cys Gly Cys Cys Thr Gly
    6770                6775                6780

Cys Cys Thr Thr Gly Cys Cys Cys Gly Cys Thr Gly Cys Thr Gly
    6785                6790                6795

Gly Ala Cys Ala Gly Gly Gly Gly Cys Thr Cys Gly Gly Cys Thr
    6800                6805                6810

Gly Thr Thr Gly Gly Gly Cys Ala Cys Thr Gly Ala Cys Ala Ala
    6815                6820                6825

Thr Thr Cys Cys Gly Thr Gly Gly Thr Gly Thr Thr Gly Thr Cys
    6830                6835                6840

Gly Gly Gly Gly Ala Ala Ala Thr Cys Ala Thr Cys Gly Thr Cys
    6845                6850                6855

Cys Thr Thr Thr Cys Cys Thr Thr Gly Gly Cys Thr Gly Cys Thr
    6860                6865                6870

Cys Gly Cys Cys Thr Gly Thr Gly Thr Thr Gly Cys Cys Ala Cys
    6875                6880                6885

Cys Thr Gly Gly Ala Thr Thr Cys Thr Gly Cys Gly Cys Gly Gly
    6890                6895                6900

Gly Ala Cys Gly Thr Cys Cys Thr Thr Cys Thr Gly Cys Thr Ala
    6905                6910                6915

Cys Gly Thr Cys Cys Cys Thr Thr Cys Gly Gly Cys Cys Cys Thr
    6920                6925                6930

Cys Ala Ala Thr Cys Cys Ala Gly Cys Gly Gly Ala Cys Cys Thr
    6935                6940                6945

Thr Cys Cys Thr Thr Cys Cys Cys Gly Cys Gly Gly Cys Cys Thr
    6950                6955                6960

Gly Cys Thr Gly Cys Cys Gly Gly Cys Thr Cys Thr Gly Cys Gly
    6965                6970                6975

Gly Cys Cys Thr Cys Thr Thr Cys Cys Gly Cys Gly Thr Cys Thr
    6980                6985                6990
```

-continued

```
Thr Cys  Gly Cys Cys Thr Thr  Cys Gly Cys Cys Cys  Thr Cys Ala
    6995                 7000                 7005

Gly Ala  Cys Gly Ala Gly Thr  Cys Gly Gly Ala Thr  Cys Thr Cys
    7010                 7015                 7020

Cys Cys  Thr Thr Thr Gly Gly  Gly Cys Cys Gly Cys  Cys Thr Cys
    7025                 7030                 7035

Cys Cys  Cys Gly Cys Ala Thr  Cys Gly Ala Thr Ala  Cys Cys Gly
    7040                 7045                 7050

Thr Cys  Gly Ala Cys Cys Thr  Cys Gly Ala Gly Ala  Cys Cys Thr
    7055                 7060                 7065

Ala Gly  Ala Ala Ala Ala Ala  Cys Ala Thr Gly Gly  Ala Gly Cys
    7070                 7075                 7080

Ala Ala  Thr Cys Ala Cys Ala  Ala Gly Thr Ala Gly  Cys Ala Ala
    7085                 7090                 7095

Thr Ala  Cys Ala Gly Cys Ala  Gly Cys Thr Ala Cys  Cys Ala Ala
    7100                 7105                 7110

Thr Gly  Cys Thr Gly Ala Thr  Thr Gly Thr Gly Cys  Cys Thr Gly
    7115                 7120                 7125

Gly Cys  Thr Ala Gly Ala Ala  Gly Cys Ala Cys Ala  Ala Gly Ala
    7130                 7135                 7140

Gly Gly  Ala Gly Gly Ala Gly  Gly Ala Gly Gly Thr  Gly Gly Gly
    7145                 7150                 7155

Thr Thr  Thr Thr Cys Cys Ala  Gly Thr Cys Ala Cys  Ala Cys Cys
    7160                 7165                 7170

Thr Cys  Ala Gly Gly Thr Ala  Cys Cys Thr Thr Thr  Ala Ala Gly
    7175                 7180                 7185

Ala Cys  Cys Ala Ala Thr Gly  Ala Cys Thr Thr Ala  Cys Ala Ala
    7190                 7195                 7200

Gly Gly  Cys Ala Gly Cys Thr  Gly Thr Ala Gly Ala  Thr Cys Thr
    7205                 7210                 7215

Thr Ala  Gly Cys Cys Ala Cys  Thr Thr Thr Thr Thr  Ala Ala Ala
    7220                 7225                 7230

Ala Gly  Ala Ala Ala Ala Gly  Gly Gly Gly Gly Gly  Ala Cys Thr
    7235                 7240                 7245

Gly Gly  Ala Ala Gly Gly Gly  Cys Thr Ala Ala Thr  Thr Cys Ala
    7250                 7255                 7260

Cys Thr  Cys Cys Cys Ala Ala  Cys Gly Ala Ala Gly  Ala Cys Ala
    7265                 7270                 7275

Ala Gly  Ala Thr Ala Thr Cys  Cys Thr Thr Gly Ala  Thr Cys Thr
    7280                 7285                 7290

Gly Thr  Gly Gly Ala Thr Cys  Thr Ala Cys Cys Ala  Cys Ala Cys
    7295                 7300                 7305

Ala Cys  Ala Ala Gly Gly Cys  Thr Ala Cys Thr Thr  Cys Cys Cys
    7310                 7315                 7320

Thr Gly  Ala Thr Thr Gly Gly  Cys Ala Gly Ala Ala  Cys Thr Ala
    7325                 7330                 7335

Cys Ala  Cys Ala Cys Cys Ala  Gly Gly Gly Cys Cys  Ala Gly Gly
    7340                 7345                 7350

Gly Ala  Thr Cys Ala Gly Ala  Thr Ala Thr Cys Cys  Ala Cys Thr
    7355                 7360                 7365

Gly Ala  Cys Cys Thr Thr Thr  Gly Gly Ala Thr Gly  Gly Thr Gly
    7370                 7375                 7380

Cys Thr  Ala Cys Ala Ala Gly  Cys Thr Ala Gly Thr  Ala Cys Cys
```

-continued

```
    7385                7390                7395

Ala Gly  Thr Thr Gly Ala Gly  Cys Ala Ala Gly Ala  Gly Ala Ala
    7400                7405                7410

Gly Gly  Thr Ala Gly Ala Ala  Gly Ala Ala Gly Cys  Cys Ala Ala
    7415                7420                7425

Thr Gly  Ala Ala Gly Gly Ala  Gly Ala Gly Ala Ala  Cys Ala Cys
    7430                7435                7440

Cys Cys  Gly Cys Thr Thr Gly  Thr Thr Ala Cys Ala  Cys Cys Cys
    7445                7450                7455

Thr Gly  Thr Gly Ala Gly Cys  Cys Thr Gly Cys Ala  Thr Gly Gly
    7460                7465                7470

Gly Ala  Thr Gly Gly Ala Thr  Gly Ala Cys Cys Cys  Gly Gly Ala
    7475                7480                7485

Gly Ala  Gly Ala Gly Ala Ala  Gly Thr Ala Thr Thr  Ala Gly Ala
    7490                7495                7500

Gly Thr  Gly Gly Ala Gly Gly  Thr Thr Thr Gly Ala  Cys Ala Gly
    7505                7510                7515

Cys Cys  Gly Cys Cys Thr Ala  Gly Cys Ala Thr Thr  Thr Cys Ala
    7520                7525                7530

Thr Cys  Ala Cys Ala Thr Gly  Gly Cys Cys Cys Gly  Ala Gly Ala
    7535                7540                7545

Gly Cys  Thr Gly Cys Ala Thr  Cys Cys Gly Gly Ala  Cys Thr Gly
    7550                7555                7560

Thr Ala  Cys Thr Gly Gly Gly  Thr Cys Thr Cys Thr  Cys Thr Gly
    7565                7570                7575

Gly Thr  Thr Ala Gly Ala Cys  Cys Ala Gly Ala Thr  Cys Thr Gly
    7580                7585                7590

Ala Gly  Cys Cys Thr Gly Gly  Gly Ala Gly Cys Thr  Cys Thr Cys
    7595                7600                7605

Thr Gly  Gly Cys Thr Ala Ala  Cys Thr Ala Gly Gly  Gly Ala Ala
    7610                7615                7620

Cys Cys  Cys Ala Cys Thr Gly  Cys Thr Thr Ala Ala  Gly Cys Cys
    7625                7630                7635

Thr Cys  Ala Ala Thr Ala Ala  Ala Gly Cys Thr Thr  Gly Cys Cys
    7640                7645                7650

Thr Thr  Gly Ala Gly Thr Gly  Cys Thr Thr Cys Ala  Ala Gly Thr
    7655                7660                7665

Ala Gly  Thr Gly Thr Gly Thr  Gly Cys Cys Cys Gly  Thr Cys Thr
    7670                7675                7680

Gly Thr  Thr Gly Thr Gly Thr  Gly Ala Cys Thr Cys  Thr Gly Gly
    7685                7690                7695

Thr Ala  Ala Cys Thr Ala Gly  Ala Gly Ala Thr Cys  Cys Cys Thr
    7700                7705                7710

Cys Ala  Gly Ala Cys Cys Cys  Thr Thr Thr Thr Ala  Gly Thr Cys
    7715                7720                7725

Ala Gly  Thr Gly Thr Gly Gly  Ala Ala Ala Ala Thr  Cys Thr Cys
    7730                7735                7740

Thr Ala  Gly Cys Ala Gly Gly  Gly Cys Cys Cys Gly  Thr Thr Thr
    7745                7750                7755

Ala Ala  Ala Cys Cys Cys Gly  Cys Thr Gly Ala Thr  Cys Ala Gly
    7760                7765                7770

Cys Cys  Thr Cys Gly Ala Cys  Thr Gly Thr Gly Cys  Cys Thr Thr
    7775                7780                7785
```

Cys Thr Ala Gly Thr Thr Gly Cys Cys Ala Gly Cys Cys Ala Thr
7790 7795 7800

Cys Thr Gly Thr Thr Gly Thr Thr Thr Gly Cys Cys Cys Cys Thr
7805 7810 7815

Cys Cys Cys Cys Cys Gly Thr Gly Cys Cys Thr Thr Cys Cys Thr
7820 7825 7830

Thr Gly Ala Cys Cys Cys Thr Gly Gly Ala Ala Gly Gly Thr Gly
7835 7840 7845

Cys Cys Ala Cys Thr Cys Cys Cys Ala Cys Thr Gly Thr Cys Cys
7850 7855 7860

Thr Thr Thr Cys Cys Thr Ala Ala Thr Ala Ala Ala Ala Thr Gly
7865 7870 7875

Ala Gly Gly Ala Ala Ala Thr Thr Gly Cys Ala Thr Cys Gly Cys
7880 7885 7890

Ala Thr Thr Gly Thr Cys Thr Gly Ala Gly Thr Ala Gly Gly Thr
7895 7900 7905

Gly Thr Cys Ala Thr Thr Cys Thr Ala Thr Thr Cys Thr Gly Gly
7910 7915 7920

Gly Gly Gly Gly Thr Gly Gly Gly Gly Thr Gly Gly Gly Gly Cys
7925 7930 7935

Ala Gly Gly Ala Cys Ala Gly Cys Ala Ala Gly Gly Gly Gly Gly
7940 7945 7950

Ala Gly Gly Ala Thr Thr Gly Gly Gly Ala Ala Gly Ala Cys Ala
7955 7960 7965

Ala Thr Ala Gly Cys Ala Gly Gly Cys Ala Thr Gly Cys Thr Gly
7970 7975 7980

Gly Gly Gly Ala Thr Gly Cys Gly Gly Thr Gly Gly Gly Cys Thr
7985 7990 7995

Cys Thr Ala Thr Gly Gly Cys Thr Thr Cys Thr Gly Ala Gly Gly
8000 8005 8010

Cys Gly Gly Ala Ala Ala Gly Ala Ala Cys Cys Ala Gly Cys Thr
8015 8020 8025

Gly Gly Gly Gly Cys Thr Cys Thr Ala Gly Gly Gly Gly Gly Thr
8030 8035 8040

Ala Thr Cys Cys Cys Cys Ala Cys Gly Cys Gly Cys Cys Cys Thr
8045 8050 8055

Gly Thr Ala Gly Cys Gly Gly Cys Gly Cys Ala Thr Thr Ala Ala
8060 8065 8070

Gly Cys Gly Cys Gly Gly Cys Gly Gly Gly Thr Gly Thr Gly Gly
8075 8080 8085

Thr Gly Gly Thr Thr Ala Cys Gly Cys Gly Cys Ala Gly Cys Gly
8090 8095 8100

Thr Gly Ala Cys Cys Gly Cys Thr Ala Cys Ala Cys Thr Thr Gly
8105 8110 8115

Cys Cys Ala Gly Cys Gly Cys Cys Cys Thr Ala Gly Cys Gly Cys
8120 8125 8130

Cys Cys Gly Cys Thr Cys Cys Thr Thr Thr Cys Gly Cys Thr Thr
8135 8140 8145

Thr Cys Thr Thr Cys Cys Cys Thr Thr Cys Cys Thr Thr Thr Cys
8150 8155 8160

Thr Cys Gly Cys Cys Ala Cys Gly Thr Thr Cys Gly Cys Cys Gly
8165 8170 8175

Gly Cys Thr Thr Thr Cys Cys Cys Cys Gly Thr Cys Ala Ala Gly
8180 8185 8190

Cys Thr Cys Thr Ala Ala Ala Thr Cys Gly Gly Gly Gly Gly Cys
8195 8200 8205

Thr Cys Cys Cys Thr Thr Thr Ala Gly Gly Gly Thr Thr Cys Cys
8210 8215 8220

Gly Ala Thr Thr Thr Ala Gly Thr Gly Cys Thr Thr Thr Ala Cys
8225 8230 8235

Gly Gly Cys Ala Cys Cys Thr Cys Gly Ala Cys Cys Cys Cys Ala
8240 8245 8250

Ala Ala Ala Ala Ala Cys Thr Thr Gly Ala Thr Thr Ala Gly Gly
8255 8260 8265

Gly Thr Gly Ala Thr Gly Gly Thr Thr Cys Ala Cys Gly Thr Ala
8270 8275 8280

Gly Thr Gly Gly Gly Cys Cys Ala Thr Cys Gly Cys Cys Cys Thr
8285 8290 8295

Gly Ala Thr Ala Gly Ala Cys Gly Gly Thr Thr Thr Thr Thr Cys
8300 8305 8310

Gly Cys Cys Cys Thr Thr Thr Gly Ala Cys Gly Thr Thr Gly Gly
8315 8320 8325

Ala Gly Thr Cys Cys Ala Cys Gly Thr Thr Cys Thr Thr Thr Ala
8330 8335 8340

Ala Thr Ala Gly Thr Gly Gly Ala Cys Thr Cys Thr Thr Gly Thr
8345 8350 8355

Thr Cys Cys Ala Ala Ala Cys Thr Gly Gly Ala Ala Cys Ala Ala
8360 8365 8370

Cys Ala Cys Thr Cys Ala Ala Cys Cys Cys Thr Ala Thr Cys Thr
8375 8380 8385

Cys Gly Gly Thr Cys Thr Ala Thr Thr Cys Thr Thr Thr Thr Gly
8390 8395 8400

Ala Thr Thr Thr Ala Thr Ala Ala Gly Gly Gly Ala Thr Thr Thr
8405 8410 8415

Thr Gly Cys Cys Gly Ala Thr Thr Thr Cys Gly Gly Cys Cys Thr
8420 8425 8430

Ala Thr Thr Gly Gly Thr Thr Ala Ala Ala Ala Ala Ala Thr Gly
8435 8440 8445

Ala Gly Cys Thr Gly Ala Thr Thr Thr Ala Ala Cys Ala Ala Ala
8450 8455 8460

Ala Ala Thr Thr Thr Ala Ala Cys Gly Cys Gly Ala Ala Thr Thr
8465 8470 8475

Ala Ala Thr Thr Cys Thr Gly Thr Gly Gly Ala Ala Thr Gly Thr
8480 8485 8490

Gly Thr Gly Thr Cys Ala Gly Thr Thr Ala Gly Gly Gly Thr Gly
8495 8500 8505

Thr Gly Gly Ala Ala Ala Gly Thr Cys Cys Cys Cys Ala Gly Gly
8510 8515 8520

Cys Thr Cys Cys Cys Cys Ala Gly Cys Ala Gly Gly Cys Ala Gly
8525 8530 8535

Ala Ala Gly Thr Ala Thr Gly Cys Ala Ala Ala Gly Cys Ala Thr
8540 8545 8550

Gly Cys Ala Thr Cys Thr Cys Ala Ala Thr Thr Ala Gly Thr Cys
8555 8560 8565

Ala Gly Cys Ala Ala Cys Cys Ala Gly Gly Thr Gly Thr Gly Gly

```
    8570                8575                8580

Ala Ala  Ala Gly Thr Cys Cys  Cys Cys Ala Gly Gly  Cys Thr Cys
    8585                8590                8595

Cys Cys  Cys Ala Gly Cys Ala  Gly Gly Cys Ala Gly  Ala Ala Gly
    8600                8605                8610

Thr Ala  Thr Gly Cys Ala Ala  Ala Gly Cys Ala Thr  Gly Cys Ala
    8615                8620                8625

Thr Cys  Thr Cys Ala Ala Thr  Thr Ala Gly Thr Cys  Ala Gly Cys
    8630                8635                8640

Ala Ala  Cys Cys Ala Thr Ala  Gly Thr Cys Cys Cys  Gly Cys Cys
    8645                8650                8655

Cys Cys  Thr Ala Ala Cys Thr  Cys Cys Gly Cys Cys  Cys Ala Thr
    8660                8665                8670

Cys Cys  Cys Gly Cys Cys Cys  Cys Thr Ala Ala Cys  Thr Cys Cys
    8675                8680                8685

Gly Cys  Cys Cys Ala Gly Thr  Thr Cys Cys Gly Cys  Cys Cys Ala
    8690                8695                8700

Thr Thr  Cys Thr Cys Cys Gly  Cys Cys Cys Cys Ala  Thr Gly Gly
    8705                8710                8715

Cys Thr  Gly Ala Cys Thr Ala  Ala Thr Thr Thr Thr  Thr Thr Thr
    8720                8725                8730

Thr Ala  Thr Thr Thr Ala Thr  Gly Cys Ala Gly Ala  Gly Gly Cys
    8735                8740                8745

Cys Gly  Ala Gly Gly Cys Cys  Gly Cys Cys Thr Cys  Thr Gly Cys
    8750                8755                8760

Cys Thr  Cys Thr Gly Ala Gly  Cys Thr Ala Thr Thr  Cys Cys Ala
    8765                8770                8775

Gly Ala  Ala Gly Thr Ala Gly  Thr Gly Ala Gly Gly  Ala Gly Gly
    8780                8785                8790

Cys Thr  Thr Thr Thr Thr Thr  Gly Gly Ala Gly Gly  Cys Cys Thr
    8795                8800                8805

Ala Gly  Gly Cys Thr Thr Thr  Thr Gly Cys Ala Ala  Ala Ala Ala
    8810                8815                8820

Gly Cys  Thr Cys Cys Cys Gly  Gly Gly Ala Gly Cys  Thr Thr Gly
    8825                8830                8835

Thr Ala  Thr Ala Thr Cys Cys  Ala Thr Thr Thr Thr  Cys Gly Gly
    8840                8845                8850

Ala Thr  Cys Thr Gly Ala Thr  Cys Ala Gly Cys Ala  Cys Gly Thr
    8855                8860                8865

Gly Thr  Thr Gly Ala Cys Ala  Ala Thr Thr Ala Ala  Thr Cys Ala
    8870                8875                8880

Thr Cys  Gly Gly Cys Ala Thr  Ala Gly Thr Ala Thr  Ala Thr Cys
    8885                8890                8895

Gly Gly  Cys Ala Thr Ala Gly  Thr Ala Thr Ala Ala  Thr Ala Cys
    8900                8905                8910

Gly Ala  Cys Ala Ala Gly Gly  Thr Gly Ala Gly Gly  Ala Ala Cys
    8915                8920                8925

Thr Ala  Ala Ala Cys Cys Ala  Thr Gly Gly Cys Cys  Ala Ala Gly
    8930                8935                8940

Thr Thr  Gly Ala Cys Cys Ala  Gly Thr Gly Cys Cys  Gly Thr Thr
    8945                8950                8955

Cys Cys  Gly Gly Thr Gly Cys  Thr Cys Ala Cys Cys  Gly Cys Gly
    8960                8965                8970
```

Cys Gly Cys Gly Ala Cys Gly Thr Cys Gly Cys Cys Gly Gly Ala
8975 8980 8985

Gly Cys Gly Gly Thr Cys Gly Ala Gly Thr Thr Cys Thr Gly Gly
8990 8995 9000

Ala Cys Cys Gly Ala Cys Cys Gly Gly Cys Thr Cys Gly Gly Gly
9005 9010 9015

Thr Thr Cys Thr Cys Cys Cys Gly Gly Gly Ala Cys Thr Thr Cys
9020 9025 9030

Gly Thr Gly Gly Ala Gly Gly Ala Cys Gly Ala Cys Thr Thr Cys
9035 9040 9045

Gly Cys Cys Gly Gly Thr Gly Thr Gly Gly Thr Cys Cys Gly Gly
9050 9055 9060

Gly Ala Cys Gly Ala Cys Gly Thr Gly Ala Cys Cys Cys Thr Gly
9065 9070 9075

Thr Thr Cys Ala Thr Cys Ala Gly Cys Gly Cys Gly Gly Thr Cys
9080 9085 9090

Cys Ala Gly Gly Ala Cys Cys Ala Gly Gly Thr Gly Gly Thr Gly
9095 9100 9105

Cys Cys Gly Gly Ala Cys Ala Ala Cys Ala Cys Cys Cys Thr Gly
9110 9115 9120

Gly Cys Cys Thr Gly Gly Gly Thr Gly Thr Gly Gly Gly Thr Gly
9125 9130 9135

Cys Gly Cys Gly Gly Cys Cys Thr Gly Gly Ala Cys Gly Ala Gly
9140 9145 9150

Cys Thr Gly Thr Ala Cys Gly Cys Cys Gly Ala Gly Thr Gly Gly
9155 9160 9165

Thr Cys Gly Gly Ala Gly Gly Thr Cys Gly Thr Gly Thr Cys Cys
9170 9175 9180

Ala Cys Gly Ala Ala Cys Thr Thr Cys Cys Gly Gly Gly Ala Cys
9185 9190 9195

Gly Cys Cys Thr Cys Cys Gly Gly Gly Cys Cys Gly Gly Cys Cys
9200 9205 9210

Ala Thr Gly Ala Cys Cys Gly Ala Gly Ala Thr Cys Gly Gly Cys
9215 9220 9225

Gly Ala Gly Cys Ala Gly Cys Cys Gly Thr Gly Gly Gly Gly Gly
9230 9235 9240

Cys Gly Gly Gly Ala Gly Thr Thr Cys Gly Cys Cys Cys Thr Gly
9245 9250 9255

Cys Gly Cys Gly Ala Cys Cys Cys Gly Gly Cys Cys Gly Gly Cys
9260 9265 9270

Ala Ala Cys Thr Gly Cys Gly Thr Gly Cys Ala Cys Thr Thr Cys
9275 9280 9285

Gly Thr Gly Gly Cys Cys Gly Ala Gly Gly Ala Gly Cys Ala Gly
9290 9295 9300

Gly Ala Cys Thr Gly Ala Cys Ala Cys Gly Thr Gly Cys Thr Ala
9305 9310 9315

Cys Gly Ala Gly Ala Thr Thr Thr Cys Gly Ala Thr Thr Cys Cys
9320 9325 9330

Ala Cys Cys Gly Cys Cys Gly Cys Cys Thr Thr Cys Thr Ala Thr
9335 9340 9345

Gly Ala Ala Ala Gly Gly Thr Thr Gly Gly Gly Cys Thr Thr Cys
9350 9355 9360

Gly Gly Ala Ala Thr Cys Gly Thr Thr Thr Thr Cys Cys Gly Gly
9365 9370 9375

Gly Ala Cys Gly Cys Cys Gly Gly Cys Thr Gly Gly Ala Thr Gly
9380 9385 9390

Ala Thr Cys Cys Thr Cys Cys Ala Gly Cys Gly Cys Gly Gly Gly
9395 9400 9405

Gly Ala Thr Cys Thr Cys Ala Thr Gly Cys Thr Gly Gly Ala Gly
9410 9415 9420

Thr Thr Cys Thr Thr Cys Gly Cys Cys Cys Ala Cys Cys Cys Cys
9425 9430 9435

Ala Ala Cys Thr Thr Gly Thr Thr Thr Ala Thr Thr Gly Cys Ala
9440 9445 9450

Gly Cys Thr Thr Ala Thr Ala Ala Thr Gly Gly Thr Thr Ala Cys
9455 9460 9465

Ala Ala Ala Thr Ala Ala Ala Gly Cys Ala Ala Thr Ala Gly Cys
9470 9475 9480

Ala Thr Cys Ala Cys Ala Ala Ala Thr Thr Thr Cys Ala Cys Ala
9485 9490 9495

Ala Ala Thr Ala Ala Ala Gly Cys Ala Thr Thr Thr Thr Thr Thr
9500 9505 9510

Thr Cys Ala Cys Thr Gly Cys Ala Thr Thr Cys Thr Ala Gly Thr
9515 9520 9525

Thr Gly Thr Gly Gly Thr Thr Thr Gly Thr Cys Cys Ala Ala Ala
9530 9535 9540

Cys Thr Cys Ala Thr Cys Ala Ala Thr Gly Thr Ala Thr Cys Thr
9545 9550 9555

Thr Ala Thr Cys Ala Thr Gly Thr Cys Thr Gly Thr Ala Thr Ala
9560 9565 9570

Cys Cys Gly Thr Cys Gly Ala Cys Cys Thr Cys Thr Ala Gly Cys
9575 9580 9585

Thr Ala Gly Ala Gly Cys Thr Thr Gly Gly Cys Gly Thr Ala Ala
9590 9595 9600

Thr Cys Ala Thr Gly Gly Thr Cys Ala Thr Ala Gly Cys Thr Gly
9605 9610 9615

Thr Thr Thr Cys Cys Thr Gly Thr Gly Thr Gly Ala Ala Ala Thr
9620 9625 9630

Thr Gly Thr Thr Ala Thr Cys Cys Gly Cys Thr Cys Ala Cys Ala
9635 9640 9645

Ala Thr Thr Cys Cys Ala Cys Ala Cys Ala Ala Cys Ala Thr Ala
9650 9655 9660

Cys Gly Ala Gly Cys Cys Gly Gly Ala Ala Gly Cys Ala Thr Ala
9665 9670 9675

Ala Ala Gly Thr Gly Thr Ala Ala Ala Gly Cys Cys Thr Gly Gly
9680 9685 9690

Gly Gly Thr Gly Cys Cys Thr Ala Ala Thr Gly Ala Gly Thr Gly
9695 9700 9705

Ala Gly Cys Thr Ala Ala Cys Thr Cys Ala Cys Ala Thr Thr Ala
9710 9715 9720

Ala Thr Thr Gly Cys Gly Thr Thr Gly Cys Gly Cys Thr Cys Ala
9725 9730 9735

Cys Thr Gly Cys Cys Cys Gly Cys Thr Thr Thr Cys Cys Ala Gly
9740 9745 9750

Thr Cys Gly Gly Gly Ala Ala Ala Cys Cys Thr Gly Thr Cys Gly

```
    9755                9760                9765

Thr Gly  Cys Cys Ala Gly Cys  Thr Gly Cys Ala Thr  Thr Ala Ala
    9770                9775                9780

Thr Gly  Ala Ala Thr Cys Gly  Gly Cys Cys Ala Ala  Cys Gly Cys
    9785                9790                9795

Gly Cys  Gly Gly Gly Gly Ala  Gly Ala Gly Gly Cys  Gly Gly Thr
    9800                9805                9810

Thr Thr  Gly Cys Gly Thr Ala  Thr Thr Gly Gly Gly  Cys Gly Cys
    9815                9820                9825

Thr Cys  Thr Thr Cys Cys Gly  Cys Thr Thr Cys Cys  Thr Cys Gly
    9830                9835                9840

Cys Thr  Cys Ala Cys Thr Gly  Ala Cys Thr Cys Gly  Cys Thr Gly
    9845                9850                9855

Cys Gly  Cys Thr Cys Gly Gly  Thr Cys Gly Thr Thr  Cys Gly Gly
    9860                9865                9870

Cys Thr  Gly Cys Gly Gly Cys  Gly Ala Gly Cys Gly  Gly Thr Ala
    9875                9880                9885

Thr Cys  Ala Gly Cys Thr Cys  Ala Cys Thr Cys Ala  Ala Ala Gly
    9890                9895                9900

Gly Cys  Gly Gly Thr Ala Ala  Thr Ala Cys Gly Gly  Thr Thr Ala
    9905                9910                9915

Thr Cys  Cys Ala Cys Ala Gly  Ala Ala Thr Cys Ala  Gly Gly Gly
    9920                9925                9930

Gly Ala  Thr Ala Ala Cys Gly  Cys Ala Gly Gly Ala  Ala Ala Gly
    9935                9940                9945

Ala Ala  Cys Ala Thr Gly Thr  Gly Ala Gly Cys Ala  Ala Ala Ala
    9950                9955                9960

Gly Gly  Cys Cys Ala Gly Cys  Ala Ala Ala Ala Gly  Gly Cys Cys
    9965                9970                9975

Ala Gly  Gly Ala Ala Cys Cys  Gly Thr Ala Ala Ala  Ala Ala Gly
    9980                9985                9990

Gly Cys  Cys Gly Cys Gly Thr  Thr Gly Cys Thr Gly  Gly Cys Gly
    9995                10000               10005

Thr Thr  Thr Thr Thr Cys Cys  Ala Thr Ala Gly Gly  Cys Thr Cys
    10010               10015               10020

Cys Gly  Cys Cys Cys Cys Cys  Cys Thr Gly Ala Cys  Gly Ala Gly
    10025               10030               10035

Cys Ala  Thr Cys Ala Cys Ala  Ala Ala Ala Ala Thr  Cys Gly Ala
    10040               10045               10050

Cys Gly  Cys Thr Cys Ala Ala  Gly Thr Cys Ala Gly  Ala Gly Gly
    10055               10060               10065

Thr Gly  Gly Cys Gly Ala Ala  Ala Cys Cys Cys Gly  Ala Cys Ala
    10070               10075               10080

Gly Gly  Ala Cys Thr Ala Thr  Ala Ala Ala Gly Ala  Thr Ala Cys
    10085               10090               10095

Cys Ala  Gly Gly Cys Gly Thr  Thr Thr Cys Cys Cys  Cys Cys Thr
    10100               10105               10110

Gly Gly  Ala Ala Gly Cys Thr  Cys Cys Cys Thr Cys  Gly Thr Gly
    10115               10120               10125

Cys Gly  Cys Thr Cys Thr Cys  Cys Thr Gly Thr Thr  Cys Cys Gly
    10130               10135               10140

Ala Cys  Cys Cys Thr Gly Cys  Cys Gly Cys Thr Thr  Ala Cys Cys
    10145               10150               10155
```

```
Gly Gly  Ala Thr Ala Cys Cys  Thr Gly Thr Cys Cys  Gly Cys Cys
    10160                10165                10170

Thr Thr  Thr Cys Thr Cys Cys  Cys Thr Thr Cys Gly  Gly Gly Ala
    10175                10180                10185

Ala Gly  Cys Gly Thr Gly Gly  Cys Gly Cys Thr Thr  Thr Cys Thr
    10190                10195                10200

Cys Ala  Thr Ala Gly Cys Thr  Cys Ala Cys Gly Cys  Thr Gly Thr
    10205                10210                10215

Ala Gly  Gly Thr Ala Thr Cys  Thr Cys Ala Gly Thr  Thr Cys Gly
    10220                10225                10230

Gly Thr  Gly Thr Ala Gly Gly  Thr Cys Gly Thr Thr  Cys Gly Cys
    10235                10240                10245

Thr Cys  Cys Ala Ala Gly Cys  Thr Gly Gly Gly Cys  Thr Gly Thr
    10250                10255                10260

Gly Thr  Gly Cys Ala Cys Gly  Ala Ala Cys Cys Cys  Cys Cys Cys
    10265                10270                10275

Gly Thr  Thr Cys Ala Gly Cys  Cys Cys Gly Ala Cys  Cys Gly Cys
    10280                10285                10290

Thr Gly  Cys Gly Cys Cys Thr  Thr Ala Thr Cys Cys  Gly Gly Thr
    10295                10300                10305

Ala Ala  Cys Thr Ala Thr Cys  Gly Thr Cys Thr Thr  Gly Ala Gly
    10310                10315                10320

Thr Cys  Cys Ala Ala Cys Cys  Cys Gly Gly Thr Ala  Ala Gly Ala
    10325                10330                10335

Cys Ala  Cys Gly Ala Cys Thr  Thr Ala Thr Cys Gly  Cys Cys Ala
    10340                10345                10350

Cys Thr  Gly Gly Cys Ala Gly  Cys Ala Gly Cys Cys  Ala Cys Thr
    10355                10360                10365

Gly Gly  Thr Ala Ala Cys Ala  Gly Gly Ala Thr Thr  Ala Gly Cys
    10370                10375                10380

Ala Gly  Ala Gly Cys Gly Ala  Gly Gly Thr Ala Thr  Gly Thr Ala
    10385                10390                10395

Gly Gly  Cys Gly Gly Thr Gly  Cys Thr Ala Cys Ala  Gly Ala Gly
    10400                10405                10410

Thr Thr  Cys Thr Thr Gly Ala  Ala Gly Thr Gly Gly  Thr Gly Gly
    10415                10420                10425

Cys Cys  Thr Ala Ala Cys Thr  Ala Cys Gly Gly Cys  Thr Ala Cys
    10430                10435                10440

Ala Cys  Thr Ala Gly Ala Ala  Gly Ala Ala Cys Ala  Gly Thr Ala
    10445                10450                10455

Thr Thr  Thr Gly Gly Thr Ala  Thr Cys Thr Gly Cys  Gly Cys Thr
    10460                10465                10470

Cys Thr  Gly Cys Thr Gly Ala  Ala Gly Cys Cys Ala  Gly Thr Thr
    10475                10480                10485

Ala Cys  Cys Thr Thr Cys Gly  Gly Ala Ala Ala Ala  Ala Gly Ala
    10490                10495                10500

Gly Thr  Thr Gly Gly Thr Ala  Gly Cys Thr Cys Thr  Thr Gly Ala
    10505                10510                10515

Thr Cys  Cys Gly Gly Cys Ala  Ala Ala Cys Ala Ala  Ala Cys Cys
    10520                10525                10530

Ala Cys  Cys Gly Cys Thr Gly  Gly Thr Ala Gly Cys  Gly Gly Thr
    10535                10540                10545
```

-continued

Gly Gly Thr Thr Thr Thr Thr Thr Thr Gly Thr Thr Thr Gly Cys
10550 10555 10560

Ala Ala Gly Cys Ala Gly Cys Ala Gly Ala Thr Thr Ala Cys Gly
10565 10570 10575

Cys Gly Cys Ala Gly Ala Ala Ala Ala Ala Ala Ala Gly Gly Ala
10580 10585 10590

Thr Cys Thr Cys Ala Ala Gly Ala Ala Gly Ala Thr Cys Cys Thr
10595 10600 10605

Thr Thr Gly Ala Thr Cys Thr Thr Thr Thr Cys Thr Ala Cys Gly
10610 10615 10620

Gly Gly Gly Thr Cys Thr Gly Ala Cys Gly Cys Thr Cys Ala Gly
10625 10630 10635

Thr Gly Gly Ala Ala Cys Gly Ala Ala Ala Ala Cys Thr Cys Ala
10640 10645 10650

Cys Gly Thr Thr Ala Ala Gly Gly Gly Ala Thr Thr Thr Thr Gly
10655 10660 10665

Gly Thr Cys Ala Thr Gly Ala Gly Ala Thr Thr Ala Thr Cys Ala
10670 10675 10680

Ala Ala Ala Ala Gly Gly Ala Thr Cys Thr Thr Cys Ala Cys Cys
10685 10690 10695

Thr Ala Gly Ala Thr Cys Cys Thr Thr Thr Thr Ala Ala Ala Thr
10700 10705 10710

Thr Ala Ala Ala Ala Ala Thr Gly Ala Ala Gly Thr Thr Thr Thr
10715 10720 10725

Ala Ala Ala Thr Cys Ala Ala Thr Cys Thr Ala Ala Ala Gly Thr
10730 10735 10740

Ala Thr Ala Thr Ala Thr Gly Ala Gly Thr Ala Ala Ala Cys Thr
10745 10750 10755

Thr Gly Gly Thr Cys Thr Gly Ala Cys Ala Gly Thr Thr Ala Cys
10760 10765 10770

Cys Ala Ala Thr Gly Cys Thr Thr Ala Ala Thr Cys Ala Gly Thr
10775 10780 10785

Gly Ala Gly Gly Cys Ala Cys Cys Thr Ala Thr Cys Thr Cys Ala
10790 10795 10800

Gly Cys Gly Ala Thr Cys Thr Gly Thr Cys Thr Ala Thr Thr Thr
10805 10810 10815

Cys Gly Thr Thr Cys Ala Thr Cys Cys Ala Thr Ala Gly Thr Thr
10820 10825 10830

Gly Cys Cys Thr Gly Ala Cys Thr Cys Cys Cys Cys Gly Thr Cys
10835 10840 10845

Gly Thr Gly Thr Ala Gly Ala Thr Ala Ala Cys Thr Ala Cys Gly
10850 10855 10860

Ala Thr Ala Cys Gly Gly Gly Ala Gly Gly Gly Cys Thr Thr Ala
10865 10870 10875

Cys Cys Ala Thr Cys Thr Gly Gly Cys Cys Cys Cys Ala Gly Thr
10880 10885 10890

Gly Cys Thr Gly Cys Ala Ala Thr Gly Ala Thr Ala Cys Cys Gly
10895 10900 10905

Cys Gly Ala Gly Ala Cys Cys Cys Ala Cys Gly Cys Thr Cys Ala
10910 10915 10920

Cys Cys Gly Gly Cys Thr Cys Cys Ala Gly Ala Thr Thr Thr Ala
10925 10930 10935

Thr Cys Ala Gly Cys Ala Ala Thr Ala Ala Ala Cys Cys Ala Gly

```
    10940               10945               10950

Cys Cys  Ala Gly Cys Cys Gly  Gly Ala Ala Gly Gly  Gly Cys Cys
    10955               10960               10965

Gly Ala  Gly Cys Gly Cys Ala  Gly Ala Ala Gly Thr  Gly Gly Thr
    10970               10975               10980

Cys Cys  Thr Gly Cys Ala Ala  Cys Thr Thr Thr Ala  Thr Cys Cys
    10985               10990               10995

Gly Cys  Cys Thr Cys Cys Ala  Thr Cys Cys Ala Gly  Thr Cys Thr
    11000               11005               11010

Ala Thr  Thr Ala Ala Thr Thr  Gly Thr Thr Gly Cys  Cys Gly Gly
    11015               11020               11025

Gly Ala  Ala Gly Cys Thr Ala  Gly Ala Gly Thr Ala  Ala Gly Thr
    11030               11035               11040

Ala Gly  Thr Thr Cys Gly Cys  Cys Ala Gly Thr Thr  Ala Ala Thr
    11045               11050               11055

Ala Gly  Thr Thr Thr Gly Cys  Gly Cys Ala Ala Cys  Gly Thr Thr
    11060               11065               11070

Gly Thr  Thr Gly Cys Cys Ala  Thr Thr Gly Cys Thr  Ala Cys Ala
    11075               11080               11085

Gly Gly  Cys Ala Thr Cys Gly  Thr Gly Gly Thr Gly  Thr Cys Ala
    11090               11095               11100

Cys Gly  Cys Thr Cys Gly Thr  Cys Gly Thr Thr Thr  Gly Gly Thr
    11105               11110               11115

Ala Thr  Gly Gly Cys Thr Thr  Cys Ala Thr Thr Cys  Ala Gly Cys
    11120               11125               11130

Thr Cys  Cys Gly Gly Thr Thr  Cys Cys Cys Ala Ala  Cys Gly Ala
    11135               11140               11145

Thr Cys  Ala Ala Gly Gly Cys  Gly Ala Gly Thr Thr  Ala Cys Ala
    11150               11155               11160

Thr Gly  Ala Thr Cys Cys Cys  Cys Cys Ala Thr Gly  Thr Thr Gly
    11165               11170               11175

Thr Gly  Cys Ala Ala Ala Ala  Ala Ala Gly Cys Gly  Gly Thr Thr
    11180               11185               11190

Ala Gly  Cys Thr Cys Cys Thr  Thr Cys Gly Gly Thr  Cys Cys Thr
    11195               11200               11205

Cys Cys  Gly Ala Thr Cys Gly  Thr Thr Gly Thr Cys  Ala Gly Ala
    11210               11215               11220

Ala Gly  Thr Ala Ala Gly Thr  Thr Gly Gly Cys Cys  Gly Cys Ala
    11225               11230               11235

Gly Thr  Gly Thr Thr Ala Thr  Cys Ala Cys Thr Cys  Ala Thr Gly
    11240               11245               11250

Gly Thr  Thr Ala Thr Gly Gly  Cys Ala Gly Cys Ala  Cys Thr Gly
    11255               11260               11265

Cys Ala  Thr Ala Ala Thr Thr  Cys Thr Cys Thr Thr  Ala Cys Thr
    11270               11275               11280

Gly Thr  Cys Ala Thr Gly Cys  Cys Ala Thr Cys Cys  Gly Thr Ala
    11285               11290               11295

Ala Gly  Ala Thr Gly Cys Thr  Thr Thr Thr Cys Thr  Gly Thr Gly
    11300               11305               11310

Ala Cys  Thr Gly Gly Thr Gly  Ala Gly Thr Ala Cys  Thr Cys Ala
    11315               11320               11325

Ala Cys  Cys Ala Ala Gly Thr  Cys Ala Thr Thr Cys  Thr Gly Ala
    11330               11335               11340
```

Gly Ala Ala Thr Ala Gly Thr Gly Thr Ala Thr Gly Cys Gly Gly
11345 11350 11355

Cys Gly Ala Cys Cys Gly Ala Gly Thr Thr Gly Cys Thr Cys Thr
11360 11365 11370

Thr Gly Cys Cys Cys Gly Gly Cys Gly Thr Cys Ala Ala Thr Ala
11375 11380 11385

Cys Gly Gly Gly Ala Thr Ala Ala Thr Ala Cys Cys Gly Cys Gly
11390 11395 11400

Cys Cys Ala Cys Ala Thr Ala Gly Cys Ala Gly Ala Ala Cys Thr
11405 11410 11415

Thr Thr Ala Ala Ala Ala Gly Thr Gly Cys Thr Cys Ala Thr Cys
11420 11425 11430

Ala Thr Thr Gly Gly Ala Ala Ala Ala Cys Gly Thr Thr Cys Thr
11435 11440 11445

Thr Cys Gly Gly Gly Gly Cys Gly Ala Ala Ala Ala Cys Thr Cys
11450 11455 11460

Thr Cys Ala Ala Gly Gly Ala Thr Cys Thr Thr Ala Cys Cys Gly
11465 11470 11475

Cys Thr Gly Thr Thr Gly Ala Gly Ala Thr Cys Cys Ala Gly Thr
11480 11485 11490

Thr Cys Gly Ala Thr Gly Thr Ala Ala Cys Cys Cys Ala Cys Thr
11495 11500 11505

Cys Gly Thr Gly Cys Ala Cys Cys Cys Ala Ala Cys Thr Gly Ala
11510 11515 11520

Thr Cys Thr Thr Cys Ala Gly Cys Ala Thr Cys Thr Thr Thr Thr
11525 11530 11535

Ala Cys Thr Thr Thr Cys Ala Cys Cys Ala Gly Cys Gly Thr Thr
11540 11545 11550

Thr Cys Thr Gly Gly Gly Thr Gly Ala Gly Cys Ala Ala Ala Ala
11555 11560 11565

Ala Cys Ala Gly Gly Ala Ala Gly Gly Cys Ala Ala Ala Ala Thr
11570 11575 11580

Gly Cys Cys Gly Cys Ala Ala Ala Ala Ala Ala Gly Gly Gly Ala
11585 11590 11595

Ala Thr Ala Ala Gly Gly Gly Cys Gly Ala Cys Ala Cys Gly Gly
11600 11605 11610

Ala Ala Ala Thr Gly Thr Thr Gly Ala Ala Thr Ala Cys Thr Cys
11615 11620 11625

Ala Thr Ala Cys Thr Cys Thr Thr Cys Cys Thr Thr Thr Thr Thr
11630 11635 11640

Cys Ala Ala Thr Ala Thr Thr Ala Thr Thr Gly Ala Ala Gly Cys
11645 11650 11655

Ala Thr Thr Thr Ala Thr Cys Ala Gly Gly Gly Thr Thr Ala Thr
11660 11665 11670

Thr Gly Thr Cys Thr Cys Ala Thr Gly Ala Gly Cys Gly Gly Ala
11675 11680 11685

Thr Ala Cys Ala Thr Ala Thr Thr Thr Gly Ala Ala Thr Gly Thr
11690 11695 11700

Ala Thr Thr Thr Ala Gly Ala Ala Ala Ala Ala Thr Ala Ala Ala
11705 11710 11715

Cys Ala Ala Ala Thr Ala Gly Gly Gly Gly Thr Thr Cys Cys Gly
11720 11725 11730

```
Cys Gly   Cys Ala Cys Ala Thr   Thr Thr Cys Cys Cys   Cys Gly Ala
    11735                11740                11745

Ala Ala   Ala Gly Thr Gly Cys   Cys Ala Cys Cys Thr   Gly Ala Cys
    11750                11755                11760
```

<210> SEQ ID NO 5
<211> LENGTH: 291
<212> TYPE: PRT
<213> ORGANISM: Artificial Sequence
<220> FEATURE:
<223> OTHER INFORMATION: synthetic constructs

<400> SEQUENCE: 5

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290
```

<210> SEQ ID NO 6
<211> LENGTH: 291
<212> TYPE: PRT
<213> ORGANISM: Artificial Sequence
<220> FEATURE:

<223> OTHER INFORMATION: synthetic constructs

<400> SEQUENCE: 6

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290
```

<210> SEQ ID NO 7
<211> LENGTH: 248
<212> TYPE: PRT
<213> ORGANISM: Artificial Sequence
<220> FEATURE:
<223> OTHER INFORMATION: synthetic constructs

<400> SEQUENCE: 7

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45
```

```
Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245
```

<210> SEQ ID NO 8
<211> LENGTH: 311
<212> TYPE: PRT
<213> ORGANISM: Artificial Sequence
<220> FEATURE:
<223> OTHER INFORMATION: synthetic constructs

<400> SEQUENCE: 8

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160
```

```
Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310


<210> SEQ ID NO 9
<211> LENGTH: 238
<212> TYPE: PRT
<213> ORGANISM: Artificial Sequence
<220> FEATURE:
<223> OTHER INFORMATION: synthetic constructs

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205
```

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 10
<211> LENGTH: 239
<212> TYPE: PRT
<213> ORGANISM: Artificial Sequence
<220> FEATURE:
<223> OTHER INFORMATION: synthetic constructs

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
<211> LENGTH: 839
<212> TYPE: PRT
<213> ORGANISM: Artificial Sequence
<220> FEATURE:
<223> OTHER INFORMATION: synthetic constructs

<400> SEQUENCE: 11

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser

```
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Ala Ala Ala Val Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Gln Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Asp Phe Lys Glu Asp Gly Asn Ile Leu Gly
            420                 425                 430

His Lys Leu Glu Tyr Asn Tyr Asn Ser His Asn Val Tyr Ile Thr Ala
        435                 440                 445

Asp Lys Gln Lys Asn Gly Ile Lys Ala Asn Phe Lys Ile Arg His Asn
    450                 455                 460
```

```
Ile Glu Asp Gly Gly Val Gln Leu Ala Asp His Tyr Gln Gln Asn Thr
465                 470                 475                 480

Pro Ile Gly Asp Gly Pro Val Leu Leu Pro Asp Asn His Tyr Leu Ser
                485                 490                 495

Tyr Gln Ser Lys Leu Ser Lys Asp Pro Asn Glu Lys Arg Asp His Met
            500                 505                 510

Val Leu Leu Glu Phe Val Thr Ala Ala Gly Gly Thr Lys Val Tyr Asp
        515                 520                 525

Pro Glu Gln Arg Lys Arg Met Ile Thr Gly Pro Gln Trp Trp Ala Arg
    530                 535                 540

Cys Lys Gln Met Asn Val Leu Asp Ser Phe Ile Asn Tyr Tyr Asp Ser
545                 550                 555                 560

Glu Lys His Ala Glu Asn Ala Val Ile Phe Leu His Gly Asn Ala Thr
                565                 570                 575

Ser Ser Tyr Leu Trp Arg His Val Val Pro His Ile Glu Pro Val Ala
            580                 585                 590

Arg Cys Ile Ile Pro Asp Leu Ile Gly Met Gly Lys Ser Gly Lys Ser
        595                 600                 605

Gly Asn Gly Ser Tyr Arg Leu Leu Asp His Tyr Lys Tyr Leu Thr Ala
    610                 615                 620

Trp Phe Glu Leu Leu Asn Leu Pro Lys Lys Ile Ile Phe Val Gly His
625                 630                 635                 640

Asp Trp Gly Ala Ala Leu Ala Phe His Tyr Ala Tyr Glu His Gln Asp
                645                 650                 655

Arg Ile Lys Ala Ile Val His Met Glu Ser Val Val Asp Val Ile Glu
            660                 665                 670

Ser Trp Asp Glu Trp Pro Asp Ile Glu Glu Asp Ile Ala Leu Ile Lys
        675                 680                 685

Ser Glu Glu Gly Glu Lys Met Val Leu Glu Asn Asn Phe Phe Val Glu
    690                 695                 700

Thr Val Leu Pro Ser Lys Ile Met Arg Lys Leu Glu Pro Glu Glu Phe
705                 710                 715                 720

Ala Ala Tyr Leu Glu Pro Phe Lys Glu Lys Gly Glu Val Arg Arg Pro
                725                 730                 735

Thr Leu Ser Trp Pro Arg Glu Ile Pro Leu Val Lys Gly Gly Lys Pro
            740                 745                 750

Asp Val Val Gln Ile Val Arg Asn Tyr Asn Ala Tyr Leu Arg Ala Ser
        755                 760                 765

Asp Asp Leu Pro Lys Leu Phe Ile Glu Gly Asp Pro Gly Phe Phe Ser
    770                 775                 780

Asn Ala Ile Val Glu Gly Ala Lys Lys Phe Pro Asn Thr Glu Phe Val
785                 790                 795                 800

Lys Val Lys Gly Leu His Phe Leu Gln Glu Asp Ala Pro Asp Glu Met
                805                 810                 815

Gly Lys Tyr Ile Lys Ser Phe Val Glu Arg Val Leu Lys Asn Glu Gln
            820                 825                 830

Phe Cys Tyr Glu Asn Glu Val
        835
```

<210> SEQ ID NO 12
<211> LENGTH: 12249
<212> TYPE: PRT
<213> ORGANISM: Artificial Sequence
<220> FEATURE:

<223> OTHER INFORMATION: synthetic constructs

<400> SEQUENCE: 12

```
Gly Thr Cys Gly Ala Cys Gly Gly Ala Thr Cys Gly Gly Gly Ala Gly
1               5                   10                  15

Ala Thr Cys Thr Cys Cys Cys Gly Ala Thr Cys Cys Cys Cys Thr Ala
            20                  25                  30

Thr Gly Gly Thr Gly Cys Ala Cys Thr Cys Thr Cys Ala Gly Thr Ala
        35                  40                  45

Cys Ala Ala Thr Cys Thr Gly Cys Thr Cys Thr Gly Ala Thr Gly Cys
    50                  55                  60

Cys Gly Cys Ala Thr Ala Gly Thr Thr Ala Ala Gly Cys Cys Ala Gly
65                  70                  75                  80

Thr Ala Thr Cys Thr Gly Cys Thr Cys Cys Cys Thr Gly Cys Thr Thr
                85                  90                  95

Gly Thr Gly Thr Gly Thr Thr Gly Gly Ala Gly Gly Thr Cys Gly Cys
            100                 105                 110

Thr Gly Ala Gly Thr Ala Gly Thr Gly Cys Gly Cys Gly Ala Gly Cys
        115                 120                 125

Ala Ala Ala Ala Thr Thr Thr Ala Ala Gly Cys Thr Ala Cys Ala Ala
    130                 135                 140

Cys Ala Ala Gly Gly Cys Ala Ala Gly Gly Cys Thr Thr Gly Ala Cys
145                 150                 155                 160

Cys Gly Ala Cys Ala Ala Thr Thr Gly Cys Ala Thr Gly Ala Ala Gly
                165                 170                 175

Ala Ala Thr Cys Thr Gly Cys Thr Thr Ala Gly Gly Gly Thr Thr Ala
            180                 185                 190

Gly Gly Cys Gly Thr Thr Thr Thr Gly Cys Gly Cys Thr Gly Cys Thr
        195                 200                 205

Thr Cys Gly Cys Gly Ala Thr Gly Thr Ala Cys Gly Gly Gly Cys Cys
    210                 215                 220

Ala Gly Ala Thr Ala Thr Ala Cys Gly Cys Gly Thr Thr Gly Ala Cys
225                 230                 235                 240

Ala Thr Thr Gly Ala Thr Thr Ala Thr Thr Gly Ala Cys Thr Ala Gly
                245                 250                 255

Thr Thr Ala Thr Thr Ala Ala Thr Ala Gly Thr Ala Ala Thr Cys Ala
            260                 265                 270

Ala Thr Thr Ala Cys Gly Gly Gly Gly Thr Cys Ala Thr Thr Ala Gly
        275                 280                 285

Thr Thr Cys Ala Thr Ala Gly Cys Cys Cys Ala Thr Ala Thr Ala Thr
    290                 295                 300

Gly Gly Ala Gly Thr Thr Cys Cys Gly Cys Gly Thr Thr Ala Cys Ala
305                 310                 315                 320

Thr Ala Ala Cys Thr Thr Ala Cys Gly Gly Thr Ala Ala Ala Thr Gly
                325                 330                 335

Gly Cys Cys Cys Gly Cys Cys Thr Gly Gly Cys Thr Gly Ala Cys Cys
            340                 345                 350

Gly Cys Cys Cys Ala Ala Cys Gly Ala Cys Cys Cys Cys Cys Gly Cys
        355                 360                 365

Cys Cys Ala Thr Thr Gly Ala Cys Gly Thr Cys Ala Ala Thr Ala Ala
    370                 375                 380

Thr Gly Ala Cys Gly Thr Ala Thr Gly Thr Thr Cys Cys Cys Ala Thr
385                 390                 395                 400
```

Ala Gly Thr Ala Ala Cys Gly Cys Cys Ala Ala Thr Ala Gly Gly Gly
405 410 415

Ala Cys Thr Thr Thr Cys Cys Ala Thr Thr Gly Ala Cys Gly Thr Cys
420 425 430

Ala Ala Thr Gly Gly Gly Thr Gly Gly Ala Gly Thr Ala Thr Thr Thr
435 440 445

Ala Cys Gly Gly Thr Ala Ala Ala Cys Thr Gly Cys Cys Cys Ala Cys
450 455 460

Thr Thr Gly Gly Cys Ala Gly Thr Ala Cys Ala Thr Cys Ala Ala Gly
465 470 475 480

Thr Gly Thr Ala Thr Cys Ala Thr Ala Thr Gly Cys Cys Ala Ala Gly
485 490 495

Thr Ala Cys Gly Cys Cys Cys Cys Cys Thr Ala Thr Thr Gly Ala Cys
500 505 510

Gly Thr Cys Ala Ala Thr Gly Ala Cys Gly Gly Thr Ala Ala Ala Thr
515 520 525

Gly Gly Cys Cys Cys Gly Cys Cys Thr Gly Gly Cys Ala Thr Thr Ala
530 535 540

Thr Gly Cys Cys Cys Ala Gly Thr Ala Cys Ala Thr Gly Ala Cys Cys
545 550 555 560

Thr Thr Ala Thr Gly Gly Gly Ala Cys Thr Thr Thr Cys Cys Thr Ala
565 570 575

Cys Thr Thr Gly Gly Cys Ala Gly Thr Ala Cys Ala Thr Cys Thr Ala
580 585 590

Cys Gly Thr Ala Thr Thr Ala Gly Thr Cys Ala Thr Cys Gly Cys Thr
595 600 605

Ala Thr Thr Ala Cys Cys Ala Thr Gly Gly Thr Gly Ala Thr Gly Cys
610 615 620

Gly Gly Thr Thr Thr Thr Gly Gly Cys Ala Gly Thr Ala Cys Ala Thr
625 630 635 640

Cys Ala Ala Thr Gly Gly Gly Cys Gly Thr Gly Gly Ala Thr Ala Gly
645 650 655

Cys Gly Gly Thr Thr Thr Gly Ala Cys Thr Cys Ala Cys Gly Gly Gly
660 665 670

Gly Ala Thr Thr Thr Cys Cys Ala Ala Gly Thr Cys Thr Cys Cys Ala
675 680 685

Cys Cys Cys Cys Ala Thr Thr Gly Ala Cys Gly Thr Cys Ala Ala Thr
690 695 700

Gly Gly Gly Ala Gly Thr Thr Thr Gly Thr Thr Thr Thr Gly Gly Cys
705 710 715 720

Ala Cys Cys Ala Ala Ala Ala Thr Cys Ala Ala Cys Gly Gly Gly Ala
725 730 735

Cys Thr Thr Thr Cys Cys Ala Ala Ala Ala Thr Gly Thr Cys Gly Thr
740 745 750

Ala Ala Cys Ala Ala Cys Thr Cys Cys Gly Cys Cys Cys Cys Ala Thr
755 760 765

Thr Gly Ala Cys Gly Cys Ala Ala Ala Thr Gly Gly Gly Cys Gly Gly
770 775 780

Thr Ala Gly Gly Cys Gly Thr Gly Thr Ala Cys Gly Gly Thr Gly Gly
785 790 795 800

Gly Ala Gly Gly Thr Cys Thr Ala Thr Ala Thr Ala Ala Gly Cys Ala
805 810 815

Gly Cys Gly Cys Gly Thr Thr Thr Thr Gly Cys Cys Thr Gly Thr Ala

```
            820                 825                 830

Cys Thr Gly Gly Gly Thr Cys Thr Cys Thr Cys Thr Gly Gly Thr Thr
        835                 840                 845

Ala Gly Ala Cys Cys Ala Gly Ala Thr Cys Thr Gly Ala Gly Cys Cys
    850                 855                 860

Thr Gly Gly Gly Ala Gly Cys Thr Cys Thr Cys Thr Gly Gly Cys Thr
865                 870                 875                 880

Ala Ala Cys Thr Ala Gly Gly Gly Ala Ala Cys Cys Cys Ala Cys Thr
                885                 890                 895

Gly Cys Thr Thr Ala Ala Gly Cys Cys Thr Cys Ala Ala Thr Ala Ala
            900                 905                 910

Ala Gly Cys Thr Thr Gly Cys Cys Thr Thr Gly Ala Gly Thr Gly Cys
        915                 920                 925

Thr Thr Cys Ala Ala Gly Thr Ala Gly Thr Gly Thr Gly Thr Gly Cys
    930                 935                 940

Cys Cys Gly Thr Cys Thr Gly Thr Thr Gly Thr Gly Thr Gly Ala Cys
945                 950                 955                 960

Thr Cys Thr Gly Gly Thr Ala Ala Cys Thr Ala Gly Ala Gly Ala Thr
                965                 970                 975

Cys Cys Cys Thr Cys Ala Gly Ala Cys Cys Cys Thr Thr Thr Thr Ala
            980                 985                 990

Gly Thr Cys Ala Gly Thr Gly Thr  Gly Gly Ala Ala Ala  Ala Thr Cys
        995                 1000                1005

Thr Cys  Thr Ala Gly Cys Ala  Gly Thr Gly Gly Cys  Gly Cys Cys
    1010                 1015                 1020

Cys Gly  Ala Ala Cys Ala Gly  Gly Gly Ala Cys Thr  Thr Gly Ala
    1025                 1030                 1035

Ala Ala  Gly Cys Gly Ala Ala  Ala Gly Gly Gly Ala  Ala Ala Cys
    1040                 1045                 1050

Cys Ala  Gly Ala Gly Gly Ala  Gly Cys Thr Cys Thr  Cys Thr Cys
    1055                 1060                 1065

Gly Ala  Cys Gly Cys Ala Gly  Gly Ala Cys Thr Cys  Gly Gly Cys
    1070                 1075                 1080

Thr Thr  Gly Cys Thr Gly Ala  Ala Gly Cys Gly Cys  Gly Cys Ala
    1085                 1090                 1095

Cys Gly  Gly Cys Ala Ala Gly  Ala Gly Gly Cys Gly  Ala Gly Gly
    1100                 1105                 1110

Gly Gly  Cys Gly Gly Cys Gly  Ala Cys Thr Gly Gly  Thr Gly Ala
    1115                 1120                 1125

Gly Thr  Ala Cys Gly Cys Cys  Ala Ala Ala Ala Ala  Thr Thr Thr
    1130                 1135                 1140

Thr Gly  Ala Cys Thr Ala Gly  Cys Gly Gly Ala Gly  Gly Cys Thr
    1145                 1150                 1155

Ala Gly  Ala Ala Gly Gly Ala  Gly Ala Gly Ala Gly  Ala Thr Gly
    1160                 1165                 1170

Gly Gly  Thr Gly Cys Gly Ala  Gly Ala Gly Cys Gly  Thr Cys Ala
    1175                 1180                 1185

Gly Thr  Ala Thr Thr Ala Ala  Gly Cys Gly Gly Gly  Gly Gly Ala
    1190                 1195                 1200

Gly Ala  Ala Thr Thr Ala Gly  Ala Thr Cys Gly Cys  Gly Ala Thr
    1205                 1210                 1215

Gly Gly  Gly Ala Ala Ala Ala  Ala Ala Thr Thr Cys  Gly Gly Thr
    1220                 1225                 1230
```

```
Thr Ala  Ala Gly Gly Cys Cys  Ala Gly Gly Gly Gly  Gly Ala Ala
    1235                 1240                 1245

Ala Gly  Ala Ala Ala Ala Ala  Ala Thr Ala Thr Ala  Ala Ala Thr
    1250                 1255                 1260

Thr Ala  Ala Ala Ala Cys Ala  Thr Ala Thr Ala Gly  Thr Ala Thr
    1265                 1270                 1275

Gly Gly  Gly Cys Ala Ala Gly  Cys Ala Gly Gly Gly  Ala Gly Cys
    1280                 1285                 1290

Thr Ala  Gly Ala Ala Cys Gly  Ala Thr Thr Cys Gly  Cys Ala Gly
    1295                 1300                 1305

Thr Thr  Ala Ala Thr Cys Cys  Thr Gly Gly Cys Cys  Thr Gly Thr
    1310                 1315                 1320

Thr Ala  Gly Ala Ala Ala Cys  Ala Thr Cys Ala Gly  Ala Ala Gly
    1325                 1330                 1335

Gly Cys  Thr Gly Thr Ala Gly  Ala Cys Ala Ala Ala  Thr Ala Cys
    1340                 1345                 1350

Thr Gly  Gly Gly Ala Cys Ala  Gly Cys Thr Ala Cys  Ala Ala Cys
    1355                 1360                 1365

Cys Ala  Thr Cys Cys Cys Thr  Thr Cys Ala Gly Ala  Cys Ala Gly
    1370                 1375                 1380

Gly Ala  Thr Cys Ala Gly Ala  Ala Gly Ala Ala Cys  Thr Thr Ala
    1385                 1390                 1395

Gly Ala  Thr Cys Ala Thr Thr  Ala Thr Ala Thr Ala  Ala Thr Ala
    1400                 1405                 1410

Cys Ala  Gly Thr Ala Gly Cys  Ala Ala Cys Cys Cys  Thr Cys Thr
    1415                 1420                 1425

Ala Thr  Thr Gly Thr Gly Thr  Gly Cys Ala Thr Cys  Ala Ala Ala
    1430                 1435                 1440

Gly Gly  Ala Thr Ala Gly Ala  Gly Ala Thr Ala Ala  Ala Ala Gly
    1445                 1450                 1455

Ala Cys  Ala Cys Cys Ala Ala  Gly Gly Ala Ala Gly  Cys Thr Thr
    1460                 1465                 1470

Thr Ala  Gly Ala Cys Ala Ala  Gly Ala Thr Ala Gly  Ala Gly Gly
    1475                 1480                 1485

Ala Ala  Gly Ala Gly Cys Ala  Ala Ala Ala Cys Ala  Ala Ala Ala
    1490                 1495                 1500

Gly Thr  Ala Ala Gly Ala Cys  Cys Ala Cys Cys Gly  Cys Ala Cys
    1505                 1510                 1515

Ala Gly  Cys Ala Ala Gly Cys  Gly Gly Cys Cys Gly  Cys Thr Gly
    1520                 1525                 1530

Ala Thr  Cys Thr Thr Cys Ala  Gly Ala Cys Cys Thr  Gly Gly Ala
    1535                 1540                 1545

Gly Gly  Ala Gly Gly Ala Gly  Ala Thr Ala Thr Gly  Ala Gly Gly
    1550                 1555                 1560

Gly Ala  Cys Ala Ala Thr Thr  Gly Gly Ala Gly Ala  Ala Gly Thr
    1565                 1570                 1575

Gly Ala  Ala Thr Thr Ala Thr  Ala Thr Ala Ala Ala  Thr Ala Thr
    1580                 1585                 1590

Ala Ala  Ala Gly Thr Ala Gly  Thr Ala Ala Ala Ala  Ala Thr Thr
    1595                 1600                 1605

Gly Ala  Ala Cys Cys Ala Thr  Thr Ala Gly Gly Ala  Gly Thr Ala
    1610                 1615                 1620
```

```
Gly Cys  Ala Cys Cys Cys Ala  Cys Cys Ala Ala Gly  Gly Cys Ala
    1625                 1630                 1635

Ala Ala  Gly Ala Gly Ala Ala  Gly Ala Gly Thr Gly  Gly Thr Gly
    1640                 1645                 1650

Cys Ala  Gly Ala Gly Ala Gly  Ala Ala Ala Ala Ala  Ala Gly Ala
    1655                 1660                 1665

Gly Cys  Ala Gly Thr Gly Gly  Gly Ala Ala Thr Ala  Gly Gly Ala
    1670                 1675                 1680

Gly Cys  Thr Thr Thr Gly Thr  Thr Cys Cys Thr Thr  Gly Gly Gly
    1685                 1690                 1695

Thr Thr  Cys Thr Thr Gly Gly  Gly Ala Gly Cys Ala  Gly Cys Ala
    1700                 1705                 1710

Gly Gly  Ala Ala Gly Cys Ala  Cys Thr Ala Thr Gly  Gly Gly Cys
    1715                 1720                 1725

Gly Cys  Ala Gly Cys Gly Thr  Cys Ala Ala Thr Gly  Ala Cys Gly
    1730                 1735                 1740

Cys Thr  Gly Ala Cys Gly Gly  Thr Ala Cys Ala Gly  Gly Cys Cys
    1745                 1750                 1755

Ala Gly  Ala Cys Ala Ala Thr  Thr Ala Thr Thr Gly  Thr Cys Thr
    1760                 1765                 1770

Gly Gly  Thr Ala Thr Ala Gly  Thr Gly Cys Ala Gly  Cys Ala Gly
    1775                 1780                 1785

Cys Ala  Gly Ala Ala Cys Ala  Ala Thr Thr Thr Gly  Cys Thr Gly
    1790                 1795                 1800

Ala Gly  Gly Gly Cys Thr Ala  Thr Thr Gly Ala Gly  Gly Cys Gly
    1805                 1810                 1815

Cys Ala  Ala Cys Ala Gly Cys  Ala Thr Cys Thr Gly  Thr Thr Gly
    1820                 1825                 1830

Cys Ala  Ala Cys Thr Cys Ala  Cys Ala Gly Thr Cys  Thr Gly Gly
    1835                 1840                 1845

Gly Gly  Cys Ala Thr Cys Ala  Ala Gly Cys Ala Gly  Cys Thr Cys
    1850                 1855                 1860

Cys Ala  Gly Gly Cys Ala Ala  Gly Ala Ala Thr Cys  Cys Thr Gly
    1865                 1870                 1875

Gly Cys  Thr Gly Thr Gly Gly  Ala Ala Ala Gly Ala  Thr Ala Cys
    1880                 1885                 1890

Cys Thr  Ala Ala Ala Gly Gly  Ala Thr Cys Ala Ala  Cys Ala Gly
    1895                 1900                 1905

Cys Thr  Cys Cys Thr Gly Gly  Gly Gly Ala Thr Thr  Thr Gly Gly
    1910                 1915                 1920

Gly Gly  Thr Thr Gly Cys Thr  Cys Thr Gly Gly Ala  Ala Ala Ala
    1925                 1930                 1935

Cys Thr  Cys Ala Thr Thr Thr  Gly Cys Ala Cys Cys  Ala Cys Thr
    1940                 1945                 1950

Gly Cys  Thr Gly Thr Gly Cys  Cys Thr Thr Gly Gly  Ala Ala Thr
    1955                 1960                 1965

Gly Cys  Thr Ala Gly Thr Thr  Gly Gly Ala Gly Thr  Ala Ala Thr
    1970                 1975                 1980

Ala Ala  Ala Thr Cys Thr Cys  Thr Gly Gly Ala Ala  Cys Ala Gly
    1985                 1990                 1995

Ala Thr  Thr Thr Gly Gly Ala  Ala Thr Cys Ala Cys  Ala Cys Gly
    2000                 2005                 2010

Ala Cys  Cys Thr Gly Gly Ala  Thr Gly Gly Ala Gly  Thr Gly Gly
```

-continued

```
    2015                2020                2025

Gly Ala  Cys Ala Gly Ala Gly  Ala Ala Ala Thr Thr  Ala Ala Cys
    2030                2035                2040

Ala Ala  Thr Thr Ala Cys Ala  Cys Ala Ala Gly Cys  Thr Thr Ala
    2045                2050                2055

Ala Thr  Ala Cys Ala Cys Thr  Cys Cys Thr Thr Ala  Ala Thr Thr
    2060                2065                2070

Gly Ala  Ala Gly Ala Ala Thr  Cys Gly Cys Ala Ala  Ala Ala Cys
    2075                2080                2085

Cys Ala  Gly Cys Ala Ala Gly  Ala Ala Ala Ala Gly  Ala Ala Thr
    2090                2095                2100

Gly Ala  Ala Cys Ala Ala Gly  Ala Ala Thr Thr Ala  Thr Thr Gly
    2105                2110                2115

Gly Ala  Ala Thr Thr Ala Gly  Ala Thr Ala Ala Ala  Thr Gly Gly
    2120                2125                2130

Gly Cys  Ala Ala Gly Thr Thr  Thr Gly Thr Gly Gly  Ala Ala Thr
    2135                2140                2145

Thr Gly  Gly Thr Thr Thr Ala  Ala Cys Ala Thr Ala  Ala Cys Ala
    2150                2155                2160

Ala Ala  Thr Thr Gly Gly Cys  Thr Gly Thr Gly Gly  Thr Ala Thr
    2165                2170                2175

Ala Thr  Ala Ala Ala Ala Thr  Thr Ala Thr Thr Cys  Ala Thr Ala
    2180                2185                2190

Ala Thr  Gly Ala Thr Ala Gly  Thr Ala Gly Gly Ala  Gly Gly Cys
    2195                2200                2205

Thr Thr  Gly Gly Thr Ala Gly  Gly Thr Thr Thr Ala  Ala Gly Ala
    2210                2215                2220

Ala Thr  Ala Gly Thr Thr Thr  Thr Thr Gly Cys Thr  Gly Thr Ala
    2225                2230                2235

Cys Thr  Thr Thr Cys Thr Ala  Thr Ala Gly Thr Gly  Ala Ala Thr
    2240                2245                2250

Ala Gly  Ala Gly Thr Thr Ala  Gly Gly Cys Ala Gly  Gly Gly Ala
    2255                2260                2265

Thr Ala  Thr Thr Cys Ala Cys  Cys Ala Thr Thr Ala  Thr Cys Gly
    2270                2275                2280

Thr Thr  Thr Cys Ala Gly Ala  Cys Cys Cys Ala Cys  Cys Thr Cys
    2285                2290                2295

Cys Cys  Ala Ala Cys Cys Cys  Cys Gly Ala Gly Gly  Gly Gly Ala
    2300                2305                2310

Cys Cys  Cys Gly Ala Cys Ala  Gly Gly Cys Cys Cys  Gly Ala Ala
    2315                2320                2325

Gly Gly  Ala Ala Thr Ala Gly  Ala Ala Gly Ala Ala  Gly Ala Ala
    2330                2335                2340

Gly Gly  Thr Gly Gly Ala Gly  Ala Gly Ala Gly Ala  Gly Ala Cys
    2345                2350                2355

Ala Gly  Ala Gly Ala Cys Ala  Gly Ala Thr Cys Cys  Ala Thr Thr
    2360                2365                2370

Cys Gly  Ala Thr Thr Ala Gly  Thr Gly Ala Ala Cys  Gly Gly Ala
    2375                2380                2385

Thr Cys  Gly Gly Cys Ala Cys  Thr Gly Cys Gly Thr  Gly Cys Gly
    2390                2395                2400

Cys Cys  Ala Ala Thr Thr Cys  Thr Gly Cys Ala Gly  Ala Cys Ala
    2405                2410                2415
```

Ala Ala Thr Gly Gly Cys Ala Gly Thr Ala Thr Thr Cys Ala Thr
2420 2425 2430

Cys Cys Ala Cys Ala Ala Thr Thr Thr Thr Ala Ala Ala Ala Gly
2435 2440 2445

Ala Ala Ala Ala Gly Gly Gly Gly Gly Gly Ala Thr Thr Gly Gly
2450 2455 2460

Gly Gly Gly Gly Thr Ala Cys Ala Gly Thr Gly Cys Ala Gly Gly
2465 2470 2475

Gly Gly Ala Ala Ala Gly Ala Ala Thr Ala Gly Thr Ala Gly Ala
2480 2485 2490

Cys Ala Thr Ala Ala Thr Ala Gly Cys Ala Ala Cys Ala Gly Ala
2495 2500 2505

Cys Ala Thr Ala Cys Ala Ala Ala Cys Thr Ala Ala Ala Gly Ala
2510 2515 2520

Ala Thr Thr Ala Cys Ala Ala Ala Ala Ala Cys Ala Ala Ala Thr
2525 2530 2535

Thr Ala Cys Ala Ala Ala Ala Ala Thr Thr Cys Ala Ala Ala Ala
2540 2545 2550

Thr Thr Thr Thr Cys Gly Gly Gly Thr Thr Thr Ala Thr Thr Ala
2555 2560 2565

Cys Ala Gly Gly Gly Ala Cys Ala Gly Cys Ala Gly Ala Gly Ala
2570 2575 2580

Thr Cys Cys Ala Gly Thr Thr Thr Gly Gly Thr Thr Ala Ala Thr
2585 2590 2595

Thr Ala Ala Gly Gly Gly Thr Gly Cys Ala Gly Cys Gly Gly Cys
2600 2605 2610

Cys Thr Cys Cys Gly Cys Gly Cys Cys Gly Gly Gly Thr Thr Thr
2615 2620 2625

Thr Gly Gly Cys Gly Cys Cys Thr Cys Cys Cys Gly Cys Gly Gly
2630 2635 2640

Gly Cys Gly Cys Cys Cys Cys Cys Cys Thr Cys Cys Thr Cys Ala
2645 2650 2655

Cys Gly Gly Cys Gly Ala Gly Cys Gly Cys Thr Gly Cys Cys Ala
2660 2665 2670

Cys Gly Thr Cys Ala Gly Ala Cys Gly Ala Ala Gly Gly Gly Cys
2675 2680 2685

Gly Cys Ala Gly Gly Ala Gly Cys Gly Thr Thr Cys Cys Thr Gly
2690 2695 2700

Ala Thr Cys Cys Thr Thr Cys Cys Gly Cys Cys Cys Gly Gly Ala
2705 2710 2715

Cys Gly Cys Thr Cys Ala Gly Gly Ala Cys Ala Gly Cys Gly Gly
2720 2725 2730

Cys Cys Cys Gly Cys Thr Gly Cys Thr Cys Ala Thr Ala Ala Gly
2735 2740 2745

Ala Cys Thr Cys Gly Gly Cys Cys Thr Thr Ala Gly Ala Ala Cys
2750 2755 2760

Cys Cys Cys Ala Gly Thr Ala Thr Cys Ala Gly Cys Ala Gly Ala
2765 2770 2775

Ala Gly Gly Ala Cys Ala Thr Thr Thr Thr Ala Gly Gly Ala Cys
2780 2785 2790

Gly Gly Gly Ala Cys Thr Thr Gly Gly Gly Thr Gly Ala Cys Thr
2795 2800 2805

-continued

```
Cys Thr  Ala Gly Gly Gly Cys  Ala Cys Thr Gly Gly  Thr Thr Thr
    2810                 2815                 2820

Thr Cys  Thr Thr Thr Cys Cys  Ala Gly Ala Gly Ala  Gly Cys Gly
    2825                 2830                 2835

Gly Ala  Ala Cys Ala Gly Gly  Cys Gly Ala Gly Gly  Ala Ala Ala
    2840                 2845                 2850

Ala Gly  Thr Ala Gly Thr Cys  Cys Cys Thr Thr Cys  Thr Cys Gly
    2855                 2860                 2865

Gly Cys  Gly Ala Thr Thr Cys  Thr Gly Cys Gly Gly  Ala Gly Gly
    2870                 2875                 2880

Gly Ala  Thr Cys Thr Cys Cys  Gly Thr Gly Gly Gly  Gly Cys Gly
    2885                 2890                 2895

Gly Thr  Gly Ala Ala Cys Gly  Cys Cys Gly Ala Thr  Gly Ala Thr
    2900                 2905                 2910

Thr Ala  Thr Ala Thr Ala Ala  Gly Gly Ala Cys Gly  Cys Gly Cys
    2915                 2920                 2925

Cys Gly  Gly Gly Thr Gly Thr  Gly Gly Cys Ala Cys  Ala Gly Cys
    2930                 2935                 2940

Thr Ala  Gly Thr Thr Cys Cys  Gly Thr Cys Gly Cys  Ala Gly Cys
    2945                 2950                 2955

Cys Gly  Gly Gly Ala Thr Thr  Thr Gly Gly Gly Thr  Cys Gly Cys
    2960                 2965                 2970

Gly Gly  Thr Thr Cys Thr Thr  Gly Thr Thr Thr Gly  Thr Gly Gly
    2975                 2980                 2985

Ala Thr  Cys Gly Cys Thr Gly  Thr Gly Ala Thr Cys  Gly Thr Cys
    2990                 2995                 3000

Ala Cys  Thr Thr Gly Gly Thr  Gly Ala Gly Thr Thr  Gly Cys Gly
    3005                 3010                 3015

Gly Gly  Cys Thr Gly Cys Thr  Gly Gly Gly Cys Thr  Gly Gly Cys
    3020                 3025                 3030

Cys Gly  Gly Gly Gly Cys Thr  Thr Thr Cys Gly Thr  Gly Gly Cys
    3035                 3040                 3045

Cys Gly  Cys Cys Gly Gly Gly  Cys Cys Gly Cys Thr  Cys Gly Gly
    3050                 3055                 3060

Thr Gly  Gly Gly Ala Cys Gly  Gly Ala Ala Gly Cys  Gly Thr Gly
    3065                 3070                 3075

Thr Gly  Gly Ala Gly Ala Gly  Ala Cys Cys Gly Cys  Cys Ala Ala
    3080                 3085                 3090

Gly Gly  Gly Cys Thr Gly Thr  Ala Gly Thr Cys Thr  Gly Gly Gly
    3095                 3100                 3105

Thr Cys  Cys Gly Cys Gly Ala  Gly Cys Ala Ala Gly  Gly Thr Thr
    3110                 3115                 3120

Gly Cys  Cys Cys Thr Gly Ala  Ala Cys Thr Gly Gly  Gly Gly Gly
    3125                 3130                 3135

Thr Thr  Gly Gly Gly Gly Gly  Gly Ala Gly Cys Gly  Cys Ala Cys
    3140                 3145                 3150

Ala Ala  Ala Ala Thr Gly Gly  Cys Gly Gly Cys Thr  Gly Thr Thr
    3155                 3160                 3165

Cys Cys  Cys Gly Ala Gly Thr  Cys Thr Thr Gly Ala  Ala Thr Gly
    3170                 3175                 3180

Gly Ala  Ala Gly Ala Cys Gly  Cys Thr Thr Gly Thr  Ala Ala Gly
    3185                 3190                 3195

Gly Cys  Gly Gly Gly Cys Thr  Gly Thr Gly Ala Gly  Gly Thr Cys
```

-continued

```
    3200                3205                3210

Gly Thr  Thr Gly Ala Ala Ala  Cys Ala Ala Gly Gly  Thr Gly Gly
    3215                3220                3225

Gly Gly  Gly Gly Cys Ala Thr  Gly Gly Thr Gly Gly  Gly Cys Gly
    3230                3235                3240

Gly Cys  Ala Ala Gly Ala Ala  Cys Cys Cys Ala Ala  Gly Gly Thr
    3245                3250                3255

Cys Thr  Thr Gly Ala Gly Gly  Cys Cys Thr Thr Cys  Gly Cys Thr
    3260                3265                3270

Ala Ala  Thr Gly Cys Gly Gly  Gly Ala Ala Ala Gly  Cys Thr Cys
    3275                3280                3285

Thr Thr  Ala Thr Thr Cys Gly  Gly Gly Thr Gly Ala  Gly Ala Thr
    3290                3295                3300

Gly Gly  Gly Cys Thr Gly Gly  Gly Gly Cys Ala Cys  Cys Ala Thr
    3305                3310                3315

Cys Thr  Gly Gly Gly Gly Ala  Cys Cys Cys Thr Gly  Ala Cys Gly
    3320                3325                3330

Thr Gly  Ala Ala Gly Thr Thr  Thr Gly Thr Cys Ala  Cys Thr Gly
    3335                3340                3345

Ala Cys  Thr Gly Gly Ala Gly  Ala Ala Cys Thr Cys  Gly Gly Gly
    3350                3355                3360

Thr Thr  Thr Gly Thr Cys Gly  Thr Cys Thr Gly Gly  Thr Thr Gly
    3365                3370                3375

Cys Gly  Gly Gly Gly Gly Cys  Gly Gly Cys Ala Gly  Thr Thr Ala
    3380                3385                3390

Thr Gly  Cys Gly Gly Thr Gly  Cys Cys Gly Thr Thr  Gly Gly Gly
    3395                3400                3405

Cys Ala  Gly Thr Gly Cys Ala  Cys Cys Cys Gly Thr  Ala Cys Cys
    3410                3415                3420

Thr Thr  Thr Gly Gly Gly Ala  Gly Cys Gly Cys Gly  Cys Gly Cys
    3425                3430                3435

Cys Thr  Cys Gly Thr Cys Gly  Thr Gly Thr Cys Gly  Thr Gly Ala
    3440                3445                3450

Cys Gly  Thr Cys Ala Cys Cys  Cys Gly Thr Thr Cys  Thr Gly Thr
    3455                3460                3465

Thr Gly  Gly Cys Thr Thr Ala  Thr Ala Ala Thr Gly  Cys Ala Gly
    3470                3475                3480

Gly Gly  Thr Gly Gly Gly Gly  Cys Cys Ala Cys Cys  Thr Gly Cys
    3485                3490                3495

Cys Gly  Gly Thr Ala Gly Gly  Thr Gly Thr Gly Cys  Gly Gly Thr
    3500                3505                3510

Ala Gly  Gly Cys Thr Thr Thr  Thr Cys Thr Cys Cys  Gly Thr Cys
    3515                3520                3525

Gly Cys  Ala Gly Gly Ala Cys  Gly Cys Ala Gly Gly  Gly Thr Thr
    3530                3535                3540

Cys Gly  Gly Gly Cys Cys Thr  Ala Gly Gly Gly Thr  Ala Gly Gly
    3545                3550                3555

Cys Thr  Cys Thr Cys Cys Thr  Gly Ala Ala Thr Cys  Gly Ala Cys
    3560                3565                3570

Ala Gly  Gly Cys Gly Cys Cys  Gly Gly Ala Cys Cys  Thr Cys Thr
    3575                3580                3585

Gly Gly  Thr Gly Ala Gly Gly  Gly Gly Ala Gly Gly  Gly Ala Thr
    3590                3595                3600
```

```
Ala Ala  Gly Thr Gly Ala Gly  Gly Cys Gly Thr Cys  Ala Gly Thr
    3605                 3610                 3615

Thr Thr  Cys Thr Thr Thr Gly  Gly Thr Cys Gly Gly  Thr Thr Thr
    3620                 3625                 3630

Thr Ala  Thr Gly Thr Ala Cys  Cys Thr Ala Thr Cys  Thr Thr Cys
    3635                 3640                 3645

Thr Thr  Ala Ala Gly Thr Ala  Gly Cys Thr Gly Ala  Ala Gly Cys
    3650                 3655                 3660

Thr Cys  Cys Gly Gly Thr Thr  Thr Thr Gly Ala Ala  Cys Thr Ala
    3665                 3670                 3675

Thr Gly  Cys Gly Cys Thr Cys  Gly Gly Gly Gly Thr  Thr Gly Gly
    3680                 3685                 3690

Cys Gly  Ala Gly Thr Gly Thr  Gly Thr Thr Thr Thr  Gly Thr Gly
    3695                 3700                 3705

Ala Ala  Gly Thr Thr Thr Thr  Thr Thr Ala Gly Gly  Cys Ala Cys
    3710                 3715                 3720

Cys Thr  Thr Thr Thr Gly Ala  Ala Ala Thr Gly Thr  Ala Ala Thr
    3725                 3730                 3735

Cys Ala  Thr Thr Thr Gly Gly  Gly Thr Cys Ala Ala  Thr Ala Thr
    3740                 3745                 3750

Gly Thr  Ala Ala Thr Thr Thr  Thr Cys Ala Gly Thr  Gly Thr Thr
    3755                 3760                 3765

Ala Gly  Ala Cys Thr Ala Gly  Thr Ala Ala Ala Gly  Cys Thr Thr
    3770                 3775                 3780

Cys Thr  Gly Cys Ala Gly Gly  Thr Cys Gly Ala Cys  Thr Cys Thr
    3785                 3790                 3795

Ala Gly  Ala Ala Ala Ala Thr  Thr Gly Thr Cys Cys  Gly Cys Thr
    3800                 3805                 3810

Ala Ala  Ala Thr Thr Cys Thr  Gly Gly Cys Cys Gly  Thr Thr Thr
    3815                 3820                 3825

Thr Thr  Gly Gly Cys Thr Thr  Thr Thr Thr Thr Gly  Thr Thr Ala
    3830                 3835                 3840

Gly Ala  Cys Ala Gly Gly Ala  Thr Cys Cys Ala Thr  Gly Ala Cys
    3845                 3850                 3855

Ala Gly  Ala Gly Ala Cys Cys  Cys Thr Gly Cys Cys  Thr Cys Cys
    3860                 3865                 3870

Cys Gly  Thr Gly Ala Cys Cys  Gly Ala Gly Ala Gly  Thr Gly Cys
    3875                 3880                 3885

Cys Gly  Thr Gly Gly Cys Cys  Cys Thr Thr Cys Ala  Ala Gly Cys
    3890                 3895                 3900

Cys Gly  Ala Gly Gly Thr Thr  Ala Cys Cys Cys Ala  Ala Ala Gly
    3905                 3910                 3915

Gly Gly  Ala Gly Thr Thr Gly  Thr Thr Cys Gly Ala  Gly Thr Thr
    3920                 3925                 3930

Cys Gly  Thr Gly Cys Thr Gly  Ala Ala Cys Gly Ala  Cys Cys Cys
    3935                 3940                 3945

Thr Thr  Thr Gly Cys Thr Thr  Gly Cys Ala Ala Gly  Cys Ala Gly
    3950                 3955                 3960

Thr Cys  Thr Cys Thr Ala Thr  Ala Thr Cys Ala Ala  Cys Ala Thr
    3965                 3970                 3975

Cys Gly  Cys Ala Cys Thr Thr  Gly Cys Ala Gly Gly  Ala Cys Thr
    3980                 3985                 3990
```

```
Gly Ala  Gly Thr Ala Thr Ala  Cys Thr Gly Cys Thr  Gly Thr Thr
    3995                 4000                 4005

Cys Gly  Thr Thr Thr Thr Thr  Ala Thr Gly Ala Cys  Cys Cys Gly
    4010                 4015                 4020

Ala Gly  Gly Ala Cys Thr Cys  Gly Ala Thr Gly Ala  Thr Cys Cys
    4025                 4030                 4035

Ala Cys  Gly Gly Gly Cys Ala  Ala Ala Ala Cys Thr  Thr Ala Thr
    4040                 4045                 4050

Thr Gly  Cys Thr Gly Thr Gly  Thr Cys Ala Ala Cys  Cys Ala Thr
    4055                 4060                 4065

Cys Cys  Thr Thr Gly Thr Gly  Cys Cys Thr Gly Thr  Cys Gly Thr
    4070                 4075                 4080

Cys Ala  Gly Cys Ala Thr Thr  Gly Cys Cys Thr Cys  Cys Thr Ala
    4085                 4090                 4095

Cys Ala  Cys Thr Gly Gly Ala  Thr Thr Gly Gly Cys  Gly Ala Gly
    4100                 4105                 4110

Cys Gly  Gly Cys Cys Thr Gly  Ala Cys Ala Ala Thr  Thr Thr Cys
    4115                 4120                 4125

Cys Gly  Thr Thr Cys Thr Thr  Gly Ala Ala Ala Thr  Gly Cys Cys
    4130                 4135                 4140

Ala Gly  Cys Gly Gly Gly Cys  Cys Ala Thr Thr Thr  Thr Gly Cys
    4145                 4150                 4155

Ala Gly  Ala Ala Gly Gly Cys  Ala Gly Cys Thr Cys  Ala Gly Thr
    4160                 4165                 4170

Gly Ala  Thr Gly Cys Thr Gly  Gly Gly Ala Gly Gly  Ala Gly Ala
    4175                 4180                 4185

Ala Gly  Ala Gly Gly Thr Ala  Gly Ala Thr Gly Gly  Thr Gly Thr
    4190                 4195                 4200

Ala Gly  Thr Cys Ala Cys Cys  Ala Thr Gly Thr Gly  Gly Gly Gly
    4205                 4210                 4215

Ala Cys  Gly Gly Thr Ala Thr  Cys Thr Cys Ala Cys  Cys Thr Gly
    4220                 4225                 4230

Gly Gly  Cys Ala Cys Thr Thr  Thr Cys Cys Ala Cys  Gly Cys Cys
    4235                 4240                 4245

Cys Ala  Thr Gly Ala Thr Thr  Cys Thr Cys Cys Thr  Cys Gly Cys
    4250                 4255                 4260

Thr Cys  Thr Gly Gly Gly Thr  Cys Thr Cys Cys Thr  Gly Gly Cys
    4265                 4270                 4275

Cys Gly  Gly Ala Ala Gly Cys  Ala Ala Thr Gly Cys  Thr Ala Cys
    4280                 4285                 4290

Ala Ala  Ala Gly Cys Thr Cys  Thr Thr Cys Ala Cys  Ala Gly Cys
    4295                 4300                 4305

Thr Ala  Thr Cys Ala Cys Thr  Thr Thr Cys Gly Ala  Thr Ala Thr
    4310                 4315                 4320

Cys Gly  Cys Thr Ala Thr Gly  Thr Gly Cys Gly Thr  Gly Ala Cys
    4325                 4330                 4335

Thr Gly  Gly Cys Cys Thr Thr  Gly Cys Cys Gly Cys  Gly Gly Cys
    4340                 4345                 4350

Cys Cys  Thr Gly Ala Cys Thr  Ala Cys Cys Thr Cys  Cys Thr Cys
    4355                 4360                 4365

Cys Cys  Ala Cys Cys Thr Cys  Ala Thr Gly Ala Gly  Ala Thr Gly
    4370                 4375                 4380

Gly Thr  Thr Cys Thr Gly Gly  Thr Ala Cys Gly Cys  Thr Ala Thr
```

```
    4385                4390                4395

Cys Ala  Gly Thr Thr Gly Thr  Gly Cys Ala Thr Gly  Cys Thr Thr
    4400                4405                4410

Thr Cys  Thr Gly Gly Thr Gly  Gly Thr Cys Thr Thr  Gly Thr Ala
    4415                4420                4425

Thr Ala  Thr Cys Cys Thr Gly  Cys Thr Gly Gly Thr  Gly Gly Ala
    4430                4435                4440

Gly Thr  Gly Gly Gly Cys Ala  Cys Ala Gly Gly Ala  Cys Gly Cys
    4445                4450                4455

Cys Ala  Ala Ala Gly Cys Cys  Gly Cys Gly Gly Gly  Ala Ala Cys
    4460                4465                4470

Cys Gly  Cys Thr Gly Ala Cys  Ala Thr Gly Thr Thr  Cys Ala Ala
    4475                4480                4485

Thr Ala  Cys Cys Cys Thr Gly  Ala Ala Gly Cys Thr  Gly Thr Thr
    4490                4495                4500

Gly Ala  Cys Ala Gly Thr Ala  Gly Thr Gly Ala Thr  Gly Thr Gly
    4505                4510                4515

Gly Cys  Thr Gly Gly Gly Gly  Thr Ala Thr Cys Cys  Ala Ala Thr
    4520                4525                4530

Thr Gly  Thr Gly Thr Gly Gly  Gly Cys Thr Cys Thr  Thr Gly Gly
    4535                4540                4545

Ala Gly  Thr Cys Gly Ala Gly  Gly Gly Thr Ala Thr  Cys Gly Cys
    4550                4555                4560

Gly Gly  Thr Gly Thr Thr Gly  Cys Cys Cys Gly Thr  Thr Gly Gly
    4565                4570                4575

Gly Gly  Thr Gly Ala Cys Gly  Ala Gly Cys Thr Gly  Gly Gly Gly
    4580                4585                4590

Ala Thr  Ala Thr Thr Cys Thr  Thr Thr Cys Cys Thr  Gly Gly Ala
    4595                4600                4605

Thr Ala  Thr Cys Gly Thr Gly  Gly Cys Ala Ala Ala  Gly Thr Ala
    4610                4615                4620

Cys Ala  Thr Thr Thr Thr Cys  Gly Cys Ala Thr Thr  Cys Thr Thr
    4625                4630                4635

Gly Cys  Thr Cys Cys Thr Gly  Ala Ala Cys Thr Ala  Thr Cys Thr
    4640                4645                4650

Gly Ala  Cys Gly Thr Cys Ala  Ala Ala Cys Gly Ala  Ala Thr Cys
    4655                4660                4665

Thr Gly  Thr Cys Gly Thr Gly  Thr Cys Cys Gly Gly  Cys Ala Gly
    4670                4675                4680

Cys Ala  Thr Thr Thr Thr Gly  Gly Ala Thr Gly Thr  Thr Cys Cys
    4685                4690                4695

Ala Thr  Cys Thr Gly Cys Thr  Thr Cys Thr Gly Gly  Gly Ala Cys
    4700                4705                4710

Cys Cys  Cys Gly Gly Cys Thr  Gly Ala Thr Gly Ala  Thr Gly Cys
    4715                4720                4725

Gly Gly  Cys Cys Gly Cys Ala  Gly Thr Gly Ala Gly  Cys Ala Ala
    4730                4735                4740

Gly Gly  Gly Cys Gly Ala Gly  Gly Ala Gly Cys Thr  Gly Thr Thr
    4745                4750                4755

Cys Ala  Cys Cys Gly Gly Gly  Gly Thr Gly Gly Thr  Gly Cys Cys
    4760                4765                4770

Cys Ala  Thr Cys Cys Thr Gly  Gly Thr Cys Gly Ala  Gly Cys Thr
    4775                4780                4785
```

Gly Gly Ala Cys Gly Gly Cys Gly Ala Cys Gly Thr Ala Ala Ala
4790 4795 4800

Cys Gly Gly Cys Cys Ala Cys Ala Ala Gly Thr Thr Cys Ala Gly
4805 4810 4815

Cys Gly Thr Gly Thr Cys Cys Gly Gly Cys Gly Ala Gly Gly Gly
4820 4825 4830

Cys Gly Ala Gly Gly Gly Cys Gly Ala Thr Gly Cys Cys Ala Cys
4835 4840 4845

Cys Thr Ala Cys Gly Gly Cys Ala Ala Gly Cys Thr Gly Ala Cys
4850 4855 4860

Cys Cys Thr Gly Ala Ala Gly Cys Thr Gly Ala Thr Cys Thr Gly
4865 4870 4875

Cys Ala Cys Cys Ala Cys Cys Gly Gly Cys Ala Ala Gly Cys Thr
4880 4885 4890

Gly Cys Cys Cys Gly Thr Gly Cys Cys Cys Thr Gly Gly Cys Cys
4895 4900 4905

Cys Ala Cys Cys Cys Thr Cys Gly Thr Gly Ala Cys Cys Ala Cys
4910 4915 4920

Cys Cys Thr Gly Gly Gly Cys Thr Ala Cys Gly Gly Cys Cys Thr
4925 4930 4935

Gly Cys Ala Gly Thr Gly Cys Thr Thr Cys Gly Cys Cys Cys Gly
4940 4945 4950

Cys Thr Ala Cys Cys Cys Cys Gly Ala Cys Cys Ala Cys Ala Thr
4955 4960 4965

Gly Ala Ala Gly Cys Ala Gly Cys Ala Cys Gly Ala Cys Thr Thr
4970 4975 4980

Cys Thr Thr Cys Ala Ala Gly Thr Cys Cys Gly Cys Cys Ala Thr
4985 4990 4995

Gly Cys Cys Cys Gly Ala Ala Gly Gly Cys Thr Ala Cys Gly Thr
5000 5005 5010

Cys Cys Ala Gly Gly Ala Gly Cys Gly Cys Ala Cys Cys Ala Thr
5015 5020 5025

Cys Thr Thr Cys Thr Thr Cys Ala Ala Gly Gly Ala Cys Gly Ala
5030 5035 5040

Cys Gly Gly Cys Ala Ala Cys Thr Ala Cys Ala Ala Gly Ala Cys
5045 5050 5055

Cys Cys Gly Cys Gly Cys Cys Gly Ala Gly Gly Thr Gly Ala Ala
5060 5065 5070

Gly Thr Thr Cys Gly Ala Gly Gly Gly Cys Gly Ala Cys Ala Cys
5075 5080 5085

Cys Cys Thr Gly Gly Thr Gly Ala Ala Cys Cys Gly Cys Ala Thr
5090 5095 5100

Cys Gly Ala Gly Cys Thr Gly Ala Ala Gly Gly Gly Cys Ala Thr
5105 5110 5115

Cys Gly Ala Cys Thr Thr Cys Ala Ala Gly Gly Ala Gly Gly Ala
5120 5125 5130

Cys Gly Gly Cys Ala Ala Cys Ala Thr Cys Cys Thr Gly Gly Gly
5135 5140 5145

Gly Cys Ala Cys Ala Ala Gly Cys Thr Gly Gly Ala Gly Thr Ala
5150 5155 5160

Cys Ala Ala Cys Thr Ala Cys Ala Ala Cys Ala Gly Cys Cys Ala
5165 5170 5175

Cys Ala Ala Cys Gly Thr Cys Thr Ala Thr Ala Thr Cys Ala Cys
5180 5185 5190

Cys Gly Cys Cys Gly Ala Cys Ala Ala Gly Cys Ala Gly Ala Ala
5195 5200 5205

Gly Ala Ala Cys Gly Gly Cys Ala Thr Cys Ala Ala Gly Gly Cys
5210 5215 5220

Cys Ala Ala Cys Thr Thr Cys Ala Ala Gly Ala Thr Cys Cys Gly
5225 5230 5235

Cys Cys Ala Cys Ala Ala Cys Ala Thr Cys Gly Ala Gly Gly Ala
5240 5245 5250

Cys Gly Gly Cys Gly Gly Cys Gly Thr Gly Cys Ala Gly Cys Thr
5255 5260 5265

Cys Gly Cys Cys Gly Ala Cys Cys Ala Cys Thr Ala Cys Cys Ala
5270 5275 5280

Gly Cys Ala Gly Ala Ala Cys Ala Cys Cys Cys Cys Cys Ala Thr
5285 5290 5295

Cys Gly Gly Cys Gly Ala Cys Gly Gly Cys Cys Cys Cys Gly Thr
5300 5305 5310

Gly Cys Thr Gly Cys Thr Gly Cys Cys Cys Gly Ala Cys Ala Ala
5315 5320 5325

Cys Cys Ala Cys Thr Ala Cys Cys Thr Gly Ala Gly Cys Thr Ala
5330 5335 5340

Cys Cys Ala Gly Thr Cys Cys Ala Ala Gly Cys Thr Gly Ala Gly
5345 5350 5355

Cys Ala Ala Ala Gly Ala Cys Cys Cys Cys Ala Ala Cys Gly Ala
5360 5365 5370

Gly Ala Ala Gly Cys Gly Cys Gly Ala Thr Cys Ala Cys Ala Thr
5375 5380 5385

Gly Gly Thr Cys Cys Thr Gly Cys Thr Gly Gly Ala Gly Thr Thr
5390 5395 5400

Cys Gly Thr Gly Ala Cys Cys Gly Cys Cys Gly Cys Cys Gly Gly
5405 5410 5415

Gly Gly Gly Thr Ala Cys Cys Ala Ala Gly Gly Thr Gly Thr Ala
5420 5425 5430

Cys Gly Ala Cys Cys Cys Cys Gly Ala Gly Cys Ala Gly Ala Gly
5435 5440 5445

Gly Ala Ala Gly Ala Gly Gly Ala Thr Gly Ala Thr Cys Ala Cys
5450 5455 5460

Cys Gly Gly Cys Cys Cys Cys Cys Ala Gly Thr Gly Gly Thr Gly
5465 5470 5475

Gly Gly Cys Cys Ala Gly Gly Thr Gly Cys Ala Ala Gly Cys Ala
5480 5485 5490

Gly Ala Thr Gly Ala Ala Cys Gly Thr Gly Cys Thr Gly Gly Ala
5495 5500 5505

Cys Ala Gly Cys Thr Thr Cys Ala Thr Cys Ala Ala Cys Thr Ala
5510 5515 5520

Cys Thr Ala Cys Gly Ala Cys Ala Gly Cys Gly Ala Gly Ala Ala
5525 5530 5535

Gly Cys Ala Cys Gly Cys Cys Gly Ala Gly Ala Ala Cys Gly Cys
5540 5545 5550

Cys Gly Thr Gly Ala Thr Cys Thr Thr Cys Cys Thr Gly Cys Ala
5555 5560 5565

Cys Gly Gly Cys Ala Ala Cys Gly Cys Cys Ala Cys Thr Ala Gly 5570 5575 5580

Cys Ala Gly Cys Thr Ala Cys Cys Thr Gly Thr Gly Gly Ala Gly
5585 5590 5595

Gly Cys Ala Cys Gly Thr Gly Gly Thr Gly Cys Cys Cys Cys Ala
5600 5605 5610

Cys Ala Thr Cys Gly Ala Gly Cys Cys Cys Gly Thr Gly Gly Cys
5615 5620 5625

Cys Ala Gly Gly Thr Gly Cys Ala Thr Cys Ala Thr Cys Cys Cys
5630 5635 5640

Cys Gly Ala Thr Cys Thr Gly Ala Thr Cys Gly Gly Cys Ala Thr
5645 5650 5655

Gly Gly Gly Cys Ala Ala Gly Ala Gly Cys Gly Gly Cys Ala Ala
5660 5665 5670

Gly Ala Gly Cys Gly Gly Cys Ala Ala Cys Gly Gly Cys Ala Gly
5675 5680 5685

Cys Thr Ala Cys Ala Gly Gly Cys Thr Gly Cys Thr Gly Gly Ala
5690 5695 5700

Cys Cys Ala Cys Thr Ala Cys Ala Ala Gly Thr Ala Cys Cys Thr
5705 5710 5715

Gly Ala Cys Cys Gly Cys Cys Thr Gly Gly Thr Thr Cys Gly Ala
5720 5725 5730

Gly Cys Thr Cys Cys Thr Gly Ala Ala Cys Cys Thr Gly Cys Cys
5735 5740 5745

Cys Ala Ala Gly Ala Ala Gly Ala Thr Cys Ala Thr Cys Thr Thr
5750 5755 5760

Cys Gly Thr Gly Gly Gly Cys Cys Ala Cys Gly Ala Cys Thr Gly
5765 5770 5775

Gly Gly Gly Cys Gly Cys Cys Gly Cys Cys Cys Thr Gly Gly Cys
5780 5785 5790

Cys Thr Thr Cys Cys Ala Cys Thr Ala Cys Gly Cys Cys Thr Ala
5795 5800 5805

Cys Gly Ala Gly Cys Ala Cys Cys Ala Gly Gly Ala Cys Ala Gly
5810 5815 5820

Gly Ala Thr Cys Ala Ala Gly Gly Cys Cys Ala Thr Cys Gly Thr
5825 5830 5835

Gly Cys Ala Cys Ala Thr Gly Gly Ala Gly Ala Gly Cys Gly Thr
5840 5845 5850

Gly Gly Thr Gly Gly Ala Cys Gly Thr Gly Ala Thr Cys Gly Ala
5855 5860 5865

Gly Ala Gly Cys Thr Gly Gly Gly Ala Cys Gly Ala Gly Thr Gly
5870 5875 5880

Gly Cys Cys Ala Gly Ala Cys Ala Thr Cys Gly Ala Gly Gly Ala
5885 5890 5895

Gly Gly Ala Cys Ala Thr Cys Gly Cys Cys Cys Thr Gly Ala Thr
5900 5905 5910

Cys Ala Ala Gly Ala Gly Cys Gly Ala Gly Gly Ala Gly Gly Gly
5915 5920 5925

Cys Gly Ala Gly Ala Ala Gly Ala Thr Gly Gly Thr Gly Cys Thr
5930 5935 5940

Gly Gly Ala Gly Ala Ala Cys Ala Ala Cys Thr Thr Cys Thr Thr
5945 5950 5955

Cys Gly Thr Gly Gly Ala Gly Ala Cys Cys Gly Thr Gly Cys Thr
5960 5965 5970

```
Gly Cys  Cys Cys Ala Gly Cys  Ala Ala Gly Ala Thr  Cys Ala Thr
    5975                 5980                 5985

Gly Ala  Gly Ala Ala Ala Gly  Cys Thr Gly Gly Ala  Gly Cys Cys
    5990                 5995                 6000

Cys Gly  Ala Gly Gly Ala Gly  Thr Thr Cys Gly Cys  Cys Gly Cys
    6005                 6010                 6015

Cys Thr  Ala Cys Cys Thr Gly  Gly Ala Gly Cys Cys  Cys Thr Thr
    6020                 6025                 6030

Cys Ala  Ala Gly Gly Ala Gly  Ala Ala Gly Gly Gly  Cys Gly Ala
    6035                 6040                 6045

Gly Gly  Thr Gly Ala Gly Ala  Ala Gly Ala Cys Cys  Cys Ala Cys
    6050                 6055                 6060

Cys Cys  Thr Gly Ala Gly Cys  Thr Gly Gly Cys Cys  Cys Ala Gly
    6065                 6070                 6075

Ala Gly  Ala Gly Ala Thr Cys  Cys Cys Cys Cys Thr  Gly Gly Thr
    6080                 6085                 6090

Gly Ala  Ala Gly Gly Gly Cys  Cys Cys Ala Thr Gly  Gly Ala Thr
    6095                 6100                 6105

Gly Cys  Ala Thr Gly Ala Cys  Cys Ala Ala Cys Thr  Gly Ala Cys
    6110                 6115                 6120

Ala Gly  Ala Ala Gly Ala Gly  Cys Ala Gly Ala Thr  Thr Gly Cys
    6125                 6130                 6135

Ala Gly  Ala Gly Thr Thr Cys  Ala Ala Ala Gly Ala  Ala Gly Cys
    6140                 6145                 6150

Cys Thr  Thr Cys Thr Cys Ala  Thr Thr Ala Thr Thr  Cys Gly Ala
    6155                 6160                 6165

Cys Ala  Ala Gly Gly Ala Thr  Gly Gly Gly Gly Ala  Cys Gly Gly
    6170                 6175                 6180

Cys Ala  Cys Cys Ala Thr Cys  Ala Cys Cys Ala Cys  Ala Ala Ala
    6185                 6190                 6195

Gly Gly  Ala Ala Cys Thr Thr  Gly Gly Cys Ala Cys  Cys Gly Thr
    6200                 6205                 6210

Thr Ala  Thr Gly Ala Gly Gly  Thr Cys Gly Cys Thr  Thr Gly Gly
    6215                 6220                 6225

Ala Cys  Ala Ala Ala Ala Cys  Cys Cys Ala Ala Cys  Gly Gly Ala
    6230                 6235                 6240

Ala Gly  Cys Ala Gly Ala Ala  Thr Thr Gly Cys Ala  Gly Gly Ala
    6245                 6250                 6255

Thr Ala  Thr Gly Ala Thr Cys  Ala Ala Thr Gly Ala  Ala Gly Thr
    6260                 6265                 6270

Cys Gly  Ala Thr Gly Cys Thr  Gly Ala Thr Gly Gly  Cys Ala Ala
    6275                 6280                 6285

Thr Gly  Gly Ala Ala Cys Gly  Ala Thr Thr Thr Ala  Cys Thr Thr
    6290                 6295                 6300

Thr Cys  Cys Thr Gly Ala Ala  Thr Thr Thr Cys Thr  Thr Ala Cys
    6305                 6310                 6315

Thr Ala  Thr Gly Ala Thr Gly  Gly Cys Thr Ala Gly  Ala Ala Ala
    6320                 6325                 6330

Ala Ala  Thr Gly Ala Ala Gly  Gly Ala Cys Ala Cys  Ala Gly Ala
    6335                 6340                 6345

Cys Ala  Gly Cys Gly Ala Ala  Gly Ala Gly Gly Ala  Ala Ala Thr
    6350                 6355                 6360
```

-continued

```
Cys Cys  Gly Ala Gly Ala Ala  Gly Cys Ala Thr Thr  Cys Cys Gly
    6365                 6370                 6375

Thr Gly  Thr Thr Thr Thr Thr  Gly Ala Cys Ala Ala  Gly Gly Ala
    6380                 6385                 6390

Thr Gly  Gly Gly Ala Ala Cys  Gly Gly Cys Thr Ala  Cys Ala Thr
    6395                 6400                 6405

Cys Ala  Gly Cys Gly Cys Thr  Gly Cys Thr Cys Ala  Gly Thr Thr
    6410                 6415                 6420

Ala Cys  Gly Thr Cys Ala Cys  Gly Thr Cys Ala Thr  Gly Ala Cys
    6425                 6430                 6435

Ala Ala  Ala Cys Cys Thr Cys  Gly Gly Gly Gly Ala  Gly Ala Ala
    6440                 6445                 6450

Gly Thr  Thr Ala Ala Cys Ala  Gly Ala Thr Gly Ala  Ala Gly Ala
    6455                 6460                 6465

Ala Gly  Thr Thr Gly Ala Thr  Gly Ala Ala Ala Thr  Gly Ala Thr
    6470                 6475                 6480

Ala Ala  Gly Gly Gly Ala Ala  Gly Cys Ala Gly Ala  Thr Ala Thr
    6485                 6490                 6495

Cys Gly  Ala Thr Gly Gly Thr  Gly Ala Thr Gly Gly  Cys Cys Ala
    6500                 6505                 6510

Ala Gly  Thr Ala Ala Ala Cys  Thr Ala Thr Gly Ala  Ala Gly Ala
    6515                 6520                 6525

Gly Thr  Thr Thr Gly Thr Ala  Cys Ala Ala Ala Thr  Gly Ala Thr
    6530                 6535                 6540

Gly Ala  Cys Ala Gly Cys Ala  Ala Ala Gly Gly Gly  Gly Gly Gly
    6545                 6550                 6555

Gly Ala  Ala Gly Ala Gly Gly  Cys Gly Cys Thr Gly  Gly Ala Ala
    6560                 6565                 6570

Gly Ala  Ala Ala Ala Ala Cys  Thr Thr Cys Ala Thr  Thr Gly Cys
    6575                 6580                 6585

Cys Gly  Thr Cys Ala Gly Cys  Gly Cys Thr Gly Cys  Cys Ala Ala
    6590                 6595                 6600

Cys Cys  Gly Gly Thr Thr Cys  Ala Ala Gly Ala Ala  Gly Ala Thr
    6605                 6610                 6615

Cys Thr  Cys Cys Ala Gly Cys  Thr Cys Cys Gly Gly  Gly Gly Cys
    6620                 6625                 6630

Ala Cys  Thr Gly Gly Ala Gly  Cys Thr Cys Gly Gly  Cys Ala Ala
    6635                 6640                 6645

Gly Cys  Cys Cys Gly Ala Cys  Gly Thr Gly Gly Thr  Gly Cys Ala
    6650                 6655                 6660

Gly Ala  Thr Cys Gly Thr Gly  Ala Gly Ala Ala Ala  Cys Thr Ala
    6665                 6670                 6675

Cys Ala  Ala Cys Gly Cys Cys  Thr Ala Cys Cys Thr  Gly Ala Gly
    6680                 6685                 6690

Ala Gly  Cys Cys Ala Gly Cys  Gly Ala Cys Gly Ala  Cys Cys Thr
    6695                 6700                 6705

Gly Cys  Cys Cys Ala Ala Gly  Cys Thr Gly Thr Thr  Cys Ala Thr
    6710                 6715                 6720

Cys Gly  Ala Gly Gly Gly Cys  Gly Ala Cys Cys Cys  Cys Gly Gly
    6725                 6730                 6735

Cys Thr  Thr Cys Thr Thr Cys  Ala Gly Cys Ala Ala  Cys Gly Cys
    6740                 6745                 6750

Cys Ala  Thr Cys Gly Thr Gly  Gly Ala Gly Gly Gly  Cys Gly Cys
```

```
    6755                6760                6765

Cys Ala  Ala Gly Ala Ala Gly  Thr Thr Cys Cys Cys  Cys Ala Ala
    6770                6775                6780

Cys Ala  Cys Cys Gly Ala Gly  Thr Thr Cys Gly Thr  Gly Ala Ala
    6785                6790                6795

Gly Gly  Thr Gly Ala Ala Gly  Gly Gly Cys Cys Thr  Gly Cys Ala
    6800                6805                6810

Cys Thr  Thr Cys Cys Thr Cys  Cys Ala Gly Gly Ala  Gly Gly Ala
    6815                6820                6825

Cys Gly  Cys Cys Cys Cys Cys  Gly Ala Cys Gly Ala  Gly Ala Thr
    6830                6835                6840

Gly Gly  Gly Cys Ala Ala Gly  Thr Ala Cys Ala Thr  Cys Ala Ala
    6845                6850                6855

Gly Ala  Gly Cys Thr Thr Cys  Gly Thr Gly Gly Ala  Gly Ala Gly
    6860                6865                6870

Ala Gly  Thr Gly Cys Thr Gly  Ala Ala Gly Ala Ala  Cys Gly Ala
    6875                6880                6885

Gly Cys  Ala Gly Thr Thr Cys  Thr Gly Cys Thr Ala  Cys Gly Ala
    6890                6895                6900

Gly Ala  Ala Cys Gly Ala Gly  Gly Thr Gly Thr Ala  Ala Gly Ala
    6905                6910                6915

Ala Thr  Thr Cys Gly Ala Thr  Ala Thr Cys Ala Ala  Gly Cys Thr
    6920                6925                6930

Thr Ala  Thr Cys Gly Ala Thr  Ala Ala Thr Cys Ala  Ala Cys Cys
    6935                6940                6945

Thr Cys  Thr Gly Gly Ala Thr  Thr Ala Cys Ala Ala  Ala Ala Thr
    6950                6955                6960

Thr Thr  Gly Thr Gly Ala Ala  Ala Gly Ala Thr Thr  Gly Ala Cys
    6965                6970                6975

Thr Gly  Gly Thr Ala Thr Thr  Cys Thr Thr Ala Ala  Cys Thr Ala
    6980                6985                6990

Thr Gly  Thr Thr Gly Cys Thr  Cys Cys Thr Thr Thr  Thr Ala Cys
    6995                7000                7005

Gly Cys  Thr Ala Thr Gly Thr  Gly Gly Ala Thr Ala  Cys Gly Cys
    7010                7015                7020

Thr Gly  Cys Thr Thr Thr Ala  Ala Thr Gly Cys Cys  Thr Thr Thr
    7025                7030                7035

Gly Thr  Ala Thr Cys Ala Thr  Gly Cys Thr Ala Thr  Thr Gly Cys
    7040                7045                7050

Thr Thr  Cys Cys Cys Gly Thr  Ala Thr Gly Gly Cys  Thr Thr Thr
    7055                7060                7065

Cys Ala  Thr Thr Thr Thr Cys  Thr Cys Cys Thr Cys  Cys Thr Thr
    7070                7075                7080

Gly Thr  Ala Thr Ala Ala Ala  Thr Cys Cys Thr Gly  Gly Thr Thr
    7085                7090                7095

Gly Cys  Thr Gly Thr Cys Thr  Cys Thr Thr Thr Ala  Thr Gly Ala
    7100                7105                7110

Gly Gly  Ala Gly Thr Thr Gly  Thr Gly Gly Cys Cys  Cys Gly Thr
    7115                7120                7125

Thr Gly  Thr Cys Ala Gly Gly  Cys Ala Ala Cys Gly  Thr Gly Gly
    7130                7135                7140

Cys Gly  Thr Gly Gly Thr Gly  Thr Gly Cys Ala Cys  Thr Gly Thr
    7145                7150                7155
```

```
Gly Thr  Thr Thr Gly Cys Thr  Gly Ala Cys Gly Cys  Ala Ala Cys
    7160                 7165                 7170

Cys Cys  Cys Cys Ala Cys Thr  Gly Gly Thr Thr Gly  Gly Gly Gly
    7175                 7180                 7185

Cys Ala  Thr Thr Gly Cys Cys  Ala Cys Cys Ala Cys  Cys Thr Gly
    7190                 7195                 7200

Thr Cys  Ala Gly Cys Thr Cys  Cys Thr Thr Thr Cys  Cys Gly Gly
    7205                 7210                 7215

Gly Ala  Cys Thr Thr Thr Cys  Gly Cys Thr Thr Thr  Cys Cys Cys
    7220                 7225                 7230

Cys Cys  Thr Cys Cys Cys Thr  Ala Thr Thr Gly Cys  Cys Ala Cys
    7235                 7240                 7245

Gly Gly  Cys Gly Gly Ala Ala  Cys Thr Cys Ala Thr  Cys Gly Cys
    7250                 7255                 7260

Cys Gly  Cys Cys Thr Gly Cys  Cys Thr Thr Gly Cys  Cys Cys Gly
    7265                 7270                 7275

Cys Thr  Gly Cys Thr Gly Gly  Ala Cys Ala Gly Gly  Gly Gly Cys
    7280                 7285                 7290

Thr Cys  Gly Gly Cys Thr Gly  Thr Thr Gly Gly Gly  Cys Ala Cys
    7295                 7300                 7305

Thr Gly  Ala Cys Ala Ala Thr  Thr Cys Cys Gly Thr  Gly Gly Thr
    7310                 7315                 7320

Gly Thr  Thr Gly Thr Cys Gly  Gly Gly Gly Ala Ala  Ala Thr Cys
    7325                 7330                 7335

Ala Thr  Cys Gly Thr Cys Cys  Thr Thr Thr Cys Cys  Thr Thr Gly
    7340                 7345                 7350

Gly Cys  Thr Gly Cys Thr Cys  Gly Cys Cys Thr Gly  Thr Gly Thr
    7355                 7360                 7365

Thr Gly  Cys Cys Ala Cys Cys  Thr Gly Gly Ala Thr  Thr Cys Thr
    7370                 7375                 7380

Gly Cys  Gly Cys Gly Gly Gly  Ala Cys Gly Thr Cys  Cys Thr Thr
    7385                 7390                 7395

Cys Thr  Gly Cys Thr Ala Cys  Gly Thr Cys Cys Cys  Thr Thr Cys
    7400                 7405                 7410

Gly Gly  Cys Cys Cys Thr Cys  Ala Ala Thr Cys Cys  Ala Gly Cys
    7415                 7420                 7425

Gly Gly  Ala Cys Cys Thr Thr  Cys Cys Thr Thr Cys  Cys Cys Gly
    7430                 7435                 7440

Cys Gly  Gly Cys Cys Thr Gly  Cys Thr Gly Cys Cys  Gly Gly Cys
    7445                 7450                 7455

Thr Cys  Thr Gly Cys Gly Gly  Cys Cys Thr Cys Thr  Thr Cys Cys
    7460                 7465                 7470

Gly Cys  Gly Thr Cys Thr Thr  Cys Gly Cys Cys Thr  Thr Cys Gly
    7475                 7480                 7485

Cys Cys  Cys Thr Cys Ala Gly  Ala Cys Gly Ala Gly  Thr Cys Gly
    7490                 7495                 7500

Gly Ala  Thr Cys Thr Cys Cys  Cys Thr Thr Thr Gly  Gly Gly Cys
    7505                 7510                 7515

Cys Gly  Cys Cys Thr Cys Cys  Cys Cys Gly Cys Ala  Thr Cys Gly
    7520                 7525                 7530

Ala Thr  Ala Cys Cys Gly Thr  Cys Gly Ala Cys Cys  Thr Cys Gly
    7535                 7540                 7545
```

Ala Gly Ala Cys Cys Thr Ala Gly Ala Ala Ala Ala Ala Cys Ala
7550 7555 7560

Thr Gly Gly Ala Gly Cys Ala Ala Thr Cys Ala Cys Ala Ala Gly
7565 7570 7575

Thr Ala Gly Cys Ala Ala Thr Ala Cys Ala Gly Cys Ala Gly Cys
7580 7585 7590

Thr Ala Cys Cys Ala Ala Thr Gly Cys Thr Gly Ala Thr Thr Gly
7595 7600 7605

Thr Gly Cys Cys Thr Gly Gly Cys Thr Ala Gly Ala Ala Gly Cys
7610 7615 7620

Ala Cys Ala Ala Gly Ala Gly Gly Ala Gly Gly Ala Gly Gly Ala
7625 7630 7635

Gly Gly Thr Gly Gly Gly Thr Thr Thr Thr Cys Cys Ala Gly Thr
7640 7645 7650

Cys Ala Cys Ala Cys Cys Thr Cys Ala Gly Gly Thr Ala Cys Cys
7655 7660 7665

Thr Thr Thr Ala Ala Gly Ala Cys Cys Ala Ala Thr Gly Ala Cys
7670 7675 7680

Thr Thr Ala Cys Ala Ala Gly Gly Cys Ala Gly Cys Thr Gly Thr
7685 7690 7695

Ala Gly Ala Thr Cys Thr Thr Ala Gly Cys Cys Ala Cys Thr Thr
7700 7705 7710

Thr Thr Thr Ala Ala Ala Ala Gly Ala Ala Ala Ala Gly Gly Gly
7715 7720 7725

Gly Gly Gly Ala Cys Thr Gly Gly Ala Ala Gly Gly Gly Cys Thr
7730 7735 7740

Ala Ala Thr Thr Cys Ala Cys Thr Cys Cys Cys Ala Ala Cys Gly
7745 7750 7755

Ala Ala Gly Ala Cys Ala Ala Gly Ala Thr Ala Thr Cys Cys Thr
7760 7765 7770

Thr Gly Ala Thr Cys Thr Gly Thr Gly Gly Ala Thr Cys Thr Ala
7775 7780 7785

Cys Cys Ala Cys Ala Cys Ala Cys Ala Ala Gly Gly Cys Thr Ala
7790 7795 7800

Cys Thr Thr Cys Cys Cys Thr Gly Ala Thr Thr Gly Gly Cys Ala
7805 7810 7815

Gly Ala Ala Cys Thr Ala Cys Ala Cys Ala Cys Cys Ala Gly Gly
7820 7825 7830

Gly Cys Cys Ala Gly Gly Gly Ala Thr Cys Ala Gly Ala Thr Ala
7835 7840 7845

Thr Cys Cys Ala Cys Thr Gly Ala Cys Cys Thr Thr Thr Gly Gly
7850 7855 7860

Ala Thr Gly Gly Thr Gly Cys Thr Ala Cys Ala Ala Gly Cys Thr
7865 7870 7875

Ala Gly Thr Ala Cys Cys Ala Gly Thr Thr Gly Ala Gly Cys Ala
7880 7885 7890

Ala Gly Ala Gly Ala Ala Gly Gly Thr Ala Gly Ala Ala Gly Ala
7895 7900 7905

Ala Gly Cys Cys Ala Ala Thr Gly Ala Ala Gly Gly Ala Gly Ala
7910 7915 7920

Gly Ala Ala Cys Ala Cys Cys Cys Gly Cys Thr Thr Gly Thr Thr
7925 7930 7935

Ala Cys Ala Cys Cys Cys Thr Gly Thr Gly Ala Gly Cys Cys Thr

-continued

```
    7940                7945                7950

Gly Cys  Ala Thr Gly Gly Gly  Ala Thr Gly Gly Ala  Thr Gly Ala
    7955                7960                7965

Cys Cys  Cys Gly Gly Ala Gly  Ala Gly Ala Gly Ala  Ala Gly Thr
    7970                7975                7980

Ala Thr  Thr Ala Gly Ala Gly  Thr Gly Gly Ala Gly  Gly Thr Thr
    7985                7990                7995

Thr Gly  Ala Cys Ala Gly Cys  Cys Gly Cys Cys Thr  Ala Gly Cys
    8000                8005                8010

Ala Thr  Thr Thr Cys Ala Thr  Cys Ala Cys Ala Thr  Gly Gly Cys
    8015                8020                8025

Cys Cys  Gly Ala Gly Ala Gly  Cys Thr Gly Cys Ala  Thr Cys Cys
    8030                8035                8040

Gly Gly  Ala Cys Thr Gly Thr  Ala Cys Thr Gly Gly  Gly Thr Cys
    8045                8050                8055

Thr Cys  Thr Cys Thr Gly Gly  Thr Thr Ala Gly Ala  Cys Cys Ala
    8060                8065                8070

Gly Ala  Thr Cys Thr Gly Ala  Gly Cys Cys Thr Gly  Gly Gly Ala
    8075                8080                8085

Gly Cys  Thr Cys Thr Cys Thr  Gly Gly Cys Thr Ala  Ala Cys Thr
    8090                8095                8100

Ala Gly  Gly Gly Ala Ala Cys  Cys Cys Ala Cys Thr  Gly Cys Thr
    8105                8110                8115

Thr Ala  Ala Gly Cys Cys Thr  Cys Ala Ala Thr Ala  Ala Ala Gly
    8120                8125                8130

Cys Thr  Thr Gly Cys Cys Thr  Thr Gly Ala Gly Thr  Gly Cys Thr
    8135                8140                8145

Thr Cys  Ala Ala Gly Thr Ala  Gly Thr Gly Thr Gly  Thr Gly Cys
    8150                8155                8160

Cys Cys  Gly Thr Cys Thr Gly  Thr Thr Gly Thr Gly  Thr Gly Ala
    8165                8170                8175

Cys Thr  Cys Thr Gly Gly Thr  Ala Ala Cys Thr Ala  Gly Ala Gly
    8180                8185                8190

Ala Thr  Cys Cys Cys Thr Cys  Ala Gly Ala Cys Cys  Cys Thr Thr
    8195                8200                8205

Thr Thr  Ala Gly Thr Cys Ala  Gly Thr Gly Thr Gly  Gly Ala Ala
    8210                8215                8220

Ala Ala  Thr Cys Thr Cys Thr  Ala Gly Cys Ala Gly  Gly Gly Cys
    8225                8230                8235

Cys Cys  Gly Thr Thr Thr Ala  Ala Ala Cys Cys Cys  Gly Cys Thr
    8240                8245                8250

Gly Ala  Thr Cys Ala Gly Cys  Cys Thr Cys Gly Ala  Cys Thr Gly
    8255                8260                8265

Thr Gly  Cys Cys Thr Thr Cys  Thr Ala Gly Thr Thr  Gly Cys Cys
    8270                8275                8280

Ala Gly  Cys Cys Ala Thr Cys  Thr Gly Thr Thr Gly  Thr Thr Thr
    8285                8290                8295

Gly Cys  Cys Cys Cys Thr Cys  Cys Cys Cys Cys Gly  Thr Gly Cys
    8300                8305                8310

Cys Thr  Thr Cys Cys Thr Thr  Gly Ala Cys Cys Cys  Thr Gly Gly
    8315                8320                8325

Ala Ala  Gly Gly Thr Gly Cys  Cys Ala Cys Thr Cys  Cys Cys Ala
    8330                8335                8340
```

Cys Thr Gly Thr Cys Cys Thr Thr Thr Cys Cys Thr Ala Ala Thr
8345 8350 8355

Ala Ala Ala Ala Thr Gly Ala Gly Gly Ala Ala Ala Thr Thr Gly
8360 8365 8370

Cys Ala Thr Cys Gly Cys Ala Thr Thr Gly Thr Cys Thr Gly Ala
8375 8380 8385

Gly Thr Ala Gly Gly Thr Gly Thr Cys Ala Thr Thr Cys Thr Ala
8390 8395 8400

Thr Thr Cys Thr Gly Gly Gly Gly Gly Gly Thr Gly Gly Gly Gly
8405 8410 8415

Thr Gly Gly Gly Gly Cys Ala Gly Gly Ala Cys Ala Gly Cys Ala
8420 8425 8430

Ala Gly Gly Gly Gly Gly Ala Gly Gly Ala Thr Thr Gly Gly Gly
8435 8440 8445

Ala Ala Gly Ala Cys Ala Ala Thr Ala Gly Cys Ala Gly Gly Cys
8450 8455 8460

Ala Thr Gly Cys Thr Gly Gly Gly Gly Ala Thr Gly Cys Gly Gly
8465 8470 8475

Thr Gly Gly Gly Cys Thr Cys Thr Ala Thr Gly Gly Cys Thr Thr
8480 8485 8490

Cys Thr Gly Ala Gly Gly Cys Gly Gly Ala Ala Ala Gly Ala Ala
8495 8500 8505

Cys Cys Ala Gly Cys Thr Gly Gly Gly Gly Cys Thr Cys Thr Ala
8510 8515 8520

Gly Gly Gly Gly Gly Thr Ala Thr Cys Cys Cys Cys Ala Cys Gly
8525 8530 8535

Cys Gly Cys Cys Cys Thr Gly Thr Ala Gly Cys Gly Gly Cys Gly
8540 8545 8550

Cys Ala Thr Thr Ala Ala Gly Cys Gly Cys Gly Gly Cys Gly Gly
8555 8560 8565

Gly Thr Gly Thr Gly Gly Thr Gly Gly Thr Thr Ala Cys Gly Cys
8570 8575 8580

Gly Cys Ala Gly Cys Gly Thr Gly Ala Cys Cys Gly Cys Thr Ala
8585 8590 8595

Cys Ala Cys Thr Thr Gly Cys Cys Ala Gly Cys Gly Cys Cys Cys
8600 8605 8610

Thr Ala Gly Cys Gly Cys Cys Cys Gly Cys Thr Cys Cys Thr Thr
8615 8620 8625

Thr Cys Gly Cys Thr Thr Thr Cys Thr Thr Cys Cys Cys Thr Thr
8630 8635 8640

Cys Cys Thr Thr Thr Cys Thr Cys Gly Cys Cys Ala Cys Gly Thr
8645 8650 8655

Thr Cys Gly Cys Cys Gly Gly Cys Thr Thr Thr Cys Cys Cys Cys
8660 8665 8670

Gly Thr Cys Ala Ala Gly Cys Thr Cys Thr Ala Ala Ala Thr Cys
8675 8680 8685

Gly Gly Gly Gly Gly Cys Thr Cys Cys Cys Thr Thr Thr Ala Gly
8690 8695 8700

Gly Gly Thr Thr Cys Cys Gly Ala Thr Thr Thr Ala Gly Thr Gly
8705 8710 8715

Cys Thr Thr Thr Ala Cys Gly Gly Cys Ala Cys Cys Thr Cys Gly
8720 8725 8730

```
Ala Cys Cys Cys Cys Ala Ala Ala Ala Ala Ala Cys Thr Thr Gly
    8735                8740                8745

Ala Thr Thr Ala Gly Gly Gly Thr Gly Ala Thr Gly Gly Thr Thr
    8750                8755                8760

Cys Ala Cys Gly Thr Ala Gly Thr Gly Gly Gly Cys Cys Ala Thr
    8765                8770                8775

Cys Gly Cys Cys Cys Thr Gly Ala Thr Ala Gly Ala Cys Gly Gly
    8780                8785                8790

Thr Thr Thr Thr Thr Cys Gly Cys Cys Cys Thr Thr Thr Gly Ala
    8795                8800                8805

Cys Gly Thr Thr Gly Gly Ala Gly Thr Cys Cys Ala Cys Gly Thr
    8810                8815                8820

Thr Cys Thr Thr Thr Ala Ala Thr Ala Gly Thr Gly Gly Ala Cys
    8825                8830                8835

Thr Cys Thr Thr Gly Thr Thr Cys Cys Ala Ala Ala Cys Thr Gly
    8840                8845                8850

Gly Ala Ala Cys Ala Ala Cys Ala Cys Thr Cys Ala Ala Cys Cys
    8855                8860                8865

Cys Thr Ala Thr Cys Thr Cys Gly Gly Thr Cys Thr Ala Thr Thr
    8870                8875                8880

Cys Thr Thr Thr Thr Gly Ala Thr Thr Thr Ala Thr Ala Ala Gly
    8885                8890                8895

Gly Gly Ala Thr Thr Thr Thr Gly Cys Cys Gly Ala Thr Thr Thr
    8900                8905                8910

Cys Gly Gly Cys Cys Thr Ala Thr Thr Gly Gly Thr Thr Ala Ala
    8915                8920                8925

Ala Ala Ala Ala Thr Gly Ala Gly Cys Thr Gly Ala Thr Thr Thr
    8930                8935                8940

Ala Ala Cys Ala Ala Ala Ala Ala Thr Thr Thr Ala Ala Cys Gly
    8945                8950                8955

Cys Gly Ala Ala Thr Thr Ala Ala Thr Thr Cys Thr Gly Thr Gly
    8960                8965                8970

Gly Ala Ala Thr Gly Thr Gly Thr Gly Thr Cys Ala Gly Thr Thr
    8975                8980                8985

Ala Gly Gly Gly Thr Gly Thr Gly Gly Ala Ala Ala Gly Thr Cys
    8990                8995                9000

Cys Cys Cys Ala Gly Gly Cys Thr Cys Cys Cys Cys Ala Gly Cys
    9005                9010                9015

Ala Gly Gly Cys Ala Gly Ala Ala Gly Thr Ala Thr Gly Cys Ala
    9020                9025                9030

Ala Ala Gly Cys Ala Thr Gly Cys Ala Thr Cys Thr Cys Ala Ala
    9035                9040                9045

Thr Thr Ala Gly Thr Cys Ala Gly Cys Ala Ala Cys Cys Ala Gly
    9050                9055                9060

Gly Thr Gly Thr Gly Gly Ala Ala Ala Gly Thr Cys Cys Cys Cys
    9065                9070                9075

Ala Gly Gly Cys Thr Cys Cys Cys Cys Ala Gly Cys Ala Gly Gly
    9080                9085                9090

Cys Ala Gly Ala Ala Gly Thr Ala Thr Gly Cys Ala Ala Ala Gly
    9095                9100                9105

Cys Ala Thr Gly Cys Ala Thr Cys Thr Cys Ala Ala Thr Thr Ala
    9110                9115                9120

Gly Thr Cys Ala Gly Cys Ala Ala Cys Cys Ala Thr Ala Gly Thr
```

```
    9125                9130                9135

Cys Cys  Cys Gly Cys Cys Cys  Cys Thr Ala Ala Cys  Thr Cys Cys
    9140                9145                9150

Gly Cys  Cys Cys Ala Thr Cys  Cys Cys Gly Cys Cys  Cys Cys Thr
    9155                9160                9165

Ala Ala  Cys Thr Cys Cys Gly  Cys Cys Cys Ala Gly  Thr Thr Cys
    9170                9175                9180

Cys Gly  Cys Cys Cys Ala Thr  Thr Cys Thr Cys Cys  Gly Cys Cys
    9185                9190                9195

Cys Cys  Ala Thr Gly Gly Cys  Thr Gly Ala Cys Thr  Ala Ala Thr
    9200                9205                9210

Thr Thr  Thr Thr Thr Thr Thr  Ala Thr Thr Thr Ala  Thr Gly Cys
    9215                9220                9225

Ala Gly  Ala Gly Gly Cys Cys  Gly Ala Gly Gly Cys  Cys Gly Cys
    9230                9235                9240

Cys Thr  Cys Thr Gly Cys Cys  Thr Cys Thr Gly Ala  Gly Cys Thr
    9245                9250                9255

Ala Thr  Thr Cys Cys Ala Gly  Ala Ala Gly Thr Ala  Gly Thr Gly
    9260                9265                9270

Ala Gly  Gly Ala Gly Gly Cys  Thr Thr Thr Thr Thr  Thr Gly Gly
    9275                9280                9285

Ala Gly  Gly Cys Cys Thr Ala  Gly Gly Cys Thr Thr  Thr Thr Gly
    9290                9295                9300

Cys Ala  Ala Ala Ala Ala Gly  Cys Thr Cys Cys Cys  Gly Gly Gly
    9305                9310                9315

Ala Gly  Cys Thr Thr Gly Thr  Ala Thr Ala Thr Cys  Cys Ala Thr
    9320                9325                9330

Thr Thr  Thr Cys Gly Gly Ala  Thr Cys Thr Gly Ala  Thr Cys Ala
    9335                9340                9345

Gly Cys  Ala Cys Gly Thr Gly  Thr Thr Gly Ala Cys  Ala Ala Thr
    9350                9355                9360

Thr Ala  Ala Thr Cys Ala Thr  Cys Gly Gly Cys Ala  Thr Ala Gly
    9365                9370                9375

Thr Ala  Thr Ala Thr Cys Gly  Gly Cys Ala Thr Ala  Gly Thr Ala
    9380                9385                9390

Thr Ala  Ala Thr Ala Cys Gly  Ala Cys Ala Ala Gly  Gly Thr Gly
    9395                9400                9405

Ala Gly  Gly Ala Ala Cys Thr  Ala Ala Ala Cys Cys  Ala Thr Gly
    9410                9415                9420

Gly Cys  Cys Ala Ala Gly Thr  Thr Gly Ala Cys Cys  Ala Gly Thr
    9425                9430                9435

Gly Cys  Cys Gly Thr Thr Cys  Cys Gly Gly Thr Gly  Cys Thr Cys
    9440                9445                9450

Ala Cys  Cys Gly Cys Gly Cys  Gly Cys Gly Ala Cys  Gly Thr Cys
    9455                9460                9465

Gly Cys  Cys Gly Gly Ala Gly  Cys Gly Gly Thr Cys  Gly Ala Gly
    9470                9475                9480

Thr Thr  Cys Thr Gly Gly Ala  Cys Cys Gly Ala Cys  Cys Gly Gly
    9485                9490                9495

Cys Thr  Cys Gly Gly Gly Thr  Thr Cys Thr Cys Cys  Cys Gly Gly
    9500                9505                9510

Gly Ala  Cys Thr Thr Cys Gly  Thr Gly Gly Ala Gly  Gly Ala Cys
    9515                9520                9525
```

Gly Ala Cys Thr Thr Cys Gly Cys Cys Gly Gly Thr Gly Thr Gly
9530 9535 9540

Gly Thr Cys Cys Gly Gly Gly Ala Cys Gly Ala Cys Gly Thr Gly
9545 9550 9555

Ala Cys Cys Cys Thr Gly Thr Thr Cys Ala Thr Cys Ala Gly Cys
9560 9565 9570

Gly Cys Gly Gly Thr Cys Cys Ala Gly Gly Ala Cys Cys Ala Gly
9575 9580 9585

Gly Thr Gly Gly Thr Gly Cys Cys Gly Gly Ala Cys Ala Ala Cys
9590 9595 9600

Ala Cys Cys Cys Thr Gly Gly Cys Cys Thr Gly Gly Gly Thr Gly
9605 9610 9615

Thr Gly Gly Gly Thr Gly Cys Gly Cys Gly Gly Cys Cys Thr Gly
9620 9625 9630

Gly Ala Cys Gly Ala Gly Cys Thr Gly Thr Ala Cys Gly Cys Cys
9635 9640 9645

Gly Ala Gly Thr Gly Gly Thr Cys Gly Gly Ala Gly Gly Thr Cys
9650 9655 9660

Gly Thr Gly Thr Cys Cys Ala Cys Gly Ala Ala Cys Thr Thr Cys
9665 9670 9675

Cys Gly Gly Gly Ala Cys Gly Cys Cys Thr Cys Cys Gly Gly Gly
9680 9685 9690

Cys Cys Gly Gly Cys Cys Ala Thr Gly Ala Cys Cys Gly Ala Gly
9695 9700 9705

Ala Thr Cys Gly Gly Cys Gly Ala Gly Cys Ala Gly Cys Cys Gly
9710 9715 9720

Thr Gly Gly Gly Gly Gly Cys Gly Gly Gly Ala Gly Thr Thr Cys
9725 9730 9735

Gly Cys Cys Cys Thr Gly Cys Gly Cys Gly Ala Cys Cys Cys Gly
9740 9745 9750

Gly Cys Cys Gly Gly Cys Ala Ala Cys Thr Gly Cys Gly Thr Gly
9755 9760 9765

Cys Ala Cys Thr Thr Cys Gly Thr Gly Gly Cys Cys Gly Ala Gly
9770 9775 9780

Gly Ala Gly Cys Ala Gly Gly Ala Cys Thr Gly Ala Cys Ala Cys
9785 9790 9795

Gly Thr Gly Cys Thr Ala Cys Gly Ala Gly Ala Thr Thr Thr Cys
9800 9805 9810

Gly Ala Thr Thr Cys Cys Ala Cys Cys Gly Cys Cys Gly Cys Cys
9815 9820 9825

Thr Thr Cys Thr Ala Thr Gly Ala Ala Ala Gly Gly Thr Thr Gly
9830 9835 9840

Gly Gly Cys Thr Thr Cys Gly Gly Ala Ala Thr Cys Gly Thr Thr
9845 9850 9855

Thr Thr Cys Cys Gly Gly Gly Ala Cys Gly Cys Cys Gly Gly Cys
9860 9865 9870

Thr Gly Gly Ala Thr Gly Ala Thr Cys Cys Thr Cys Cys Ala Gly
9875 9880 9885

Cys Gly Cys Gly Gly Gly Gly Ala Thr Cys Thr Cys Ala Thr Gly
9890 9895 9900

Cys Thr Gly Gly Ala Gly Thr Thr Cys Thr Thr Cys Gly Cys Cys
9905 9910 9915

Cys Ala Cys Cys Cys Cys Ala Ala Cys Thr Thr Gly Thr Thr Thr
9920 9925 9930

Ala Thr Thr Gly Cys Ala Gly Cys Thr Thr Ala Thr Ala Ala Thr
9935 9940 9945

Gly Gly Thr Thr Ala Cys Ala Ala Ala Thr Ala Ala Ala Gly Cys
9950 9955 9960

Ala Ala Thr Ala Gly Cys Ala Thr Cys Ala Cys Ala Ala Ala Thr
9965 9970 9975

Thr Thr Cys Ala Cys Ala Ala Ala Thr Ala Ala Ala Gly Cys Ala
9980 9985 9990

Thr Thr Thr Thr Thr Thr Thr Cys Ala Cys Thr Gly Cys Ala Thr
9995 10000 10005

Thr Cys Thr Ala Gly Thr Thr Gly Thr Gly Gly Thr Thr Thr Gly
10010 10015 10020

Thr Cys Cys Ala Ala Ala Cys Thr Cys Ala Thr Cys Ala Ala Thr
10025 10030 10035

Gly Thr Ala Thr Cys Thr Thr Ala Thr Cys Ala Thr Gly Thr Cys
10040 10045 10050

Thr Gly Thr Ala Thr Ala Cys Cys Gly Thr Cys Gly Ala Cys Cys
10055 10060 10065

Thr Cys Thr Ala Gly Cys Thr Ala Gly Ala Gly Cys Thr Thr Gly
10070 10075 10080

Gly Cys Gly Thr Ala Ala Thr Cys Ala Thr Gly Gly Thr Cys Ala
10085 10090 10095

Thr Ala Gly Cys Thr Gly Thr Thr Thr Cys Cys Thr Gly Thr Gly
10100 10105 10110

Thr Gly Ala Ala Ala Thr Thr Gly Thr Thr Ala Thr Cys Cys Gly
10115 10120 10125

Cys Thr Cys Ala Cys Ala Ala Thr Thr Cys Cys Ala Cys Ala Cys
10130 10135 10140

Ala Ala Cys Ala Thr Ala Cys Gly Ala Gly Cys Cys Gly Gly Ala
10145 10150 10155

Ala Gly Cys Ala Thr Ala Ala Ala Gly Thr Gly Thr Ala Ala Ala
10160 10165 10170

Gly Cys Cys Thr Gly Gly Gly Gly Thr Gly Cys Cys Thr Ala Ala
10175 10180 10185

Thr Gly Ala Gly Thr Gly Ala Gly Cys Thr Ala Ala Cys Thr Cys
10190 10195 10200

Ala Cys Ala Thr Thr Ala Ala Thr Thr Gly Cys Gly Thr Thr Gly
10205 10210 10215

Cys Gly Cys Thr Cys Ala Cys Thr Gly Cys Cys Cys Gly Cys Thr
10220 10225 10230

Thr Thr Cys Cys Ala Gly Thr Cys Gly Gly Gly Ala Ala Ala Cys
10235 10240 10245

Cys Thr Gly Thr Cys Gly Thr Gly Cys Cys Ala Gly Cys Thr Gly
10250 10255 10260

Cys Ala Thr Thr Ala Ala Thr Gly Ala Ala Thr Cys Gly Gly Cys
10265 10270 10275

Cys Ala Ala Cys Gly Cys Gly Cys Gly Gly Gly Gly Ala Gly Ala
10280 10285 10290

Gly Gly Cys Gly Gly Thr Thr Thr Gly Cys Gly Thr Ala Thr Thr
10295 10300 10305

Gly Gly Gly Cys Gly Cys Thr Cys Thr Thr Cys Cys Gly Cys Thr

```
    10310               10315               10320

Thr Cys  Cys Thr Cys Gly Cys  Thr Cys Ala Cys Thr  Gly Ala Cys
    10325               10330               10335

Thr Cys  Gly Cys Thr Gly Cys  Gly Cys Thr Cys Gly  Gly Thr Cys
    10340               10345               10350

Gly Thr  Thr Cys Gly Gly Cys  Thr Gly Cys Gly Gly  Cys Gly Ala
    10355               10360               10365

Gly Cys  Gly Gly Thr Ala Thr  Cys Ala Gly Cys Thr  Cys Ala Cys
    10370               10375               10380

Thr Cys  Ala Ala Ala Gly Gly  Cys Gly Gly Thr Ala  Ala Thr Ala
    10385               10390               10395

Cys Gly  Gly Thr Thr Ala Thr  Cys Cys Ala Cys Ala  Gly Ala Ala
    10400               10405               10410

Thr Cys  Ala Gly Gly Gly Gly  Ala Thr Ala Ala Cys  Gly Cys Ala
    10415               10420               10425

Gly Gly  Ala Ala Ala Gly Ala  Ala Cys Ala Thr Gly  Thr Gly Ala
    10430               10435               10440

Gly Cys  Ala Ala Ala Ala Gly  Gly Cys Cys Ala Gly  Cys Ala Ala
    10445               10450               10455

Ala Ala  Gly Gly Cys Cys Ala  Gly Gly Ala Ala Cys  Cys Gly Thr
    10460               10465               10470

Ala Ala  Ala Ala Ala Gly Gly  Cys Cys Gly Cys Gly  Thr Thr Gly
    10475               10480               10485

Cys Thr  Gly Gly Cys Gly Thr  Thr Thr Thr Thr Cys  Cys Ala Thr
    10490               10495               10500

Ala Gly  Gly Cys Thr Cys Cys  Gly Cys Cys Cys Cys  Cys Cys Thr
    10505               10510               10515

Gly Ala  Cys Gly Ala Gly Cys  Ala Thr Cys Ala Cys  Ala Ala Ala
    10520               10525               10530

Ala Ala  Thr Cys Gly Ala Cys  Gly Cys Thr Cys Ala  Ala Gly Thr
    10535               10540               10545

Cys Ala  Gly Ala Gly Gly Thr  Gly Gly Cys Gly Ala  Ala Ala Cys
    10550               10555               10560

Cys Cys  Gly Ala Cys Ala Gly  Gly Ala Cys Thr Ala  Thr Ala Ala
    10565               10570               10575

Ala Gly  Ala Thr Ala Cys Cys  Ala Gly Gly Cys Gly  Thr Thr Thr
    10580               10585               10590

Cys Cys  Cys Cys Cys Thr Gly  Gly Ala Ala Gly Cys  Thr Cys Cys
    10595               10600               10605

Cys Thr  Cys Gly Thr Gly Cys  Gly Cys Thr Cys Thr  Cys Cys Thr
    10610               10615               10620

Gly Thr  Thr Cys Cys Gly Ala  Cys Cys Cys Thr Gly  Cys Cys Gly
    10625               10630               10635

Cys Thr  Thr Ala Cys Cys Gly  Gly Ala Thr Ala Cys  Cys Thr Gly
    10640               10645               10650

Thr Cys  Cys Gly Cys Cys Thr  Thr Thr Cys Thr Cys  Cys Cys Thr
    10655               10660               10665

Thr Cys  Gly Gly Gly Ala Ala  Gly Cys Gly Thr Gly  Gly Cys Gly
    10670               10675               10680

Cys Thr  Thr Thr Cys Thr Cys  Ala Thr Ala Gly Cys  Thr Cys Ala
    10685               10690               10695

Cys Gly  Cys Thr Gly Thr Ala  Gly Gly Thr Ala Thr  Cys Thr Cys
    10700               10705               10710
```

```
Ala Gly Thr Thr Cys Gly Gly Thr Gly Thr Ala Gly Gly Thr Cys
    10715               10720               10725

Gly Thr Thr Cys Gly Cys Thr Cys Cys Ala Ala Gly Cys Thr Gly
    10730               10735               10740

Gly Gly Cys Thr Gly Thr Gly Thr Gly Cys Ala Cys Gly Ala Ala
    10745               10750               10755

Cys Cys Cys Cys Cys Cys Gly Thr Thr Cys Ala Gly Cys Cys Cys
    10760               10765               10770

Gly Ala Cys Cys Gly Cys Thr Gly Cys Gly Cys Cys Thr Thr Ala
    10775               10780               10785

Thr Cys Cys Gly Gly Thr Ala Ala Cys Thr Ala Thr Cys Gly Thr
    10790               10795               10800

Cys Thr Thr Gly Ala Gly Thr Cys Cys Ala Ala Cys Cys Cys Gly
    10805               10810               10815

Gly Thr Ala Ala Gly Ala Cys Ala Cys Gly Ala Cys Thr Thr Ala
    10820               10825               10830

Thr Cys Gly Cys Cys Ala Cys Thr Gly Gly Cys Ala Gly Cys Ala
    10835               10840               10845

Gly Cys Cys Ala Cys Thr Gly Gly Thr Ala Ala Cys Ala Gly Gly
    10850               10855               10860

Ala Thr Thr Ala Gly Cys Ala Gly Ala Gly Cys Gly Ala Gly Gly
    10865               10870               10875

Thr Ala Thr Gly Thr Ala Gly Gly Cys Gly Gly Thr Gly Cys Thr
    10880               10885               10890

Ala Cys Ala Gly Ala Gly Thr Thr Cys Thr Thr Gly Ala Ala Gly
    10895               10900               10905

Thr Gly Gly Thr Gly Gly Cys Cys Thr Ala Ala Cys Thr Ala Cys
    10910               10915               10920

Gly Gly Cys Thr Ala Cys Ala Cys Thr Ala Gly Ala Ala Gly Ala
    10925               10930               10935

Ala Cys Ala Gly Thr Ala Thr Thr Thr Gly Gly Thr Ala Thr Cys
    10940               10945               10950

Thr Gly Cys Gly Cys Thr Cys Thr Gly Cys Thr Gly Ala Ala Gly
    10955               10960               10965

Cys Cys Ala Gly Thr Thr Ala Cys Cys Thr Thr Cys Gly Gly Ala
    10970               10975               10980

Ala Ala Ala Ala Gly Ala Gly Thr Thr Gly Gly Thr Ala Gly Cys
    10985               10990               10995

Thr Cys Thr Thr Gly Ala Thr Cys Cys Gly Gly Cys Ala Ala Ala
    11000               11005               11010

Cys Ala Ala Ala Cys Cys Ala Cys Cys Gly Cys Thr Gly Gly Thr
    11015               11020               11025

Ala Gly Cys Gly Gly Thr Gly Gly Thr Thr Thr Thr Thr Thr Thr
    11030               11035               11040

Gly Thr Thr Thr Gly Cys Ala Ala Gly Cys Ala Gly Cys Ala Gly
    11045               11050               11055

Ala Thr Thr Ala Cys Gly Cys Gly Cys Ala Gly Ala Ala Ala Ala
    11060               11065               11070

Ala Ala Ala Gly Gly Ala Thr Cys Thr Cys Ala Ala Gly Ala Ala
    11075               11080               11085

Gly Ala Thr Cys Cys Thr Thr Thr Gly Ala Thr Cys Thr Thr Thr
    11090               11095               11100
```

Thr Cys Thr Ala Cys Gly Gly Gly Gly Thr Cys Thr Gly Ala Cys
11105 11110 11115

Gly Cys Thr Cys Ala Gly Thr Gly Gly Ala Ala Cys Gly Ala Ala
11120 11125 11130

Ala Ala Cys Thr Cys Ala Cys Gly Thr Thr Ala Ala Gly Gly Gly
11135 11140 11145

Ala Thr Thr Thr Thr Gly Gly Thr Cys Ala Thr Gly Ala Gly Ala
11150 11155 11160

Thr Thr Ala Thr Cys Ala Ala Ala Ala Ala Gly Gly Ala Thr Cys
11165 11170 11175

Thr Thr Cys Ala Cys Cys Thr Ala Gly Ala Thr Cys Cys Thr Thr
11180 11185 11190

Thr Thr Ala Ala Ala Thr Thr Ala Ala Ala Ala Ala Thr Gly Ala
11195 11200 11205

Ala Gly Thr Thr Thr Thr Ala Ala Ala Thr Cys Ala Ala Thr Cys
11210 11215 11220

Thr Ala Ala Ala Gly Thr Ala Thr Ala Thr Ala Thr Gly Ala Gly
11225 11230 11235

Thr Ala Ala Ala Cys Thr Thr Gly Gly Thr Cys Thr Gly Ala Cys
11240 11245 11250

Ala Gly Thr Thr Ala Cys Cys Ala Ala Thr Gly Cys Thr Thr Ala
11255 11260 11265

Ala Thr Cys Ala Gly Thr Gly Ala Gly Gly Cys Ala Cys Cys Thr
11270 11275 11280

Ala Thr Cys Thr Cys Ala Gly Cys Gly Ala Thr Cys Thr Gly Thr
11285 11290 11295

Cys Thr Ala Thr Thr Thr Cys Gly Thr Thr Cys Ala Thr Cys Cys
11300 11305 11310

Ala Thr Ala Gly Thr Thr Gly Cys Cys Thr Gly Ala Cys Thr Cys
11315 11320 11325

Cys Cys Cys Gly Thr Cys Gly Thr Gly Thr Ala Gly Ala Thr Ala
11330 11335 11340

Ala Cys Thr Ala Cys Gly Ala Thr Ala Cys Gly Gly Gly Ala Gly
11345 11350 11355

Gly Gly Cys Thr Thr Ala Cys Cys Ala Thr Cys Thr Gly Gly Cys
11360 11365 11370

Cys Cys Cys Ala Gly Thr Gly Cys Thr Gly Cys Ala Ala Thr Gly
11375 11380 11385

Ala Thr Ala Cys Cys Gly Cys Gly Ala Gly Ala Cys Cys Cys Ala
11390 11395 11400

Cys Gly Cys Thr Cys Ala Cys Cys Gly Gly Cys Thr Cys Cys Ala
11405 11410 11415

Gly Ala Thr Thr Thr Ala Thr Cys Ala Gly Cys Ala Ala Thr Ala
11420 11425 11430

Ala Ala Cys Cys Ala Gly Cys Cys Ala Gly Cys Cys Gly Gly Ala
11435 11440 11445

Ala Gly Gly Gly Cys Cys Gly Ala Gly Cys Gly Cys Ala Gly Ala
11450 11455 11460

Ala Gly Thr Gly Gly Thr Cys Cys Thr Gly Cys Ala Ala Cys Thr
11465 11470 11475

Thr Thr Ala Thr Cys Cys Gly Cys Cys Thr Cys Cys Ala Thr Cys
11480 11485 11490

Cys Ala Gly Thr Cys Thr Ala Thr Thr Ala Ala Thr Thr Gly Thr

```
    11495               11500               11505

Thr Gly   Cys Cys Gly Gly Gly   Ala Ala Gly Cys Thr   Ala Gly Ala
    11510               11515               11520

Gly Thr   Ala Ala Gly Thr Ala   Gly Thr Thr Cys Gly   Cys Cys Ala
    11525               11530               11535

Gly Thr   Thr Ala Ala Thr Ala   Gly Thr Thr Thr Gly   Cys Gly Cys
    11540               11545               11550

Ala Ala   Cys Gly Thr Thr Gly   Thr Thr Gly Cys Cys   Ala Thr Thr
    11555               11560               11565

Gly Cys   Thr Ala Cys Ala Gly   Gly Cys Ala Thr Cys   Gly Thr Gly
    11570               11575               11580

Gly Thr   Gly Thr Cys Ala Cys   Gly Cys Thr Cys Gly   Thr Cys Gly
    11585               11590               11595

Thr Thr   Thr Gly Gly Thr Ala   Thr Gly Gly Cys Thr   Thr Cys Ala
    11600               11605               11610

Thr Thr   Cys Ala Gly Cys Thr   Cys Cys Gly Gly Thr   Thr Cys Cys
    11615               11620               11625

Cys Ala   Ala Cys Gly Ala Thr   Cys Ala Ala Gly Gly   Cys Gly Ala
    11630               11635               11640

Gly Thr   Thr Ala Cys Ala Thr   Gly Ala Thr Cys Cys   Cys Cys Cys
    11645               11650               11655

Ala Thr   Gly Thr Thr Gly Thr   Gly Cys Ala Ala Ala   Ala Ala Ala
    11660               11665               11670

Gly Cys   Gly Gly Thr Thr Ala   Gly Cys Thr Cys Cys   Thr Thr Cys
    11675               11680               11685

Gly Gly   Thr Cys Cys Thr Cys   Cys Gly Ala Thr Cys   Gly Thr Thr
    11690               11695               11700

Gly Thr   Cys Ala Gly Ala Ala   Gly Thr Ala Ala Gly   Thr Thr Gly
    11705               11710               11715

Gly Cys   Cys Gly Cys Ala Gly   Thr Gly Thr Thr Ala   Thr Cys Ala
    11720               11725               11730

Cys Thr   Cys Ala Thr Gly Gly   Thr Thr Ala Thr Gly   Gly Cys Ala
    11735               11740               11745

Gly Cys   Ala Cys Thr Gly Cys   Ala Thr Ala Ala Thr   Thr Cys Thr
    11750               11755               11760

Cys Thr   Thr Ala Cys Thr Gly   Thr Cys Ala Thr Gly   Cys Cys Ala
    11765               11770               11775

Thr Cys   Cys Gly Thr Ala Ala   Gly Ala Thr Gly Cys   Thr Thr Thr
    11780               11785               11790

Thr Cys   Thr Gly Thr Gly Ala   Cys Thr Gly Gly Thr   Gly Ala Gly
    11795               11800               11805

Thr Ala   Cys Thr Cys Ala Ala   Cys Cys Ala Ala Gly   Thr Cys Ala
    11810               11815               11820

Thr Thr   Cys Thr Gly Ala Gly   Ala Ala Thr Ala Gly   Thr Gly Thr
    11825               11830               11835

Ala Thr   Gly Cys Gly Gly Cys   Gly Ala Cys Cys Gly   Ala Gly Thr
    11840               11845               11850

Thr Gly   Cys Thr Cys Thr Thr   Gly Cys Cys Cys Gly   Gly Cys Gly
    11855               11860               11865

Thr Cys   Ala Ala Thr Ala Cys   Gly Gly Gly Ala Thr   Ala Ala Thr
    11870               11875               11880

Ala Cys   Cys Gly Cys Gly Cys   Cys Ala Cys Ala Thr   Ala Gly Cys
    11885               11890               11895
```

```
Ala Gly   Ala Ala Cys Thr Thr   Thr Ala Ala Ala Ala   Gly Thr Gly
    11900                 11905                 11910

Cys Thr   Cys Ala Thr Cys Ala   Thr Thr Gly Gly Ala   Ala Ala Ala
    11915                 11920                 11925

Cys Gly   Thr Thr Cys Thr Thr   Cys Gly Gly Gly Gly   Cys Gly Ala
    11930                 11935                 11940

Ala Ala   Ala Cys Thr Cys Thr   Cys Ala Ala Gly Gly   Ala Thr Cys
    11945                 11950                 11955

Thr Thr   Ala Cys Cys Gly Cys   Thr Gly Thr Thr Gly   Ala Gly Ala
    11960                 11965                 11970

Thr Cys   Cys Ala Gly Thr Thr   Cys Gly Ala Thr Gly   Thr Ala Ala
    11975                 11980                 11985

Cys Cys   Cys Ala Cys Thr Cys   Gly Thr Gly Cys Ala   Cys Cys Cys
    11990                 11995                 12000

Ala Ala   Cys Thr Gly Ala Thr   Cys Thr Thr Cys Ala   Gly Cys Ala
    12005                 12010                 12015

Thr Cys   Thr Thr Thr Thr Ala   Cys Thr Thr Thr Cys   Ala Cys Cys
    12020                 12025                 12030

Ala Gly   Cys Gly Thr Thr Thr   Cys Thr Gly Gly Gly   Thr Gly Ala
    12035                 12040                 12045

Gly Cys   Ala Ala Ala Ala Ala   Cys Ala Gly Gly Ala   Ala Gly Gly
    12050                 12055                 12060

Cys Ala   Ala Ala Ala Thr Gly   Cys Cys Gly Cys Ala   Ala Ala Ala
    12065                 12070                 12075

Ala Ala   Gly Gly Gly Ala Ala   Thr Ala Ala Gly Gly   Gly Cys Gly
    12080                 12085                 12090

Ala Cys   Ala Cys Gly Gly Ala   Ala Ala Thr Gly Thr   Thr Gly Ala
    12095                 12100                 12105

Ala Thr   Ala Cys Thr Cys Ala   Thr Ala Cys Thr Cys   Thr Thr Cys
    12110                 12115                 12120

Cys Thr   Thr Thr Thr Thr Cys   Ala Ala Thr Ala Thr   Thr Ala Thr
    12125                 12130                 12135

Thr Gly   Ala Ala Gly Cys Ala   Thr Thr Thr Ala Thr   Cys Ala Gly
    12140                 12145                 12150

Gly Gly   Thr Thr Ala Thr Thr   Gly Thr Cys Thr Cys   Ala Thr Gly
    12155                 12160                 12165

Ala Gly   Cys Gly Gly Ala Thr   Ala Cys Ala Thr Ala   Thr Thr Thr
    12170                 12175                 12180

Gly Ala   Ala Thr Gly Thr Ala   Thr Thr Thr Ala Gly   Ala Ala Ala
    12185                 12190                 12195

Ala Ala   Thr Ala Ala Ala Cys   Ala Ala Ala Thr Ala   Gly Gly Gly
    12200                 12205                 12210

Gly Thr   Thr Cys Cys Gly Cys   Gly Cys Ala Cys Ala   Thr Thr Thr
    12215                 12220                 12225

Cys Cys   Cys Cys Gly Ala Ala   Ala Ala Gly Thr Gly   Cys Cys Ala
    12230                 12235                 12240

Cys Cys   Thr Gly Ala Cys
    12245
```

<210> SEQ ID NO 13
<211> LENGTH: 11706
<212> TYPE: PRT
<213> ORGANISM: Artificial Sequence
<220> FEATURE:

<223> OTHER INFORMATION: synthetic constructs

<400> SEQUENCE: 13

```
Gly Thr Cys Gly Ala Cys Gly Gly Ala Thr Cys Gly Gly Gly Ala Gly
1               5                   10                  15

Ala Thr Cys Thr Cys Cys Cys Gly Ala Thr Cys Cys Cys Cys Thr Ala
            20                  25                  30

Thr Gly Gly Thr Gly Cys Ala Cys Thr Cys Thr Cys Ala Gly Thr Ala
        35                  40                  45

Cys Ala Ala Thr Cys Thr Gly Cys Thr Cys Thr Gly Ala Thr Gly Cys
    50                  55                  60

Cys Gly Cys Ala Thr Ala Gly Thr Thr Ala Ala Gly Cys Cys Ala Gly
65                  70                  75                  80

Thr Ala Thr Cys Thr Gly Cys Thr Cys Cys Cys Thr Gly Cys Thr Thr
                85                  90                  95

Gly Thr Gly Thr Gly Thr Thr Gly Gly Ala Gly Gly Thr Cys Gly Cys
            100                 105                 110

Thr Gly Ala Gly Thr Ala Gly Thr Gly Cys Gly Cys Gly Ala Gly Cys
        115                 120                 125

Ala Ala Ala Ala Thr Thr Thr Ala Ala Gly Cys Thr Ala Cys Ala Ala
    130                 135                 140

Cys Ala Ala Gly Gly Cys Ala Ala Gly Gly Cys Thr Thr Gly Ala Cys
145                 150                 155                 160

Cys Gly Ala Cys Ala Ala Thr Thr Gly Cys Ala Thr Gly Ala Ala Gly
                165                 170                 175

Ala Ala Thr Cys Thr Gly Cys Thr Thr Ala Gly Gly Gly Thr Thr Ala
            180                 185                 190

Gly Gly Cys Gly Thr Thr Thr Thr Gly Cys Gly Cys Thr Gly Cys Thr
        195                 200                 205

Thr Cys Gly Cys Gly Ala Thr Gly Thr Ala Cys Gly Gly Gly Cys Cys
    210                 215                 220

Ala Gly Ala Thr Ala Thr Ala Cys Gly Cys Gly Thr Thr Gly Ala Cys
225                 230                 235                 240

Ala Thr Thr Gly Ala Thr Thr Ala Thr Thr Gly Ala Cys Thr Ala Gly
                245                 250                 255

Thr Thr Ala Thr Thr Ala Ala Thr Ala Gly Thr Ala Ala Thr Cys Ala
            260                 265                 270

Ala Thr Thr Ala Cys Gly Gly Gly Gly Thr Cys Ala Thr Thr Ala Gly
        275                 280                 285

Thr Thr Cys Ala Thr Ala Gly Cys Cys Cys Ala Thr Ala Thr Ala Thr
    290                 295                 300

Gly Gly Ala Gly Thr Thr Cys Cys Gly Cys Gly Thr Thr Ala Cys Ala
305                 310                 315                 320

Thr Ala Ala Cys Thr Thr Ala Cys Gly Gly Thr Ala Ala Ala Thr Gly
                325                 330                 335

Gly Cys Cys Cys Gly Cys Cys Thr Gly Gly Cys Thr Gly Ala Cys Cys
            340                 345                 350

Gly Cys Cys Cys Ala Ala Cys Gly Ala Cys Cys Cys Cys Cys Gly Cys
        355                 360                 365

Cys Cys Ala Thr Thr Gly Ala Cys Gly Thr Cys Ala Ala Thr Ala Ala
    370                 375                 380

Thr Gly Ala Cys Gly Thr Ala Thr Gly Thr Thr Cys Cys Cys Ala Thr
385                 390                 395                 400
```

```
Ala Gly Thr Ala Ala Cys Gly Cys Cys Ala Ala Thr Ala Gly Gly Gly
                405                 410                 415

Ala Cys Thr Thr Thr Cys Cys Ala Thr Thr Gly Ala Cys Gly Thr Cys
            420                 425                 430

Ala Ala Thr Gly Gly Gly Thr Gly Gly Ala Gly Thr Ala Thr Thr Thr
        435                 440                 445

Ala Cys Gly Gly Thr Ala Ala Ala Cys Thr Gly Cys Cys Cys Ala Cys
    450                 455                 460

Thr Thr Gly Gly Cys Ala Gly Thr Ala Cys Ala Thr Cys Ala Ala Gly
465                 470                 475                 480

Thr Gly Thr Ala Thr Cys Ala Thr Ala Thr Gly Cys Cys Ala Ala Gly
                485                 490                 495

Thr Ala Cys Gly Cys Cys Cys Cys Cys Thr Ala Thr Thr Gly Ala Cys
            500                 505                 510

Gly Thr Cys Ala Ala Thr Gly Ala Cys Gly Gly Thr Ala Ala Ala Thr
        515                 520                 525

Gly Gly Cys Cys Cys Gly Cys Cys Thr Gly Gly Cys Ala Thr Thr Ala
    530                 535                 540

Thr Gly Cys Cys Cys Ala Gly Thr Ala Cys Ala Thr Gly Ala Cys Cys
545                 550                 555                 560

Thr Thr Ala Thr Gly Gly Gly Ala Cys Thr Thr Thr Cys Cys Thr Ala
                565                 570                 575

Cys Thr Thr Gly Gly Cys Ala Gly Thr Ala Cys Ala Thr Cys Thr Ala
            580                 585                 590

Cys Gly Thr Ala Thr Thr Ala Gly Thr Cys Ala Thr Cys Gly Cys Thr
        595                 600                 605

Ala Thr Thr Ala Cys Cys Ala Thr Gly Gly Thr Gly Ala Thr Gly Cys
    610                 615                 620

Gly Gly Thr Thr Thr Thr Gly Gly Cys Ala Gly Thr Ala Cys Ala Thr
625                 630                 635                 640

Cys Ala Ala Thr Gly Gly Gly Cys Gly Thr Gly Gly Ala Thr Ala Gly
                645                 650                 655

Cys Gly Gly Thr Thr Thr Gly Ala Cys Thr Cys Ala Cys Gly Gly Gly
            660                 665                 670

Gly Ala Thr Thr Thr Cys Cys Ala Ala Gly Thr Cys Thr Cys Cys Ala
        675                 680                 685

Cys Cys Cys Cys Ala Thr Thr Gly Ala Cys Gly Thr Cys Ala Ala Thr
    690                 695                 700

Gly Gly Gly Ala Gly Thr Thr Thr Gly Thr Thr Thr Thr Gly Gly Cys
705                 710                 715                 720

Ala Cys Cys Ala Ala Ala Ala Thr Cys Ala Ala Cys Gly Gly Gly Ala
                725                 730                 735

Cys Thr Thr Thr Cys Cys Ala Ala Ala Ala Thr Gly Thr Cys Gly Thr
            740                 745                 750

Ala Ala Cys Ala Ala Cys Thr Cys Cys Gly Cys Cys Cys Cys Ala Thr
        755                 760                 765

Thr Gly Ala Cys Gly Cys Ala Ala Ala Thr Gly Gly Gly Cys Gly Gly
    770                 775                 780

Thr Ala Gly Gly Cys Gly Thr Gly Thr Ala Cys Gly Gly Thr Gly Gly
785                 790                 795                 800

Gly Ala Gly Gly Thr Cys Thr Ala Thr Ala Thr Ala Ala Gly Cys Ala
                805                 810                 815

Gly Cys Gly Cys Gly Thr Thr Thr Thr Gly Cys Cys Thr Gly Thr Ala
```

```
            820                 825                 830

Cys Thr Gly Gly Gly Thr Cys Thr Cys Thr Cys Thr Gly Gly Thr Thr
        835                 840                 845

Ala Gly Ala Cys Cys Ala Gly Ala Thr Cys Thr Gly Ala Gly Cys Cys
    850                 855                 860

Thr Gly Gly Gly Ala Gly Cys Thr Cys Thr Cys Thr Gly Gly Cys Thr
865                 870                 875                 880

Ala Ala Cys Thr Ala Gly Gly Gly Ala Ala Cys Cys Cys Ala Cys Thr
                885                 890                 895

Gly Cys Thr Thr Ala Ala Gly Cys Cys Thr Cys Ala Ala Thr Ala Ala
            900                 905                 910

Ala Gly Cys Thr Thr Gly Cys Cys Thr Thr Gly Ala Gly Thr Gly Cys
        915                 920                 925

Thr Thr Cys Ala Ala Gly Thr Ala Gly Thr Gly Thr Gly Thr Gly Cys
    930                 935                 940

Cys Cys Gly Thr Cys Thr Gly Thr Thr Gly Thr Gly Thr Gly Ala Cys
945                 950                 955                 960

Thr Cys Thr Gly Gly Thr Ala Ala Cys Thr Ala Gly Ala Gly Ala Thr
                965                 970                 975

Cys Cys Cys Thr Cys Ala Gly Ala Cys Cys Cys Thr Thr Thr Thr Ala
            980                 985                 990

Gly Thr Cys Ala Gly Thr Gly Thr  Gly Gly Ala Ala Ala  Ala Thr Cys
        995                 1000                1005

Thr Cys  Thr Ala Gly Cys Ala  Gly Thr Gly Gly Cys  Gly Cys Cys
    1010                 1015                 1020

Cys Gly  Ala Ala Cys Ala Gly  Gly Gly Ala Cys Thr  Thr Gly Ala
    1025                 1030                 1035

Ala Ala  Gly Cys Gly Ala Ala  Ala Gly Gly Gly Ala  Ala Ala Cys
    1040                 1045                 1050

Cys Ala  Gly Ala Gly Gly Ala  Gly Cys Thr Cys Thr  Cys Thr Cys
    1055                 1060                 1065

Gly Ala  Cys Gly Cys Ala Gly  Gly Ala Cys Thr Cys  Gly Gly Cys
    1070                 1075                 1080

Thr Thr  Gly Cys Thr Gly Ala  Ala Gly Cys Gly Cys  Gly Cys Ala
    1085                 1090                 1095

Cys Gly  Gly Cys Ala Ala Gly  Ala Gly Gly Cys Gly  Ala Gly Gly
    1100                 1105                 1110

Gly Gly  Cys Gly Gly Cys Gly  Ala Cys Thr Gly Gly  Thr Gly Ala
    1115                 1120                 1125

Gly Thr  Ala Cys Gly Cys Cys  Ala Ala Ala Ala Ala  Thr Thr Thr
    1130                 1135                 1140

Thr Gly  Ala Cys Thr Ala Gly  Cys Gly Gly Ala Gly  Gly Cys Thr
    1145                 1150                 1155

Ala Gly  Ala Ala Gly Gly Ala  Gly Ala Gly Ala Gly  Ala Thr Gly
    1160                 1165                 1170

Gly Gly  Thr Gly Cys Gly Ala  Gly Ala Gly Cys Gly  Thr Cys Ala
    1175                 1180                 1185

Gly Thr  Ala Thr Thr Ala Ala  Gly Cys Gly Gly Gly  Gly Gly Ala
    1190                 1195                 1200

Gly Ala  Ala Thr Thr Ala Gly  Ala Thr Cys Gly Cys  Gly Ala Thr
    1205                 1210                 1215

Gly Gly  Gly Ala Ala Ala Ala  Ala Ala Thr Thr Cys  Gly Gly Thr
    1220                 1225                 1230
```

-continued

```
Thr Ala  Ala Gly Gly Cys Cys  Ala Gly Gly Gly Gly  Gly Ala Ala
    1235                 1240                 1245

Ala Gly  Ala Ala Ala Ala Ala  Ala Thr Ala Thr Ala  Ala Ala Thr
    1250                 1255                 1260

Thr Ala  Ala Ala Ala Cys Ala  Thr Ala Thr Ala Gly  Thr Ala Thr
    1265                 1270                 1275

Gly Gly  Gly Cys Ala Ala Gly  Cys Ala Gly Gly Gly  Ala Gly Cys
    1280                 1285                 1290

Thr Ala  Gly Ala Ala Cys Gly  Ala Thr Thr Cys Gly  Cys Ala Gly
    1295                 1300                 1305

Thr Thr  Ala Ala Thr Cys Cys  Thr Gly Gly Cys Cys  Thr Gly Thr
    1310                 1315                 1320

Thr Ala  Gly Ala Ala Ala Cys  Ala Thr Cys Ala Gly  Ala Ala Gly
    1325                 1330                 1335

Gly Cys  Thr Gly Thr Ala Gly  Ala Cys Ala Ala Ala  Thr Ala Cys
    1340                 1345                 1350

Thr Gly  Gly Gly Ala Cys Ala  Gly Cys Thr Ala Cys  Ala Ala Cys
    1355                 1360                 1365

Cys Ala  Thr Cys Cys Cys Thr  Thr Cys Ala Gly Ala  Cys Ala Gly
    1370                 1375                 1380

Gly Ala  Thr Cys Ala Gly Ala  Ala Gly Ala Ala Cys  Thr Thr Ala
    1385                 1390                 1395

Gly Ala  Thr Cys Ala Thr Thr  Ala Thr Ala Thr Ala  Ala Thr Ala
    1400                 1405                 1410

Cys Ala  Gly Thr Ala Gly Cys  Ala Ala Cys Cys Cys  Thr Cys Thr
    1415                 1420                 1425

Ala Thr  Thr Gly Thr Gly Thr  Gly Cys Ala Thr Cys  Ala Ala Ala
    1430                 1435                 1440

Gly Gly  Ala Thr Ala Gly Ala  Gly Ala Thr Ala Ala  Ala Ala Gly
    1445                 1450                 1455

Ala Cys  Ala Cys Cys Ala Ala  Gly Gly Ala Ala Gly  Cys Thr Thr
    1460                 1465                 1470

Thr Ala  Gly Ala Cys Ala Ala  Gly Ala Thr Ala Gly  Ala Gly Gly
    1475                 1480                 1485

Ala Ala  Gly Ala Gly Cys Ala  Ala Ala Ala Cys Ala  Ala Ala Ala
    1490                 1495                 1500

Gly Thr  Ala Ala Gly Ala Cys  Cys Ala Cys Cys Gly  Cys Ala Cys
    1505                 1510                 1515

Ala Gly  Cys Ala Ala Gly Cys  Gly Gly Cys Cys Gly  Cys Thr Gly
    1520                 1525                 1530

Ala Thr  Cys Thr Thr Cys Ala  Gly Ala Cys Cys Thr  Gly Gly Ala
    1535                 1540                 1545

Gly Gly  Ala Gly Gly Ala Gly  Ala Thr Ala Thr Gly  Ala Gly Gly
    1550                 1555                 1560

Gly Ala  Cys Ala Ala Thr Thr  Gly Gly Ala Gly Ala  Ala Gly Thr
    1565                 1570                 1575

Gly Ala  Ala Thr Thr Ala Thr  Ala Thr Ala Ala Ala  Thr Ala Thr
    1580                 1585                 1590

Ala Ala  Ala Gly Thr Ala Gly  Thr Ala Ala Ala Ala  Ala Thr Thr
    1595                 1600                 1605

Gly Ala  Ala Cys Cys Ala Thr  Thr Ala Gly Gly Ala  Gly Thr Ala
    1610                 1615                 1620
```

```
Gly Cys  Ala Cys Cys Cys Ala  Cys Cys Ala Ala Gly  Gly Cys Ala
    1625                 1630                 1635

Ala Ala  Gly Ala Gly Ala Ala  Gly Ala Gly Thr Gly  Gly Thr Gly
    1640                 1645                 1650

Cys Ala  Gly Ala Gly Ala Gly  Ala Ala Ala Ala Ala  Ala Gly Ala
    1655                 1660                 1665

Gly Cys  Ala Gly Thr Gly Gly  Gly Ala Ala Thr Ala  Gly Gly Ala
    1670                 1675                 1680

Gly Cys  Thr Thr Thr Gly Thr  Thr Cys Cys Thr Thr  Gly Gly Gly
    1685                 1690                 1695

Thr Thr  Cys Thr Thr Gly Gly  Gly Ala Gly Cys Ala  Gly Cys Ala
    1700                 1705                 1710

Gly Gly  Ala Ala Gly Cys Ala  Cys Thr Ala Thr Gly  Gly Gly Cys
    1715                 1720                 1725

Gly Cys  Ala Gly Cys Gly Thr  Cys Ala Ala Thr Gly  Ala Cys Gly
    1730                 1735                 1740

Cys Thr  Gly Ala Cys Gly Gly  Thr Ala Cys Ala Gly  Gly Cys Cys
    1745                 1750                 1755

Ala Gly  Ala Cys Ala Ala Thr  Thr Ala Thr Thr Gly  Thr Cys Thr
    1760                 1765                 1770

Gly Gly  Thr Ala Thr Ala Gly  Thr Gly Cys Ala Gly  Cys Ala Gly
    1775                 1780                 1785

Cys Ala  Gly Ala Ala Cys Ala  Ala Thr Thr Thr Gly  Cys Thr Gly
    1790                 1795                 1800

Ala Gly  Gly Gly Cys Thr Ala  Thr Thr Gly Ala Gly  Gly Cys Gly
    1805                 1810                 1815

Cys Ala  Ala Cys Ala Gly Cys  Ala Thr Cys Thr Gly  Thr Thr Gly
    1820                 1825                 1830

Cys Ala  Ala Cys Thr Cys Ala  Cys Ala Gly Thr Cys  Thr Gly Gly
    1835                 1840                 1845

Gly Gly  Cys Ala Thr Cys Ala  Ala Gly Cys Ala Gly  Cys Thr Cys
    1850                 1855                 1860

Cys Ala  Gly Gly Cys Ala Ala  Gly Ala Ala Thr Cys  Cys Thr Gly
    1865                 1870                 1875

Gly Cys  Thr Gly Thr Gly Gly  Ala Ala Ala Gly Ala  Thr Ala Cys
    1880                 1885                 1890

Cys Thr  Ala Ala Ala Gly Gly  Ala Thr Cys Ala Ala  Cys Ala Gly
    1895                 1900                 1905

Cys Thr  Cys Cys Thr Gly Gly  Gly Gly Ala Thr Thr  Thr Gly Gly
    1910                 1915                 1920

Gly Gly  Thr Thr Gly Cys Thr  Cys Thr Gly Gly Ala  Ala Ala Ala
    1925                 1930                 1935

Cys Thr  Cys Ala Thr Thr Thr  Gly Cys Ala Cys Cys  Ala Cys Thr
    1940                 1945                 1950

Gly Cys  Thr Gly Thr Gly Cys  Cys Thr Thr Gly Gly  Ala Ala Thr
    1955                 1960                 1965

Gly Cys  Thr Ala Gly Thr Thr  Gly Gly Ala Gly Thr  Ala Ala Thr
    1970                 1975                 1980

Ala Ala  Ala Thr Cys Thr Cys  Thr Gly Gly Ala Ala  Cys Ala Gly
    1985                 1990                 1995

Ala Thr  Thr Thr Gly Gly Ala  Ala Thr Cys Ala Cys  Ala Cys Gly
    2000                 2005                 2010

Ala Cys  Cys Thr Gly Gly Ala  Thr Gly Gly Ala Gly  Thr Gly Gly
```

```
    2015                2020                2025

Gly Ala  Cys Ala Gly Ala Gly  Ala Ala Ala Thr Thr  Ala Ala Cys
    2030                2035                2040

Ala Ala  Thr Thr Ala Cys Ala  Cys Ala Ala Gly Cys  Thr Thr Ala
    2045                2050                2055

Ala Thr  Ala Cys Ala Cys Thr  Cys Cys Thr Thr Ala  Ala Thr Thr
    2060                2065                2070

Gly Ala  Ala Gly Ala Ala Thr  Cys Gly Cys Ala Ala  Ala Ala Cys
    2075                2080                2085

Cys Ala  Gly Cys Ala Ala Gly  Ala Ala Ala Ala Gly  Ala Ala Thr
    2090                2095                2100

Gly Ala  Ala Cys Ala Ala Gly  Ala Ala Thr Thr Ala  Thr Thr Gly
    2105                2110                2115

Gly Ala  Ala Thr Thr Ala Gly  Ala Thr Ala Ala Ala  Thr Gly Gly
    2120                2125                2130

Gly Cys  Ala Ala Gly Thr Thr  Thr Gly Thr Gly Gly  Ala Ala Thr
    2135                2140                2145

Thr Gly  Gly Thr Thr Thr Ala  Ala Cys Ala Thr Ala  Ala Cys Ala
    2150                2155                2160

Ala Ala  Thr Thr Gly Gly Cys  Thr Gly Thr Gly Gly  Thr Ala Thr
    2165                2170                2175

Ala Thr  Ala Ala Ala Ala Thr  Thr Ala Thr Thr Cys  Ala Thr Ala
    2180                2185                2190

Ala Thr  Gly Ala Thr Ala Gly  Thr Ala Gly Gly Ala  Gly Gly Cys
    2195                2200                2205

Thr Thr  Gly Gly Thr Ala Gly  Gly Thr Thr Thr Ala  Ala Gly Ala
    2210                2215                2220

Ala Thr  Ala Gly Thr Thr Thr  Thr Thr Gly Cys Thr  Gly Thr Ala
    2225                2230                2235

Cys Thr  Thr Thr Cys Thr Ala  Thr Ala Gly Thr Gly  Ala Ala Thr
    2240                2245                2250

Ala Gly  Ala Gly Thr Thr Ala  Gly Gly Cys Ala Gly  Gly Gly Ala
    2255                2260                2265

Thr Ala  Thr Thr Cys Ala Cys  Cys Ala Thr Thr Ala  Thr Cys Gly
    2270                2275                2280

Thr Thr  Thr Cys Ala Gly Ala  Cys Cys Cys Ala Cys  Cys Thr Cys
    2285                2290                2295

Cys Cys  Ala Ala Cys Cys Cys  Cys Gly Ala Gly Gly  Gly Gly Ala
    2300                2305                2310

Cys Cys  Cys Gly Ala Cys Ala  Gly Gly Cys Cys Cys  Gly Ala Ala
    2315                2320                2325

Gly Gly  Ala Ala Thr Ala Gly  Ala Ala Gly Ala Ala  Gly Ala Ala
    2330                2335                2340

Gly Gly  Thr Gly Gly Ala Gly  Ala Gly Ala Gly Ala  Gly Ala Cys
    2345                2350                2355

Ala Gly  Ala Gly Ala Cys Ala  Gly Ala Thr Cys Cys  Ala Thr Thr
    2360                2365                2370

Cys Gly  Ala Thr Thr Ala Gly  Thr Gly Ala Ala Cys  Gly Gly Ala
    2375                2380                2385

Thr Cys  Gly Gly Cys Ala Cys  Thr Gly Cys Gly Thr  Gly Cys Gly
    2390                2395                2400

Cys Cys  Ala Ala Thr Thr Cys  Thr Gly Cys Ala Gly  Ala Cys Ala
    2405                2410                2415
```

```
Ala Ala  Thr Gly Gly Cys Ala  Gly Thr Ala Thr Thr  Cys Ala Thr
    2420                 2425                 2430

Cys Cys  Ala Cys Ala Ala Thr  Thr Thr Thr Ala Ala  Ala Ala Gly
    2435                 2440                 2445

Ala Ala  Ala Ala Gly Gly Gly  Gly Gly Gly Ala Thr  Thr Gly Gly
    2450                 2455                 2460

Gly Gly  Gly Gly Thr Ala Cys  Ala Gly Thr Gly Cys  Ala Gly Gly
    2465                 2470                 2475

Gly Gly  Ala Ala Ala Gly Ala  Ala Thr Ala Gly Thr  Ala Gly Ala
    2480                 2485                 2490

Cys Ala  Thr Ala Ala Thr Ala  Gly Cys Ala Ala Cys  Ala Gly Ala
    2495                 2500                 2505

Cys Ala  Thr Ala Cys Ala Ala  Ala Cys Thr Ala Ala  Ala Gly Ala
    2510                 2515                 2520

Ala Thr  Thr Ala Cys Ala Ala  Ala Ala Ala Cys Ala  Ala Ala Thr
    2525                 2530                 2535

Thr Ala  Cys Ala Ala Ala Ala  Ala Thr Thr Cys Ala  Ala Ala Ala
    2540                 2545                 2550

Thr Thr  Thr Thr Cys Gly Gly  Gly Thr Thr Thr Ala  Thr Thr Ala
    2555                 2560                 2565

Cys Ala  Gly Gly Gly Ala Cys  Ala Gly Cys Ala Gly  Ala Gly Ala
    2570                 2575                 2580

Thr Cys  Cys Ala Gly Thr Thr  Thr Gly Gly Thr Thr  Ala Ala Thr
    2585                 2590                 2595

Thr Ala  Ala Gly Gly Gly Thr  Gly Cys Ala Gly Cys  Gly Gly Cys
    2600                 2605                 2610

Cys Thr  Cys Cys Gly Cys Gly  Cys Cys Gly Gly Gly  Thr Thr Thr
    2615                 2620                 2625

Thr Gly  Gly Cys Gly Cys Cys  Thr Cys Cys Cys Gly  Cys Gly Gly
    2630                 2635                 2640

Gly Cys  Gly Cys Cys Cys Cys  Cys Cys Thr Cys Cys  Thr Cys Ala
    2645                 2650                 2655

Cys Gly  Gly Cys Gly Ala Gly  Cys Gly Cys Thr Gly  Cys Cys Ala
    2660                 2665                 2670

Cys Gly  Thr Cys Ala Gly Ala  Cys Gly Ala Ala Gly  Gly Gly Cys
    2675                 2680                 2685

Gly Cys  Ala Gly Gly Ala Gly  Cys Gly Thr Thr Cys  Cys Thr Gly
    2690                 2695                 2700

Ala Thr  Cys Cys Thr Thr Cys  Cys Gly Cys Cys Cys  Gly Gly Ala
    2705                 2710                 2715

Cys Gly  Cys Thr Cys Ala Gly  Gly Ala Cys Ala Gly  Cys Gly Gly
    2720                 2725                 2730

Cys Cys  Cys Gly Cys Thr Gly  Cys Thr Cys Ala Thr  Ala Ala Gly
    2735                 2740                 2745

Ala Cys  Thr Cys Gly Gly Cys  Cys Thr Thr Ala Gly  Ala Ala Cys
    2750                 2755                 2760

Cys Cys  Cys Ala Gly Thr Ala  Thr Cys Ala Gly Cys  Ala Gly Ala
    2765                 2770                 2775

Ala Gly  Gly Ala Cys Ala Thr  Thr Thr Thr Ala Gly  Gly Ala Cys
    2780                 2785                 2790

Gly Gly  Gly Ala Cys Thr Thr  Gly Gly Gly Thr Gly  Ala Cys Thr
    2795                 2800                 2805
```

```
Cys Thr  Ala Gly Gly Gly Cys  Ala Cys Thr Gly Gly  Thr Thr Thr
    2810                 2815                 2820

Thr Cys  Thr Thr Thr Cys Cys  Ala Gly Ala Gly Ala  Gly Cys Gly
    2825                 2830                 2835

Gly Ala  Ala Cys Ala Gly Gly  Cys Gly Ala Gly Gly  Ala Ala Ala
    2840                 2845                 2850

Ala Gly  Thr Ala Gly Thr Cys  Cys Cys Thr Thr Cys  Thr Cys Gly
    2855                 2860                 2865

Gly Cys  Gly Ala Thr Thr Cys  Thr Gly Cys Gly Gly  Ala Gly Gly
    2870                 2875                 2880

Gly Ala  Thr Cys Thr Cys Cys  Gly Thr Gly Gly Gly  Gly Cys Gly
    2885                 2890                 2895

Gly Thr  Gly Ala Ala Cys Gly  Cys Cys Gly Ala Thr  Gly Ala Thr
    2900                 2905                 2910

Thr Ala  Thr Ala Thr Ala Ala  Gly Gly Ala Cys Gly  Cys Gly Cys
    2915                 2920                 2925

Cys Gly  Gly Gly Thr Gly Thr  Gly Gly Cys Ala Cys  Ala Gly Cys
    2930                 2935                 2940

Thr Ala  Gly Thr Thr Cys Cys  Gly Thr Cys Gly Cys  Ala Gly Cys
    2945                 2950                 2955

Cys Gly  Gly Gly Ala Thr Thr  Thr Gly Gly Gly Thr  Cys Gly Cys
    2960                 2965                 2970

Gly Gly  Thr Thr Cys Thr Thr  Gly Thr Thr Thr Gly  Thr Gly Gly
    2975                 2980                 2985

Ala Thr  Cys Gly Cys Thr Gly  Thr Gly Ala Thr Cys  Gly Thr Cys
    2990                 2995                 3000

Ala Cys  Thr Thr Gly Gly Thr  Gly Ala Gly Thr Thr  Gly Cys Gly
    3005                 3010                 3015

Gly Gly  Cys Thr Gly Cys Thr  Gly Gly Gly Cys Thr  Gly Gly Cys
    3020                 3025                 3030

Cys Gly  Gly Gly Gly Cys Thr  Thr Thr Cys Gly Thr  Gly Gly Cys
    3035                 3040                 3045

Cys Gly  Cys Cys Gly Gly Gly  Cys Cys Gly Cys Thr  Cys Gly Gly
    3050                 3055                 3060

Thr Gly  Gly Gly Ala Cys Gly  Gly Ala Ala Gly Cys  Gly Thr Gly
    3065                 3070                 3075

Thr Gly  Gly Ala Gly Ala Gly  Ala Cys Cys Gly Cys  Cys Ala Ala
    3080                 3085                 3090

Gly Gly  Gly Cys Thr Gly Thr  Ala Gly Thr Cys Thr  Gly Gly Gly
    3095                 3100                 3105

Thr Cys  Cys Gly Cys Gly Ala  Gly Cys Ala Ala Gly  Gly Thr Thr
    3110                 3115                 3120

Gly Cys  Cys Cys Thr Gly Ala  Ala Cys Thr Gly Gly  Gly Gly Gly
    3125                 3130                 3135

Thr Thr  Gly Gly Gly Gly Gly  Gly Ala Gly Cys Gly  Cys Ala Cys
    3140                 3145                 3150

Ala Ala  Ala Ala Thr Gly Gly  Cys Gly Gly Cys Thr  Gly Thr Thr
    3155                 3160                 3165

Cys Cys  Cys Gly Ala Gly Thr  Cys Thr Thr Gly Ala  Ala Thr Gly
    3170                 3175                 3180

Gly Ala  Ala Gly Ala Cys Gly  Cys Thr Thr Gly Thr  Ala Ala Gly
    3185                 3190                 3195

Gly Cys  Gly Gly Gly Cys Thr  Gly Thr Gly Ala Gly  Gly Thr Cys
```

```
    3200                3205                3210

Gly Thr  Thr Gly Ala Ala Ala  Cys Ala Ala Gly Gly  Thr Gly Gly
    3215                3220                3225

Gly Gly  Gly Gly Cys Ala Thr  Gly Gly Thr Gly Gly  Gly Cys Gly
    3230                3235                3240

Gly Cys  Ala Ala Gly Ala Ala  Cys Cys Cys Ala Ala  Gly Gly Thr
    3245                3250                3255

Cys Thr  Thr Gly Ala Gly Gly  Cys Cys Thr Thr Cys  Gly Cys Thr
    3260                3265                3270

Ala Ala  Thr Gly Cys Gly Gly  Gly Ala Ala Ala Gly  Cys Thr Cys
    3275                3280                3285

Thr Thr  Ala Thr Thr Cys Gly  Gly Gly Thr Gly Ala  Gly Ala Thr
    3290                3295                3300

Gly Gly  Gly Cys Thr Gly Gly  Gly Gly Cys Ala Cys  Cys Ala Thr
    3305                3310                3315

Cys Thr  Gly Gly Gly Gly Ala  Cys Cys Cys Thr Gly  Ala Cys Gly
    3320                3325                3330

Thr Gly  Ala Ala Gly Thr Thr  Thr Gly Thr Cys Ala  Cys Thr Gly
    3335                3340                3345

Ala Cys  Thr Gly Gly Ala Gly  Ala Ala Cys Thr Cys  Gly Gly Gly
    3350                3355                3360

Thr Thr  Thr Gly Thr Cys Gly  Thr Cys Thr Gly Gly  Thr Thr Gly
    3365                3370                3375

Cys Gly  Gly Gly Gly Gly Cys  Gly Gly Cys Ala Gly  Thr Thr Ala
    3380                3385                3390

Thr Gly  Cys Gly Gly Thr Gly  Cys Cys Gly Thr Thr  Gly Gly Gly
    3395                3400                3405

Cys Ala  Gly Thr Gly Cys Ala  Cys Cys Cys Gly Thr  Ala Cys Cys
    3410                3415                3420

Thr Thr  Thr Gly Gly Gly Ala  Gly Cys Gly Cys Gly  Cys Gly Cys
    3425                3430                3435

Cys Thr  Cys Gly Thr Cys Gly  Thr Gly Thr Cys Gly  Thr Gly Ala
    3440                3445                3450

Cys Gly  Thr Cys Ala Cys Cys  Cys Gly Thr Thr Cys  Thr Gly Thr
    3455                3460                3465

Thr Gly  Gly Cys Thr Thr Ala  Thr Ala Ala Thr Gly  Cys Ala Gly
    3470                3475                3480

Gly Gly  Thr Gly Gly Gly Gly  Cys Cys Ala Cys Cys  Thr Gly Cys
    3485                3490                3495

Cys Gly  Gly Thr Ala Gly Gly  Thr Gly Thr Gly Cys  Gly Gly Thr
    3500                3505                3510

Ala Gly  Gly Cys Thr Thr Thr  Thr Cys Thr Cys Cys  Gly Thr Cys
    3515                3520                3525

Gly Cys  Ala Gly Gly Ala Cys  Gly Cys Ala Gly Gly  Gly Thr Thr
    3530                3535                3540

Cys Gly  Gly Gly Cys Cys Thr  Ala Gly Gly Gly Thr  Ala Gly Gly
    3545                3550                3555

Cys Thr  Cys Thr Cys Cys Thr  Gly Ala Ala Thr Cys  Gly Ala Cys
    3560                3565                3570

Ala Gly  Gly Cys Gly Cys Cys  Gly Gly Ala Cys Cys  Thr Cys Thr
    3575                3580                3585

Gly Gly  Thr Gly Ala Gly Gly  Gly Gly Ala Gly Gly  Gly Ala Thr
    3590                3595                3600
```

Ala Ala Gly Thr Gly Ala Gly Gly Cys Gly Thr Cys Ala Gly Thr
3605 3610 3615

Thr Thr Cys Thr Thr Thr Gly Gly Thr Cys Gly Gly Thr Thr Thr
3620 3625 3630

Thr Ala Thr Gly Thr Ala Cys Cys Thr Ala Thr Cys Thr Thr Cys
3635 3640 3645

Thr Thr Ala Ala Gly Thr Ala Gly Cys Thr Gly Ala Ala Gly Cys
3650 3655 3660

Thr Cys Cys Gly Gly Thr Thr Thr Thr Gly Ala Ala Cys Thr Ala
3665 3670 3675

Thr Gly Cys Gly Cys Thr Cys Gly Gly Gly Gly Thr Thr Gly Gly
3680 3685 3690

Cys Gly Ala Gly Thr Gly Thr Gly Thr Thr Thr Thr Gly Thr Gly
3695 3700 3705

Ala Ala Gly Thr Thr Thr Thr Thr Thr Ala Gly Gly Cys Ala Cys
3710 3715 3720

Cys Thr Thr Thr Thr Gly Ala Ala Ala Thr Gly Thr Ala Ala Thr
3725 3730 3735

Cys Ala Thr Thr Thr Gly Gly Gly Thr Cys Ala Ala Thr Ala Thr
3740 3745 3750

Gly Thr Ala Ala Thr Thr Thr Thr Cys Ala Gly Thr Gly Thr Thr
3755 3760 3765

Ala Gly Ala Cys Thr Ala Gly Thr Ala Ala Ala Gly Cys Thr Thr
3770 3775 3780

Cys Thr Gly Cys Ala Gly Gly Thr Cys Gly Ala Cys Thr Cys Thr
3785 3790 3795

Ala Gly Ala Ala Ala Ala Thr Thr Gly Thr Cys Cys Gly Cys Thr
3800 3805 3810

Ala Ala Ala Thr Thr Cys Thr Gly Gly Cys Cys Gly Thr Thr Thr
3815 3820 3825

Thr Thr Gly Gly Cys Thr Thr Thr Thr Thr Thr Gly Thr Thr Ala
3830 3835 3840

Gly Ala Cys Ala Gly Gly Ala Thr Cys Cys Ala Thr Gly Ala Cys
3845 3850 3855

Ala Gly Ala Gly Ala Cys Cys Cys Thr Gly Cys Cys Thr Cys Cys
3860 3865 3870

Cys Gly Thr Gly Ala Cys Cys Gly Ala Gly Ala Gly Thr Gly Cys
3875 3880 3885

Cys Gly Thr Gly Gly Cys Cys Cys Thr Thr Cys Ala Ala Gly Cys
3890 3895 3900

Cys Gly Ala Gly Gly Thr Thr Ala Cys Cys Cys Ala Ala Ala Gly
3905 3910 3915

Gly Gly Ala Gly Thr Thr Gly Thr Thr Cys Gly Ala Gly Thr Thr
3920 3925 3930

Cys Gly Thr Gly Cys Thr Gly Ala Ala Cys Gly Ala Cys Cys Cys
3935 3940 3945

Thr Thr Thr Gly Cys Thr Thr Gly Cys Ala Ala Gly Cys Ala Gly
3950 3955 3960

Thr Cys Thr Cys Thr Ala Thr Ala Thr Cys Ala Ala Cys Ala Thr
3965 3970 3975

Cys Gly Cys Ala Cys Thr Thr Gly Cys Ala Gly Gly Ala Cys Thr
3980 3985 3990

```
Gly Ala  Gly Thr Ala Thr Ala  Cys Thr Gly Cys Thr  Gly Thr Thr
    3995                 4000                 4005

Cys Gly  Thr Thr Thr Thr Thr  Ala Thr Gly Ala Cys  Cys Cys Gly
    4010                 4015                 4020

Ala Gly  Gly Ala Cys Thr Cys  Gly Ala Thr Gly Ala  Thr Cys Cys
    4025                 4030                 4035

Ala Cys  Gly Gly Gly Cys Ala  Ala Ala Ala Cys Thr  Thr Ala Thr
    4040                 4045                 4050

Thr Gly  Cys Thr Gly Thr Gly  Thr Cys Ala Ala Cys  Cys Ala Thr
    4055                 4060                 4065

Cys Cys  Thr Thr Gly Thr Gly  Cys Cys Thr Gly Thr  Cys Gly Thr
    4070                 4075                 4080

Cys Ala  Gly Cys Ala Thr Thr  Gly Cys Cys Thr Cys  Cys Thr Ala
    4085                 4090                 4095

Cys Ala  Cys Thr Gly Gly Ala  Thr Thr Gly Gly Cys  Gly Ala Gly
    4100                 4105                 4110

Cys Gly  Gly Cys Cys Thr Gly  Ala Cys Ala Ala Thr  Thr Thr Cys
    4115                 4120                 4125

Cys Gly  Thr Thr Cys Thr Thr  Gly Ala Ala Ala Thr  Gly Cys Cys
    4130                 4135                 4140

Ala Gly  Cys Gly Gly Gly Cys  Cys Ala Thr Thr Thr  Thr Gly Cys
    4145                 4150                 4155

Ala Gly  Ala Ala Gly Gly Cys  Ala Gly Cys Thr Cys  Ala Gly Thr
    4160                 4165                 4170

Gly Ala  Thr Gly Cys Thr Gly  Gly Gly Ala Gly Gly  Ala Gly Ala
    4175                 4180                 4185

Ala Gly  Ala Gly Gly Thr Ala  Gly Ala Thr Gly Gly  Thr Gly Thr
    4190                 4195                 4200

Ala Gly  Thr Cys Ala Cys Cys  Ala Thr Gly Thr Gly  Gly Gly Gly
    4205                 4210                 4215

Ala Cys  Gly Gly Thr Ala Thr  Cys Thr Cys Ala Cys  Cys Thr Gly
    4220                 4225                 4230

Gly Gly  Cys Ala Cys Thr Thr  Thr Cys Cys Ala Cys  Gly Cys Cys
    4235                 4240                 4245

Cys Ala  Thr Gly Ala Thr Thr  Cys Thr Cys Cys Thr  Cys Gly Cys
    4250                 4255                 4260

Thr Cys  Thr Gly Gly Gly Thr  Cys Thr Cys Cys Thr  Gly Gly Cys
    4265                 4270                 4275

Cys Gly  Gly Ala Ala Gly Cys  Ala Ala Thr Gly Cys  Thr Ala Cys
    4280                 4285                 4290

Ala Ala  Ala Gly Cys Thr Cys  Thr Thr Cys Ala Cys  Ala Gly Cys
    4295                 4300                 4305

Thr Ala  Thr Cys Ala Cys Thr  Thr Thr Cys Gly Ala  Thr Ala Thr
    4310                 4315                 4320

Cys Gly  Cys Thr Ala Thr Gly  Thr Gly Cys Gly Thr  Gly Ala Cys
    4325                 4330                 4335

Thr Gly  Gly Cys Cys Thr Thr  Gly Cys Cys Gly Cys  Gly Gly Cys
    4340                 4345                 4350

Cys Cys  Thr Gly Ala Cys Thr  Ala Cys Cys Thr Cys  Cys Thr Cys
    4355                 4360                 4365

Cys Cys  Ala Cys Cys Thr Cys  Ala Thr Gly Ala Gly  Ala Thr Gly
    4370                 4375                 4380

Gly Thr  Thr Cys Thr Gly Gly  Thr Ala Cys Gly Cys  Thr Ala Thr
```

```
    4385                4390                4395

Cys Ala  Gly Thr Thr Gly Thr  Gly Cys Ala Thr Gly  Cys Thr Thr
    4400                4405                4410

Thr Cys  Thr Gly Gly Thr Gly  Gly Thr Cys Thr Thr  Gly Thr Ala
    4415                4420                4425

Thr Ala  Thr Cys Cys Thr Gly  Cys Thr Gly Gly Thr  Gly Gly Ala
    4430                4435                4440

Gly Thr  Gly Gly Gly Cys Ala  Cys Ala Gly Gly Ala  Cys Gly Cys
    4445                4450                4455

Cys Ala  Ala Ala Gly Cys Cys  Gly Cys Gly Gly Gly  Ala Ala Cys
    4460                4465                4470

Cys Gly  Cys Thr Gly Ala Cys  Ala Thr Gly Thr Thr  Cys Ala Ala
    4475                4480                4485

Thr Ala  Cys Cys Cys Thr Gly  Ala Ala Gly Cys Thr  Gly Thr Thr
    4490                4495                4500

Gly Ala  Cys Ala Gly Thr Ala  Gly Thr Gly Ala Thr  Gly Thr Gly
    4505                4510                4515

Gly Cys  Thr Gly Gly Gly Gly  Thr Ala Thr Cys Cys  Ala Ala Thr
    4520                4525                4530

Thr Gly  Thr Gly Thr Gly Gly  Gly Cys Thr Cys Thr  Thr Gly Gly
    4535                4540                4545

Ala Gly  Thr Cys Gly Ala Gly  Gly Gly Thr Ala Thr  Cys Gly Cys
    4550                4555                4560

Gly Gly  Thr Gly Thr Thr Gly  Cys Cys Cys Gly Thr  Thr Gly Gly
    4565                4570                4575

Gly Gly  Thr Gly Ala Cys Gly  Ala Gly Cys Thr Gly  Gly Gly Gly
    4580                4585                4590

Ala Thr  Ala Thr Thr Cys Thr  Thr Thr Cys Cys Thr  Gly Gly Ala
    4595                4600                4605

Thr Ala  Thr Cys Gly Thr Gly  Gly Cys Ala Ala Ala  Gly Thr Ala
    4610                4615                4620

Cys Ala  Thr Thr Thr Thr Cys  Gly Cys Ala Thr Thr  Cys Thr Thr
    4625                4630                4635

Gly Cys  Thr Cys Cys Thr Gly  Ala Ala Cys Thr Ala  Thr Cys Thr
    4640                4645                4650

Gly Ala  Cys Gly Thr Cys Ala  Ala Ala Cys Gly Ala  Ala Thr Cys
    4655                4660                4665

Thr Gly  Thr Cys Gly Thr Gly  Thr Cys Cys Gly Gly  Cys Ala Gly
    4670                4675                4680

Cys Ala  Thr Thr Thr Thr Gly  Gly Ala Thr Gly Thr  Thr Cys Cys
    4685                4690                4695

Ala Thr  Cys Thr Gly Cys Thr  Thr Cys Thr Gly Gly  Gly Ala Cys
    4700                4705                4710

Cys Cys  Cys Gly Gly Cys Thr  Gly Ala Thr Gly Ala  Thr Gly Cys
    4715                4720                4725

Gly Gly  Cys Cys Gly Cys Ala  Gly Thr Gly Ala Gly  Cys Ala Ala
    4730                4735                4740

Gly Gly  Gly Cys Gly Ala Gly  Gly Ala Gly Cys Thr  Gly Thr Thr
    4745                4750                4755

Cys Ala  Cys Cys Gly Gly Gly  Gly Thr Gly Gly Thr  Gly Cys Cys
    4760                4765                4770

Cys Ala  Thr Cys Cys Thr Gly  Gly Thr Cys Gly Ala  Gly Cys Thr
    4775                4780                4785
```

Gly Gly Ala Cys Gly Gly Cys Gly Ala Cys Gly Thr Ala Ala Ala
4790 4795 4800

Cys Gly Gly Cys Cys Ala Cys Ala Ala Gly Thr Thr Cys Ala Gly
4805 4810 4815

Cys Gly Thr Gly Thr Cys Cys Gly Gly Cys Gly Ala Gly Gly Gly
4820 4825 4830

Cys Gly Ala Gly Gly Gly Cys Gly Ala Thr Gly Cys Cys Ala Cys
4835 4840 4845

Cys Thr Ala Cys Gly Gly Cys Ala Ala Gly Cys Thr Gly Ala Cys
4850 4855 4860

Cys Cys Thr Gly Ala Ala Gly Cys Thr Gly Ala Thr Cys Thr Gly
4865 4870 4875

Cys Ala Cys Cys Ala Cys Cys Gly Gly Cys Ala Ala Gly Cys Thr
4880 4885 4890

Gly Cys Cys Cys Gly Thr Gly Cys Cys Cys Thr Gly Gly Cys Cys
4895 4900 4905

Cys Ala Cys Cys Cys Thr Cys Gly Thr Gly Ala Cys Cys Ala Cys
4910 4915 4920

Cys Cys Thr Gly Gly Gly Cys Thr Ala Cys Gly Gly Cys Cys Thr
4925 4930 4935

Gly Cys Ala Gly Thr Gly Cys Thr Thr Cys Gly Cys Cys Cys Gly
4940 4945 4950

Cys Thr Ala Cys Cys Cys Cys Gly Ala Cys Cys Ala Cys Ala Thr
4955 4960 4965

Gly Ala Ala Gly Cys Ala Gly Cys Ala Cys Gly Ala Cys Thr Thr
4970 4975 4980

Cys Thr Thr Cys Ala Ala Gly Thr Cys Cys Gly Cys Cys Ala Thr
4985 4990 4995

Gly Cys Cys Cys Gly Ala Ala Gly Gly Cys Thr Ala Cys Gly Thr
5000 5005 5010

Cys Cys Ala Gly Gly Ala Gly Cys Gly Cys Ala Cys Cys Ala Thr
5015 5020 5025

Cys Thr Thr Cys Thr Thr Cys Ala Ala Gly Gly Ala Cys Gly Ala
5030 5035 5040

Cys Gly Gly Cys Ala Ala Cys Thr Ala Cys Ala Ala Gly Ala Cys
5045 5050 5055

Cys Cys Gly Cys Gly Cys Cys Gly Ala Gly Gly Thr Gly Ala Ala
5060 5065 5070

Gly Thr Thr Cys Gly Ala Gly Gly Gly Cys Gly Ala Cys Ala Cys
5075 5080 5085

Cys Cys Thr Gly Gly Thr Gly Ala Ala Cys Cys Gly Cys Ala Thr
5090 5095 5100

Cys Gly Ala Gly Cys Thr Gly Ala Ala Gly Gly Gly Cys Ala Thr
5105 5110 5115

Cys Gly Ala Cys Thr Thr Cys Ala Ala Gly Gly Ala Gly Gly Ala
5120 5125 5130

Cys Gly Gly Cys Ala Ala Cys Ala Thr Cys Cys Thr Gly Gly Gly
5135 5140 5145

Gly Cys Ala Cys Ala Ala Gly Cys Thr Gly Gly Ala Gly Thr Ala
5150 5155 5160

Cys Ala Ala Cys Thr Ala Cys Ala Ala Cys Ala Gly Cys Cys Ala
5165 5170 5175

```
Cys Ala  Ala Cys Gly Thr Cys  Thr Ala Thr Ala Thr  Cys Ala Cys
    5180                 5185                 5190

Cys Gly  Cys Cys Gly Ala Cys  Ala Ala Gly Cys Ala  Gly Ala Ala
    5195                 5200                 5205

Gly Ala  Ala Cys Gly Gly Cys  Ala Thr Cys Ala Ala  Gly Gly Cys
    5210                 5215                 5220

Cys Ala  Ala Cys Thr Thr Cys  Ala Ala Gly Ala Thr  Cys Cys Gly
    5225                 5230                 5235

Cys Cys  Ala Cys Ala Ala Cys  Ala Thr Cys Gly Ala  Gly Gly Ala
    5240                 5245                 5250

Cys Gly  Gly Cys Gly Gly Cys  Gly Thr Gly Cys Ala  Gly Cys Thr
    5255                 5260                 5265

Cys Gly  Cys Cys Gly Ala Cys  Cys Ala Cys Thr Ala  Cys Cys Ala
    5270                 5275                 5280

Gly Cys  Ala Gly Ala Ala Cys  Ala Cys Cys Cys Cys  Cys Ala Thr
    5285                 5290                 5295

Cys Gly  Gly Cys Gly Ala Cys  Gly Gly Cys Cys Cys  Cys Gly Thr
    5300                 5305                 5310

Gly Cys  Thr Gly Cys Thr Gly  Cys Cys Cys Gly Ala  Cys Ala Ala
    5315                 5320                 5325

Cys Cys  Ala Cys Thr Ala Cys  Cys Thr Gly Ala Gly  Cys Thr Ala
    5330                 5335                 5340

Cys Cys  Ala Gly Thr Cys Cys  Ala Ala Gly Cys Thr  Gly Ala Gly
    5345                 5350                 5355

Cys Ala  Ala Ala Gly Ala Cys  Cys Cys Cys Ala Ala  Cys Gly Ala
    5360                 5365                 5370

Gly Ala  Ala Gly Cys Gly Cys  Gly Ala Thr Cys Ala  Cys Ala Thr
    5375                 5380                 5385

Gly Gly  Thr Cys Cys Thr Gly  Cys Thr Gly Gly Ala  Gly Thr Thr
    5390                 5395                 5400

Cys Gly  Thr Gly Ala Cys Cys  Gly Cys Cys Gly Cys  Cys Gly Gly
    5405                 5410                 5415

Gly Gly  Gly Thr Ala Cys Cys  Ala Ala Gly Gly Thr  Gly Thr Ala
    5420                 5425                 5430

Cys Gly  Ala Cys Cys Cys Cys  Gly Ala Gly Cys Ala  Gly Ala Gly
    5435                 5440                 5445

Gly Ala  Ala Gly Ala Gly Gly  Ala Thr Gly Ala Thr  Cys Ala Cys
    5450                 5455                 5460

Cys Gly  Gly Cys Cys Cys Cys  Cys Ala Gly Thr Gly  Gly Thr Gly
    5465                 5470                 5475

Gly Gly  Cys Cys Ala Gly Gly  Thr Gly Cys Ala Ala  Gly Cys Ala
    5480                 5485                 5490

Gly Ala  Thr Gly Ala Ala Cys  Gly Thr Gly Cys Thr  Gly Gly Ala
    5495                 5500                 5505

Cys Ala  Gly Cys Thr Thr Cys  Ala Thr Cys Ala Ala  Cys Thr Ala
    5510                 5515                 5520

Cys Thr  Ala Cys Gly Ala Cys  Ala Gly Cys Gly Ala  Gly Ala Ala
    5525                 5530                 5535

Gly Cys  Ala Cys Gly Cys Cys  Gly Ala Gly Ala Ala  Cys Gly Cys
    5540                 5545                 5550

Cys Gly  Thr Gly Ala Thr Cys  Thr Thr Cys Cys Thr  Gly Cys Ala
    5555                 5560                 5565

Cys Gly  Gly Cys Ala Ala Cys  Gly Cys Cys Ala Cys  Thr Ala Gly
```

```
                5570                5575                5580

Cys Ala Gly Cys Thr Ala Cys Cys Thr Gly Thr Gly Gly Ala Gly
    5585                5590                5595

Gly Cys Ala Cys Gly Thr Gly Gly Thr Gly Cys Cys Cys Cys Ala
    5600                5605                5610

Cys Ala Thr Cys Gly Ala Gly Cys Cys Cys Gly Thr Gly Gly Cys
    5615                5620                5625

Cys Ala Gly Gly Thr Gly Cys Ala Thr Cys Ala Thr Cys Cys Cys
    5630                5635                5640

Cys Gly Ala Thr Cys Thr Gly Ala Thr Cys Gly Gly Cys Ala Thr
    5645                5650                5655

Gly Gly Gly Cys Ala Ala Gly Ala Gly Cys Gly Gly Cys Ala Ala
    5660                5665                5670

Gly Ala Gly Cys Gly Gly Cys Ala Ala Cys Gly Gly Cys Ala Gly
    5675                5680                5685

Cys Thr Ala Cys Ala Gly Gly Cys Thr Gly Cys Thr Gly Gly Ala
    5690                5695                5700

Cys Cys Ala Cys Thr Ala Cys Ala Ala Gly Thr Ala Cys Cys Thr
    5705                5710                5715

Gly Ala Cys Cys Gly Cys Cys Thr Gly Gly Thr Thr Cys Gly Ala
    5720                5725                5730

Gly Cys Thr Thr Cys Thr Gly Ala Ala Cys Cys Thr Gly Cys Cys
    5735                5740                5745

Cys Ala Ala Gly Ala Ala Gly Ala Thr Cys Ala Thr Cys Thr Thr
    5750                5755                5760

Cys Gly Thr Gly Gly Gly Cys Cys Ala Cys Gly Ala Cys Thr Gly
    5765                5770                5775

Gly Gly Gly Cys Gly Cys Cys Gly Cys Cys Cys Thr Gly Gly Cys
    5780                5785                5790

Cys Thr Thr Cys Cys Ala Cys Thr Ala Cys Gly Cys Cys Thr Ala
    5795                5800                5805

Cys Gly Ala Gly Cys Ala Cys Cys Ala Gly Gly Ala Cys Ala Gly
    5810                5815                5820

Gly Ala Thr Cys Ala Ala Gly Gly Cys Cys Ala Thr Cys Gly Thr
    5825                5830                5835

Gly Cys Ala Cys Ala Thr Gly Gly Ala Gly Ala Gly Cys Gly Thr
    5840                5845                5850

Gly Gly Thr Gly Gly Ala Cys Gly Thr Gly Ala Thr Cys Gly Ala
    5855                5860                5865

Gly Ala Gly Cys Thr Gly Gly Gly Ala Cys Gly Ala Gly Thr Gly
    5870                5875                5880

Gly Cys Cys Ala Gly Ala Cys Ala Thr Cys Gly Ala Gly Gly Ala
    5885                5890                5895

Gly Gly Ala Cys Ala Thr Cys Gly Cys Cys Cys Thr Gly Ala Thr
    5900                5905                5910

Cys Ala Ala Gly Ala Gly Cys Gly Ala Gly Gly Ala Gly Gly Gly
    5915                5920                5925

Cys Gly Ala Gly Ala Ala Gly Ala Thr Gly Gly Thr Gly Cys Thr
    5930                5935                5940

Gly Gly Ala Gly Ala Ala Cys Ala Ala Cys Thr Thr Cys Thr Thr
    5945                5950                5955

Cys Gly Thr Gly Gly Ala Gly Ala Cys Cys Gly Thr Gly Cys Thr
    5960                5965                5970
```

```
Gly Cys  Cys Cys Ala Gly Cys  Ala Ala Gly Ala Thr  Cys Ala Thr
    5975                 5980                 5985

Gly Ala  Gly Ala Ala Ala Gly  Cys Thr Gly Gly Ala  Gly Cys Cys
    5990                 5995                 6000

Cys Gly  Ala Gly Gly Ala Gly  Thr Thr Cys Gly Cys  Cys Gly Cys
    6005                 6010                 6015

Cys Thr  Ala Cys Cys Thr Gly  Gly Ala Gly Cys Cys  Cys Thr Thr
    6020                 6025                 6030

Cys Ala  Ala Gly Gly Ala Gly  Ala Ala Gly Gly Gly  Cys Gly Ala
    6035                 6040                 6045

Gly Gly  Thr Gly Ala Gly Ala  Ala Gly Ala Cys Cys  Cys Ala Cys
    6050                 6055                 6060

Cys Cys  Thr Gly Ala Gly Cys  Thr Gly Gly Cys Cys  Cys Ala Gly
    6065                 6070                 6075

Ala Gly  Ala Gly Ala Thr Cys  Cys Cys Cys Cys Thr  Gly Gly Thr
    6080                 6085                 6090

Gly Ala  Ala Gly Gly Gly Cys  Gly Gly Cys Ala Ala  Gly Cys Cys
    6095                 6100                 6105

Cys Gly  Ala Cys Gly Thr Gly  Gly Thr Gly Cys Ala  Gly Ala Thr
    6110                 6115                 6120

Cys Gly  Thr Gly Ala Gly Ala  Ala Ala Cys Thr Ala  Cys Ala Ala
    6125                 6130                 6135

Cys Gly  Cys Cys Thr Ala Cys  Cys Thr Gly Ala Gly  Ala Gly Cys
    6140                 6145                 6150

Cys Ala  Gly Cys Gly Ala Cys  Gly Ala Cys Cys Thr  Gly Cys Cys
    6155                 6160                 6165

Cys Ala  Ala Gly Cys Thr Gly  Thr Thr Cys Ala Thr  Cys Gly Ala
    6170                 6175                 6180

Gly Gly  Gly Cys Gly Ala Cys  Cys Cys Cys Gly Gly  Cys Thr Thr
    6185                 6190                 6195

Cys Thr  Thr Cys Ala Gly Cys  Ala Ala Cys Gly Cys  Cys Ala Thr
    6200                 6205                 6210

Cys Gly  Thr Gly Gly Ala Gly  Gly Gly Cys Gly Cys  Cys Ala Ala
    6215                 6220                 6225

Gly Ala  Ala Gly Thr Thr Cys  Cys Cys Cys Ala Ala  Cys Ala Cys
    6230                 6235                 6240

Cys Gly  Ala Gly Thr Thr Cys  Gly Thr Gly Ala Ala  Gly Gly Thr
    6245                 6250                 6255

Gly Ala  Ala Gly Gly Gly Cys  Cys Thr Gly Cys Ala  Cys Thr Thr
    6260                 6265                 6270

Cys Cys  Thr Cys Cys Ala Gly  Gly Ala Gly Gly Ala  Cys Gly Cys
    6275                 6280                 6285

Cys Cys  Cys Cys Gly Ala Cys  Gly Ala Gly Ala Thr  Gly Gly Gly
    6290                 6295                 6300

Cys Ala  Ala Gly Thr Ala Cys  Ala Thr Cys Ala Ala  Gly Ala Gly
    6305                 6310                 6315

Cys Thr  Thr Cys Gly Thr Gly  Gly Ala Gly Ala Gly  Ala Gly Thr
    6320                 6325                 6330

Gly Cys  Thr Gly Ala Ala Gly  Ala Ala Cys Gly Ala  Gly Cys Ala
    6335                 6340                 6345

Gly Thr  Thr Cys Thr Gly Cys  Thr Ala Cys Gly Ala  Gly Ala Ala
    6350                 6355                 6360
```

```
Cys Gly  Ala Gly Gly Thr Gly  Thr Ala Ala Gly Ala  Ala Thr Thr
    6365                 6370                 6375

Cys Gly  Ala Thr Ala Thr Cys  Ala Ala Gly Cys Thr  Thr Ala Thr
    6380                 6385                 6390

Cys Gly  Ala Thr Ala Ala Thr  Cys Ala Ala Cys Cys  Thr Cys Thr
    6395                 6400                 6405

Gly Gly  Ala Thr Thr Ala Cys  Ala Ala Ala Ala Thr  Thr Thr Gly
    6410                 6415                 6420

Thr Gly  Ala Ala Ala Gly Ala  Thr Thr Gly Ala Cys  Thr Gly Gly
    6425                 6430                 6435

Thr Ala  Thr Thr Cys Thr Thr  Ala Ala Cys Thr Ala  Thr Gly Thr
    6440                 6445                 6450

Thr Gly  Cys Thr Cys Cys Thr  Thr Thr Thr Ala Cys  Gly Cys Thr
    6455                 6460                 6465

Ala Thr  Gly Thr Gly Gly Ala  Thr Ala Cys Gly Cys  Thr Gly Cys
    6470                 6475                 6480

Thr Thr  Thr Ala Ala Thr Gly  Cys Cys Thr Thr Thr  Gly Thr Ala
    6485                 6490                 6495

Thr Cys  Ala Thr Gly Cys Thr  Ala Thr Thr Gly Cys  Thr Thr Cys
    6500                 6505                 6510

Cys Cys  Gly Thr Ala Thr Gly  Gly Cys Thr Thr Thr  Cys Ala Thr
    6515                 6520                 6525

Thr Thr  Thr Cys Thr Cys Cys  Thr Cys Cys Thr Thr  Gly Thr Ala
    6530                 6535                 6540

Thr Ala  Ala Ala Thr Cys Cys  Thr Gly Gly Thr Thr  Gly Cys Thr
    6545                 6550                 6555

Gly Thr  Cys Thr Cys Thr Thr  Thr Ala Thr Gly Ala  Gly Gly Ala
    6560                 6565                 6570

Gly Thr  Thr Gly Thr Gly Gly  Cys Cys Cys Gly Thr  Thr Gly Thr
    6575                 6580                 6585

Cys Ala  Gly Gly Cys Ala Ala  Cys Gly Thr Gly Gly  Cys Gly Thr
    6590                 6595                 6600

Gly Gly  Thr Gly Thr Gly Cys  Ala Cys Thr Gly Thr  Gly Thr Thr
    6605                 6610                 6615

Thr Gly  Cys Thr Gly Ala Cys  Gly Cys Ala Ala Cys  Cys Cys Cys
    6620                 6625                 6630

Cys Ala  Cys Thr Gly Gly Thr  Thr Gly Gly Gly Gly  Cys Ala Thr
    6635                 6640                 6645

Thr Gly  Cys Cys Ala Cys Cys  Ala Cys Cys Thr Gly  Thr Cys Ala
    6650                 6655                 6660

Gly Cys  Thr Cys Cys Thr Thr  Thr Cys Cys Gly Gly  Gly Ala Cys
    6665                 6670                 6675

Thr Thr  Thr Cys Gly Cys Thr  Thr Thr Cys Cys Cys  Cys Cys Thr
    6680                 6685                 6690

Cys Cys  Cys Thr Ala Thr Thr  Gly Cys Cys Ala Cys  Gly Gly Cys
    6695                 6700                 6705

Gly Gly  Ala Ala Cys Thr Cys  Ala Thr Cys Gly Cys  Cys Gly Cys
    6710                 6715                 6720

Cys Thr  Gly Cys Cys Thr Thr  Gly Cys Cys Cys Gly  Cys Thr Gly
    6725                 6730                 6735

Cys Thr  Gly Gly Ala Cys Ala  Gly Gly Gly Gly Cys  Thr Cys Gly
    6740                 6745                 6750

Gly Cys  Thr Gly Thr Thr Gly  Gly Gly Cys Ala Cys  Thr Gly Ala
```

-continued

```
    6755                6760                6765

Cys Ala  Ala Thr Thr Cys Cys  Gly Thr Gly Gly Thr  Gly Thr Thr
    6770                6775                6780

Gly Thr  Cys Gly Gly Gly Gly  Ala Ala Ala Thr Cys  Ala Thr Cys
    6785                6790                6795

Gly Thr  Cys Cys Thr Thr Thr  Cys Cys Thr Thr Gly  Gly Cys Thr
    6800                6805                6810

Gly Cys  Thr Cys Gly Cys Cys  Thr Gly Thr Gly Thr  Thr Gly Cys
    6815                6820                6825

Cys Ala  Cys Cys Thr Gly Gly  Ala Thr Thr Cys Thr  Gly Cys Gly
    6830                6835                6840

Cys Gly  Gly Gly Ala Cys Gly  Thr Cys Cys Thr Thr  Cys Thr Gly
    6845                6850                6855

Cys Thr  Ala Cys Gly Thr Cys  Cys Cys Thr Thr Cys  Gly Gly Cys
    6860                6865                6870

Cys Cys  Thr Cys Ala Ala Thr  Cys Cys Ala Gly Cys  Gly Gly Ala
    6875                6880                6885

Cys Cys  Thr Thr Cys Cys Thr  Thr Cys Cys Cys Gly  Cys Gly Gly
    6890                6895                6900

Cys Cys  Thr Gly Cys Thr Gly  Cys Cys Gly Gly Cys  Thr Cys Thr
    6905                6910                6915

Gly Cys  Gly Gly Cys Cys Thr  Cys Thr Thr Cys Cys  Gly Cys Gly
    6920                6925                6930

Thr Cys  Thr Thr Cys Gly Cys  Cys Thr Thr Cys Gly  Cys Cys Cys
    6935                6940                6945

Thr Cys  Ala Gly Ala Cys Gly  Ala Gly Thr Cys Gly  Gly Ala Thr
    6950                6955                6960

Cys Thr  Cys Cys Cys Thr Thr  Thr Gly Gly Gly Cys  Cys Gly Cys
    6965                6970                6975

Cys Thr  Cys Cys Cys Cys Gly  Cys Ala Thr Cys Gly  Ala Thr Ala
    6980                6985                6990

Cys Cys  Gly Thr Cys Gly Ala  Cys Cys Thr Cys Gly  Ala Gly Ala
    6995                7000                7005

Cys Cys  Thr Ala Gly Ala Ala  Ala Ala Ala Cys Ala  Thr Gly Gly
    7010                7015                7020

Ala Gly  Cys Ala Ala Thr Cys  Ala Cys Ala Ala Gly  Thr Ala Gly
    7025                7030                7035

Cys Ala  Ala Thr Ala Cys Ala  Gly Cys Ala Gly Cys  Thr Ala Cys
    7040                7045                7050

Cys Ala  Ala Thr Gly Cys Thr  Gly Ala Thr Thr Gly  Thr Gly Cys
    7055                7060                7065

Cys Thr  Gly Gly Cys Thr Ala  Gly Ala Ala Gly Cys  Ala Cys Ala
    7070                7075                7080

Ala Gly  Ala Gly Gly Ala Gly  Gly Ala Gly Gly Ala  Gly Gly Thr
    7085                7090                7095

Gly Gly  Gly Thr Thr Thr Thr  Cys Cys Ala Gly Thr  Cys Ala Cys
    7100                7105                7110

Ala Cys  Cys Thr Cys Ala Gly  Gly Thr Ala Cys Cys  Thr Thr Thr
    7115                7120                7125

Ala Ala  Gly Ala Cys Cys Ala  Ala Thr Gly Ala Cys  Thr Thr Ala
    7130                7135                7140

Cys Ala  Ala Gly Gly Cys Ala  Gly Cys Thr Gly Thr  Ala Gly Ala
    7145                7150                7155
```

Thr Cys Thr Thr Ala Gly Cys Cys Ala Cys Thr Thr Thr Thr Thr
7160 7165 7170

Ala Ala Ala Ala Gly Ala Ala Ala Ala Gly Gly Gly Gly Gly Gly
7175 7180 7185

Ala Cys Thr Gly Gly Ala Ala Gly Gly Gly Cys Thr Ala Ala Thr
7190 7195 7200

Thr Cys Ala Cys Thr Cys Cys Cys Ala Ala Cys Gly Ala Ala Gly
7205 7210 7215

Ala Cys Ala Ala Gly Ala Thr Ala Thr Cys Cys Thr Thr Gly Ala
7220 7225 7230

Thr Cys Thr Gly Thr Gly Gly Ala Thr Cys Thr Ala Cys Cys Ala
7235 7240 7245

Cys Ala Cys Ala Cys Ala Ala Gly Gly Cys Thr Ala Cys Thr Thr
7250 7255 7260

Cys Cys Cys Thr Gly Ala Thr Thr Gly Gly Cys Ala Gly Ala Ala
7265 7270 7275

Cys Thr Ala Cys Ala Cys Ala Cys Cys Ala Gly Gly Gly Cys Cys
7280 7285 7290

Ala Gly Gly Gly Ala Thr Cys Ala Gly Ala Thr Ala Thr Cys Cys
7295 7300 7305

Ala Cys Thr Gly Ala Cys Cys Thr Thr Thr Gly Gly Ala Thr Gly
7310 7315 7320

Gly Thr Gly Cys Thr Ala Cys Ala Ala Gly Cys Thr Ala Gly Thr
7325 7330 7335

Ala Cys Cys Ala Gly Thr Thr Gly Ala Gly Cys Ala Ala Gly Ala
7340 7345 7350

Gly Ala Ala Gly Gly Thr Ala Gly Ala Ala Gly Ala Ala Gly Cys
7355 7360 7365

Cys Ala Ala Thr Gly Ala Ala Gly Gly Ala Gly Ala Gly Ala Ala
7370 7375 7380

Cys Ala Cys Cys Cys Gly Cys Thr Thr Gly Thr Thr Ala Cys Ala
7385 7390 7395

Cys Cys Cys Thr Gly Thr Gly Ala Gly Cys Cys Thr Gly Cys Ala
7400 7405 7410

Thr Gly Gly Gly Ala Thr Gly Gly Ala Thr Gly Ala Cys Cys Cys
7415 7420 7425

Gly Gly Ala Gly Ala Gly Ala Gly Ala Ala Gly Thr Ala Thr Thr
7430 7435 7440

Ala Gly Ala Gly Thr Gly Gly Ala Gly Gly Thr Thr Thr Gly Ala
7445 7450 7455

Cys Ala Gly Cys Cys Gly Cys Cys Thr Ala Gly Cys Ala Thr Thr
7460 7465 7470

Thr Cys Ala Thr Cys Ala Cys Ala Thr Gly Gly Cys Cys Cys Gly
7475 7480 7485

Ala Gly Ala Gly Cys Thr Gly Cys Ala Thr Cys Cys Gly Gly Ala
7490 7495 7500

Cys Thr Gly Thr Ala Cys Thr Gly Gly Gly Thr Cys Thr Cys Thr
7505 7510 7515

Cys Thr Gly Gly Thr Thr Ala Gly Ala Cys Cys Ala Gly Ala Thr
7520 7525 7530

Cys Thr Gly Ala Gly Cys Cys Thr Gly Gly Gly Ala Gly Cys Thr
7535 7540 7545

Cys Thr Cys Thr Gly Gly Cys Thr Ala Ala Cys Thr Ala Gly Gly
7550 7555 7560

Gly Ala Ala Cys Cys Cys Ala Cys Thr Gly Cys Thr Thr Ala Ala
7565 7570 7575

Gly Cys Cys Thr Cys Ala Ala Thr Ala Ala Ala Gly Cys Thr Thr
7580 7585 7590

Gly Cys Cys Thr Thr Gly Ala Gly Thr Gly Cys Thr Thr Cys Ala
7595 7600 7605

Ala Gly Thr Ala Gly Thr Gly Thr Gly Thr Gly Cys Cys Cys Gly
7610 7615 7620

Thr Cys Thr Gly Thr Thr Gly Thr Gly Thr Gly Ala Cys Thr Cys
7625 7630 7635

Thr Gly Gly Thr Ala Ala Cys Thr Ala Gly Ala Gly Ala Thr Cys
7640 7645 7650

Cys Cys Thr Cys Ala Gly Ala Cys Cys Cys Thr Thr Thr Thr Ala
7655 7660 7665

Gly Thr Cys Ala Gly Thr Gly Thr Gly Gly Ala Ala Ala Ala Thr
7670 7675 7680

Cys Thr Cys Thr Ala Gly Cys Ala Gly Gly Gly Cys Cys Cys Gly
7685 7690 7695

Thr Thr Thr Ala Ala Ala Cys Cys Cys Gly Cys Thr Gly Ala Thr
7700 7705 7710

Cys Ala Gly Cys Cys Thr Cys Gly Ala Cys Thr Gly Thr Gly Cys
7715 7720 7725

Cys Thr Thr Cys Thr Ala Gly Thr Thr Gly Cys Cys Ala Gly Cys
7730 7735 7740

Cys Ala Thr Cys Thr Gly Thr Thr Gly Thr Thr Thr Gly Cys Cys
7745 7750 7755

Cys Cys Thr Cys Cys Cys Cys Cys Gly Thr Gly Cys Cys Thr Thr
7760 7765 7770

Cys Cys Thr Thr Gly Ala Cys Cys Cys Thr Gly Gly Ala Ala Gly
7775 7780 7785

Gly Thr Gly Cys Cys Ala Cys Thr Cys Cys Cys Ala Cys Thr Gly
7790 7795 7800

Thr Cys Cys Thr Thr Thr Cys Cys Thr Ala Ala Thr Ala Ala Ala
7805 7810 7815

Ala Thr Gly Ala Gly Gly Ala Ala Ala Thr Thr Gly Cys Ala Thr
7820 7825 7830

Cys Gly Cys Ala Thr Thr Gly Thr Cys Thr Gly Ala Gly Thr Ala
7835 7840 7845

Gly Gly Thr Gly Thr Cys Ala Thr Thr Cys Thr Ala Thr Thr Cys
7850 7855 7860

Thr Gly Gly Gly Gly Gly Gly Thr Gly Gly Gly Gly Thr Gly Gly
7865 7870 7875

Gly Gly Cys Ala Gly Gly Ala Cys Ala Gly Cys Ala Ala Gly Gly
7880 7885 7890

Gly Gly Gly Ala Gly Gly Ala Thr Thr Gly Gly Gly Ala Ala Gly
7895 7900 7905

Ala Cys Ala Ala Thr Ala Gly Cys Ala Gly Gly Cys Ala Thr Gly
7910 7915 7920

Cys Thr Gly Gly Gly Gly Ala Thr Gly Cys Gly Gly Thr Gly Gly
7925 7930 7935

Gly Cys Thr Cys Thr Ala Thr Gly Gly Cys Thr Thr Cys Thr Gly

```
    7940                7945                7950

Ala Gly  Gly Cys Gly Gly Ala  Ala Ala Gly Ala Ala  Cys Cys Ala
    7955                7960                7965

Gly Cys  Thr Gly Gly Gly Gly  Cys Thr Cys Thr Ala  Gly Gly Gly
    7970                7975                7980

Gly Gly  Thr Ala Thr Cys Cys  Cys Cys Ala Cys Gly  Cys Gly Cys
    7985                7990                7995

Cys Cys  Thr Gly Thr Ala Gly  Cys Gly Gly Cys Gly  Cys Ala Thr
    8000                8005                8010

Thr Ala  Ala Gly Cys Gly Cys  Gly Gly Cys Gly Gly  Gly Thr Gly
    8015                8020                8025

Thr Gly  Gly Thr Gly Gly Thr  Thr Ala Cys Gly Cys  Gly Cys Ala
    8030                8035                8040

Gly Cys  Gly Thr Gly Ala Cys  Cys Gly Cys Thr Ala  Cys Ala Cys
    8045                8050                8055

Thr Thr  Gly Cys Cys Ala Gly  Cys Gly Cys Cys Cys  Thr Ala Gly
    8060                8065                8070

Cys Gly  Cys Cys Cys Gly Cys  Thr Cys Cys Thr Thr  Thr Cys Gly
    8075                8080                8085

Cys Thr  Thr Thr Cys Thr Thr  Cys Cys Cys Thr Thr  Cys Cys Thr
    8090                8095                8100

Thr Thr  Cys Thr Cys Gly Cys  Cys Ala Cys Gly Thr  Thr Cys Gly
    8105                8110                8115

Cys Cys  Gly Gly Cys Thr Thr  Thr Cys Cys Cys Cys  Gly Thr Cys
    8120                8125                8130

Ala Ala  Gly Cys Thr Cys Thr  Ala Ala Ala Thr Cys  Gly Gly Gly
    8135                8140                8145

Gly Gly  Cys Thr Cys Cys Cys  Thr Thr Thr Ala Gly  Gly Gly Thr
    8150                8155                8160

Thr Cys  Cys Gly Ala Thr Thr  Thr Ala Gly Thr Gly  Cys Thr Thr
    8165                8170                8175

Thr Ala  Cys Gly Gly Cys Ala  Cys Cys Thr Cys Gly  Ala Cys Cys
    8180                8185                8190

Cys Cys  Ala Ala Ala Ala Ala  Ala Cys Thr Thr Gly  Ala Thr Thr
    8195                8200                8205

Ala Gly  Gly Gly Thr Gly Ala  Thr Gly Gly Thr Thr  Cys Ala Cys
    8210                8215                8220

Gly Thr  Ala Gly Thr Gly Gly  Gly Cys Cys Ala Thr  Cys Gly Cys
    8225                8230                8235

Cys Cys  Thr Gly Ala Thr Ala  Gly Ala Cys Gly Gly  Thr Thr Thr
    8240                8245                8250

Thr Thr  Cys Gly Cys Cys Cys  Thr Thr Thr Gly Ala  Cys Gly Thr
    8255                8260                8265

Thr Gly  Gly Ala Gly Thr Cys  Cys Ala Cys Gly Thr  Thr Cys Thr
    8270                8275                8280

Thr Thr  Ala Ala Thr Ala Gly  Thr Gly Gly Ala Cys  Thr Cys Thr
    8285                8290                8295

Thr Gly  Thr Thr Cys Cys Ala  Ala Ala Cys Thr Gly  Gly Ala Ala
    8300                8305                8310

Cys Ala  Ala Cys Ala Cys Thr  Cys Ala Ala Cys Cys  Cys Thr Ala
    8315                8320                8325

Thr Cys  Thr Cys Gly Gly Thr  Cys Thr Ala Thr Thr  Cys Thr Thr
    8330                8335                8340
```

```
Thr Thr  Gly Ala Thr Thr Thr  Ala Thr Ala Ala Gly  Gly Gly Ala
    8345                 8350                 8355

Thr Thr  Thr Thr Gly Cys Cys  Gly Ala Thr Thr Thr  Cys Gly Gly
    8360                 8365                 8370

Cys Cys  Thr Ala Thr Thr Gly  Gly Thr Thr Ala Ala  Ala Ala Ala
    8375                 8380                 8385

Ala Thr  Gly Ala Gly Cys Thr  Gly Ala Thr Thr Thr  Ala Ala Cys
    8390                 8395                 8400

Ala Ala  Ala Ala Ala Thr Thr  Thr Ala Ala Cys Gly  Cys Gly Ala
    8405                 8410                 8415

Ala Thr  Thr Ala Ala Thr Thr  Cys Thr Gly Thr Gly  Gly Ala Ala
    8420                 8425                 8430

Thr Gly  Thr Gly Thr Gly Thr  Cys Ala Gly Thr Thr  Ala Gly Gly
    8435                 8440                 8445

Gly Thr  Gly Thr Gly Gly Ala  Ala Ala Gly Thr Cys  Cys Cys Cys
    8450                 8455                 8460

Ala Gly  Gly Cys Thr Cys Cys  Cys Cys Ala Gly Cys  Ala Gly Gly
    8465                 8470                 8475

Cys Ala  Gly Ala Ala Gly Thr  Ala Thr Gly Cys Ala  Ala Ala Gly
    8480                 8485                 8490

Cys Ala  Thr Gly Cys Ala Thr  Cys Thr Cys Ala Ala  Thr Thr Ala
    8495                 8500                 8505

Gly Thr  Cys Ala Gly Cys Ala  Ala Cys Cys Ala Gly  Gly Thr Gly
    8510                 8515                 8520

Thr Gly  Gly Ala Ala Ala Gly  Thr Cys Cys Cys Cys  Ala Gly Gly
    8525                 8530                 8535

Cys Thr  Cys Cys Cys Cys Ala  Gly Cys Ala Gly Gly  Cys Ala Gly
    8540                 8545                 8550

Ala Ala  Gly Thr Ala Thr Gly  Cys Ala Ala Ala Gly  Cys Ala Thr
    8555                 8560                 8565

Gly Cys  Ala Thr Cys Thr Cys  Ala Ala Thr Thr Ala  Gly Thr Cys
    8570                 8575                 8580

Ala Gly  Cys Ala Ala Cys Cys  Ala Thr Ala Gly Thr  Cys Cys Cys
    8585                 8590                 8595

Gly Cys  Cys Cys Cys Thr Ala  Ala Cys Thr Cys Cys  Gly Cys Cys
    8600                 8605                 8610

Cys Ala  Thr Cys Cys Cys Gly  Cys Cys Cys Cys Thr  Ala Ala Cys
    8615                 8620                 8625

Thr Cys  Cys Gly Cys Cys Cys  Ala Gly Thr Thr Cys  Cys Gly Cys
    8630                 8635                 8640

Cys Cys  Ala Thr Thr Cys Thr  Cys Cys Gly Cys Cys  Cys Cys Ala
    8645                 8650                 8655

Thr Gly  Gly Cys Thr Gly Ala  Cys Thr Ala Ala Thr  Thr Thr Thr
    8660                 8665                 8670

Thr Thr  Thr Thr Ala Thr Thr  Thr Ala Thr Gly Cys  Ala Gly Ala
    8675                 8680                 8685

Gly Gly  Cys Cys Gly Ala Gly  Gly Cys Cys Gly Cys  Cys Thr Cys
    8690                 8695                 8700

Thr Gly  Cys Cys Thr Cys Thr  Gly Ala Gly Cys Thr  Ala Thr Thr
    8705                 8710                 8715

Cys Cys  Ala Gly Ala Ala Gly  Thr Ala Gly Thr Gly  Ala Gly Gly
    8720                 8725                 8730
```

Ala Gly Gly Cys Thr Thr Thr Thr Thr Thr Gly Gly Ala Gly Gly
8735 8740 8745

Cys Cys Thr Ala Gly Gly Cys Thr Thr Thr Thr Gly Cys Ala Ala
8750 8755 8760

Ala Ala Ala Gly Cys Thr Cys Cys Cys Gly Gly Gly Ala Gly Cys
8765 8770 8775

Thr Thr Gly Thr Ala Thr Ala Thr Cys Cys Ala Thr Thr Thr Thr
8780 8785 8790

Cys Gly Gly Ala Thr Cys Thr Gly Ala Thr Cys Ala Gly Cys Ala
8795 8800 8805

Cys Gly Thr Gly Thr Thr Gly Ala Cys Ala Ala Thr Thr Ala Ala
8810 8815 8820

Thr Cys Ala Thr Cys Gly Gly Cys Ala Thr Ala Gly Thr Ala Thr
8825 8830 8835

Ala Thr Cys Gly Gly Cys Ala Thr Ala Gly Thr Ala Thr Ala Ala
8840 8845 8850

Thr Ala Cys Gly Ala Cys Ala Ala Gly Gly Thr Gly Ala Gly Gly
8855 8860 8865

Ala Ala Cys Thr Ala Ala Ala Cys Cys Ala Thr Gly Gly Cys Cys
8870 8875 8880

Ala Ala Gly Thr Thr Gly Ala Cys Cys Ala Gly Thr Gly Cys Cys
8885 8890 8895

Gly Thr Thr Cys Cys Gly Gly Thr Gly Cys Thr Cys Ala Cys Cys
8900 8905 8910

Gly Cys Gly Cys Gly Cys Gly Ala Cys Gly Thr Cys Gly Cys Cys
8915 8920 8925

Gly Gly Ala Gly Cys Gly Gly Thr Cys Gly Ala Gly Thr Thr Cys
8930 8935 8940

Thr Gly Gly Ala Cys Cys Gly Ala Cys Cys Gly Gly Cys Thr Cys
8945 8950 8955

Gly Gly Gly Thr Thr Cys Thr Cys Cys Cys Gly Gly Gly Ala Cys
8960 8965 8970

Thr Thr Cys Gly Thr Gly Gly Ala Gly Gly Ala Cys Gly Ala Cys
8975 8980 8985

Thr Thr Cys Gly Cys Cys Gly Gly Thr Gly Thr Gly Gly Thr Cys
8990 8995 9000

Cys Gly Gly Gly Ala Cys Gly Ala Cys Gly Thr Gly Ala Cys Cys
9005 9010 9015

Cys Thr Gly Thr Thr Cys Ala Thr Cys Ala Gly Cys Gly Cys Gly
9020 9025 9030

Gly Thr Cys Cys Ala Gly Gly Ala Cys Cys Ala Gly Gly Thr Gly
9035 9040 9045

Gly Thr Gly Cys Cys Gly Gly Ala Cys Ala Ala Cys Ala Cys Cys
9050 9055 9060

Cys Thr Gly Gly Cys Cys Thr Gly Gly Gly Thr Gly Thr Gly Gly
9065 9070 9075

Gly Thr Gly Cys Gly Cys Gly Gly Cys Cys Thr Gly Gly Ala Cys
9080 9085 9090

Gly Ala Gly Cys Thr Gly Thr Ala Cys Gly Cys Cys Gly Ala Gly
9095 9100 9105

Thr Gly Gly Thr Cys Gly Gly Ala Gly Gly Thr Cys Gly Thr Gly
9110 9115 9120

Thr Cys Cys Ala Cys Gly Ala Ala Cys Thr Thr Cys Cys Gly Gly 9125 9130 9135

Gly Ala Cys Gly Cys Cys Thr Cys Cys Gly Gly Gly Cys Cys Gly
9140 9145 9150

Gly Cys Cys Ala Thr Gly Ala Cys Cys Gly Ala Gly Ala Thr Cys
9155 9160 9165

Gly Gly Cys Gly Ala Gly Cys Ala Gly Cys Cys Gly Thr Gly Gly
9170 9175 9180

Gly Gly Gly Cys Gly Gly Gly Ala Gly Thr Thr Cys Gly Cys Cys
9185 9190 9195

Cys Thr Gly Cys Gly Cys Gly Ala Cys Cys Cys Gly Gly Cys Cys
9200 9205 9210

Gly Gly Cys Ala Ala Cys Thr Gly Cys Gly Thr Gly Cys Ala Cys
9215 9220 9225

Thr Thr Cys Gly Thr Gly Gly Cys Cys Gly Ala Gly Gly Ala Gly
9230 9235 9240

Cys Ala Gly Gly Ala Cys Thr Gly Ala Cys Ala Cys Gly Thr Gly
9245 9250 9255

Cys Thr Ala Cys Gly Ala Gly Ala Thr Thr Thr Cys Gly Ala Thr
9260 9265 9270

Thr Cys Cys Ala Cys Cys Gly Cys Cys Gly Cys Cys Thr Thr Cys
9275 9280 9285

Thr Ala Thr Gly Ala Ala Ala Gly Gly Thr Thr Gly Gly Gly Cys
9290 9295 9300

Thr Thr Cys Gly Gly Ala Ala Thr Cys Gly Thr Thr Thr Thr Cys
9305 9310 9315

Cys Gly Gly Gly Ala Cys Gly Cys Cys Gly Gly Cys Thr Gly Gly
9320 9325 9330

Ala Thr Gly Ala Thr Cys Cys Thr Cys Cys Ala Gly Cys Gly Cys
9335 9340 9345

Gly Gly Gly Gly Ala Thr Cys Thr Cys Ala Thr Gly Cys Thr Gly
9350 9355 9360

Gly Ala Gly Thr Thr Cys Thr Thr Cys Gly Cys Cys Cys Ala Cys
9365 9370 9375

Cys Cys Cys Ala Ala Cys Thr Thr Gly Thr Thr Thr Ala Thr Thr
9380 9385 9390

Gly Cys Ala Gly Cys Thr Thr Ala Thr Ala Ala Thr Gly Gly Thr
9395 9400 9405

Thr Ala Cys Ala Ala Ala Thr Ala Ala Ala Gly Cys Ala Ala Thr
9410 9415 9420

Ala Gly Cys Ala Thr Cys Ala Cys Ala Ala Ala Thr Thr Thr Cys
9425 9430 9435

Ala Cys Ala Ala Ala Thr Ala Ala Ala Gly Cys Ala Thr Thr Thr
9440 9445 9450

Thr Thr Thr Thr Cys Ala Cys Thr Gly Cys Ala Thr Thr Cys Thr
9455 9460 9465

Ala Gly Thr Thr Gly Thr Gly Gly Thr Thr Thr Gly Thr Cys Cys
9470 9475 9480

Ala Ala Ala Cys Thr Cys Ala Thr Cys Ala Ala Thr Gly Thr Ala
9485 9490 9495

Thr Cys Thr Thr Ala Thr Cys Ala Thr Gly Thr Cys Thr Gly Thr
9500 9505 9510

Ala Thr Ala Cys Cys Gly Thr Cys Gly Ala Cys Cys Thr Cys Thr
9515 9520 9525

Ala Gly Cys Thr Ala Gly Ala Gly Cys Thr Thr Gly Gly Cys Gly
9530 9535 9540

Thr Ala Ala Thr Cys Ala Thr Gly Gly Thr Cys Ala Thr Ala Gly
9545 9550 9555

Cys Thr Gly Thr Thr Thr Cys Cys Thr Gly Thr Gly Thr Gly Ala
9560 9565 9570

Ala Ala Thr Thr Gly Thr Thr Ala Thr Cys Cys Gly Cys Thr Cys
9575 9580 9585

Ala Cys Ala Ala Thr Thr Cys Cys Ala Cys Ala Cys Ala Ala Cys
9590 9595 9600

Ala Thr Ala Cys Gly Ala Gly Cys Cys Gly Gly Ala Ala Gly Cys
9605 9610 9615

Ala Thr Ala Ala Ala Gly Thr Gly Thr Ala Ala Ala Gly Cys Cys
9620 9625 9630

Thr Gly Gly Gly Gly Thr Gly Cys Cys Thr Ala Ala Thr Gly Ala
9635 9640 9645

Gly Thr Gly Ala Gly Cys Thr Ala Ala Cys Thr Cys Ala Cys Ala
9650 9655 9660

Thr Thr Ala Ala Thr Thr Gly Cys Gly Thr Thr Gly Cys Gly Cys
9665 9670 9675

Thr Cys Ala Cys Thr Gly Cys Cys Cys Gly Cys Thr Thr Thr Cys
9680 9685 9690

Cys Ala Gly Thr Cys Gly Gly Gly Ala Ala Ala Cys Cys Thr Gly
9695 9700 9705

Thr Cys Gly Thr Gly Cys Cys Ala Gly Cys Thr Gly Cys Ala Thr
9710 9715 9720

Thr Ala Ala Thr Gly Ala Ala Thr Cys Gly Gly Cys Cys Ala Ala
9725 9730 9735

Cys Gly Cys Gly Cys Gly Gly Gly Gly Ala Gly Ala Gly Gly Cys
9740 9745 9750

Gly Gly Thr Thr Thr Gly Cys Gly Thr Ala Thr Thr Gly Gly Gly
9755 9760 9765

Cys Gly Cys Thr Cys Thr Thr Cys Cys Gly Cys Thr Thr Cys Cys
9770 9775 9780

Thr Cys Gly Cys Thr Cys Ala Cys Thr Gly Ala Cys Thr Cys Gly
9785 9790 9795

Cys Thr Gly Cys Gly Cys Thr Cys Gly Gly Thr Cys Gly Thr Thr
9800 9805 9810

Cys Gly Gly Cys Thr Gly Cys Gly Gly Cys Gly Ala Gly Cys Gly
9815 9820 9825

Gly Thr Ala Thr Cys Ala Gly Cys Thr Cys Ala Cys Thr Cys Ala
9830 9835 9840

Ala Ala Gly Gly Cys Gly Gly Thr Ala Ala Thr Ala Cys Gly Gly
9845 9850 9855

Thr Thr Ala Thr Cys Cys Ala Cys Ala Gly Ala Ala Thr Cys Ala
9860 9865 9870

Gly Gly Gly Gly Ala Thr Ala Ala Cys Gly Cys Ala Gly Gly Ala
9875 9880 9885

Ala Ala Gly Ala Ala Cys Ala Thr Gly Thr Gly Ala Gly Cys Ala
9890 9895 9900

Ala Ala Ala Gly Gly Cys Cys Ala Gly Cys Ala Ala Ala Ala Gly
9905 9910 9915

```
Gly Cys  Cys Ala Gly Gly Ala  Ala Cys Cys Gly Thr  Ala Ala Ala
    9920                9925                9930

Ala Ala  Gly Gly Cys Cys Gly  Cys Gly Thr Thr Gly  Cys Thr Gly
    9935                9940                9945

Gly Cys  Gly Thr Thr Thr Thr  Thr Cys Cys Ala Thr  Ala Gly Gly
    9950                9955                9960

Cys Thr  Cys Cys Gly Cys Cys  Cys Cys Cys Cys Thr  Gly Ala Cys
    9965                9970                9975

Gly Ala  Gly Cys Ala Thr Cys  Ala Cys Ala Ala Ala  Ala Ala Thr
    9980                9985                9990

Cys Gly  Ala Cys Gly Cys Thr   Cys Ala Ala Gly Thr   Cys Ala Gly
    9995                10000                10005

Ala Gly   Gly Thr Gly Gly Cys   Gly Ala Ala Ala Cys   Cys Cys Gly
    10010                10015                10020

Ala Cys   Ala Gly Gly Ala Cys   Thr Ala Thr Ala Ala   Ala Gly Ala
    10025                10030                10035

Thr Ala   Cys Cys Ala Gly Gly   Cys Gly Thr Thr Thr   Cys Cys Cys
    10040                10045                10050

Cys Cys   Thr Gly Gly Ala Ala   Gly Cys Thr Cys Cys   Cys Thr Cys
    10055                10060                10065

Gly Thr   Gly Cys Gly Cys Thr   Cys Thr Cys Cys Thr   Gly Thr Thr
    10070                10075                10080

Cys Cys   Gly Ala Cys Cys Cys   Thr Gly Cys Cys Gly   Cys Thr Thr
    10085                10090                10095

Ala Cys   Cys Gly Gly Ala Thr   Ala Cys Cys Thr Gly   Thr Cys Cys
    10100                10105                10110

Gly Cys   Cys Thr Thr Thr Cys   Thr Cys Cys Cys Thr   Thr Cys Gly
    10115                10120                10125

Gly Gly   Ala Ala Gly Cys Gly   Thr Gly Gly Cys Gly   Cys Thr Thr
    10130                10135                10140

Thr Cys   Thr Cys Ala Thr Ala   Gly Cys Thr Cys Ala   Cys Gly Cys
    10145                10150                10155

Thr Gly   Thr Ala Gly Gly Thr   Ala Thr Cys Thr Cys   Ala Gly Thr
    10160                10165                10170

Thr Cys   Gly Gly Thr Gly Thr   Ala Gly Gly Thr Cys   Gly Thr Thr
    10175                10180                10185

Cys Gly   Cys Thr Cys Cys Ala   Ala Gly Cys Thr Gly   Gly Gly Cys
    10190                10195                10200

Thr Gly   Thr Gly Thr Gly Cys   Ala Cys Gly Ala Ala   Cys Cys Cys
    10205                10210                10215

Cys Cys   Cys Gly Thr Thr Cys   Ala Gly Cys Cys Cys   Gly Ala Cys
    10220                10225                10230

Cys Gly   Cys Thr Gly Cys Gly   Cys Cys Thr Thr Ala   Thr Cys Cys
    10235                10240                10245

Gly Gly   Thr Ala Ala Cys Thr   Ala Thr Cys Gly Thr   Cys Thr Thr
    10250                10255                10260

Gly Ala   Gly Thr Cys Cys Ala   Ala Cys Cys Cys Gly   Gly Thr Ala
    10265                10270                10275

Ala Gly   Ala Cys Ala Cys Gly   Ala Cys Thr Thr Ala   Thr Cys Gly
    10280                10285                10290

Cys Cys   Ala Cys Thr Gly Gly   Cys Ala Gly Cys Ala   Gly Cys Cys
    10295                10300                10305

Ala Cys   Thr Gly Gly Thr Ala   Ala Cys Ala Gly Gly   Ala Thr Thr
```

```
    10310               10315               10320

Ala Gly  Cys Ala Gly Ala Gly  Cys Gly Ala Gly Gly  Thr Ala Thr
    10325               10330               10335

Gly Thr  Ala Gly Gly Cys Gly  Gly Thr Gly Cys Thr  Ala Cys Ala
    10340               10345               10350

Gly Ala  Gly Thr Thr Cys Thr  Thr Gly Ala Ala Gly  Thr Gly Gly
    10355               10360               10365

Thr Gly  Gly Cys Cys Thr Ala  Ala Cys Thr Ala Cys  Gly Gly Cys
    10370               10375               10380

Thr Ala  Cys Ala Cys Thr Ala  Gly Ala Ala Gly Ala  Ala Cys Ala
    10385               10390               10395

Gly Thr  Ala Thr Thr Thr Gly  Gly Thr Ala Thr Cys  Thr Gly Cys
    10400               10405               10410

Gly Cys  Thr Cys Thr Gly Cys  Thr Gly Ala Ala Gly  Cys Cys Ala
    10415               10420               10425

Gly Thr  Thr Ala Cys Cys Thr  Thr Cys Gly Gly Ala  Ala Ala Ala
    10430               10435               10440

Ala Gly  Ala Gly Thr Thr Gly  Gly Thr Ala Gly Cys  Thr Cys Thr
    10445               10450               10455

Thr Gly  Ala Thr Cys Cys Gly  Gly Cys Ala Ala Ala  Cys Ala Ala
    10460               10465               10470

Ala Cys  Cys Ala Cys Cys Gly  Cys Thr Gly Gly Thr  Ala Gly Cys
    10475               10480               10485

Gly Gly  Thr Gly Gly Thr Thr  Thr Thr Thr Thr Thr  Gly Thr Thr
    10490               10495               10500

Thr Gly  Cys Ala Ala Gly Cys  Ala Gly Cys Ala Gly  Ala Thr Thr
    10505               10510               10515

Ala Cys  Gly Cys Gly Cys Ala  Gly Ala Ala Ala Ala  Ala Ala Ala
    10520               10525               10530

Gly Gly  Ala Thr Cys Thr Cys  Ala Ala Gly Ala Ala  Gly Ala Thr
    10535               10540               10545

Cys Cys  Thr Thr Thr Gly Ala  Thr Cys Thr Thr Thr  Thr Cys Thr
    10550               10555               10560

Ala Cys  Gly Gly Gly Gly Thr  Cys Thr Gly Ala Cys  Gly Cys Thr
    10565               10570               10575

Cys Ala  Gly Thr Gly Gly Ala  Ala Cys Gly Ala Ala  Ala Ala Cys
    10580               10585               10590

Thr Cys  Ala Cys Gly Thr Thr  Ala Ala Gly Gly Gly  Ala Thr Thr
    10595               10600               10605

Thr Thr  Gly Gly Thr Cys Ala  Thr Gly Ala Gly Ala  Thr Thr Ala
    10610               10615               10620

Thr Cys  Ala Ala Ala Ala Ala  Gly Gly Ala Thr Cys  Thr Thr Cys
    10625               10630               10635

Ala Cys  Cys Thr Ala Gly Ala  Thr Cys Cys Thr Thr  Thr Thr Ala
    10640               10645               10650

Ala Ala  Thr Thr Ala Ala Ala  Ala Ala Thr Gly Ala  Ala Gly Thr
    10655               10660               10665

Thr Thr  Thr Ala Ala Ala Thr  Cys Ala Ala Thr Cys  Thr Ala Ala
    10670               10675               10680

Ala Gly  Thr Ala Thr Ala Thr  Ala Thr Gly Ala Gly  Thr Ala Ala
    10685               10690               10695

Ala Cys  Thr Thr Gly Gly Thr  Cys Thr Gly Ala Cys  Ala Gly Thr
    10700               10705               10710
```

```
Thr Ala  Cys Cys Ala Ala Thr  Gly Cys Thr Thr Ala  Ala Thr Cys
    10715                10720                10725

Ala Gly  Thr Gly Ala Gly Gly  Cys Ala Cys Cys Thr  Ala Thr Cys
    10730                10735                10740

Thr Cys  Ala Gly Cys Gly Ala  Thr Cys Thr Gly Thr  Cys Thr Ala
    10745                10750                10755

Thr Thr  Thr Cys Gly Thr Thr  Cys Ala Thr Cys Cys  Ala Thr Ala
    10760                10765                10770

Gly Thr  Thr Gly Cys Cys Thr  Gly Ala Cys Thr Cys  Cys Cys Cys
    10775                10780                10785

Gly Thr  Cys Gly Thr Gly Thr  Ala Gly Ala Thr Ala  Ala Cys Thr
    10790                10795                10800

Ala Cys  Gly Ala Thr Ala Cys  Gly Gly Gly Ala Gly  Gly Gly Cys
    10805                10810                10815

Thr Thr  Ala Cys Cys Ala Thr  Cys Thr Gly Gly Cys  Cys Cys Cys
    10820                10825                10830

Ala Gly  Thr Gly Cys Thr Gly  Cys Ala Ala Thr Gly  Ala Thr Ala
    10835                10840                10845

Cys Cys  Gly Cys Gly Ala Gly  Ala Cys Cys Cys Ala  Cys Gly Cys
    10850                10855                10860

Thr Cys  Ala Cys Cys Gly Gly  Cys Thr Cys Cys Ala  Gly Ala Thr
    10865                10870                10875

Thr Thr  Ala Thr Cys Ala Gly  Cys Ala Ala Thr Ala  Ala Ala Cys
    10880                10885                10890

Cys Ala  Gly Cys Cys Ala Gly  Cys Cys Gly Gly Ala  Ala Gly Gly
    10895                10900                10905

Gly Cys  Cys Gly Ala Gly Cys  Gly Cys Ala Gly Ala  Ala Gly Thr
    10910                10915                10920

Gly Gly  Thr Cys Cys Thr Gly  Cys Ala Ala Cys Thr  Thr Thr Ala
    10925                10930                10935

Thr Cys  Cys Gly Cys Cys Thr  Cys Cys Ala Thr Cys  Cys Ala Gly
    10940                10945                10950

Thr Cys  Thr Ala Thr Thr Ala  Ala Thr Thr Gly Thr  Thr Gly Cys
    10955                10960                10965

Cys Gly  Gly Gly Ala Ala Gly  Cys Thr Ala Gly Ala  Gly Thr Ala
    10970                10975                10980

Ala Gly  Thr Ala Gly Thr Thr  Cys Gly Cys Cys Ala  Gly Thr Thr
    10985                10990                10995

Ala Ala  Thr Ala Gly Thr Thr  Thr Gly Cys Gly Cys  Ala Ala Cys
    11000                11005                11010

Gly Thr  Thr Gly Thr Thr Gly  Cys Cys Ala Thr Thr  Gly Cys Thr
    11015                11020                11025

Ala Cys  Ala Gly Gly Cys Ala  Thr Cys Gly Thr Gly  Gly Thr Gly
    11030                11035                11040

Thr Cys  Ala Cys Gly Cys Thr  Cys Gly Thr Cys Gly  Thr Thr Thr
    11045                11050                11055

Gly Gly  Thr Ala Thr Gly Gly  Cys Thr Thr Cys Ala  Thr Thr Cys
    11060                11065                11070

Ala Gly  Cys Thr Cys Cys Gly  Gly Thr Thr Cys Cys  Cys Ala Ala
    11075                11080                11085

Cys Gly  Ala Thr Cys Ala Ala  Gly Gly Cys Gly Ala  Gly Thr Thr
    11090                11095                11100
```

Ala Cys Ala Thr Gly Ala Thr Cys Cys Cys Cys Cys Ala Thr Gly
11105 11110 11115

Thr Thr Gly Thr Gly Cys Ala Ala Ala Ala Ala Ala Gly Cys Gly
11120 11125 11130

Gly Thr Thr Ala Gly Cys Thr Cys Cys Thr Thr Cys Gly Gly Thr
11135 11140 11145

Cys Cys Thr Cys Cys Gly Ala Thr Cys Gly Thr Thr Gly Thr Cys
11150 11155 11160

Ala Gly Ala Ala Gly Thr Ala Ala Gly Thr Thr Gly Gly Cys Cys
11165 11170 11175

Gly Cys Ala Gly Thr Gly Thr Thr Ala Thr Cys Ala Cys Thr Cys
11180 11185 11190

Ala Thr Gly Gly Thr Thr Ala Thr Gly Gly Cys Ala Gly Cys Ala
11195 11200 11205

Cys Thr Gly Cys Ala Thr Ala Ala Thr Thr Cys Thr Cys Thr Thr
11210 11215 11220

Ala Cys Thr Gly Thr Cys Ala Thr Gly Cys Cys Ala Thr Cys Cys
11225 11230 11235

Gly Thr Ala Ala Gly Ala Thr Gly Cys Thr Thr Thr Thr Cys Thr
11240 11245 11250

Gly Thr Gly Ala Cys Thr Gly Gly Thr Gly Ala Gly Thr Ala Cys
11255 11260 11265

Thr Cys Ala Ala Cys Cys Ala Ala Gly Thr Cys Ala Thr Thr Cys
11270 11275 11280

Thr Gly Ala Gly Ala Ala Thr Ala Gly Thr Gly Thr Ala Thr Gly
11285 11290 11295

Cys Gly Gly Cys Gly Ala Cys Cys Gly Ala Gly Thr Thr Gly Cys
11300 11305 11310

Thr Cys Thr Thr Gly Cys Cys Cys Gly Gly Cys Gly Thr Cys Ala
11315 11320 11325

Ala Thr Ala Cys Gly Gly Gly Ala Thr Ala Ala Thr Ala Cys Cys
11330 11335 11340

Gly Cys Gly Cys Cys Ala Cys Ala Thr Ala Gly Cys Ala Gly Ala
11345 11350 11355

Ala Cys Thr Thr Thr Ala Ala Ala Ala Gly Thr Gly Cys Thr Cys
11360 11365 11370

Ala Thr Cys Ala Thr Thr Gly Gly Ala Ala Ala Ala Cys Gly Thr
11375 11380 11385

Thr Cys Thr Thr Cys Gly Gly Gly Gly Cys Gly Ala Ala Ala Ala
11390 11395 11400

Cys Thr Cys Thr Cys Ala Ala Gly Gly Ala Thr Cys Thr Thr Ala
11405 11410 11415

Cys Cys Gly Cys Thr Gly Thr Thr Gly Ala Gly Ala Thr Cys Cys
11420 11425 11430

Ala Gly Thr Thr Cys Gly Ala Thr Gly Thr Ala Ala Cys Cys Cys
11435 11440 11445

Ala Cys Thr Cys Gly Thr Gly Cys Ala Cys Cys Cys Ala Ala Cys
11450 11455 11460

Thr Gly Ala Thr Cys Thr Thr Cys Ala Gly Cys Ala Thr Cys Thr
11465 11470 11475

Thr Thr Thr Ala Cys Thr Thr Thr Cys Ala Cys Cys Ala Gly Cys
11480 11485 11490

Gly Thr Thr Thr Cys Thr Gly Gly Gly Thr Gly Ala Gly Cys Ala 11495 11500 11505

Ala Ala Ala Ala Cys Ala Gly Gly Ala Ala Gly Gly Cys Ala Ala
11510 11515 11520

Ala Ala Thr Gly Cys Cys Gly Cys Ala Ala Ala Ala Ala Ala Gly
11525 11530 11535

Gly Gly Ala Ala Thr Ala Ala Gly Gly Gly Cys Gly Ala Cys Ala
11540 11545 11550

Cys Gly Gly Ala Ala Ala Thr Gly Thr Thr Gly Ala Ala Thr Ala
11555 11560 11565

Cys Thr Cys Ala Thr Ala Cys Thr Cys Thr Thr Cys Cys Thr Thr
11570 11575 11580

Thr Thr Thr Cys Ala Ala Thr Ala Thr Thr Ala Thr Thr Gly Ala
11585 11590 11595

Ala Gly Cys Ala Thr Thr Thr Ala Thr Cys Ala Gly Gly Gly Thr
11600 11605 11610

Thr Ala Thr Thr Gly Thr Cys Thr Cys Ala Thr Gly Ala Gly Cys
11615 11620 11625

Gly Gly Ala Thr Ala Cys Ala Thr Ala Thr Thr Thr Gly Ala Ala
11630 11635 11640

Thr Gly Thr Ala Thr Thr Thr Ala Gly Ala Ala Ala Ala Ala Thr
11645 11650 11655

Ala Ala Ala Cys Ala Ala Ala Thr Ala Gly Gly Gly Gly Thr Thr
11660 11665 11670

Cys Cys Gly Cys Gly Cys Ala Cys Ala Thr Thr Thr Cys Cys Cys
11675 11680 11685

Cys Gly Ala Ala Ala Ala Gly Thr Gly Cys Cys Ala Cys Cys Thr
11690 11695 11700

Gly Ala Cys
11705

<210> SEQ ID NO 14
<211> LENGTH: 7886
<212> TYPE: PRT
<213> ORGANISM: Artificial Sequence
<220> FEATURE:
<223> OTHER INFORMATION: synthetic constructs

<400> SEQUENCE: 14

Cys Cys Thr Gly Cys Ala Gly Gly Cys Ala Gly Cys Thr Gly Cys Gly
1 5 10 15

Cys Gly Cys Thr Cys Gly Cys Thr Cys Gly Cys Thr Cys Ala Cys Thr
20 25 30

Gly Ala Gly Gly Cys Cys Gly Cys Cys Cys Gly Gly Gly Cys Ala Ala
35 40 45

Ala Gly Cys Cys Cys Gly Gly Gly Cys Gly Thr Cys Gly Gly Gly Cys
50 55 60

Gly Ala Cys Cys Thr Thr Thr Gly Gly Thr Cys Gly Cys Cys Cys Gly
65 70 75 80

Gly Cys Cys Thr Cys Ala Gly Thr Gly Ala Gly Cys Gly Ala Gly Cys
85 90 95

Gly Ala Gly Cys Gly Cys Gly Cys Ala Gly Ala Gly Ala Gly Gly Gly
100 105 110

Ala Gly Thr Gly Gly Cys Cys Ala Ala Cys Thr Cys Cys Ala Thr Cys
115 120 125

Ala Cys Thr Ala Gly Gly Gly Gly Thr Thr Cys Cys Thr Gly Cys Gly

```
    130                 135                 140

Gly Cys Cys Gly Cys Ala Cys Gly Cys Gly Thr Thr Thr Ala Ala Cys
145                 150                 155                 160

Ala Thr Thr Ala Thr Gly Gly Cys Cys Thr Thr Ala Gly Gly Thr Cys
                165                 170                 175

Ala Cys Thr Thr Cys Ala Thr Cys Thr Cys Cys Ala Thr Gly Gly Gly
            180                 185                 190

Gly Thr Thr Cys Thr Thr Cys Thr Thr Cys Thr Gly Ala Thr Thr Thr
        195                 200                 205

Thr Cys Thr Ala Gly Ala Ala Ala Ala Thr Gly Ala Gly Ala Thr Gly
    210                 215                 220

Gly Gly Gly Gly Thr Gly Cys Ala Gly Ala Gly Ala Gly Cys Thr Thr
225                 230                 235                 240

Cys Cys Thr Cys Ala Gly Thr Gly Ala Cys Cys Thr Gly Cys Cys Cys
                245                 250                 255

Ala Gly Gly Gly Thr Cys Ala Cys Ala Thr Cys Ala Gly Ala Ala Ala
            260                 265                 270

Thr Gly Thr Cys Ala Gly Ala Gly Cys Thr Ala Gly Ala Ala Cys Thr
        275                 280                 285

Thr Gly Ala Ala Cys Thr Cys Ala Gly Ala Thr Thr Ala Cys Thr Ala
    290                 295                 300

Ala Thr Cys Thr Thr Ala Ala Ala Thr Thr Cys Cys Ala Thr Gly Cys
305                 310                 315                 320

Cys Thr Thr Gly Gly Gly Gly Gly Cys Ala Thr Gly Cys Ala Ala Gly
                325                 330                 335

Thr Ala Cys Gly Ala Thr Ala Thr Ala Cys Ala Gly Ala Ala Gly Gly
            340                 345                 350

Ala Gly Thr Gly Ala Ala Cys Thr Cys Ala Thr Thr Ala Gly Gly Gly
        355                 360                 365

Cys Ala Gly Ala Thr Gly Ala Cys Cys Ala Ala Thr Gly Ala Gly Thr
    370                 375                 380

Thr Thr Ala Gly Gly Ala Ala Ala Gly Ala Ala Gly Ala Gly Thr Cys
385                 390                 395                 400

Cys Ala Gly Gly Gly Cys Ala Gly Gly Gly Thr Ala Cys Ala Thr Cys
                405                 410                 415

Thr Ala Cys Ala Cys Cys Ala Cys Cys Cys Gly Cys Cys Cys Ala Gly
            420                 425                 430

Cys Cys Cys Thr Gly Gly Gly Thr Gly Ala Gly Thr Cys Cys Ala Gly
        435                 440                 445

Cys Cys Ala Cys Gly Thr Thr Cys Ala Cys Cys Thr Cys Ala Thr Thr
    450                 455                 460

Ala Thr Ala Gly Thr Thr Gly Cys Cys Thr Cys Thr Cys Thr Cys Cys
465                 470                 475                 480

Ala Gly Thr Cys Cys Thr Ala Cys Cys Thr Thr Gly Ala Cys Gly Gly
                485                 490                 495

Gly Ala Ala Gly Cys Ala Cys Ala Ala Gly Cys Ala Gly Ala Ala Ala
            500                 505                 510

Cys Thr Gly Gly Gly Ala Cys Ala Gly Gly Ala Gly Cys Cys Cys Cys
        515                 520                 525

Ala Gly Gly Ala Gly Ala Cys Cys Ala Ala Ala Thr Cys Thr Thr Cys
    530                 535                 540

Ala Thr Gly Gly Thr Cys Cys Cys Thr Cys Thr Gly Gly Gly Ala Gly
545                 550                 555                 560
```

```
Gly Ala Thr Gly Gly Gly Thr Gly Gly Gly Gly Ala Gly Ala Gly Cys
                565                 570                 575

Thr Gly Thr Gly Gly Cys Ala Gly Ala Gly Gly Cys Cys Thr Cys Ala
            580                 585                 590

Gly Gly Ala Gly Gly Gly Gly Cys Cys Cys Thr Gly Cys Thr Gly Cys
        595                 600                 605

Thr Cys Ala Gly Thr Gly Gly Thr Gly Ala Cys Ala Gly Ala Thr Ala
    610                 615                 620

Gly Gly Gly Gly Thr Gly Ala Gly Ala Ala Ala Gly Cys Ala Gly Ala
625                 630                 635                 640

Cys Ala Gly Ala Gly Thr Cys Ala Thr Thr Cys Cys Gly Thr Cys Ala
                645                 650                 655

Gly Cys Ala Thr Thr Cys Thr Gly Gly Gly Thr Cys Thr Gly Thr Thr
            660                 665                 670

Thr Gly Gly Thr Ala Cys Thr Thr Cys Thr Thr Cys Thr Cys Ala Cys
        675                 680                 685

Gly Cys Thr Ala Ala Gly Gly Thr Gly Gly Cys Gly Gly Thr Gly Thr
    690                 695                 700

Gly Ala Thr Ala Thr Gly Cys Ala Cys Ala Ala Thr Gly Gly Cys Thr
705                 710                 715                 720

Ala Ala Ala Ala Ala Gly Cys Ala Gly Gly Gly Ala Gly Ala Gly Cys
                725                 730                 735

Thr Gly Gly Ala Ala Ala Gly Ala Ala Ala Cys Ala Ala Gly Gly Ala
            740                 745                 750

Cys Ala Gly Ala Gly Ala Cys Ala Gly Ala Gly Gly Cys Cys Ala Ala
        755                 760                 765

Gly Thr Cys Ala Ala Cys Cys Ala Gly Ala Cys Cys Ala Ala Thr Thr
    770                 775                 780

Cys Cys Cys Ala Gly Ala Gly Gly Ala Ala Gly Cys Ala Ala Ala Gly
785                 790                 795                 800

Ala Ala Ala Cys Cys Ala Thr Thr Ala Cys Ala Gly Ala Gly Ala Cys
                805                 810                 815

Thr Ala Cys Ala Ala Gly Gly Gly Gly Gly Ala Ala Gly Gly Gly Ala
            820                 825                 830

Ala Gly Gly Ala Gly Ala Gly Ala Thr Gly Ala Ala Thr Thr Ala Gly
        835                 840                 845

Cys Thr Thr Cys Cys Cys Cys Thr Gly Thr Ala Ala Ala Cys Cys Thr
    850                 855                 860

Thr Ala Gly Ala Ala Cys Cys Cys Ala Gly Cys Thr Gly Thr Thr Gly
865                 870                 875                 880

Cys Cys Ala Gly Gly Gly Cys Ala Ala Cys Gly Gly Gly Gly Cys Ala
                885                 890                 895

Ala Thr Ala Cys Cys Thr Gly Thr Cys Thr Cys Thr Thr Cys Ala Gly
            900                 905                 910

Ala Gly Gly Ala Gly Ala Thr Gly Ala Ala Gly Thr Thr Gly Cys Cys
        915                 920                 925

Ala Gly Gly Gly Thr Ala Ala Cys Thr Ala Cys Ala Thr Cys Cys Thr
    930                 935                 940

Gly Thr Cys Thr Thr Thr Cys Thr Cys Ala Ala Gly Gly Ala Cys Cys
945                 950                 955                 960

Ala Thr Cys Cys Cys Ala Gly Ala Ala Thr Gly Thr Gly Gly Cys Ala
                965                 970                 975
```

```
Cys Cys Cys Ala Cys Thr Ala Gly Cys Cys Gly Thr Thr Ala Cys Cys
            980                 985                 990

Ala Thr Ala Gly Cys Ala Ala Cys  Thr Gly Cys Cys Thr  Cys Thr Thr
        995                 1000                1005

Thr Gly  Cys Cys Cys Cys Ala  Cys Thr Thr Ala Ala  Thr Cys Cys
    1010                 1015                 1020

Cys Ala  Thr Cys Cys Cys Gly  Thr Cys Thr Gly Thr  Thr Ala Ala
    1025                 1030                 1035

Ala Ala  Gly Gly Gly Cys Cys  Cys Thr Ala Thr Ala  Gly Thr Thr
    1040                 1045                 1050

Gly Gly  Ala Gly Gly Thr Gly  Gly Gly Gly Gly Ala  Gly Gly Thr
    1055                 1060                 1065

Ala Gly  Gly Ala Ala Gly Ala  Gly Cys Gly Ala Thr  Gly Ala Thr
    1070                 1075                 1080

Cys Ala  Cys Thr Thr Gly Thr  Gly Gly Ala Cys Thr  Ala Ala Gly
    1085                 1090                 1095

Thr Thr  Thr Gly Thr Thr Cys  Gly Cys Ala Thr Cys  Cys Cys Cys
    1100                 1105                 1110

Thr Thr  Cys Thr Cys Cys Ala  Ala Cys Cys Cys Cys  Cys Thr Cys
    1115                 1120                 1125

Ala Gly  Thr Ala Cys Ala Thr  Cys Ala Cys Cys Cys  Thr Gly Gly
    1130                 1135                 1140

Gly Gly  Gly Ala Ala Cys Ala  Gly Gly Gly Thr Cys  Cys Ala Cys
    1145                 1150                 1155

Thr Thr  Gly Cys Thr Cys Cys  Thr Gly Gly Gly Cys  Cys Cys Ala
    1160                 1165                 1170

Cys Ala  Cys Ala Gly Thr Cys  Cys Thr Gly Cys Ala  Gly Thr Ala
    1175                 1180                 1185

Thr Thr  Gly Thr Gly Thr Ala  Thr Ala Thr Ala Ala  Gly Gly Cys
    1190                 1195                 1200

Cys Ala  Gly Gly Gly Cys Ala  Ala Ala Gly Ala Gly  Gly Ala Gly
    1205                 1210                 1215

Cys Ala  Gly Gly Thr Thr Thr  Thr Ala Ala Ala Gly  Thr Gly Ala
    1220                 1225                 1230

Ala Ala  Gly Gly Cys Ala Gly  Gly Cys Ala Gly Gly  Thr Gly Thr
    1235                 1240                 1245

Thr Gly  Gly Gly Gly Ala Gly  Gly Cys Ala Gly Thr  Thr Ala Cys
    1250                 1255                 1260

Cys Gly  Gly Gly Gly Cys Ala  Ala Cys Gly Gly Gly  Ala Ala Cys
    1265                 1270                 1275

Ala Gly  Gly Gly Cys Gly Thr  Thr Thr Cys Gly Gly  Ala Gly Gly
    1280                 1285                 1290

Thr Gly  Gly Thr Thr Gly Cys  Cys Ala Thr Gly Gly  Gly Gly Ala
    1295                 1300                 1305

Cys Cys  Thr Gly Gly Ala Thr  Gly Cys Thr Gly Ala  Cys Gly Ala
    1310                 1315                 1320

Ala Gly  Gly Cys Thr Cys Gly  Cys Gly Ala Gly Gly  Cys Thr Gly
    1325                 1330                 1335

Thr Gly  Ala Gly Cys Ala Gly  Cys Cys Ala Cys Ala  Gly Thr Gly
    1340                 1345                 1350

Cys Cys  Cys Thr Gly Cys Thr  Cys Ala Gly Ala Ala  Gly Cys Cys
    1355                 1360                 1365

Cys Cys  Ala Ala Gly Cys Thr  Cys Gly Thr Cys Ala  Gly Thr Cys
```

```
    1370                1375                1380

Ala Ala  Gly Cys Cys Gly Gly  Thr Thr Cys Thr Cys  Cys Gly Thr
    1385                1390                1395

Thr Thr  Gly Cys Ala Cys Thr  Cys Ala Gly Gly Ala  Gly Cys Ala
    1400                1405                1410

Cys Gly  Gly Gly Cys Ala Gly  Gly Cys Gly Ala Gly  Thr Gly Gly
    1415                1420                1425

Cys Cys  Cys Cys Thr Ala Gly  Thr Thr Cys Thr Gly  Gly Gly Gly
    1430                1435                1440

Gly Cys  Ala Gly Cys Thr Cys  Thr Ala Gly Ala Gly  Cys Gly Gly
    1445                1450                1455

Thr Ala  Cys Cys Gly Gly Ala  Thr Cys Cys Ala Thr  Gly Ala Cys
    1460                1465                1470

Ala Gly  Ala Gly Ala Cys Cys  Cys Thr Gly Cys Cys  Thr Cys Cys
    1475                1480                1485

Cys Gly  Thr Gly Ala Cys Cys  Gly Ala Gly Ala Gly  Thr Gly Cys
    1490                1495                1500

Cys Gly  Thr Gly Gly Cys Cys  Cys Thr Thr Cys Ala  Ala Gly Cys
    1505                1510                1515

Cys Gly  Ala Gly Gly Thr Thr  Ala Cys Cys Cys Ala  Ala Ala Gly
    1520                1525                1530

Gly Gly  Ala Gly Thr Thr Gly  Thr Thr Cys Gly Ala  Gly Thr Thr
    1535                1540                1545

Cys Gly  Thr Gly Cys Thr Gly  Ala Ala Cys Gly Ala  Cys Cys Cys
    1550                1555                1560

Thr Thr  Thr Gly Cys Thr Thr  Gly Cys Ala Ala Gly  Cys Ala Gly
    1565                1570                1575

Thr Cys  Thr Cys Thr Ala Thr  Ala Thr Cys Ala Ala  Cys Ala Thr
    1580                1585                1590

Cys Gly  Cys Ala Cys Thr Thr  Gly Cys Ala Gly Gly  Ala Cys Thr
    1595                1600                1605

Gly Ala  Gly Thr Ala Thr Ala  Cys Thr Gly Cys Thr  Gly Thr Thr
    1610                1615                1620

Cys Gly  Thr Thr Thr Thr Thr  Ala Thr Gly Ala Cys  Cys Cys Gly
    1625                1630                1635

Ala Gly  Gly Ala Cys Thr Cys  Gly Ala Thr Gly Ala  Thr Cys Cys
    1640                1645                1650

Ala Cys  Gly Gly Gly Cys Ala  Ala Ala Ala Cys Thr  Thr Ala Thr
    1655                1660                1665

Thr Gly  Cys Thr Gly Thr Gly  Thr Cys Ala Ala Cys  Cys Ala Thr
    1670                1675                1680

Cys Cys  Thr Thr Gly Thr Gly  Cys Cys Thr Gly Thr  Cys Gly Thr
    1685                1690                1695

Cys Ala  Gly Cys Ala Thr Thr  Gly Cys Cys Thr Cys  Cys Thr Ala
    1700                1705                1710

Cys Ala  Cys Thr Gly Gly Ala  Thr Thr Gly Gly Cys  Gly Ala Gly
    1715                1720                1725

Cys Gly  Gly Cys Cys Thr Gly  Ala Cys Ala Ala Thr  Thr Thr Cys
    1730                1735                1740

Cys Gly  Thr Thr Cys Thr Thr  Gly Ala Ala Ala Thr  Gly Cys Cys
    1745                1750                1755

Ala Gly  Cys Gly Gly Gly Cys  Cys Ala Thr Thr Thr  Thr Gly Cys
    1760                1765                1770
```

```
Ala Gly Ala Ala Gly Gly Cys Ala Gly Cys Thr Cys Ala Gly Thr
    1775                1780                1785

Gly Ala Thr Gly Cys Thr Gly Gly Gly Ala Gly Gly Ala Gly Ala
    1790                1795                1800

Ala Gly Ala Gly Gly Thr Ala Gly Ala Thr Gly Gly Thr Gly Thr
    1805                1810                1815

Ala Gly Thr Cys Ala Cys Cys Ala Thr Gly Thr Gly Gly Gly Gly
    1820                1825                1830

Ala Cys Gly Gly Thr Ala Thr Cys Thr Cys Ala Cys Cys Thr Gly
    1835                1840                1845

Gly Gly Cys Ala Cys Thr Thr Thr Cys Cys Ala Cys Gly Cys Cys
    1850                1855                1860

Cys Ala Thr Gly Ala Thr Thr Cys Thr Cys Cys Thr Cys Gly Cys
    1865                1870                1875

Thr Cys Thr Gly Gly Gly Thr Cys Thr Cys Cys Thr Gly Gly Cys
    1880                1885                1890

Cys Gly Gly Ala Ala Gly Cys Ala Ala Thr Gly Cys Thr Ala Cys
    1895                1900                1905

Ala Ala Ala Gly Cys Thr Cys Thr Thr Cys Ala Cys Ala Gly Cys
    1910                1915                1920

Thr Ala Thr Cys Ala Cys Thr Thr Thr Cys Gly Ala Thr Ala Thr
    1925                1930                1935

Cys Gly Cys Thr Ala Thr Gly Thr Gly Cys Gly Thr Gly Ala Cys
    1940                1945                1950

Thr Gly Gly Cys Cys Thr Thr Gly Cys Cys Gly Cys Gly Gly Cys
    1955                1960                1965

Cys Cys Thr Gly Ala Cys Thr Ala Cys Cys Thr Cys Cys Thr Cys
    1970                1975                1980

Cys Cys Ala Cys Cys Thr Cys Ala Thr Gly Ala Gly Ala Thr Gly
    1985                1990                1995

Gly Thr Thr Cys Thr Gly Gly Thr Ala Cys Gly Cys Thr Ala Thr
    2000                2005                2010

Cys Ala Gly Thr Thr Gly Thr Gly Cys Ala Thr Gly Cys Thr Thr
    2015                2020                2025

Thr Cys Thr Gly Gly Thr Gly Gly Thr Cys Thr Thr Gly Thr Ala
    2030                2035                2040

Thr Ala Thr Cys Cys Thr Gly Cys Thr Gly Gly Thr Gly Gly Ala
    2045                2050                2055

Gly Thr Gly Gly Gly Cys Ala Cys Ala Gly Gly Ala Cys Gly Cys
    2060                2065                2070

Cys Ala Ala Ala Gly Cys Cys Gly Cys Gly Gly Gly Ala Ala Cys
    2075                2080                2085

Cys Gly Cys Thr Gly Ala Cys Ala Thr Gly Thr Thr Cys Ala Ala
    2090                2095                2100

Thr Ala Cys Cys Cys Thr Gly Ala Ala Gly Cys Thr Gly Thr Thr
    2105                2110                2115

Gly Ala Cys Ala Gly Thr Ala Gly Thr Gly Ala Thr Gly Thr Gly
    2120                2125                2130

Gly Cys Thr Gly Gly Gly Gly Thr Ala Thr Cys Cys Ala Ala Thr
    2135                2140                2145

Thr Gly Thr Gly Thr Gly Gly Gly Cys Thr Cys Thr Thr Gly Gly
    2150                2155                2160
```

```
Ala Gly Thr Cys Gly Ala Gly Gly Gly Thr Ala Thr Cys Gly Cys
    2165                2170                2175

Gly Gly Thr Gly Thr Thr Gly Cys Cys Cys Gly Thr Thr Gly Gly
    2180                2185                2190

Gly Gly Thr Gly Ala Cys Gly Ala Gly Cys Thr Gly Gly Gly Gly
    2195                2200                2205

Ala Thr Ala Thr Thr Cys Thr Thr Thr Cys Cys Thr Gly Gly Ala
    2210                2215                2220

Thr Ala Thr Cys Gly Thr Gly Gly Cys Ala Ala Ala Gly Thr Ala
    2225                2230                2235

Cys Ala Thr Thr Thr Thr Cys Gly Cys Ala Thr Thr Cys Thr Thr
    2240                2245                2250

Gly Cys Thr Cys Cys Thr Gly Ala Ala Cys Thr Ala Thr Cys Thr
    2255                2260                2265

Gly Ala Cys Gly Thr Cys Ala Ala Ala Cys Gly Ala Ala Thr Cys
    2270                2275                2280

Thr Gly Thr Cys Gly Thr Gly Thr Cys Cys Gly Gly Cys Ala Gly
    2285                2290                2295

Cys Ala Thr Thr Thr Thr Gly Gly Ala Thr Gly Thr Thr Cys Cys
    2300                2305                2310

Ala Thr Cys Thr Gly Cys Thr Thr Cys Thr Gly Gly Gly Ala Cys
    2315                2320                2325

Cys Cys Cys Gly Gly Cys Thr Gly Ala Thr Gly Ala Thr Gly Cys
    2330                2335                2340

Gly Gly Cys Cys Gly Cys Ala Gly Thr Gly Ala Gly Cys Ala Ala
    2345                2350                2355

Gly Gly Gly Cys Gly Ala Gly Gly Ala Gly Cys Thr Gly Thr Thr
    2360                2365                2370

Cys Ala Cys Cys Gly Gly Gly Gly Thr Gly Gly Thr Gly Cys Cys
    2375                2380                2385

Cys Ala Thr Cys Cys Thr Gly Gly Thr Cys Gly Ala Gly Cys Thr
    2390                2395                2400

Gly Gly Ala Cys Gly Gly Cys Gly Ala Cys Gly Thr Ala Ala Ala
    2405                2410                2415

Cys Gly Gly Cys Cys Ala Cys Ala Ala Gly Thr Thr Cys Ala Gly
    2420                2425                2430

Cys Gly Thr Gly Thr Cys Cys Gly Gly Cys Gly Ala Gly Gly Gly
    2435                2440                2445

Cys Gly Ala Gly Gly Gly Cys Gly Ala Thr Gly Cys Cys Ala Cys
    2450                2455                2460

Cys Thr Ala Cys Gly Gly Cys Ala Ala Gly Cys Thr Gly Ala Cys
    2465                2470                2475

Cys Cys Thr Gly Ala Ala Gly Cys Thr Gly Ala Thr Cys Thr Gly
    2480                2485                2490

Cys Ala Cys Cys Ala Cys Cys Gly Gly Cys Ala Ala Gly Cys Thr
    2495                2500                2505

Gly Cys Cys Cys Gly Thr Gly Cys Cys Cys Thr Gly Gly Cys Cys
    2510                2515                2520

Cys Ala Cys Cys Cys Thr Cys Gly Thr Gly Ala Cys Cys Ala Cys
    2525                2530                2535

Cys Cys Thr Gly Gly Gly Cys Thr Ala Cys Gly Gly Cys Cys Thr
    2540                2545                2550

Gly Cys Ala Gly Thr Gly Cys Thr Thr Cys Gly Cys Cys Cys Gly
```

```
    2555                2560                2565

Cys Thr  Ala Cys Cys Cys Cys  Gly Ala Cys Cys Ala  Cys Ala Thr
    2570                2575                2580

Gly Ala  Ala Gly Cys Ala Gly  Cys Ala Cys Gly Ala  Cys Thr Thr
    2585                2590                2595

Cys Thr  Thr Cys Ala Ala Gly  Thr Cys Cys Gly Cys  Cys Ala Thr
    2600                2605                2610

Gly Cys  Cys Cys Gly Ala Ala  Gly Gly Cys Thr Ala  Cys Gly Thr
    2615                2620                2625

Cys Cys  Ala Gly Gly Ala Gly  Cys Gly Cys Ala Cys  Cys Ala Thr
    2630                2635                2640

Cys Thr  Thr Cys Thr Thr Cys  Ala Ala Gly Gly Ala  Cys Gly Ala
    2645                2650                2655

Cys Gly  Gly Cys Ala Ala Cys  Thr Ala Cys Ala Ala  Gly Ala Cys
    2660                2665                2670

Cys Cys  Gly Cys Gly Cys Cys  Gly Ala Gly Gly Thr  Gly Ala Ala
    2675                2680                2685

Gly Thr  Thr Cys Gly Ala Gly  Gly Gly Cys Gly Ala  Cys Ala Cys
    2690                2695                2700

Cys Cys  Thr Gly Gly Thr Gly  Ala Ala Cys Cys Gly  Cys Ala Thr
    2705                2710                2715

Cys Gly  Ala Gly Cys Thr Gly  Ala Ala Gly Gly Gly  Cys Ala Thr
    2720                2725                2730

Cys Gly  Ala Cys Thr Thr Cys  Ala Ala Gly Gly Ala  Gly Gly Ala
    2735                2740                2745

Cys Gly  Gly Cys Ala Ala Cys  Ala Thr Cys Cys Thr  Gly Gly Gly
    2750                2755                2760

Gly Cys  Ala Cys Ala Ala Gly  Cys Thr Gly Gly Ala  Gly Thr Ala
    2765                2770                2775

Cys Ala  Ala Cys Thr Ala Cys  Ala Ala Cys Ala Gly  Cys Cys Ala
    2780                2785                2790

Cys Ala  Ala Cys Gly Thr Cys  Thr Ala Thr Ala Thr  Cys Ala Cys
    2795                2800                2805

Cys Gly  Cys Cys Gly Ala Cys  Ala Ala Gly Cys Ala  Gly Ala Ala
    2810                2815                2820

Gly Ala  Ala Cys Gly Gly Cys  Ala Thr Cys Ala Ala  Gly Gly Cys
    2825                2830                2835

Cys Ala  Ala Cys Thr Thr Cys  Ala Ala Gly Ala Thr  Cys Cys Gly
    2840                2845                2850

Cys Cys  Ala Cys Ala Ala Cys  Ala Thr Cys Gly Ala  Gly Gly Ala
    2855                2860                2865

Cys Gly  Gly Cys Gly Gly Cys  Gly Thr Gly Cys Ala  Gly Cys Thr
    2870                2875                2880

Cys Gly  Cys Cys Gly Ala Cys  Cys Ala Cys Thr Ala  Cys Cys Ala
    2885                2890                2895

Gly Cys  Ala Gly Ala Ala Cys  Ala Cys Cys Cys Cys  Cys Ala Thr
    2900                2905                2910

Cys Gly  Gly Cys Gly Ala Cys  Gly Gly Cys Cys Cys  Cys Gly Thr
    2915                2920                2925

Gly Cys  Thr Gly Cys Thr Gly  Cys Cys Cys Gly Ala  Cys Ala Ala
    2930                2935                2940

Cys Cys  Ala Cys Thr Ala Cys  Cys Thr Gly Ala Gly  Cys Thr Ala
    2945                2950                2955
```

```
Cys Cys  Ala Gly Thr Cys Cys  Ala Ala Gly Cys Thr  Gly Ala Gly
    2960                 2965                 2970

Cys Ala  Ala Ala Gly Ala Cys  Cys Cys Cys Ala Ala  Cys Gly Ala
    2975                 2980                 2985

Gly Ala  Ala Gly Cys Gly Cys  Gly Ala Thr Cys Ala  Cys Ala Thr
    2990                 2995                 3000

Gly Gly  Thr Cys Cys Thr Gly  Cys Thr Gly Gly Ala  Gly Thr Thr
    3005                 3010                 3015

Cys Gly  Thr Gly Ala Cys Cys  Gly Cys Cys Gly Cys  Cys Gly Gly
    3020                 3025                 3030

Gly Gly  Gly Thr Ala Cys Cys  Ala Ala Gly Gly Thr  Gly Thr Ala
    3035                 3040                 3045

Cys Gly  Ala Cys Cys Cys Cys  Gly Ala Gly Cys Ala  Gly Ala Gly
    3050                 3055                 3060

Gly Ala  Ala Gly Ala Gly Gly  Ala Thr Gly Ala Thr  Cys Ala Cys
    3065                 3070                 3075

Cys Gly  Gly Cys Cys Cys Cys  Cys Ala Gly Thr Gly  Gly Thr Gly
    3080                 3085                 3090

Gly Gly  Cys Cys Ala Gly Gly  Thr Gly Cys Ala Ala  Gly Cys Ala
    3095                 3100                 3105

Gly Ala  Thr Gly Ala Ala Cys  Gly Thr Gly Cys Thr  Gly Gly Ala
    3110                 3115                 3120

Cys Ala  Gly Cys Thr Thr Cys  Ala Thr Cys Ala Ala  Cys Thr Ala
    3125                 3130                 3135

Cys Thr  Ala Cys Gly Ala Cys  Ala Gly Cys Gly Ala  Gly Ala Ala
    3140                 3145                 3150

Gly Cys  Ala Cys Gly Cys Cys  Gly Ala Gly Ala Ala  Cys Gly Cys
    3155                 3160                 3165

Cys Gly  Thr Gly Ala Thr Cys  Thr Thr Cys Cys Thr  Gly Cys Ala
    3170                 3175                 3180

Cys Gly  Gly Cys Ala Ala Cys  Gly Cys Cys Ala Cys  Thr Ala Gly
    3185                 3190                 3195

Cys Ala  Gly Cys Thr Ala Cys  Cys Thr Gly Thr Gly  Gly Ala Gly
    3200                 3205                 3210

Gly Cys  Ala Cys Gly Thr Gly  Gly Thr Gly Cys Cys  Cys Cys Ala
    3215                 3220                 3225

Cys Ala  Thr Cys Gly Ala Gly  Cys Cys Cys Gly Thr  Gly Gly Cys
    3230                 3235                 3240

Cys Ala  Gly Gly Thr Gly Cys  Ala Thr Cys Ala Thr  Cys Cys Cys
    3245                 3250                 3255

Cys Gly  Ala Thr Cys Thr Gly  Ala Thr Cys Gly Gly  Cys Ala Thr
    3260                 3265                 3270

Gly Gly  Gly Cys Ala Ala Gly  Ala Gly Cys Gly Gly  Cys Ala Ala
    3275                 3280                 3285

Gly Ala  Gly Cys Gly Gly Cys  Ala Ala Cys Gly Gly  Cys Ala Gly
    3290                 3295                 3300

Cys Thr  Ala Cys Ala Gly Gly  Cys Thr Gly Cys Thr  Gly Gly Ala
    3305                 3310                 3315

Cys Cys  Ala Cys Thr Ala Cys  Ala Ala Gly Thr Ala  Cys Cys Thr
    3320                 3325                 3330

Gly Ala  Cys Cys Gly Cys Cys  Thr Gly Gly Thr Thr  Cys Gly Ala
    3335                 3340                 3345
```

```
Gly Cys  Thr Thr Cys Thr Gly  Ala Ala Cys Cys Thr  Gly Cys Cys
    3350                 3355                 3360

Cys Ala  Ala Gly Ala Ala Gly  Ala Thr Cys Ala Thr  Cys Thr Thr
    3365                 3370                 3375

Cys Gly  Thr Gly Gly Gly Cys  Cys Ala Cys Gly Ala  Cys Thr Gly
    3380                 3385                 3390

Gly Gly  Gly Cys Gly Cys Cys  Gly Cys Cys Cys Thr  Gly Gly Cys
    3395                 3400                 3405

Cys Thr  Thr Cys Cys Ala Cys  Thr Ala Cys Gly Cys  Cys Thr Ala
    3410                 3415                 3420

Cys Gly  Ala Gly Cys Ala Cys  Cys Ala Gly Gly Ala  Cys Ala Gly
    3425                 3430                 3435

Gly Ala  Thr Cys Ala Ala Gly  Gly Cys Cys Ala Thr  Cys Gly Thr
    3440                 3445                 3450

Gly Cys  Ala Cys Ala Thr Gly  Gly Ala Gly Ala Gly  Cys Gly Thr
    3455                 3460                 3465

Gly Gly  Thr Gly Gly Ala Cys  Gly Thr Gly Ala Thr  Cys Gly Ala
    3470                 3475                 3480

Gly Ala  Gly Cys Thr Gly Gly  Gly Ala Cys Gly Ala  Gly Thr Gly
    3485                 3490                 3495

Gly Cys  Cys Ala Gly Ala Cys  Ala Thr Cys Gly Ala  Gly Gly Ala
    3500                 3505                 3510

Gly Gly  Ala Cys Ala Thr Cys  Gly Cys Cys Cys Thr  Gly Ala Thr
    3515                 3520                 3525

Cys Ala  Ala Gly Ala Gly Cys  Gly Ala Gly Gly Ala  Gly Gly Gly
    3530                 3535                 3540

Cys Gly  Ala Gly Ala Ala Gly  Ala Thr Gly Gly Thr  Gly Cys Thr
    3545                 3550                 3555

Gly Gly  Ala Gly Ala Ala Cys  Ala Ala Cys Thr Thr  Cys Thr Thr
    3560                 3565                 3570

Cys Gly  Thr Gly Gly Ala Gly  Ala Cys Cys Gly Thr  Gly Cys Thr
    3575                 3580                 3585

Gly Cys  Cys Cys Ala Gly Cys  Ala Ala Gly Ala Thr  Cys Ala Thr
    3590                 3595                 3600

Gly Ala  Gly Ala Ala Ala Gly  Cys Thr Gly Gly Ala  Gly Cys Cys
    3605                 3610                 3615

Cys Gly  Ala Gly Gly Ala Gly  Thr Thr Cys Gly Cys  Cys Gly Cys
    3620                 3625                 3630

Cys Thr  Ala Cys Cys Thr Gly  Gly Ala Gly Cys Cys  Cys Thr Thr
    3635                 3640                 3645

Cys Ala  Ala Gly Gly Ala Gly  Ala Ala Gly Gly Gly  Cys Gly Ala
    3650                 3655                 3660

Gly Gly  Thr Gly Ala Gly Ala  Ala Gly Ala Cys Cys  Cys Ala Cys
    3665                 3670                 3675

Cys Cys  Thr Gly Ala Gly Cys  Thr Gly Gly Cys Cys  Cys Ala Gly
    3680                 3685                 3690

Ala Gly  Ala Gly Ala Thr Cys  Cys Cys Cys Cys Thr  Gly Gly Thr
    3695                 3700                 3705

Gly Ala  Ala Gly Gly Gly Cys  Gly Gly Cys Ala Ala  Gly Cys Cys
    3710                 3715                 3720

Cys Gly  Ala Cys Gly Thr Gly  Gly Thr Gly Cys Ala  Gly Ala Thr
    3725                 3730                 3735

Cys Gly  Thr Gly Ala Gly Ala  Ala Ala Cys Thr Ala  Cys Ala Ala
```

3740 3745 3750

Cys Gly Cys Cys Thr Ala Cys Cys Thr Gly Ala Gly Ala Gly Cys
3755 3760 3765

Cys Ala Gly Cys Gly Ala Cys Gly Ala Cys Cys Thr Gly Cys Cys
3770 3775 3780

Cys Ala Ala Gly Cys Thr Gly Thr Thr Cys Ala Thr Cys Gly Ala
3785 3790 3795

Gly Gly Gly Cys Gly Ala Cys Cys Cys Cys Gly Gly Cys Thr Thr
3800 3805 3810

Cys Thr Thr Cys Ala Gly Cys Ala Ala Cys Gly Cys Cys Ala Thr
3815 3820 3825

Cys Gly Thr Gly Gly Ala Gly Gly Gly Cys Gly Cys Cys Ala Ala
3830 3835 3840

Gly Ala Ala Gly Thr Thr Cys Cys Cys Cys Ala Ala Cys Ala Cys
3845 3850 3855

Cys Gly Ala Gly Thr Thr Cys Gly Thr Gly Ala Ala Gly Gly Thr
3860 3865 3870

Gly Ala Ala Gly Gly Gly Cys Cys Thr Gly Cys Ala Cys Thr Thr
3875 3880 3885

Cys Cys Thr Cys Cys Ala Gly Gly Ala Gly Gly Ala Cys Gly Cys
3890 3895 3900

Cys Cys Cys Cys Gly Ala Cys Gly Ala Gly Ala Thr Gly Gly Gly
3905 3910 3915

Cys Ala Ala Gly Thr Ala Cys Ala Thr Cys Ala Ala Gly Ala Gly
3920 3925 3930

Cys Thr Thr Cys Gly Thr Gly Gly Ala Gly Ala Gly Ala Gly Thr
3935 3940 3945

Gly Cys Thr Gly Ala Ala Gly Ala Ala Cys Gly Ala Gly Cys Ala
3950 3955 3960

Gly Thr Thr Cys Thr Gly Cys Thr Ala Cys Gly Ala Gly Ala Ala
3965 3970 3975

Cys Gly Ala Gly Gly Thr Gly Thr Ala Ala Gly Ala Ala Thr Thr
3980 3985 3990

Cys Gly Ala Thr Ala Thr Cys Ala Ala Gly Cys Thr Thr Ala Thr
3995 4000 4005

Cys Gly Ala Thr Ala Ala Thr Cys Ala Ala Cys Cys Thr Cys Thr
4010 4015 4020

Gly Gly Ala Thr Thr Ala Cys Ala Ala Ala Ala Thr Thr Thr Gly
4025 4030 4035

Thr Gly Ala Ala Ala Gly Ala Thr Thr Gly Ala Cys Thr Gly Gly
4040 4045 4050

Thr Ala Thr Thr Cys Thr Thr Ala Ala Cys Thr Ala Thr Gly Thr
4055 4060 4065

Thr Gly Cys Thr Cys Cys Thr Thr Thr Thr Ala Cys Gly Cys Thr
4070 4075 4080

Ala Thr Gly Thr Gly Gly Ala Thr Ala Cys Gly Cys Thr Gly Cys
4085 4090 4095

Thr Thr Thr Ala Ala Thr Gly Cys Cys Thr Thr Thr Gly Thr Ala
4100 4105 4110

Thr Cys Ala Thr Gly Cys Thr Ala Thr Thr Gly Cys Thr Thr Cys
4115 4120 4125

Cys Cys Gly Thr Ala Thr Gly Gly Cys Thr Thr Thr Cys Ala Thr
4130 4135 4140

```
Thr Thr  Thr Cys Thr Cys Cys  Thr Cys Cys Thr Thr  Gly Thr Ala
    4145                 4150                 4155

Thr Ala  Ala Ala Thr Cys Cys  Thr Gly Gly Thr Thr  Gly Cys Thr
    4160                 4165                 4170

Gly Thr  Cys Thr Cys Thr Thr  Thr Ala Thr Gly Ala  Gly Gly Ala
    4175                 4180                 4185

Gly Thr  Thr Gly Thr Gly Gly  Cys Cys Cys Gly Thr  Thr Gly Thr
    4190                 4195                 4200

Cys Ala  Gly Gly Cys Ala Ala  Cys Gly Thr Gly Gly  Cys Gly Thr
    4205                 4210                 4215

Gly Gly  Thr Gly Thr Gly Cys  Ala Cys Thr Gly Thr  Gly Thr Thr
    4220                 4225                 4230

Thr Gly  Cys Thr Gly Ala Cys  Gly Cys Ala Ala Cys  Cys Cys Cys
    4235                 4240                 4245

Cys Ala  Cys Thr Gly Gly Thr  Thr Gly Gly Gly Gly  Cys Ala Thr
    4250                 4255                 4260

Thr Gly  Cys Cys Ala Cys Cys  Ala Cys Cys Thr Gly  Thr Cys Ala
    4265                 4270                 4275

Gly Cys  Thr Cys Cys Thr Thr  Thr Cys Cys Gly Gly  Gly Ala Cys
    4280                 4285                 4290

Thr Thr  Thr Cys Gly Cys Thr  Thr Thr Cys Cys Cys  Cys Cys Thr
    4295                 4300                 4305

Cys Cys  Cys Thr Ala Thr Thr  Gly Cys Cys Ala Cys  Gly Gly Cys
    4310                 4315                 4320

Gly Gly  Ala Ala Cys Thr Cys  Ala Thr Cys Gly Cys  Cys Gly Cys
    4325                 4330                 4335

Cys Thr  Gly Cys Cys Thr Thr  Gly Cys Cys Cys Gly  Cys Thr Gly
    4340                 4345                 4350

Cys Thr  Gly Gly Ala Cys Ala  Gly Gly Gly Gly Cys  Thr Cys Gly
    4355                 4360                 4365

Gly Cys  Thr Gly Thr Thr Gly  Gly Gly Cys Ala Cys  Thr Gly Ala
    4370                 4375                 4380

Cys Ala  Ala Thr Thr Cys Cys  Gly Thr Gly Gly Thr  Gly Thr Thr
    4385                 4390                 4395

Gly Thr  Cys Gly Gly Gly Gly  Ala Ala Ala Thr Cys  Ala Thr Cys
    4400                 4405                 4410

Gly Thr  Cys Cys Thr Thr Thr  Cys Cys Thr Thr Gly  Gly Cys Thr
    4415                 4420                 4425

Gly Cys  Thr Cys Gly Cys Cys  Thr Gly Thr Gly Thr  Thr Gly Cys
    4430                 4435                 4440

Cys Ala  Cys Cys Thr Gly Gly  Ala Thr Thr Cys Thr  Gly Cys Gly
    4445                 4450                 4455

Cys Gly  Gly Gly Ala Cys Gly  Thr Cys Cys Thr Thr  Cys Thr Gly
    4460                 4465                 4470

Cys Thr  Ala Cys Gly Thr Cys  Cys Cys Thr Thr Cys  Gly Gly Cys
    4475                 4480                 4485

Cys Cys  Thr Cys Ala Ala Thr  Cys Cys Ala Gly Cys  Gly Gly Ala
    4490                 4495                 4500

Cys Cys  Thr Thr Cys Cys Thr  Thr Cys Cys Cys Gly  Cys Gly Gly
    4505                 4510                 4515

Cys Cys  Thr Gly Cys Thr Gly  Cys Cys Gly Gly Cys  Thr Cys Thr
    4520                 4525                 4530
```

Gly Cys Gly Gly Cys Cys Thr Cys Thr Thr Cys Cys Gly Cys Gly
4535 4540 4545

Thr Cys Thr Thr Cys Gly Cys Cys Thr Thr Cys Gly Cys Cys Cys
4550 4555 4560

Thr Cys Ala Gly Ala Cys Gly Ala Gly Thr Cys Gly Gly Ala Thr
4565 4570 4575

Cys Thr Cys Cys Cys Thr Thr Thr Gly Gly Gly Cys Cys Gly Cys
4580 4585 4590

Cys Thr Cys Cys Cys Cys Gly Cys Ala Thr Cys Gly Ala Thr Ala
4595 4600 4605

Cys Cys Gly Ala Gly Cys Gly Cys Thr Gly Cys Thr Cys Gly Ala
4610 4615 4620

Gly Ala Gly Ala Thr Cys Thr Ala Cys Gly Gly Gly Thr Gly Gly
4625 4630 4635

Cys Ala Thr Cys Cys Cys Thr Gly Thr Gly Ala Cys Cys Cys Cys
4640 4645 4650

Thr Cys Cys Cys Cys Ala Gly Thr Gly Cys Cys Thr Cys Thr Cys
4655 4660 4665

Cys Thr Gly Gly Cys Cys Cys Thr Gly Gly Ala Ala Gly Thr Thr
4670 4675 4680

Gly Cys Cys Ala Cys Thr Cys Cys Ala Gly Thr Gly Cys Cys Cys
4685 4690 4695

Ala Cys Cys Ala Gly Cys Cys Thr Thr Gly Thr Cys Cys Thr Ala
4700 4705 4710

Ala Thr Ala Ala Ala Ala Thr Thr Ala Ala Gly Thr Thr Gly Cys
4715 4720 4725

Ala Thr Cys Ala Thr Thr Thr Thr Gly Thr Cys Thr Gly Ala Cys
4730 4735 4740

Thr Ala Gly Gly Thr Gly Thr Cys Cys Thr Thr Cys Thr Ala Thr
4745 4750 4755

Ala Ala Thr Ala Thr Thr Ala Thr Gly Gly Gly Gly Thr Gly Gly
4760 4765 4770

Ala Gly Gly Gly Gly Gly Gly Thr Gly Gly Thr Ala Thr Gly Gly
4775 4780 4785

Ala Gly Cys Ala Ala Gly Gly Gly Gly Cys Ala Ala Gly Thr Thr
4790 4795 4800

Gly Gly Gly Ala Ala Gly Ala Cys Ala Ala Cys Cys Thr Gly Thr
4805 4810 4815

Ala Gly Gly Gly Cys Cys Thr Gly Cys Gly Gly Gly Gly Thr Cys
4820 4825 4830

Thr Ala Thr Thr Gly Gly Gly Ala Ala Cys Cys Ala Ala Gly Cys
4835 4840 4845

Thr Gly Gly Ala Gly Thr Gly Cys Ala Gly Thr Gly Gly Cys Ala
4850 4855 4860

Cys Ala Ala Thr Cys Thr Thr Gly Gly Cys Thr Cys Ala Cys Thr
4865 4870 4875

Gly Cys Ala Ala Thr Cys Thr Cys Cys Gly Cys Cys Thr Cys Cys
4880 4885 4890

Thr Gly Gly Gly Thr Thr Cys Ala Ala Gly Cys Gly Ala Thr Thr
4895 4900 4905

Cys Thr Cys Cys Thr Gly Cys Cys Thr Cys Ala Gly Cys Cys Thr
4910 4915 4920

Cys Cys Cys Gly Ala Gly Thr Thr Gly Thr Thr Gly Gly Gly Ala 4925 4930 4935

Thr Thr Cys Cys Ala Gly Gly Cys Ala Thr Gly Cys Ala Thr Gly
4940 4945 4950

Ala Cys Cys Ala Gly Gly Cys Thr Cys Ala Gly Cys Thr Ala Ala
4955 4960 4965

Thr Thr Thr Thr Thr Gly Thr Thr Thr Thr Thr Thr Thr Gly Gly
4970 4975 4980

Thr Ala Gly Ala Gly Ala Cys Gly Gly Gly Gly Thr Thr Thr Cys
4985 4990 4995

Ala Cys Cys Ala Thr Ala Thr Thr Gly Gly Cys Cys Ala Gly Gly
5000 5005 5010

Cys Thr Gly Gly Thr Cys Thr Cys Cys Ala Ala Cys Thr Cys Cys
5015 5020 5025

Thr Ala Ala Thr Cys Thr Cys Ala Gly Gly Thr Gly Ala Thr Cys
5030 5035 5040

Thr Ala Cys Cys Cys Ala Cys Cys Thr Thr Gly Gly Cys Cys Thr
5045 5050 5055

Cys Cys Cys Ala Ala Ala Thr Thr Gly Cys Thr Gly Gly Gly Ala
5060 5065 5070

Thr Thr Ala Cys Ala Gly Gly Cys Gly Thr Gly Ala Ala Cys Cys
5075 5080 5085

Ala Cys Thr Gly Cys Thr Cys Cys Cys Thr Thr Cys Cys Cys Thr
5090 5095 5100

Gly Thr Cys Cys Thr Thr Cys Thr Gly Ala Thr Thr Thr Thr Gly
5105 5110 5115

Thr Ala Gly Gly Thr Ala Ala Cys Cys Ala Cys Gly Thr Gly Cys
5120 5125 5130

Gly Gly Ala Cys Cys Gly Ala Gly Cys Gly Gly Cys Cys Gly Cys
5135 5140 5145

Ala Gly Gly Ala Ala Cys Cys Cys Cys Thr Ala Gly Thr Gly Ala
5150 5155 5160

Thr Gly Gly Ala Gly Thr Thr Gly Gly Cys Cys Ala Cys Thr Cys
5165 5170 5175

Cys Cys Thr Cys Thr Cys Thr Gly Cys Gly Cys Gly Cys Thr Cys
5180 5185 5190

Gly Cys Thr Cys Gly Cys Thr Cys Ala Cys Thr Gly Ala Gly Gly
5195 5200 5205

Cys Cys Gly Gly Gly Cys Gly Ala Cys Cys Ala Ala Ala Gly Gly
5210 5215 5220

Thr Cys Gly Cys Cys Cys Gly Ala Cys Gly Cys Cys Cys Gly Gly
5225 5230 5235

Gly Cys Thr Thr Thr Gly Cys Cys Cys Gly Gly Gly Cys Gly Gly
5240 5245 5250

Cys Cys Thr Cys Ala Gly Thr Gly Ala Gly Cys Gly Ala Gly Cys
5255 5260 5265

Gly Ala Gly Cys Gly Cys Gly Cys Ala Gly Cys Thr Gly Cys Cys
5270 5275 5280

Thr Gly Cys Ala Gly Gly Gly Gly Cys Gly Cys Cys Thr Gly Ala
5285 5290 5295

Thr Gly Cys Gly Gly Thr Ala Thr Thr Thr Thr Cys Thr Cys Cys
5300 5305 5310

Thr Thr Ala Cys Gly Cys Ala Thr Cys Thr Gly Thr Gly Cys Gly
5315 5320 5325

```
Gly Thr  Ala Thr Thr Thr Cys  Ala Cys Ala Cys Cys  Gly Cys Ala
    5330                 5335                 5340

Thr Ala  Cys Gly Thr Cys Ala  Ala Ala Gly Cys Ala  Ala Cys Cys
    5345                 5350                 5355

Ala Thr  Ala Gly Thr Ala Cys  Gly Cys Gly Cys Cys  Cys Thr Gly
    5360                 5365                 5370

Thr Ala  Gly Cys Gly Gly Cys  Gly Cys Ala Thr Thr  Ala Ala Gly
    5375                 5380                 5385

Cys Gly  Cys Gly Gly Cys Gly  Gly Gly Thr Gly Thr  Gly Gly Thr
    5390                 5395                 5400

Gly Gly  Thr Thr Ala Cys Gly  Cys Gly Cys Ala Gly  Cys Gly Thr
    5405                 5410                 5415

Gly Ala  Cys Cys Gly Cys Thr  Ala Cys Ala Cys Thr  Thr Gly Cys
    5420                 5425                 5430

Cys Ala  Gly Cys Gly Cys Cys  Cys Thr Ala Gly Cys  Gly Cys Cys
    5435                 5440                 5445

Cys Gly  Cys Thr Cys Cys Thr  Thr Thr Cys Gly Cys  Thr Thr Thr
    5450                 5455                 5460

Cys Thr  Thr Cys Cys Cys Thr  Thr Cys Cys Thr Thr  Thr Cys Thr
    5465                 5470                 5475

Cys Gly  Cys Cys Ala Cys Gly  Thr Thr Cys Gly Cys  Cys Gly Gly
    5480                 5485                 5490

Cys Thr  Thr Thr Cys Cys Cys  Cys Gly Thr Cys Ala  Ala Gly Cys
    5495                 5500                 5505

Thr Cys  Thr Ala Ala Ala Thr  Cys Gly Gly Gly Gly  Gly Cys Thr
    5510                 5515                 5520

Cys Cys  Cys Thr Thr Thr Ala  Gly Gly Gly Thr Thr  Cys Cys Gly
    5525                 5530                 5535

Ala Thr  Thr Thr Ala Gly Thr  Gly Cys Thr Thr Thr  Ala Cys Gly
    5540                 5545                 5550

Gly Cys  Ala Cys Cys Thr Cys  Gly Ala Cys Cys Cys  Cys Ala Ala
    5555                 5560                 5565

Ala Ala  Ala Ala Cys Thr Thr  Gly Ala Thr Thr Thr  Gly Gly Gly
    5570                 5575                 5580

Thr Gly  Ala Thr Gly Gly Thr  Thr Cys Ala Cys Gly  Thr Ala Gly
    5585                 5590                 5595

Thr Gly  Gly Gly Cys Cys Ala  Thr Cys Gly Cys Cys  Cys Thr Gly
    5600                 5605                 5610

Ala Thr  Ala Gly Ala Cys Gly  Gly Thr Thr Thr Thr  Thr Cys Gly
    5615                 5620                 5625

Cys Cys  Cys Thr Thr Thr Gly  Ala Cys Gly Thr Thr  Gly Gly Ala
    5630                 5635                 5640

Gly Thr  Cys Cys Ala Cys Gly  Thr Thr Cys Thr Thr  Thr Ala Ala
    5645                 5650                 5655

Thr Ala  Gly Thr Gly Gly Ala  Cys Thr Cys Thr Thr  Gly Thr Thr
    5660                 5665                 5670

Cys Cys  Ala Ala Ala Cys Thr  Gly Gly Ala Ala Cys  Ala Ala Cys
    5675                 5680                 5685

Ala Cys  Thr Cys Ala Ala Cys  Cys Cys Thr Ala Thr  Cys Thr Cys
    5690                 5695                 5700

Gly Gly  Gly Cys Thr Ala Thr  Thr Cys Thr Thr Thr  Thr Gly Ala
    5705                 5710                 5715
```

```
Thr Thr  Thr Ala Thr Ala Ala  Gly Gly Gly Ala Thr  Thr Thr Thr
    5720                 5725                 5730

Gly Cys  Cys Gly Ala Thr Thr  Thr Cys Gly Gly Cys  Cys Thr Ala
    5735                 5740                 5745

Thr Thr  Gly Gly Thr Thr Ala  Ala Ala Ala Ala Ala  Thr Gly Ala
    5750                 5755                 5760

Gly Cys  Thr Gly Ala Thr Thr  Thr Ala Ala Cys Ala  Ala Ala Ala
    5765                 5770                 5775

Ala Thr  Thr Thr Ala Ala Cys  Gly Cys Gly Ala Ala  Thr Thr Thr
    5780                 5785                 5790

Thr Ala  Ala Cys Ala Ala Ala  Ala Thr Ala Thr Thr  Ala Ala Cys
    5795                 5800                 5805

Gly Thr  Thr Thr Ala Cys Ala  Ala Thr Thr Thr Thr  Ala Thr Gly
    5810                 5815                 5820

Gly Thr  Gly Cys Ala Cys Thr  Cys Thr Cys Ala Gly  Thr Ala Cys
    5825                 5830                 5835

Ala Ala  Thr Cys Thr Gly Cys  Thr Cys Thr Gly Ala  Thr Gly Cys
    5840                 5845                 5850

Cys Gly  Cys Ala Thr Ala Gly  Thr Thr Ala Ala Gly  Cys Cys Ala
    5855                 5860                 5865

Gly Cys  Cys Cys Cys Gly Ala  Cys Ala Cys Cys Cys  Gly Cys Cys
    5870                 5875                 5880

Ala Ala  Cys Ala Cys Cys Cys  Gly Cys Thr Gly Ala  Cys Gly Cys
    5885                 5890                 5895

Gly Cys  Cys Cys Thr Gly Ala  Cys Gly Gly Gly Cys  Thr Thr Gly
    5900                 5905                 5910

Thr Cys  Thr Gly Cys Thr Cys  Cys Cys Gly Gly Cys  Ala Thr Cys
    5915                 5920                 5925

Cys Gly  Cys Thr Thr Ala Cys  Ala Gly Ala Cys Ala  Ala Gly Cys
    5930                 5935                 5940

Thr Gly  Thr Gly Ala Cys Cys  Gly Thr Cys Thr Cys  Cys Gly Gly
    5945                 5950                 5955

Gly Ala  Gly Cys Thr Gly Cys  Ala Thr Gly Thr Gly  Thr Cys Ala
    5960                 5965                 5970

Gly Ala  Gly Gly Thr Thr Thr  Thr Cys Ala Cys Cys  Gly Thr Cys
    5975                 5980                 5985

Ala Thr  Cys Ala Cys Cys Gly  Ala Ala Ala Cys Gly  Cys Gly Cys
    5990                 5995                 6000

Gly Ala  Gly Ala Cys Gly Ala  Ala Ala Gly Gly Gly  Cys Cys Thr
    6005                 6010                 6015

Cys Gly  Thr Gly Ala Thr Ala  Cys Gly Cys Cys Thr  Ala Thr Thr
    6020                 6025                 6030

Thr Thr  Thr Ala Thr Ala Gly  Gly Thr Thr Ala Ala  Thr Gly Thr
    6035                 6040                 6045

Cys Ala  Thr Gly Ala Thr Ala  Ala Thr Ala Ala Thr  Gly Gly Thr
    6050                 6055                 6060

Thr Thr  Cys Thr Thr Ala Gly  Ala Cys Gly Thr Cys  Ala Gly Gly
    6065                 6070                 6075

Thr Gly  Gly Cys Ala Cys Thr  Thr Thr Thr Cys Gly  Gly Gly Gly
    6080                 6085                 6090

Ala Ala  Ala Thr Gly Thr Gly  Cys Gly Cys Gly Gly  Ala Ala Cys
    6095                 6100                 6105

Cys Cys  Cys Thr Ala Thr Thr  Thr Gly Thr Thr Thr  Ala Thr Thr
```

6110 6115 6120

Thr Thr Thr Cys Thr Ala Ala Ala Thr Ala Cys Ala Thr Thr Cys
6125 6130 6135

Ala Ala Ala Thr Ala Thr Gly Thr Ala Thr Cys Cys Gly Cys Thr
6140 6145 6150

Cys Ala Thr Gly Ala Gly Ala Cys Ala Ala Thr Ala Ala Cys Cys
6155 6160 6165

Cys Thr Gly Ala Thr Ala Ala Ala Thr Gly Cys Thr Thr Cys Ala
6170 6175 6180

Ala Thr Ala Ala Thr Ala Thr Thr Gly Ala Ala Ala Ala Ala Gly
6185 6190 6195

Gly Ala Ala Gly Ala Gly Thr Ala Thr Gly Ala Gly Thr Ala Thr
6200 6205 6210

Thr Cys Ala Ala Cys Ala Thr Thr Thr Cys Cys Gly Thr Gly Thr
6215 6220 6225

Cys Gly Cys Cys Cys Thr Thr Ala Thr Thr Cys Cys Cys Thr Thr
6230 6235 6240

Thr Thr Thr Thr Gly Cys Gly Gly Cys Ala Thr Thr Thr Thr Gly
6245 6250 6255

Cys Cys Thr Thr Cys Cys Thr Gly Thr Thr Thr Thr Thr Gly Cys
6260 6265 6270

Thr Cys Ala Cys Cys Cys Ala Gly Ala Ala Ala Cys Gly Cys Thr
6275 6280 6285

Gly Gly Thr Gly Ala Ala Ala Gly Thr Ala Ala Ala Ala Gly Ala
6290 6295 6300

Thr Gly Cys Thr Gly Ala Ala Gly Ala Thr Cys Ala Gly Thr Thr
6305 6310 6315

Gly Gly Gly Thr Gly Cys Ala Cys Gly Ala Gly Thr Gly Gly Gly
6320 6325 6330

Thr Thr Ala Cys Ala Thr Cys Gly Ala Ala Cys Thr Gly Gly Ala
6335 6340 6345

Thr Cys Thr Cys Ala Ala Cys Ala Gly Cys Gly Gly Thr Ala Ala
6350 6355 6360

Gly Ala Thr Cys Cys Thr Thr Gly Ala Gly Ala Gly Thr Thr Thr
6365 6370 6375

Thr Cys Gly Cys Cys Cys Cys Gly Ala Ala Gly Ala Ala Cys Gly
6380 6385 6390

Thr Thr Thr Thr Cys Cys Ala Ala Thr Gly Ala Thr Gly Ala Gly
6395 6400 6405

Cys Ala Cys Thr Thr Thr Thr Ala Ala Ala Gly Thr Thr Cys Thr
6410 6415 6420

Gly Cys Thr Ala Thr Gly Thr Gly Gly Cys Gly Cys Gly Gly Thr
6425 6430 6435

Ala Thr Thr Ala Thr Cys Cys Cys Gly Thr Ala Thr Thr Gly Ala
6440 6445 6450

Cys Gly Cys Cys Gly Gly Gly Cys Ala Ala Gly Ala Gly Cys Ala
6455 6460 6465

Ala Cys Thr Cys Gly Gly Thr Cys Gly Cys Cys Gly Cys Ala Thr
6470 6475 6480

Ala Cys Ala Cys Thr Ala Thr Thr Cys Thr Cys Ala Gly Ala Ala
6485 6490 6495

Thr Gly Ala Cys Thr Thr Gly Gly Thr Thr Gly Ala Gly Thr Ala
6500 6505 6510

Cys Thr Cys Ala Cys Cys Ala Gly Thr Cys Ala Cys Ala Gly Ala
6515 6520 6525

Ala Ala Ala Gly Cys Ala Thr Cys Thr Thr Ala Cys Gly Gly Ala
6530 6535 6540

Thr Gly Gly Cys Ala Thr Gly Ala Cys Ala Gly Thr Ala Ala Gly
6545 6550 6555

Ala Gly Ala Ala Thr Thr Ala Thr Gly Cys Ala Gly Thr Gly Cys
6560 6565 6570

Thr Gly Cys Cys Ala Thr Ala Ala Cys Cys Ala Thr Gly Ala Gly
6575 6580 6585

Thr Gly Ala Thr Ala Ala Cys Ala Cys Thr Gly Cys Gly Gly Cys
6590 6595 6600

Cys Ala Ala Cys Thr Thr Ala Cys Thr Thr Cys Thr Gly Ala Cys
6605 6610 6615

Ala Ala Cys Gly Ala Thr Cys Gly Gly Ala Gly Gly Ala Cys Cys
6620 6625 6630

Gly Ala Ala Gly Gly Ala Gly Cys Thr Ala Ala Cys Cys Gly Cys
6635 6640 6645

Thr Thr Thr Thr Thr Thr Gly Cys Ala Cys Ala Ala Cys Ala Thr
6650 6655 6660

Gly Gly Gly Gly Gly Ala Thr Cys Ala Thr Gly Thr Ala Ala Cys
6665 6670 6675

Thr Cys Gly Cys Cys Thr Thr Gly Ala Thr Cys Gly Thr Thr Gly
6680 6685 6690

Gly Gly Ala Ala Cys Cys Gly Gly Ala Gly Cys Thr Gly Ala Ala
6695 6700 6705

Thr Gly Ala Ala Gly Cys Cys Ala Thr Ala Cys Cys Ala Ala Ala
6710 6715 6720

Cys Gly Ala Cys Gly Ala Gly Cys Gly Thr Gly Ala Cys Ala Cys
6725 6730 6735

Cys Ala Cys Gly Ala Thr Gly Cys Cys Thr Gly Thr Ala Gly Cys
6740 6745 6750

Ala Ala Thr Gly Gly Cys Ala Ala Cys Ala Ala Cys Gly Thr Thr
6755 6760 6765

Gly Cys Gly Cys Ala Ala Ala Cys Thr Ala Thr Thr Ala Ala Cys
6770 6775 6780

Thr Gly Gly Cys Gly Ala Ala Cys Thr Ala Cys Thr Thr Ala Cys
6785 6790 6795

Thr Cys Thr Ala Gly Cys Thr Thr Cys Cys Cys Gly Gly Cys Ala
6800 6805 6810

Ala Cys Ala Ala Thr Thr Ala Ala Thr Ala Gly Ala Cys Thr Gly
6815 6820 6825

Gly Ala Thr Gly Gly Ala Gly Gly Cys Gly Gly Ala Thr Ala Ala
6830 6835 6840

Ala Gly Thr Thr Gly Cys Ala Gly Gly Ala Cys Cys Ala Cys Thr
6845 6850 6855

Thr Cys Thr Gly Cys Gly Cys Thr Cys Gly Gly Cys Cys Cys Thr
6860 6865 6870

Thr Cys Cys Gly Gly Cys Thr Gly Gly Cys Thr Gly Gly Thr Thr
6875 6880 6885

Thr Ala Thr Thr Gly Cys Thr Gly Ala Thr Ala Ala Ala Thr Cys
6890 6895 6900

```
Thr Gly  Gly Ala Gly Cys Cys  Gly Gly Thr Gly Ala  Gly Cys Gly
    6905                 6910                 6915

Thr Gly  Gly Gly Thr Cys Thr  Cys Gly Cys Gly Gly  Thr Ala Thr
    6920                 6925                 6930

Cys Ala  Thr Thr Gly Cys Ala  Gly Cys Ala Cys Thr  Gly Gly Gly
    6935                 6940                 6945

Gly Cys  Cys Ala Gly Ala Thr  Gly Gly Thr Ala Ala  Gly Cys Cys
    6950                 6955                 6960

Cys Thr  Cys Cys Cys Gly Thr  Ala Thr Cys Gly Thr  Ala Gly Thr
    6965                 6970                 6975

Thr Ala  Thr Cys Thr Ala Cys  Ala Cys Gly Ala Cys  Gly Gly Gly
    6980                 6985                 6990

Gly Ala  Gly Thr Cys Ala Gly  Gly Cys Ala Ala Cys  Thr Ala Thr
    6995                 7000                 7005

Gly Gly  Ala Thr Gly Ala Ala  Cys Gly Ala Ala Ala  Thr Ala Gly
    7010                 7015                 7020

Ala Cys  Ala Gly Ala Thr Cys  Gly Cys Thr Gly Ala  Gly Ala Thr
    7025                 7030                 7035

Ala Gly  Gly Thr Gly Cys Cys  Thr Cys Ala Cys Thr  Gly Ala Thr
    7040                 7045                 7050

Thr Ala  Ala Gly Cys Ala Thr  Thr Gly Gly Thr Ala  Ala Cys Thr
    7055                 7060                 7065

Gly Thr  Cys Ala Gly Ala Cys  Cys Ala Ala Gly Thr  Thr Thr Ala
    7070                 7075                 7080

Cys Thr  Cys Ala Thr Ala Thr  Ala Thr Ala Cys Thr  Thr Thr Ala
    7085                 7090                 7095

Gly Ala  Thr Thr Gly Ala Thr  Thr Thr Ala Ala Ala  Ala Cys Thr
    7100                 7105                 7110

Thr Cys  Ala Thr Thr Thr Thr  Thr Ala Ala Thr Thr  Thr Ala Ala
    7115                 7120                 7125

Ala Ala  Gly Gly Ala Thr Cys  Thr Ala Gly Gly Thr  Gly Ala Ala
    7130                 7135                 7140

Gly Ala  Thr Cys Cys Thr Thr  Thr Thr Thr Gly Ala  Thr Ala Ala
    7145                 7150                 7155

Thr Cys  Thr Cys Ala Thr Gly  Ala Cys Cys Ala Ala  Ala Ala Thr
    7160                 7165                 7170

Cys Cys  Cys Thr Thr Ala Ala  Cys Gly Thr Gly Ala  Gly Thr Thr
    7175                 7180                 7185

Thr Thr  Cys Gly Thr Thr Cys  Cys Ala Cys Thr Gly  Ala Gly Cys
    7190                 7195                 7200

Gly Thr  Cys Ala Gly Ala Cys  Cys Cys Cys Gly Thr  Ala Gly Ala
    7205                 7210                 7215

Ala Ala  Ala Gly Ala Thr Cys  Ala Ala Ala Gly Gly  Ala Thr Cys
    7220                 7225                 7230

Thr Thr  Cys Thr Thr Gly Ala  Gly Ala Thr Cys Cys  Thr Thr Thr
    7235                 7240                 7245

Thr Thr  Thr Thr Cys Thr Gly  Cys Gly Cys Gly Thr  Ala Ala Thr
    7250                 7255                 7260

Cys Thr  Gly Cys Thr Gly Cys  Thr Thr Gly Cys Ala  Ala Ala Cys
    7265                 7270                 7275

Ala Ala  Ala Ala Ala Ala Ala  Cys Cys Ala Cys Cys  Gly Cys Thr
    7280                 7285                 7290

Ala Cys  Cys Ala Gly Cys Gly  Gly Thr Gly Gly Thr  Thr Thr Gly
```

```
    7295                7300                7305

Thr Thr  Thr Gly Cys Cys Gly  Gly Ala Thr Cys Ala  Ala Gly Ala
    7310                7315                7320

Gly Cys  Thr Ala Cys Cys Ala  Ala Cys Thr Cys Thr  Thr Thr Thr
    7325                7330                7335

Thr Cys  Cys Gly Ala Ala Gly  Gly Thr Ala Ala Cys  Thr Gly Gly
    7340                7345                7350

Cys Thr  Thr Cys Ala Gly Cys  Ala Gly Ala Gly Cys  Gly Cys Ala
    7355                7360                7365

Gly Ala  Thr Ala Cys Cys Ala  Ala Ala Thr Ala Cys  Thr Gly Thr
    7370                7375                7380

Cys Cys  Thr Thr Cys Thr Ala  Gly Thr Gly Thr Ala  Gly Cys Cys
    7385                7390                7395

Gly Thr  Ala Gly Thr Thr Ala  Gly Gly Cys Cys Ala  Cys Cys Ala
    7400                7405                7410

Cys Thr  Thr Cys Ala Ala Gly  Ala Ala Cys Thr Cys  Thr Gly Thr
    7415                7420                7425

Ala Gly  Cys Ala Cys Cys Gly  Cys Cys Thr Ala Cys  Ala Thr Ala
    7430                7435                7440

Cys Cys  Thr Cys Gly Cys Thr  Cys Thr Gly Cys Thr  Ala Ala Thr
    7445                7450                7455

Cys Cys  Thr Gly Thr Thr Ala  Cys Cys Ala Gly Thr  Gly Gly Cys
    7460                7465                7470

Thr Gly  Cys Thr Gly Cys Cys  Ala Gly Thr Gly Gly  Cys Gly Ala
    7475                7480                7485

Thr Ala  Ala Gly Thr Cys Gly  Thr Gly Thr Cys Thr  Thr Ala Cys
    7490                7495                7500

Cys Gly  Gly Gly Thr Thr Gly  Gly Ala Cys Thr Cys  Ala Ala Gly
    7505                7510                7515

Ala Cys  Gly Ala Thr Ala Gly  Thr Thr Ala Cys Cys  Gly Gly Ala
    7520                7525                7530

Thr Ala  Ala Gly Gly Cys Gly  Cys Ala Gly Cys Gly  Gly Thr Cys
    7535                7540                7545

Gly Gly  Gly Cys Thr Gly Ala  Ala Cys Gly Gly Gly  Gly Gly Gly
    7550                7555                7560

Thr Thr  Cys Gly Thr Gly Cys  Ala Cys Ala Cys Ala  Gly Cys Cys
    7565                7570                7575

Cys Ala  Gly Cys Thr Thr Gly  Gly Ala Gly Cys Gly  Ala Ala Cys
    7580                7585                7590

Gly Ala  Cys Cys Thr Ala Cys  Ala Cys Cys Gly Ala  Ala Cys Thr
    7595                7600                7605

Gly Ala  Gly Ala Thr Ala Cys  Cys Thr Ala Cys Ala  Gly Cys Gly
    7610                7615                7620

Thr Gly  Ala Gly Cys Thr Ala  Thr Gly Ala Gly Ala  Ala Ala Gly
    7625                7630                7635

Cys Gly  Cys Cys Ala Cys Gly  Cys Thr Thr Cys Cys  Cys Gly Ala
    7640                7645                7650

Ala Gly  Gly Gly Ala Gly Ala  Ala Ala Gly Gly Cys  Gly Gly Ala
    7655                7660                7665

Cys Ala  Gly Gly Thr Ala Thr  Cys Cys Gly Gly Thr  Ala Ala Gly
    7670                7675                7680

Cys Gly  Gly Cys Ala Gly Gly  Gly Thr Cys Gly Gly  Ala Ala Cys
    7685                7690                7695
```

-continued

| | | | | | | | | | | | | | | |
|---|---|---|---|---|---|---|---|---|---|---|---|---|---|---|
| Ala | Gly | Gly | Ala | Gly | Ala | Gly | Cys | Gly | Cys | Ala | Cys | Gly | Ala | Gly |
| | 7700 | | | | | 7705 | | | | | 7710 | | | |
| Gly | Gly | Ala | Gly | Cys | Thr | Thr | Cys | Cys | Ala | Gly | Gly | Gly | Gly | Gly |
| | 7715 | | | | | 7720 | | | | | 7725 | | | |
| Ala | Ala | Ala | Cys | Gly | Cys | Cys | Thr | Gly | Gly | Thr | Ala | Thr | Cys | Thr |
| | 7730 | | | | | 7735 | | | | | 7740 | | | |
| Thr | Thr | Ala | Thr | Ala | Gly | Thr | Cys | Cys | Thr | Gly | Thr | Cys | Gly | Gly |
| | 7745 | | | | | 7750 | | | | | 7755 | | | |
| Gly | Thr | Thr | Thr | Cys | Gly | Cys | Cys | Ala | Cys | Cys | Thr | Cys | Thr | Gly |
| | 7760 | | | | | 7765 | | | | | 7770 | | | |
| Ala | Cys | Thr | Thr | Gly | Ala | Gly | Cys | Gly | Thr | Cys | Gly | Ala | Thr | Thr |
| | 7775 | | | | | 7780 | | | | | 7785 | | | |
| Thr | Thr | Thr | Gly | Thr | Gly | Ala | Thr | Gly | Cys | Thr | Cys | Gly | Thr | Cys |
| | 7790 | | | | | 7795 | | | | | 7800 | | | |
| Ala | Gly | Gly | Gly | Gly | Gly | Gly | Cys | Gly | Gly | Ala | Gly | Cys | Cys | Thr |
| | 7805 | | | | | 7810 | | | | | 7815 | | | |
| Ala | Thr | Gly | Gly | Ala | Ala | Ala | Ala | Ala | Cys | Gly | Cys | Cys | Ala | Gly |
| | 7820 | | | | | 7825 | | | | | 7830 | | | |
| Cys | Ala | Ala | Cys | Gly | Cys | Gly | Gly | Cys | Cys | Thr | Thr | Thr | Thr | Thr |
| | 7835 | | | | | 7840 | | | | | 7845 | | | |
| Ala | Cys | Gly | Gly | Thr | Thr | Cys | Cys | Thr | Gly | Gly | Cys | Cys | Thr | Thr |
| | 7850 | | | | | 7855 | | | | | 7860 | | | |
| Thr | Thr | Gly | Cys | Thr | Gly | Gly | Cys | Cys | Thr | Thr | Thr | Thr | Gly | Cys |
| | 7865 | | | | | 7870 | | | | | 7875 | | | |
| Thr | Cys | Ala | Cys | Ala | Thr | Gly | Thr | | | | | | | |
| | 7880 | | | | | 7885 | | | | | | | | |